US010947601B2

(12) United States Patent
Neilan et al.

(10) Patent No.: US 10,947,601 B2
(45) Date of Patent: *Mar. 16, 2021

(54) DETECTION OF SAXITOXIN-PRODUCING DINOFLAGELLATES

(71) Applicants: NewSouth Innovations Pty Limited, New South Wales (AU); Universitetet i Oslo, Oslo (NO)

(72) Inventors: Brett A. Neilan, Maroubra (AU); Shauna Ann Murray, Erskineville (AU); Anke Stuken, Oslo (NO); Kjetill S. Jakobsen, Oslo (NO); Russel J. S. Orr, Stabekk (NO); Ralf Kellmann, Nesttun (NO)

(73) Assignees: EWSOUTH INNOVATIONS PTY LIMITED, New South Wales (AU); UNIVERSITETET I OSLO, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/370,752

(22) Filed: Dec. 6, 2016

(65) Prior Publication Data
US 2017/0081733 A1 Mar. 23, 2017

Related U.S. Application Data

(63) Continuation of application No. 14/114,850, filed as application No. PCT/AU2012/000541 on May 16, 2012, now Pat. No. 9,580,759.

(60) Provisional application No. 61/486,633, filed on May 16, 2011.

(51) Int. Cl.
| C12Q 1/68 | (2018.01) |
| C12Q 1/6893 | (2018.01) |
| C07K 14/44 | (2006.01) |
| C12N 15/52 | (2006.01) |
| C12Q 1/04 | (2006.01) |
| C12P 17/18 | (2006.01) |

(52) U.S. Cl.
CPC .......... *C12Q 1/6893* (2013.01); *C07K 14/44* (2013.01); *C12N 15/52* (2013.01); *C12P 17/182* (2013.01); *C12Q 1/04* (2013.01); *C12Q 2600/158* (2013.01); *C12Q 2600/16* (2013.01)

(58) Field of Classification Search
CPC .................................................. C12Q 1/6893
See application file for complete search history.

(56) References Cited

U.S. PATENT DOCUMENTS

2011/0129842 A1* 6/2011 Neilan .............. C12N 9/90
435/6.12

FOREIGN PATENT DOCUMENTS

WO 2009/129558 10/2009

OTHER PUBLICATIONS

Genbank Accession No. JF343238—Alexandrium fundyense strain CCMP1719 SxtA short isoform precursor (sxtA) mRNA, complete cds, submitted Feb. 10, 2011, retrieved on Apr. 24, 2020 from https://www.ncbi.nlm.nih.gov/nuccore/JF343238. (Year: 2011).*
Genbank Accession No. JF343239—Alexandrium fundyense strain CCMP1719 SxtA long isoform precursor (sxtA) mRNA, complete cds, submitted Feb. 10, 2011, retrieved on Apr. 24, 2020 from https://www.ncbi.nlm.nih.gov/nuccore/JF343239. (Year: 2011).*
Stuken A, Orr RJ, Kellmann R, Murray SA, Neilan BA, Jakobsen KS. Discovery of nuclear-encoded genes for the neurotoxin saxitoxin in dinoflagellates. PLoS One. 2011; 6(5):e20096 pp. 1-12. Epub May 18, 2011. (Year: 2011).*
Yang, Ines. Investigations into the transcriptome of the toxigenic marine dinoflagellate Alexandrium minutum. PhD diss., Universitat Bremen, 2010. (Year: 2010).*
Database GenBank (online), Apr. 14, 2011 uploaded, Accession No. JF343238, Definition:Alexandrium fundyense strain CCMP1719 SxtA short isoform precursor (sxtA) mRNA, complete cds. [retrieved on May 25, 2012] Retrieved from the Internet: <URL:http://www.ncbi.nlm.nih.gov/nuccore/324962888?sat=14&satkey=8099465>.
Database GenBank (online), Apr. 14, 2011 uploaded, Accession No. JF343239, Definition:Alexandrium fundyense strain CCMP1719 SxtA long isoform precursor (sxtA) mRNA, complete cds. [retrieved on May 25, 2012] Retrieved from the Internet: <URL:http://www.ncbi.nlm.nih.gov/nuccore/324962890?sat=14&satkey=8099466>.
Database GenBank (online), Apr. 14, 2011 uploaded, Accession Nos. JF343292-JF343302, JF343308-JF-343309, JF343337-JF343346, JF343352-JF343432, [retrieved on Jun. 12, 2012] Retrieved from the Internet: <URL:http://www.ncbi.nlm.nih.gov/pmc>.
Database GenBank (online), Apr. 14, 2011 uploaded, Accession No. JF343250, Definition:Alexandrium tamarense strain ATEB01 SxtA (sxtA) gene, partial sequence [retrieved on Jun. 29, 2012] Retrieved from the Internet: <URL:http://www.ncbi.nlm.nih.gov/nuccore/324962902?sat=14&satkey=8099477>.
Ishida, Y. et. al., "PSP Toxins: Their Biosyntheis by Marine Dinoflagellates and Molecular Identification", Microbial Foodborne Diseases, 2000, 383-401.
Stuken, A. et al., "Discovery of Nuclear-Encoded Genes for the Neurotoxin Saxitoxin in Dinoflagellates", PLoS One, May 18, 2011, 6(5), e20096.

(Continued)

*Primary Examiner* — Teresa E Strzelecka
*Assistant Examiner* — Olayinka A Oyeyemi
(74) *Attorney, Agent, or Firm* — Casimir Jones, S.C.; Tanya Arenson

(57) ABSTRACT

The invention generally relates to the field of saxitoxins and the identification of microorganisms capable of producing them. More specifically, the invention relates to the identification of genes encoding saxitoxin in dinoflagellates, and methods for the specific detection of dinoflagellates that are producers of saxitoxins.

8 Claims, 14 Drawing Sheets
Specification includes a Sequence Listing.

(56) References Cited

OTHER PUBLICATIONS

Murray, S.A. et al., "sxtA-Based Quantitative Molecular Assay to Identify Saxitoxin-Producing Harmful Algal Blooms in Marine Waters", Applied and Environmental Microbiology, 2011, 77(19), 7050-7057.

International Search Report, PCT/AU2012/000541 dated Jul. 3, 2012.

Database GenBank (online) JF343240 and JF343347 through JF343351, pp. 1-123.

Kellmann et al. "Biosynthesis and Molecular Genetics of Polyketides in Marine Dinoflagellates" Mar. Drugs 2010, 8, pp. 1011-1048.

Stuken et al. "Novel hydrolysis-probe based qPCR assay to detect saxitoxin transcripts of dinoflagellates in environmental samples" Harmful Algae 28 (2013), 108-117.

Genbank Accession No. JF343238.1 Alexandrium funyense strain CCMP1719 SxtA short isoform precursor (sxtA) nRNA, complete cds (GI: 324962888, submitted by Stuken et al. Feb. 10, 2011, available online Apr. 14, 2011, retrieved on Mar. 23, 2015 from http://www.ncbi.nlm.nih.gov/nuccore/JF343238).

Genbank Accession No. JF343239.1 Alexandrium funyense strain CCMP1719 SxtA short isoform precursor (sxtA) nRNA, complete cds (GI: 324962890, submitted by Stuken et al. Feb. 10, 2011, available online Apr. 14, 2011, retrieved on Mar. 23, 2015 from http://www.ncbi.nlm.nih.gov/nuccore/JF343239).

Lowe, et al. A computer program for selection of oligonucleotide primers for polymerase chain reactions. Nucleic Acids Res. Apr. 11, 1990; 18(7): 1757-61.

Al-Tebrineh et al. Detection of saxitoxin-producing cyanobacteria and Anabaena circinalis in environmental water blooms by quantitative PCR. Appl Environ Microbial. Dec. 2010; 76(23): 7836-42. Epub Oct. 8, 2010.

Hosoi-Tanabe et al. Species-specific detection and quantification of toxic marine dinoflagellates Alexandrium tamarense and A. catenella by Real-time PCR assay. Mar Biotechnol (NY). Sep.-Oct. 2005; 7(5):506-14. Epub Jul. 5, 2005.

Kellmann et al. Biosynthetic intermediate analysis and functional homology reveal a saxitoxin gene cluster in cyanabacteria. Appl Environ Microbial. Jul. 2008; 74(13):4044-53 Epub May 16, 2008.

Llewellyn, LE. Saxitoxin, a toxic marine natural product that targets a multitude of receptors. Nat Prod Rep. Apr. 2006; 23(2):200-22. Epub Feb. 23, 2006.

* cited by examiner

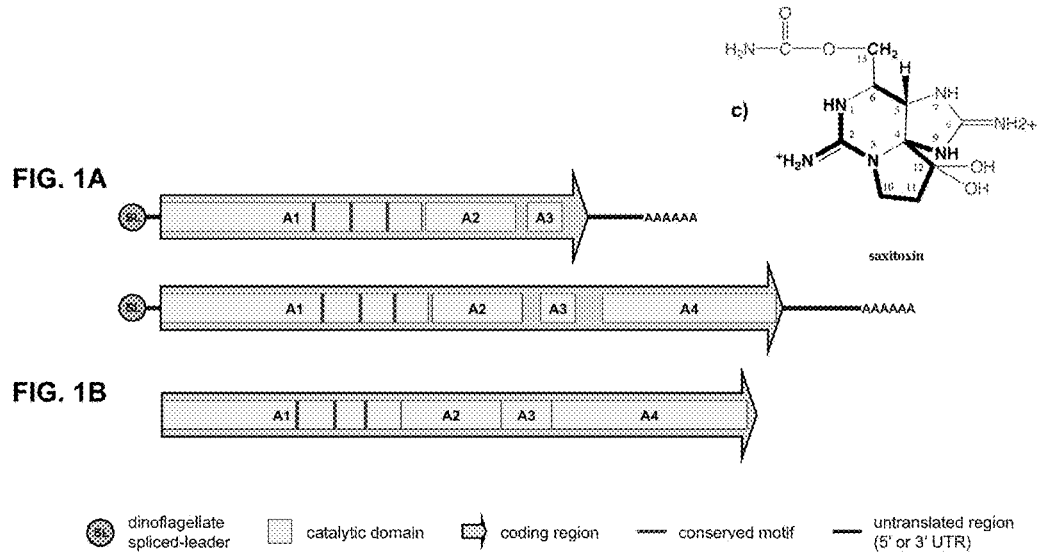
FIG. 1A
FIG. 1B
FIG. 2
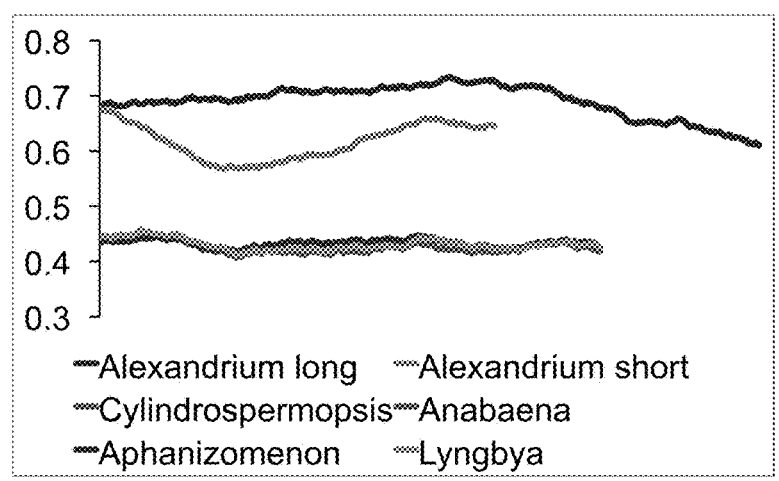

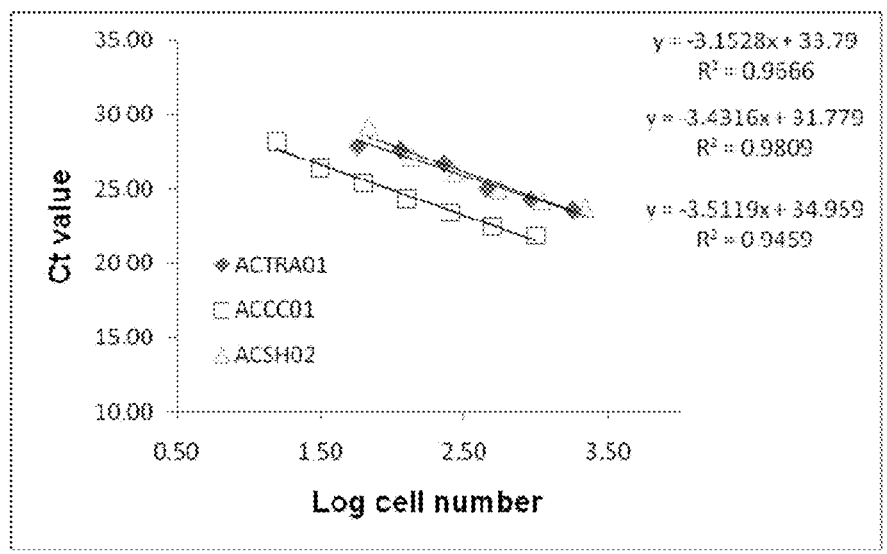
FIG. 8
FIG. 9A
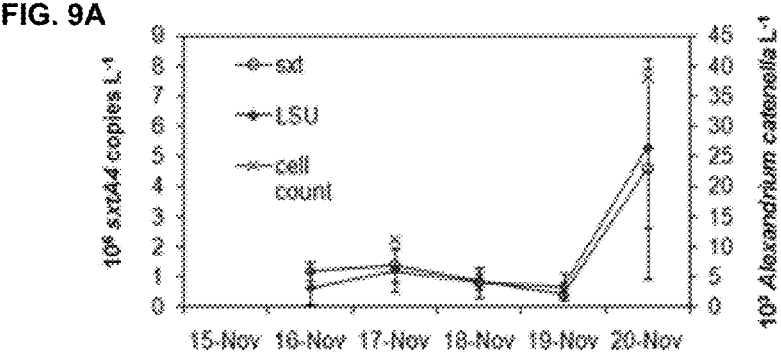
FIG. 9B
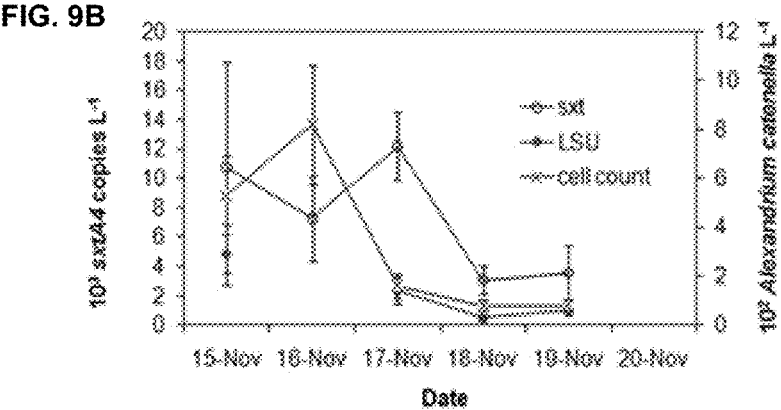

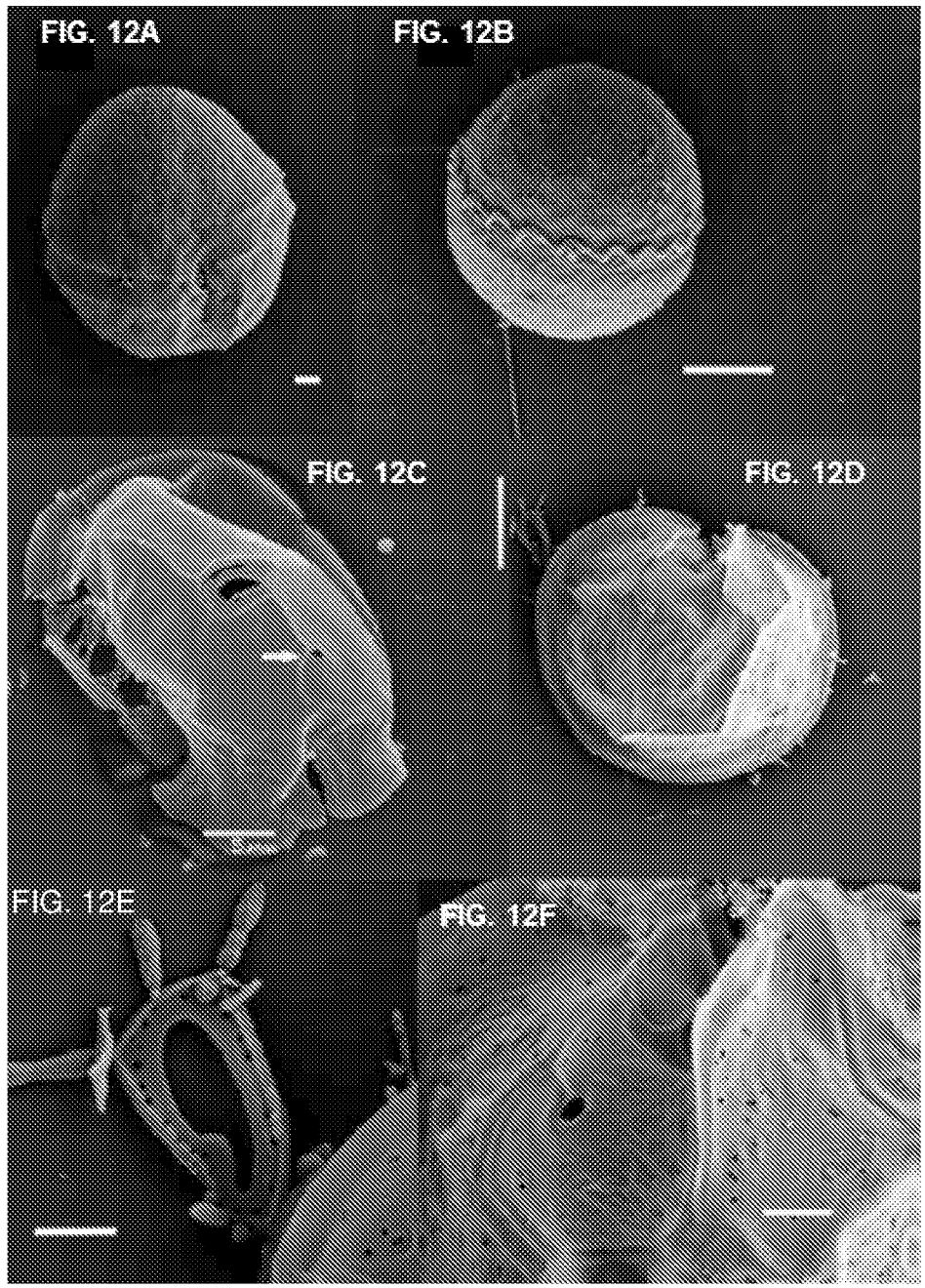

FIG. 13A  FIG. 13B  FIG. 13C  FIG. 13D
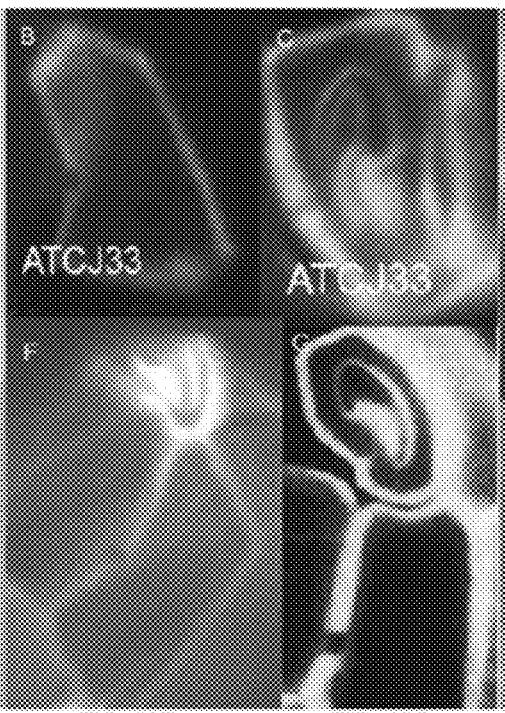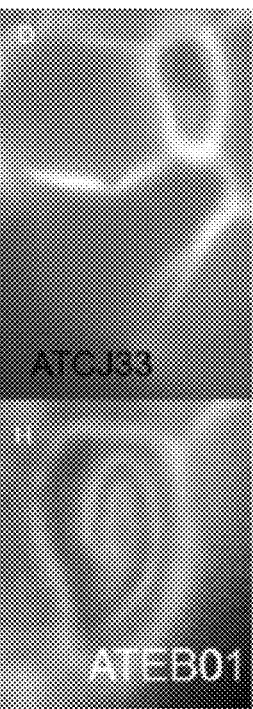
FIG. 13E  FIG. 13F  FIG. 13G  FIG. 13H

SEQUENCE LISTING

<160> NUMBER OF SEQ ID NOS: 247

<210> SEQ ID NO 1
<211> LENGTH: 3166
<212> TYPE: DNA
<213> ORGANISM: Alexandrium fundyense

<400> SEQUENCE: 1

```
accgtagcca ttttggctca agccaaactc ggatcattcc tggccactgc gccgccatcc      60
gtgccggcgc cccgaccggg ggcacctcat gtccgtggag catgcgacga tcgcggacgc     120
ggtcccgaac gggatcgacc tggcgacaaa tgccttcatg ctcgtccacg gctggacggc     180
ggcgcccctg ctcctggagc tcgtggccaa cttcagcgcg ccctggagg gcgggccca      240 gaccgcgggg gagctggccg cggagacggg cgccgaggag gggcccctgg cgatcctcct     300
ccgcgcctgc agcgtcctgg gctacgtgcg cttcgacgcc cagagcaggg cgtactccct     360
ggtcccgggg ccggagctgg acgagctcag gaccgtgctc caccctgcgt cggaggtcgc     420
gaggggcctg caggagctgt acagcgaggt cgcccccccc ttccagctgc cctcggagga     480 cgcggcgcgcg tgcctggccc tctgggagga gcagcggccc tcctggagcc agtgcaggag     540
cagggccctg ggcgtcctgc tggacggcgc tgtgctggcg ccgctgcttg tgtccgtgac     600
gtactcctcg aggtgggacg aggagggcca ggagcacggc agggataacg tcatggagcg     660
cttcgacttc agcaagatgt tgccggcgca gcggtccgcg ctcggggaca tcttcgagca     720
gttgggcgtc ggcactatga acgcgaaggg cgtgatcatg atgtcgtcaa aggggggccat     780 ggcgttgcag cgatgctact cctactacgt cccactgtcg tacgcaccgc tgatggccca     840
gatctcgccg atcctgtttg atgatgcggg ctggggttc actgacgcgg gacagactc     900 cttcgacgac gtggaggagc atgttgacag aatcttgaat gttgttggca gtggtgcgca     960
acaccggacc ctctttaagg atatgatgcg acacatcagt accgtgttca agggcgaggc    1020
attgcccttg cagccaagtt tcgttgtgga cactggctgt ggcgacggga gcctgctcat    1080
acatatctat gaacatatca aacagcacac accccggggg aaagtgcttg atcagttccc    1140
tctgacgatg gtcggcgttg acctcaatga ggatccgcga gtgacaacag ctgtgaatct    1200
gagcaagcag ggcgtcccgc acgtggtcat ctctggcgat gtgggtaagc ctgcggagat    1260
acttgccgcg ctgaagaaga agaaggtgga cgcgtcgagg acgcttcatg tccgctcctt    1320
cctagaccac gaccgtactt acatcccacc ggtcatgaga atagaggaag agagcagcac    1380
agccaggttt gcccgcactc agatggcaga ctttgtgcat ctggacaagc gtggaaagcc    1440
catcacggct ctggagctgt ttgcatccct ggtggaacat tttgaaagat gggctgatgc    1500
gctggaggtc tccttcggac tgtgtgtgct ggaggttatg atgctggatg tgcccacgac    1560
```

```
gcagcgctgg ttcaacgact gcgtgtcctt ccctctggac ttcgtccagt gtctttcgcg    1620
gcagtacatg gtatcggcgg cggcatttac aatgggagct gccatggcgg gcctcctgcc    1680
tgcggacttc cgcgccgtgg agacgtatcc tgagcatggg aggtacaacc gaatgttgag    1740
ccagcacctg gtcaagaggc cgttcaggct gcgccttgca gaggttgccg acctccagag    1800
cctcgttcat gtcgaagagc tggcatggcc caagcagatg cagggaagcc tggaggtgct    1860
ccgcagacga ctggaggcgt ccccaccac caacctggtc tgcgagctgg agggcagggt    1920
cgttgccgtg ctttacatgc aacggatcga gagtcttgcc gtcctcgatg gggtgcagtt    1980
catggacgta tcgtctgcgc actcccccag gggtcgtctg ctgcagctca tctcgatagc    2040
ggtccatccg gactttgcag gcatgaatct gggccgcgag ctgaaggagt ttggccttca    2100
cttggctcgg ttggacagca ccatcgagag ggtcatcggt gtcacaaggt gcagcaagga    2160
gtttcggcag tacgatggcc ccatgagtga gtacgtcaat gcgcacttct ctggggcccg    2220
gaccgacagc acgctggact tccactcctc cgccggagcg cagttcgtcc gcttggtgga    2280
gggcttccgc cccgaggaca ccgacaacgg cggcacagga gtggtcatcg cctacgacat    2340
caggagggct ctgcccaggg aggcggctgc gggcgcgccc ccgagcaggc cgccgccgag    2400
gacgaaggtc ccctcgctgc agctggtcca ggacgtcatg accagcatcg gctacccccc    2460
caacctcaat gacctcacca agggcttctt cgactacggc atggactccc tggagctcgt    2520
ccgcatccgg aacaagctga gcctcgccct gcagacggag ctccccgcga cgctgctcct    2580
cgacttcccc accgtgcacg acctcgtgga cggctggac caggaccggg cccccgagtc    2640
cgatgaggag gaggaggtgc gggaggaggc caaggccacg gccagagccc cggccaaggc    2700
caaggccctg gccaagggcg cgcgaggcgac ccagcgcttc gggccctcgg agatcatcag    2760
cgtgcagaag cgctgcctca acgtctacgc ccagcccatc taccagaagc ggttcacgga    2820
catggccaag aagtgcttcc cggacatgct caagtacatc ctcgccatag agtccatcct    2880
ggtcgaggtc gaggggccgg tcctgcagga gttccagctg atccaagatc tcgagtacaa    2940
gtcggtccag agaggccgcg agaatttgat gtactacatg tcaagctatt ggctggccca    3000
cccagagata cgcgatcaga gccagcagtt actcctcctc acgctgcagg accagtgctg    3060 ggcaataac cacttgtagg ctggcgctcc gcgggcacct cgaatctgcg gagccacata    3120
cgagagtctc agtgcgaaaa aaaaaaaaa aaaaaaaaa aaaaaa          3166
```

<210> SEQ ID NO 2
<211> LENGTH: 973
<212> TYPE: PRT
<213> ORGANISM: Alexandrium fundyense

<400> SEQUENCE: 2

```
Met Leu Val His Gly Trp Thr Ala Ala Pro Leu Leu Glu Leu Val
1               5                   10                  15

Ala Asn Phe Ser Ala Pro Leu Glu Gly Arg Ala Gln Thr Ala Gly Glu
            20                  25                  30

Leu Ala Ala Glu Thr Gly Ala Glu Gly Pro Leu Ala Ile Leu Leu
        35                  40                  45

Arg Ala Cys Ser Val Leu Gly Tyr Val Arg Phe Asp Ala Gln Ser Arg
    50                  55                  60

Ala Tyr Ser Leu Val Pro Gly Pro Glu Leu Asp Glu Leu Arg Thr Val
65                  70                  75                  80

Leu His Pro Ala Ser Glu Val Ala Arg Gly Leu Gln Glu Leu Tyr Ser
```

-continued

```
                85                  90                  95
Glu Val Ala Pro Pro Phe Gln Leu Pro Ser Glu Asp Ala Ala Arg Cys
            100                 105                 110

Leu Ala Leu Trp Glu Glu Gln Arg Pro Ser Trp Ser Gln Cys Arg Ser
        115                 120                 125

Arg Ala Leu Gly Val Leu Leu Asp Gly Ala Val Leu Ala Pro Leu Leu
    130                 135                 140

Val Ser Val Thr Tyr Ser Ser Arg Trp Asp Glu Glu Gly Gln Glu His
145                 150                 155                 160

Gly Arg Asp Asn Val Met Glu Arg Phe Asp Phe Ser Lys Met Leu Pro
                165                 170                 175

Ala Gln Arg Ser Ala Leu Gly Asp Ile Phe Glu Gln Leu Gly Val Gly
            180                 185                 190

Thr Met Asn Ala Lys Gly Val Ile Met Met Ser Ser Lys Gly Ala Met
        195                 200                 205

Ala Leu Gln Arg Cys Tyr Ser Tyr Tyr Val Pro Leu Ser Tyr Ala Pro
    210                 215                 220

Leu Met Ala Gln Ile Ser Pro Ile Leu Phe Asp Asp Ala Gly Trp Gly
225                 230                 235                 240

Phe Thr Asp Ala Gly Thr Asp Ser Phe Asp Asp Val Glu Glu His Val
                245                 250                 255

Asp Arg Ile Leu Asn Val Val Gly Ser Gly Ala Gln His Arg Thr Leu
            260                 265                 270

Phe Lys Asp Met Met Arg His Ile Ser Thr Val Phe Lys Gly Glu Ala
        275                 280                 285

Phe Ala Leu Gln Pro Ser Phe Val Asp Thr Gly Cys Gly Asp Gly
    290                 295                 300

Ser Leu Leu Ile His Ile Tyr Glu His Ile Lys Gln His Thr Pro Arg
305                 310                 315                 320

Gly Lys Val Leu Asp Gln Phe Pro Leu Thr Met Val Gly Val Asp Leu
                325                 330                 335

Asn Glu Asp Pro Arg Val Thr Thr Ala Val Asn Leu Ser Lys Gln Gly
            340                 345                 350

Val Pro His Val Val Ile Ser Gly Asp Val Gly Lys Pro Ala Glu Ile
        355                 360                 365

Leu Ala Ala Leu Lys Lys Lys Val Asp Ala Ser Arg Thr Leu His
    370                 375                 380

Val Arg Ser Phe Leu Asp His Asp Arg Thr Tyr Ile Pro Pro Val Met
385                 390                 395                 400

Arg Ile Glu Glu Glu Ser Ser Thr Ala Arg Phe Ala Arg Thr Gln Met
                405                 410                 415

Ala Asp Phe Val His Leu Asp Lys Arg Gly Lys Pro Ile Thr Ala Leu
            420                 425                 430

Glu Leu Phe Ala Ser Leu Val Glu His Phe Glu Arg Trp Ala Asp Ala
        435                 440                 445

Leu Glu Val Ser Phe Gly Leu Cys Val Leu Glu Val Met Met Leu Asp
    450                 455                 460

Val Pro Thr Thr Gln Arg Trp Phe Asn Asp Cys Val Ser Phe Pro Leu
465                 470                 475                 480

Asp Phe Val Gln Cys Leu Ser Arg Gln Tyr Met Val Ser Ala Ala Ala
                485                 490                 495

Phe Thr Met Gly Ala Ala Met Ala Gly Leu Leu Pro Ala Asp Phe Arg
            500                 505                 510
```

```
Ala Val Glu Thr Tyr Pro Glu His Gly Arg Tyr Asn Arg Met Leu Ser
            515                 520                 525

Gln His Leu Val Lys Arg Pro Phe Arg Leu Arg Leu Ala Glu Val Ala
        530                 535                 540

Asp Leu Gln Ser Leu Val His Val Glu Leu Ala Trp Pro Lys Gln
545                 550                 555                 560

Met Gln Gly Ser Leu Glu Val Leu Arg Arg Leu Glu Ala Ser Pro
                565                 570                 575

Thr Thr Asn Leu Val Cys Glu Leu Glu Gly Arg Val Ala Val Leu
            580                 585                 590

Tyr Met Gln Arg Ile Glu Ser Leu Ala Val Leu Asp Gly Val Gln Phe
        595                 600                 605

Met Asp Val Ser Ser Ala His Ser Pro Arg Gly Arg Leu Leu Gln Leu
        610                 615                 620

Ile Ser Ile Ala Val His Pro Asp Phe Ala Gly Met Asn Leu Gly Arg
625                 630                 635                 640

Glu Leu Lys Glu Phe Gly Leu His Leu Ala Arg Leu Asp Ser Thr Ile
                645                 650                 655

Glu Arg Val Ile Gly Val Thr Arg Cys Ser Lys Glu Phe Arg Gln Tyr
            660                 665                 670

Asp Gly Pro Met Ser Glu Tyr Val Asn Ala His Phe Ser Gly Ala Arg
        675                 680                 685

Thr Asp Ser Thr Leu Asp Phe His Ser Ser Ala Gly Ala Gln Phe Val
        690                 695                 700

Arg Leu Val Glu Gly Phe Arg Pro Glu Asp Thr Asp Asn Gly Gly Thr
705                 710                 715                 720

Gly Val Val Ile Ala Tyr Asp Ile Arg Arg Ala Leu Pro Arg Glu Ala
                725                 730                 735

Ala Ala Gly Ala Pro Pro Ser Arg Pro Pro Arg Thr Lys Val Pro
            740                 745                 750

Ser Leu Gln Leu Val Gln Asp Val Met Thr Ser Ile Gly Tyr Pro Pro
        755                 760                 765

Asn Leu Asn Asp Leu Thr Lys Gly Phe Phe Asp Tyr Gly Met Asp Ser
        770                 775                 780

Leu Glu Leu Val Arg Ile Arg Asn Lys Leu Ser Leu Ala Leu Gln Thr
785                 790                 795                 800

Glu Leu Pro Ala Thr Leu Leu Asp Phe Pro Thr Val His Asp Leu
                805                 810                 815

Val Glu Arg Leu Asp Gln Asp Arg Ala Pro Glu Ser Asp Glu Glu
            820                 825                 830

Glu Val Arg Glu Glu Ala Lys Ala Thr Ala Arg Ala Pro Ala Lys Ala
        835                 840                 845

Lys Ala Leu Ala Lys Gly Gly Glu Ala Thr Gln Arg Phe Gly Pro Ser
850                 855                 860

Glu Ile Ile Ser Val Gln Lys Arg Cys Leu Asn Val Tyr Ala Gln Pro
865                 870                 875                 880

Ile Tyr Gln Lys Arg Phe Thr Asp Met Ala Lys Lys Cys Phe Pro Asp
                885                 890                 895

Met Leu Lys Tyr Ile Leu Ala Ile Glu Ser Ile Leu Val Glu Val Glu
            900                 905                 910

Gly Pro Val Leu Gln Glu Phe Gln Leu Ile Gln Asp Leu Glu Tyr Lys
        915                 920                 925
```

```
Ser Val Gln Arg Gly Arg Glu Asn Leu Met Tyr Tyr Met Ser Ser Tyr
    930             935                 940

Trp Leu Ala His Pro Glu Ile Arg Asp Gln Ser Gln Gln Leu Leu Leu
945             950                 955                 960

Leu Thr Leu Gln Asp Gln Cys Trp Gly Asn Asn His Leu
            965                 970
```

<210> SEQ ID NO 3
<211> LENGTH: 4648
<212> TYPE: DNA
<213> ORGANISM: Alexandrium fundyense

<400> SEQUENCE: 3

```
tccgtagcca ttttggctca agagttggat cccaagctgc tcttccgcag ccaggcggcc      60
ggcgcacccg ctcccgccga tcggtccgcc tctgctcccg ttcctcccaa gccaagcgca     120
tgccgcagct tctgagcacc cttgtagcac cggacagcgc tggatcttgt gagagcgtcg     180
cgggggacag gcacggggcc tccggacgca acgagctcga ggaggcttcc gccaagtcga     240
acatccacgg cctcgacctc ggcaccgatg ccttcatgct ggtgcacggg tggacttgcg     300
ggcccttgct cctggagttt gttgcgagct cctgcagcc cttgcagcgg cagcccatga     360
ccgccgagca gctcgccgcg gagacaaacg cggggggaagg gcccgtggcg atcactctgc     420
ggacaatggc catcctcggg tacttggacc tggaccctga gccgatgtg tatgccgtgg      480
tccccgggcc ggggattgag gcgctcgccg cgctcctccg gccagcggcg cccaccagcg     540
cggccttgcg aagcatctac cagcacgccc agccgccgtt cagggtgccc tcatccgagg     600
cggcgcactg cttgcggatt tgggcggagc accgcccac ctggagaagg gcggcttgca      660
agcggctggc cctcctgctc gacggggccg tcctcgtccc gttgttgacc tcgatcacat     720
actttgcgag gtgggacgag gaggggctgg attccggcaa ggagggcgcc ttggaccgcc     780
tcgacttcag caaggccaat gccgcggcaa gggcggccct cggggggcatc ttcggcgagt     840
tgggcgtggg cacagtggac ggcgagggca ccgtgacctt gaccgcggag ggctcgttcg     900
ccctgcagcg tcgctactcc tactacgtcc cgacgtccta cgccccactg ctggacaggt     960
accacagcat cctcttcgag aatcccggct ggggggttcgc cggtgccggc cgggactcgc    1020
aggagcagga gatccacgtc caccggacgc tgaacgtggt gggcagcggg gcgcagcacc    1080
agacgctctt cacggacctc gtgcggctca ttgactcggt cttcgcgggc ggggacttcg    1140
cgtcgcagcc ggcgttcgtc gtggacacgg ggtgcggcga cggccgcttg ctcaggcgca    1200
tctacgagca cgtgaagagc aacacgccgc gcgggaaggc gctcgccgag cacccgctca    1260
cgatggtcgg cgtcgacttc aacaaggact ctcgggtggc gacggagctc aacctgagca    1320
ggcacgcagt cccgcacctg gtgctgttcg ggacgtcgg caagcccgcc gacatcatgg     1380
agatcctcgg gcggaagggg gtggacccga gcaggtccct ccacgtgcgc tccttcctgg    1440
accacgaccg gccgtacgtc cccccggcc gcgagatgga cccggacagc gcggccggga     1500
ggttcgcgag gctgcagctg tcggactgcg cccacctcga cggcgagggc aagcggatcg    1560
cgccgagcga gatgttcgcc tgctggtgg agcacttcca gcgctggggc ggcgcccctgc    1620
agggctcgtt cggcctctgc atgctggagg tcatgatgct ggacgtgccg acgacgaggg    1680
cgtccctgaa cgattgcgtc tcgctccact tcgacctcgt gcagtgcctc tcccggcagt    1740
acatggtgtc gccggcggcc ttcgccttgg gcctggccat ggccgcctc ctgcccggga     1800
gctacgaggg cgtccagacc caccccggcgc ggggggcggta ctgccgcgtg atgagccagc    1860
```

```
acctcgtgcg ccggccgtac cagatccgcc tcgccgaggt cggtgacctg ccgaggctcg    1920
cgcgcctgga ggagctggcg tggggccgcc tcggcgccac gccggaggtc ctgcggaggc    1980
gcctggagac gtctccgacc acgtgcctgg ccgtcgagat ggaccagctg gtcgtggccg    2040
tgctctacac gcagcgggtg gacagcgccg atgtggtgga ccagcagaag ttcatgcagg    2100
tctccgactg gcacagcccg agcggccgca tcatgcagct catcgcgatc tgctccgacc    2160
cggccgccaa gcacctgggc gtcgcggcgg acctgctcgc cttcgcgctc cacctggccc    2220
gcctcagccc ggacgtggac agcgtcatcg gggtgacgcg ctgccaaaac ttcgagacat    2280
tcgccgggtc gatgcgggac tacgtggacg agcacatcgc cggcacccgc gtagatccca    2340
tcatcggcct ccacaccggc aacggagctc gggtagtccg cctcgtgcac ggcttcaggc    2400
cggaggacgt gggcaaccgc ggggacggcg tgctcataca gtacgacacg agcaagctcg    2460
gcgcggcaac cggcgagcgc gcggcccccg gcgtcgggcc tgctgcggcg ccccccccg     2520
ggccggctcc cgcgccatgc cccacggact acgagcacca cgaggctctt gtcctggccg    2580
ctctgggcag cctgatgctg aagaacggcg gcaccgaggc ggcggccgcg ggcagcgccg    2640
acgtcagatt tgtggacatg gacctcctgg actccctcaa cttcaccgac ttcgcaggcc    2700
agctggacgc cgcgctcccc gtgcccgtct ccgtcgggct gctcttcgag gcgtccacgc    2760
ccaggaagct ggccgcgcac ctccaccgcg agatgcagcg gctggccggc caggcggacg    2820
gggggccgcg cctcggcccc gcaccggccg ccgccgccgc gccgccgccc gctgcggcca    2880
gggaggaggc cgcggaggct ccgctggcct ccttcgactc ggtgtgcacc aagctcgagg    2940
ggtgctccgc gctggtcgac ggctgctggt gcatcgacgt ggcgaactgc agctacctcg    3000
gcttccagtg gcgggacgag atcgccgatg gcgtggaccg ggacgtgcgc acttggggcg    3060
tccacccccc gtggaccagg ctcgtctcgt ctccgaagct gtacgacgac gtcgaggcgc    3120
gctgttgcga gctgaccggc atctggaagt gcgttctgta cccgagcgtt accatgctca    3180
acatgggagt catcccgagc ctcgtgggcg agagcgggtt cctcctcctg gacataaacg    3240
cccacgactg cgtgcagacg gccgccaggc tctgcaagaa gggcgccacc gtggtgcgcc    3300
tgaggcacaa cgacgcggag cagctcgagc acatgctctc gtcgatcccg caggggggcc    3360
acatcaccta cgtgtgcgac ggcgtgtact ccacggacgg agagctcgcc gacttgcccg    3420
ccatatgtgc ttgtttgagg ccgcgcgggg ccaagatact cgtagacgac tcgcatggct    3480
gcggcgttct tggccgcaac cccgactcgg agcaacccct cgggtatggt ggcggcggcg    3540
tcgtcgagta cttcgggctg gactacgcgg agaacaacat catctacgcc gggcagctga    3600
gcaaggcgtt caattcgccc ggcggattcg tcggctgtgc gcgcgagacc gacgagaagt    3660
tcggcattct gaacttggcc aagaactcga acacactcgt gttcacaggg ccgatctgta    3720
ctgccggcct gtcgagtgcg atgacgaccc tcgacctcaa cgccgccgag ggggaccttc    3780
agcgcaagcg gcttctggcg cgcaccctcg aattctgcga ggggctcaag cgctcgggt    3840
gccccacac ctaccacggg ttccccatcg tcaacatcta ctggacccg gtcgaggtgt     3900
gcgcagaggt gtacagggag ctgatgagcg cgaggcaggg cgcgttccag cagggcgtcg    3960
tcacgacccc catgtggcac cccatcgccc gaaggccca cgagatgctg cgcttccagt    4020
tcacgtcgct ccacgacgag gccgccgtgc gccacatcct cgtgatcctc gaggacctga    4080
tcaagcgcta cccgccctcc gccgtgccgc cgcgcatctg atcggccgcc cgagccgcag    4140
gaccagcgcg gctcatccca gggggttgttt aagggattgt tgagtctttt caatctagtc    4200
agcgtgtttt taatgtgcaa gcagcaaggg tcaggcggat tctgggcttg tacaccaagg    4260
```

```
gccaggcagg ttttggctgc cgccgttttg atcctgctgt gttgtcgtag cgtgcaagca    4320
gcaagggtca ggcggagtcc tgggcttgta caccaagggc caggcaggtt tggctgccgc    4380
cgttttgatc ctgctgtgtt gtggtagcat gcaagcagca agggtcaggc ggattttggg    4440
ctttgctgat cctgatccaa ggtatgacca gccatggcgc atcatcgcgt ctaaggtagc    4500
gcctgtccat gtctgccatc ttagctggtc actattcgca tcaacactcg caaggtacgc    4560
gtctgctacg cacaggtgac aattgacatt gtggatcgag ccacggaagg gagaaaaaaa    4620
aaaaaaaaaa aaaaaaaaaa aaaaaaaa                                        4648
```

<210> SEQ ID NO 4
<211> LENGTH: 1281
<212> TYPE: PRT
<213> ORGANISM: Alexandrium fundyense

<400> SEQUENCE: 4

```
Met Leu Val His Gly Trp Thr Cys Gly Pro Leu Leu Glu Phe Val
1               5                   10                  15

Ala Ser Phe Leu Gln Pro Leu Gln Arg Gln Pro Met Thr Ala Glu Gln
            20                  25                  30

Leu Ala Ala Glu Thr Asn Ala Gly Glu Gly Pro Val Ala Ile Thr Leu
        35                  40                  45

Arg Thr Met Ala Ile Leu Gly Tyr Leu Asp Leu Asp Pro Glu Thr Asp
    50                  55                  60

Val Tyr Ala Val Val Pro Gly Pro Gly Ile Glu Ala Leu Ala Ala Leu
65                  70                  75                  80

Leu Arg Pro Ala Ala Pro Thr Ser Ala Ala Leu Arg Ser Ile Tyr Gln
                85                  90                  95

His Ala Gln Pro Pro Phe Arg Val Pro Ser Ser Glu Ala Ala His Cys
            100                 105                 110

Leu Arg Ile Trp Ala Glu His Arg Pro Thr Trp Arg Arg Ala Ala Cys
        115                 120                 125

Lys Arg Leu Ala Leu Leu Leu Asp Gly Ala Val Leu Val Pro Leu Leu
    130                 135                 140

Thr Ser Ile Thr Tyr Phe Ala Arg Trp Asp Glu Glu Gly Leu Asp Ser
145                 150                 155                 160

Gly Lys Glu Gly Ala Leu Asp Arg Leu Asp Phe Ser Lys Ala Asn Ala
                165                 170                 175

Ala Ala Arg Ala Ala Leu Gly Gly Ile Phe Gly Glu Leu Gly Val Gly
            180                 185                 190

Thr Val Asp Gly Glu Gly Thr Val Thr Leu Thr Ala Glu Gly Ser Phe
        195                 200                 205

Ala Leu Gln Arg Arg Tyr Ser Tyr Tyr Val Pro Thr Ser Tyr Ala Pro
    210                 215                 220

Leu Leu Asp Arg Tyr His Ser Ile Leu Phe Glu Asn Pro Gly Trp Gly
225                 230                 235                 240

Phe Ala Gly Ala Gly Arg Asp Ser Gln Glu Gln Glu Ile His Val His
                245                 250                 255

Arg Thr Leu Asn Val Val Gly Ser Gly Ala Gln His Gln Thr Leu Phe
            260                 265                 270

Thr Asp Leu Val Arg Leu Ile Asp Ser Val Phe Ala Gly Gly Asp Phe
        275                 280                 285

Ala Ser Gln Pro Ala Phe Val Val Asp Thr Gly Cys Gly Asp Gly Arg
    290                 295                 300
```

```
Leu Leu Arg Arg Ile Tyr Glu His Val Lys Ser Asn Thr Pro Arg Gly
305                 310                 315                 320

Lys Ala Leu Ala Glu His Pro Leu Thr Met Val Gly Val Asp Phe Asn
                325                 330                 335

Lys Asp Ser Arg Val Ala Thr Glu Leu Asn Leu Ser Arg His Ala Val
                340                 345                 350

Pro His Leu Val Leu Phe Gly Asp Val Gly Lys Pro Ala Asp Ile Met
                355                 360                 365

Glu Ile Leu Gly Arg Lys Gly Val Asp Pro Ser Arg Ser Leu His Val
370                 375                 380

Arg Ser Phe Leu Asp His Asp Arg Pro Tyr Val Pro Pro Ala Arg Glu
385                 390                 395                 400

Met Asp Pro Asp Ser Ala Ala Gly Arg Phe Ala Arg Leu Gln Leu Ser
                405                 410                 415

Asp Cys Ala His Leu Asp Gly Glu Gly Lys Arg Ile Ala Pro Ser Glu
                420                 425                 430

Met Phe Ala Ser Leu Val Glu His Phe Gln Arg Trp Gly Gly Ala Leu
                435                 440                 445

Gln Gly Ser Phe Gly Leu Cys Met Leu Glu Val Met Met Leu Asp Val
450                 455                 460

Pro Thr Thr Arg Ala Ser Leu Asn Asp Cys Val Ser Leu His Phe Asp
465                 470                 475                 480

Leu Val Gln Cys Leu Ser Arg Gln Tyr Met Val Ser Pro Ala Ala Phe
                485                 490                 495

Ala Leu Gly Leu Ala Met Ala Gly Leu Leu Pro Gly Ser Tyr Glu Gly
                500                 505                 510

Val Gln Thr His Pro Ala Arg Gly Arg Tyr Cys Arg Val Met Ser Gln
                515                 520                 525

His Leu Val Arg Arg Pro Tyr Gln Ile Arg Leu Ala Glu Val Gly Asp
                530                 535                 540

Leu Pro Arg Leu Ala Arg Leu Glu Glu Leu Ala Trp Gly Arg Leu Gly
545                 550                 555                 560

Ala Thr Pro Glu Val Leu Arg Arg Leu Glu Thr Ser Pro Thr Thr
                565                 570                 575

Cys Leu Ala Val Glu Met Asp Gln Leu Val Val Ala Val Leu Tyr Thr
                580                 585                 590

Gln Arg Val Asp Ser Ala Asp Val Val Asp Gln Gln Lys Phe Met Gln
                595                 600                 605

Val Ser Asp Trp His Ser Pro Ser Gly Arg Ile Met Gln Leu Ile Ala
                610                 615                 620

Ile Cys Ser Asp Pro Ala Ala Lys His Leu Gly Val Ala Ala Asp Leu
625                 630                 635                 640

Leu Ala Phe Ala Leu His Leu Ala Arg Leu Ser Pro Asp Val Asp Ser
                645                 650                 655

Val Ile Gly Val Thr Arg Cys Gln Asn Phe Glu Thr Phe Ala Gly Ser
                660                 665                 670

Met Arg Asp Tyr Val Asp Glu His Ile Ala Gly Thr Arg Val Asp Pro
                675                 680                 685

Ile Ile Gly Leu His Thr Gly Asn Gly Ala Arg Val Val Arg Leu Val
                690                 695                 700

His Gly Phe Arg Pro Glu Asp Val Gly Asn Arg Gly Asp Gly Val Leu
705                 710                 715                 720
```

-continued

| | | | | | | | | | | | |
|---|---|---|---|---|---|---|---|---|---|---|---|
|Ile|Gln|Tyr|Asp|Thr|Ser|Lys|Leu|Gly|Ala|Ala|Thr|Gly|Glu|Arg|Ala|
| | | |725| | | |730| | | | |735| | | |

```
Ile Gln Tyr Asp Thr Ser Lys Leu Gly Ala Ala Thr Gly Glu Arg Ala
            725                 730                 735

Ala Pro Gly Val Gly Pro Ala Ala Pro Pro Gly Pro Ala Pro
            740                 745                 750

Ala Pro Cys Pro Thr Asp Tyr Glu His His Glu Ala Leu Val Leu Ala
            755                 760                 765

Ala Leu Gly Ser Leu Met Leu Lys Asn Gly Gly Thr Glu Ala Ala Ala
            770                 775                 780

Ala Gly Ser Ala Asp Val Arg Phe Val Asp Met Asp Leu Leu Asp Ser
785                 790                 795                 800

Leu Asn Phe Thr Asp Phe Ala Gly Gln Leu Asp Ala Ala Leu Pro Val
                    805                 810                 815

Pro Val Ser Val Gly Leu Leu Phe Glu Ala Ser Thr Pro Arg Lys Leu
            820                 825                 830

Ala Ala His Leu His Arg Glu Met Gln Arg Leu Ala Gly Gln Ala Asp
            835                 840                 845

Gly Gly Pro Arg Leu Gly Pro Ala Pro Ala Ala Ala Ala Pro Pro
    850                 855                 860

Pro Ala Ala Ala Arg Glu Glu Ala Ala Glu Ala Pro Leu Ala Ser Phe
865                 870                 875                 880

Asp Ser Val Cys Thr Lys Leu Glu Gly Cys Ser Ala Leu Val Asp Gly
                    885                 890                 895

Cys Trp Cys Ile Asp Val Ala Asn Cys Ser Tyr Leu Gly Phe Gln Trp
                    900                 905                 910

Arg Asp Glu Ile Ala Asp Gly Val Asp Arg Asp Val Arg Thr Trp Gly
                    915                 920                 925

Val His Pro Pro Trp Thr Arg Leu Val Ser Ser Pro Lys Leu Tyr Asp
            930                 935                 940

Asp Val Glu Ala Arg Cys Cys Glu Leu Thr Gly Ile Trp Lys Cys Val
945                 950                 955                 960

Leu Tyr Pro Ser Val Thr Met Leu Asn Met Gly Val Ile Pro Ser Leu
                    965                 970                 975

Val Gly Glu Ser Gly Phe Leu Leu Leu Asp Ile Asn Ala His Asp Cys
            980                 985                 990

Val Gln Thr Ala Ala Arg Leu Cys Lys Lys Gly Ala Thr Val Val Arg
            995                 1000                1005

Leu Arg His Asn Asp Ala Glu Gln Leu Glu His Met Leu Ser Ser
    1010                1015                1020

Ile Pro Gln Gly Ala Asp Ile Thr Tyr Val Cys Asp Gly Val Tyr
    1025                1030                1035

Ser Thr Asp Gly Glu Leu Ala Asp Leu Pro Ala Ile Cys Ala Cys
    1040                1045                1050

Leu Arg Pro Arg Gly Ala Lys Ile Leu Val Asp Asp Ser His Gly
    1055                1060                1065

Cys Gly Val Leu Gly Arg Asn Pro Asp Ser Glu Gln Pro Phe Gly
    1070                1075                1080

Tyr Gly Gly Gly Gly Val Val Glu Tyr Phe Gly Leu Asp Tyr Ala
    1085                1090                1095

Glu Asn Asn Ile Ile Tyr Ala Gly Gln Leu Ser Lys Ala Phe Asn
    1100                1105                1110

Ser Pro Gly Gly Phe Val Gly Cys Ala Arg Glu Thr Asp Glu Lys
    1115                1120                1125

Phe Gly Ile Leu Asn Leu Ala Lys Asn Ser Asn Thr Leu Val Phe
```

| | | | | | | | | | |
|---|---|---|---|---|---|---|---|---|---|
| | 1130 | | | 1135 | | | 1140 | | |

Thr Gly Pro Ile Cys Thr Ala Gly Leu Ser Ser Ala Met Thr Thr
   1145                    1150                    1155

Leu Asp Leu Asn Ala Ala Glu Gly Asp Leu Gln Arg Lys Arg Leu
   1160                    1165                    1170

Leu Ala Ala Thr Leu Glu Phe Cys Glu Gly Leu Lys Ala Leu Gly
   1175                    1180                    1185

Cys Pro His Thr Tyr His Gly Phe Pro Ile Val Asn Ile Tyr Trp
   1190                    1195                    1200

Thr Pro Val Glu Val Cys Ala Glu Val Tyr Arg Glu Leu Met Ser
   1205                    1210                    1215

Ala Arg Gln Gly Ala Phe Gln Gln Gly Val Val Thr Thr Pro Met
   1220                    1225                    1230

Trp His Pro Ile Ala Pro Lys Gly His Glu Met Leu Arg Phe Gln
   1235                    1240                    1245

Phe Thr Ser Leu His Asp Glu Ala Ala Val Arg His Ile Leu Val
   1250                    1255                    1260

Ile Leu Glu Asp Leu Ile Lys Arg Tyr Pro Pro Ser Ala Val Pro
   1265                    1270                    1275

Pro Arg Ile
   1280

<210> SEQ ID NO 5
<211> LENGTH: 504
<212> TYPE: DNA
<213> ORGANISM: Alexandrium catenella

<400> SEQUENCE: 5

```
gtcccgacct cctacgcccc actgctggac aggtaccacc gcatcctctt cgagaatccc    60
ggctgggggt tcgccggcgc cggccgggac tcgcaggagc aggaggtcca cgtccaccgg   120
acgctgaacg tggtgggcag cggggcgcag caccagacgc tcttcacgga tctcgtgcgg   180
ctgattgact cggtcttcgc gggcggggac ttcgcggcgc agccggcgtt cgtcgtggac   240
acagggtgcg gcgacggccg cttgctcagg cgcatctacg agcacgtgaa gagcaacacg   300
ccgcgcggga aggcgctcgg cgagcacccg ctcacgatgg tcggcgtcga cttcaacaag   360
gactctcggg tggccacgga gctcaacctg agcaggcacg cggtcccgca cctggtgctg   420
ttcggggacg tcggcaagcc cgccgacatc atggagctcc tcgggcggag ggggtggac   480 ccgagcaggt ccctccacgt gcgc                                         504
```

<210> SEQ ID NO 6
<211> LENGTH: 504
<212> TYPE: DNA
<213> ORGANISM: Alexandrium catenella

<400> SEQUENCE: 6

```
gtcccgacct cctacgcccc actgctggac aggtaccacc gcatcctctt cgagaatccc    60
ggctgggggt tcgccggcgc cggccgggac tcgcaggagc aggaggtcca cgtccaccgg   120
acgctgaacg tggtgggcag cggggcgcag caccagacgc tcttcacgga tctcgtgcgg   180
ctgattgact cagtcttcgc gggcggggac ttcgcggcgc agccggcgtt cgtcgtggac   240
acagggtgcg gcgacggccg cttgctcagg cgcatctacg agcacgtgaa gagcaacacg   300
ccgcgcggga aggcgctcgg cgagcacccg ctcacgatgg tcggcgtcga cttcaacaag   360
gactctcggg tggccacgga gctcaacctg agcaggcacg cggtcccgca cctggtgctg   420
```
ttcggggacg tcagcaagcc cgccgacatc atggagctcc tcgggcggaa tggggtggac    480
ccgagcaggt ccctccacgt gcgc    504

<210> SEQ ID NO 7
<211> LENGTH: 402
<212> TYPE: DNA
<213> ORGANISM: Alexandrium catenella

<400> SEQUENCE: 7
gaggagcatg ttgacagaat cttgaatgtc gttggcagtg gtgcgcaaca ccggaccctc    60
tttaaggatc tgatgcgaca catcagtgcc gtgttcaagg gcgaggcatt tgcctcgcag    120
ccaaattttg ttgtggacac tggctgtggc gacgggagcc tgctcataca cgtctacgag    180
cacatcaagg agcacacgcc ccggggggaaa gtgctcgacg agttccctct gacgatggtc    240
ggcgtggacc tcaacgagga gccgcgagtg acgacggccg tgaatctgag caagcagggc    300
gtcccgcacg tggtcatctc cggcgacgtg gcaagcccg cggagatcat ggccgcgctg    360
aagaagaaga aggtggaccc gtcgaggacg cttcatgtcc gc    402

<210> SEQ ID NO 8
<211> LENGTH: 505
<212> TYPE: DNA
<213> ORGANISM: Alexandrium catenella

<400> SEQUENCE: 8
gtcccgacct cctacgcccc actgctggac aggtaccaca gcatcctctt cgagaatccc    60
ggctgggggt tcgccggcgc cggccgggac tcgcaggagc aggaggtcca cgtccaccgg    120
acgctgaacg tggtgggcag cggggcgcag caccagacgc tcttcacgga cctcgtgcgg    180
ctgatcgact cggtcttcgc gggcggggac ttcgcggcgc agccggcgtt cgtcgtggac    240
acggggtgcg gcgacggccg cttgctcagg cgcatctacg agcacgtgaa gagcaacacg    300
ccgcgcggga aggcgctcgg cgagcacccg ctcacgatgg tcggcgtcga cttcaacaag    360
gactctcggg tggccacgga gctcaacctg agcaggcacg cggtcccgca caatggtgct    420
gttcggcgac gtcggcaagc ccgccgacat cacggagctc ctcgggcgga agggggtgga    480
ccctagcagg tccctccacg tgcgc    505

<210> SEQ ID NO 9
<211> LENGTH: 504
<212> TYPE: DNA
<213> ORGANISM: Alexandrium catenella

<400> SEQUENCE: 9
gtcccgacct cctacgcccc actgctggac aggtaccacc gcatcctctt cgagaatccc    60
ggctgggggt tcgccggcgc cggccgggac tcgcaggagc aggaggtcca cgtccaccgg    120
acgctgaacg tggtgggcag cggggcgcag caccagacgc tcttcacgga tctcgtgcgg    180
ctcattgact cggtcttcgc gggcgggac ttcgcggcgc agccggcgtt cgtcgtggac    240
acggggtgcg gcgacggccg cttgctcagg cgcatctacg agcacgtgaa gagcaacacg    300
ccgcgcggga aggcgctcgg cgagcacccg ctcacgatgg tcggcgtcga cttcaacaag    360
gactctcggg tggccacgga gctcaacctg agcaggcacg cggtcccgca cctggtgctg    420
ttcggggacg tcggcaagcc cgccgacatc atggagctcc tcgggcggag gggggtggac    480
ccgagcaagt ccctccacgt gcgc    504

<210> SEQ ID NO 10
<211> LENGTH: 504
<212> TYPE: DNA
<213> ORGANISM: Alexandrium catenella

<400> SEQUENCE: 10

```
gtcccagtgt cgtacgcacc actgatggcc cagatctcac cgatcctctt tgatgatgcg      60
ggctgggggt tcactgacgc ggggacagac tccttcgacg tggaggagca tgttgacaga     120
atcttgaatg tcgtgggcag tggtgcgcaa caccggaccc tctttaagga tctgatgcga     180
cacatcagtg ccgtgttcaa gggcgaggca tttgcctcgc agccaaattt tgttgtggac     240
actggctgtg gcgacgggag cctgctcata cacgtctacg agcacatcaa ggagcacacg     300
ccccggggga aagtgctcga cgagttccct ctgacgatgg tcggcgtgga cctcaacgag     360
gagccgcgag tgacgacggc cgtgaatctg agcaagcagg gcgtcccgca cgtggtcatc     420
tccggcgacg tgggcaagcc cgcggagatc aaggccgcgc tgaagaagaa gaaggtggac     480
ccgtcgagga cgcttcatgt ccgc                                            504
```

<210> SEQ ID NO 11
<211> LENGTH: 504
<212> TYPE: DNA
<213> ORGANISM: Alexandrium catenella

<400> SEQUENCE: 11

```
gtcccgacct cctacgcccc accgctggac atgtaccacc gcatcctctt cgagaatccc      60
agctgggggt tcgccggcgc cggccgggac tcgcaggagc aggaggtcca cgtccaccgg     120
acgctgaacg tggtgggcag cggggcgcag caccagacgc tcttcacgga tctcgtgcgg     180
ctgattgact cggtcttcgc gggcggggac ttcgcggcgc agccggcgtt cgtcgtggac     240
acagggtgcg gcgacggccg cttgctcagg cgcatctacg agcacgtgaa gagcaacacg     300
ccgcgcggga aggcgctcgg cgagcacccg ctcacgatgg tcggcgtcga cttcaacaag     360
gactctcggg tggccacgga gctcaacctg agcaggcacg cggtcccgca cctggtgctg     420
ttcggggacg tcggcaagcc cgccgacatc atggagctcc tcgggcggag gggggtggac     480
ccgagcaggt ccctccacgt gcgc                                            504
```

<210> SEQ ID NO 12
<211> LENGTH: 448
<212> TYPE: DNA
<213> ORGANISM: Alexandrium tamarense

<400> SEQUENCE: 12

```
cccggttggg ggttcgccgg cgccggccgg gactcgcagg agcaggaggt ccacgtccac      60
cggacgctga acgtggtggg cagcggggcg cagcaccaga cgctcttcac ggatctcgtg     120
cggctcattg actcggtctt cgcggcgggg acttcgcgt cgcagccggc gttcgtcgtg     180
gacacggggt gcggcgacgg ccgcttgctc aggcgcatct acgagcacgt gaagagcaac     240
acgccgcgcg ggaaggcgct cgccgagcac ccgctcacga tggtcggcgt cgacttcaac     300
aaggactctc gggtggcgac ggagctcaac ctgagcaggc acgcggtccc gcacctggtg     360
ctgttcgggg acgttcggca agcccgccga catcatggag atcctcgggc ggaagggggt     420
ggacccgagc aggtccctcc acgtgcgc                                        448
```

<210> SEQ ID NO 13
<211> LENGTH: 504

<212> TYPE: DNA
<213> ORGANISM: Alexandrium tamarense

<400> SEQUENCE: 13

```
gtcccgacgt cctacgcccc actgctggac aggtaccaca gcatcctctt cgagaatccc      60
ggctggggt tcgctggtgc cggccgggac tcgcaggagc aggaggtcca cgtccaccgg      120
acgctgaacg tggtgggcag cggggcgcag caccagacgc tcttcacgga cctcgtgcgg      180
ctcattgact cggtcttcgc gggcggggac ttcgcatcgc agccggcgtt catcgtggac      240
acggggtgcg gcgacggccg cttgctcagg cgcatctacg agcacgtgaa gagcaacacg      300
ccgcgcggga aggcgctcgc cgagcacccg ctcacgatgg tcggcgtcga cttcaacaag      360
gactctcggg tggcgacgga gctcaacctg agcaggcacg cggtcccgca cctggtgctc      420
ttcggggacg tcggcaagcc cgccgacatc atggagaccc tcgggcggaa tggggtggac      480
ccgagcaggt ccctccacgt gcgc                                            504
```

<210> SEQ ID NO 14
<211> LENGTH: 504
<212> TYPE: DNA
<213> ORGANISM: Alexandrium tamarense

<400> SEQUENCE: 14

```
gtcccgacgt cctacgcccc actgctggac aggtaccaca gcatcctctt cgagaatccc      60
ggctggggt tcgctggtgc cggccgggac tcgcaggagc aggaggtcca cgtccaccgg      120
acgctgaacg tggtgggcag cggggcgcag caccagacgc tcttcacgga cctcgtgcgg      180
ctcattgact cggtcttcgc gggcggggac ttcgcatcgc agccggcgtt catcgtggac      240
acggggtgcg gcgacggccg cttgctcagg cgcatctacg agcacgtgaa gagcaacacg      300
ccgcgcggga aggcgctcgc cgagcacccg ctcacgatgg tcggcgtcga cttcaacaag      360
gactctcggg tggcgacgga gctcaacctg agcaggcacg cggtcccgca cctggtgctc      420
ttcggggacg tcggcaagcc cgccgacatc atggagaccc tcgggcggaa tggggtggac      480
ccgagcaggt ccctccacgt gcgc                                            504
```

<210> SEQ ID NO 15
<211> LENGTH: 505
<212> TYPE: DNA
<213> ORGANISM: Alexandrium tamarense

<400> SEQUENCE: 15

```
gtcccgacgt cctacgcccc actgctggac aggtaccaca gcatcctctt cgagaatccc      60
ggctggggt tcgctggtgc cggccgggac tcgcaggagc aggaggtcca cgtccaccgg      120
acgctgaacg tggtgggcag cggggcgcag caccagacgc tcttcacgga cctcgtgcgg      180
ctcattgact cggtcttcgc gggcggggac ttcgcatcgc agccggcgtt catcgtggac      240
acggggtgcg gcgacggccg cttgctcagg cgcatctacg agcacgtgaa gagcaacacg      300
ccgcgcggga aggcgctcgc cgagcacccg ctcacgatgg tcggcgtcga cttcaacaag      360
gactctcggg tggcgacgga gctcaacctg agcaggcacg cggtcccgca cctggtgctc      420
ttcggggacg tcggcaagcc cgccgacgat catggagacc ctcgggcgga atggggtgga      480
cccgagcagg tccctccacg tgcgc                                           505
```

<210> SEQ ID NO 16
<211> LENGTH: 505
<212> TYPE: DNA

-continued

<213> ORGANISM: Alexandrium tamarense

<400> SEQUENCE: 16

| gtcccgacgt cctacgcccc cctgctggac aggtaccaca gcatcctctt cgagaatccc | 60 |
| ggctgggggt tcgccggcgc cggcgggac tcgcaggagc aagaggtcca cgtccaccgg | 120 |
| acgctgaacg tggtgggcag cggggcgcag caccagacgc tcttcacgga cctcgtgcgg | 180 |
| ctcattgact cggtcttcgc gggcgggac ttcgcgtcgc agccggcgtt cgtcgtggac | 240 |
| acggggtgcg gcgacggccg cttgctcagg cgcatctacg agcacgtgaa gagcaacacg | 300 |
| ccgcgcggga aggcgctcgc cgagcacccg ctcacgatgg tcggcgtcga cttcaacaag | 360 |
| gactctcggg tggcgacgga gctcaacctg agcaggcacg cggtcccgca ccatggtgct | 420 |
| gttcggggac gtcggcaagc ccgccgacat catggagctc ctcgggcgga atggggtgga | 480 |
| cccgagcagg tccctccacg tgcgc | 505 |

<210> SEQ ID NO 17
<211> LENGTH: 442
<212> TYPE: DNA
<213> ORGANISM: Alexandrium minutum

<400> SEQUENCE: 17

| gtcccgacgt cctacgcccc cctgctggac aagtaccaca gcatcctctt cgagaatccc | 60 |
| ggctgggggt tcgccggcgc cggcgggac tcgcaggagc aagaggtcca cgtccaccgg | 120 |
| acgctgaacg tgttgggcag cggggcgcag caccagacgc tcttcacgga cctcgtgcgg | 180 |
| ctcattgact ccgtcttcgc gggcgggac ttcgctgtcg cagccggcgt tcgtcgtgga | 240 |
| tacagggtgt ggcgacggcc gcttgttcag gcgcttctac gagcacgtga aagagcaaca | 300 |
| cttctcgcgc gggaaggcgc tcgccgagca cccgctcacg atggtcggcg tcgacttcaa | 360 |
| caaggactct cgggtggcga cggagctcaa cctgagcagg cacgcagtcc cgcaccaagg | 420 |
| gctgttcggg gacgtcggca ag | 442 |

<210> SEQ ID NO 18
<211> LENGTH: 505
<212> TYPE: DNA
<213> ORGANISM: Gymnodinium catenatum

<400> SEQUENCE: 18

| gtcccgacgt cctatgcccc cctgctggac aagtaccaca gcatcctctt cgagaaccct | 60 |
| ggttgggggt tcgtcggcgc cggccaggac tcgcaggagc aagagatcca cgtccaccgg | 120 |
| acgctgaacg tggttggcag cggggcgcag caccagacgc tcttcactga cctcgtgcgg | 180 |
| cacatcgact ccctcttcac tggagggac ttcatgtcgc agccggcgtt cgtcgtggat | 240 |
| acagggtgtg gcgacggccg cttgctcagg cgcatctacg agcacgtgaa gagcaacacg | 300 |
| ccgcgcggga aggctctcgc cgaacacccg ctcacgatgg ttggcgtcga cttcaacaag | 360 |
| gactcccgcg tggcgacgga gctcaacttg agcaagcatg cagtcccaca cctagtgctg | 420 |
| ttcggggatg ttggcaagcc cgccgacatc atggagctct ctcaggcaga atggggtgga | 480 |
| cccgagcagg gccctccacg tgcgc | 505 |

<210> SEQ ID NO 19
<211> LENGTH: 504
<212> TYPE: DNA
<213> ORGANISM: Gymnodinium catenatum

<400> SEQUENCE: 19

-continued

```
gtcccgacgt cctacgcccc cctgctggac aagtaccaca gcatcctctt cgagaatcct     60
ggctgggggt tcgtcggcgc cggccaggac tcgcaggagc aggaaattca cgtccaccgg    120
acgctgaacg tggtgggcag cggggcgcag caccagacgc tcttcactga cctcgtgcgg    180
cacatcgact ccctcttcac gggaggggac ttcatgtcgc agccggcgtt cgtcgtggat    240
acagggtgtg gcgacggccg cttgctcagg cgcatctacg agcacgtgaa gagcaacacg    300
ccgcgcggga aggcgctcgc cgaacacccg ctcacgatgg ttggcgtcga cttcaacaag    360
gactcccgcg tggcgacgga gctcaacttg agcaagcatg cagtcccaca cctagtgctg    420
ttcggggatg taggcaaacc cgccgacatc atggagctcc tcaggcagaa tggggtggac    480
ccgagcaggg ccctccacgt gcgc                                           504
```

<210> SEQ ID NO 20
<211> LENGTH: 504
<212> TYPE: DNA
<213> ORGANISM: Gymnodinium catenatum

<400> SEQUENCE: 20

```
gtcccgacgt cctacgcccc cctgctggac aaataccaca gcatcctctt cgagaatcct     60
ggctgggggt tcgtcggcgc cggccaggac tcgcaggagc aggaaattca cgtccaccgg    120
acgctgaatg tggtgggcag cggggcgcag caccagacgc tcttcactga cctcgtgcgg    180
cacatcgact ccctcttcac tggaggggac ttcatgtcgc agccggcgtt cgtcgtggat    240
acagggtgtg gcgacggccg cttgctcagg cgcatctacg agcacgtgaa gagcaacacg    300
ccgcgcggga aggctctcgc cgaacacccg ctcacgatgg ttggcgtcga cttcaacaag    360
gactcccgcg tggcgacgga gctcaacttg agcaaacatg cagtcccaca cctagtgctg    420
ttcggggatg ttggcaggcc cggcgacatc atggagctcc tcaggcagaa tggagtggac    480
ccgagcaggg ccctccacgt gcgc                                           504
```

<210> SEQ ID NO 21
<211> LENGTH: 504
<212> TYPE: DNA
<213> ORGANISM: Gymnodinium catenatum

<400> SEQUENCE: 21

```
gtcccgacgt cctacgcccc cctgctggac aagtaccaca gcatcctctt cgagaatcct     60
ggctgggggt tcgtcggcgc cggccaggac tcgcaggagc aggaaattca cgtccaccgg    120
acgctgaacg tggtgggcag cggggcgcag caccagacgc tcttcactga cctcgtgcgg    180
cacatcgact ccctcttcac gggaggggac ttcatgtcgc agccggcgtt cgtcgtggat    240
acagggtgtg gcgacggccg cttgctcagg cgcatctacg agcacgtgaa gagcaacacg    300
ccgcgcggga aggcgctcgc cgaacacccg ctcacgatgg ttggcgtcga cttcaacaag    360
gactcccgcg tggcgacgga gctcaacttg agcaagcatg cagtcccaca cctagtgctg    420
ttcggggatg taggcaaacc cgccgacatc atggagctcc tcaggcagaa tggggtggac    480
ccgagcaggg ccctccacgt gcgc                                           504
```

<210> SEQ ID NO 22
<211> LENGTH: 504
<212> TYPE: DNA
<213> ORGANISM: Gymnodinium catenatum

<400> SEQUENCE: 22

```
gtcccgacgt cctacgcccc cctgctggac aagtaccaca gcatcctctt cgagaatcct    60
ggctgggggt tcgtcggcgc cggccaggac tcgcaggagc aggaaattca cgtccaccgg   120
acgctgaacg tggtgggcag cggggcgcag caccagacgc tcttcactga cctcgtgcgg   180
cacatcgact ccctcttcac gggagggac  ttcatgtcgc agccggcgtt cgtcgtggat   240
acagggtgtg gcgacggccg cttgctcagg cgcatctacg agcacgtgaa gagcaacacg   300
ccgcgcggga aggcgctcgc cgaacacccg ctcacgatgg ttggcgtcga cttcaacaag   360
gactcccgcg tggcgacgga gctcaacttg agcaagcatg cagtcccaca cctagtgctg   420
ttcggggatg taggcaaacc cgccgacatc atggagctcc tcaggcagaa tggggtggac   480
ccgagcaggg ccctccacgt gcgc                                          504

<210> SEQ ID NO 23
<211> LENGTH: 447
<212> TYPE: DNA
<213> ORGANISM: Gymnodinium catenatum

<400> SEQUENCE: 23
cctggttggg ggttcgtcgg cgccggccag gactcgcagg agcaggaaat ccacgtccac    60
cggacgctga acgtggtggg cagcggggcg cagcaccaga cgctcttcac tgacctcgtg   120
cggcacatcg actccctctt cacgggaggg gacttcatgt cgcagccggc gttcgtcgtg   180
gatacagggt gtggcgacgg ccgcttgctc aggcgcatct acgagcacgt gaagagcaac   240
acgccgcgcg ggaaggcgct cgccgaacac ccgctcacga tggttggcgt cgacttcaac   300
aaggactccc gcgtggcgac ggagctcaac ttgagcaagc atgcagtccc acacctagtg   360
ctgttcgggg atgttggcaa gcccgccgac atcatggagc cctcaggca  gaatggggtg   420 gacccgagca gggccctcca cgtgcgc                                       447

<210> SEQ ID NO 24
<211> LENGTH: 649
<212> TYPE: DNA
<213> ORGANISM: Alexandrium catenella

<400> SEQUENCE: 24
gttcctcctc ctgtacataa acgcccacga ctgcgtgcag acggccgcca ggctctgcaa    60
gaagggcgcc accgtggtgc gcctgaagca caacgacacg gaacagcccg agcacatgct   120
ctcgtcgatc ccgcaggggg ccgacatcac ctacgtgtgc gacggcgtgt actccacgga   180
cgaagagctc gccgacttgc cgccatatg  tgcttgtttg aggccgcgcg gggccaagat   240
actcgtagac gactcgcatg gctgcggcgt tcttggccgc aaccccaact cggagcaacc   300
cctcgggtat ggtggcggcg gcgtcatcga gtacttcggg ctggactacg cggagaacaa   360
catcatctac gccgggcagc tgagcaaggc gttcaattcg cccggcggat tcgtcagctg   420
tgcgcgcgag accgacgaga atttcggcgt tctgaacttg gccaagaact cgaacacact   480
cgtgttcaca gggccgatct gtactgccgg cctgtcgagt gcgaagacga ccttcgacct   540
caacgccgcc gaggggacct tcagcgcaa  gcggcttctg gcggctaccc tcgaattctg   600
cgaggggctc aaggcgctcg ggtgccccca cacctaccac gagttcccc              649

<210> SEQ ID NO 25
<211> LENGTH: 576
<212> TYPE: DNA
<213> ORGANISM: Alexandrium catenella

<400> SEQUENCE: 25
```

```
tggtgcgcct gaagcacaac gacacggaac agcccgagca catgctctcg tcgatcccgc    60
agggggccga catcacctac gtgtgcgacg gcgtgtactc cacggacgaa gagctcgccg   120
acttgccccc catatgtgct tgtttgaggc cgcgcggggc caagatactc gtagacgact   180
cgcatggctg cggcgttctt ggccgcaacc ccaactcgga gcaacccctc gggtatggtg   240
gcggcggcgt catcgagtac ttcgggctgg actacgcgga gaacaacatc atctacgccg   300
ggcagctgag caaggcgttc aattcgcccg gcggattcgt cagctgtgcg cgcgagaccg   360
acgagaattt cggcgttctg aacttggcca agaactcgaa cacactcgtg tatcacaggg   420
ccgatctgta ctgccgccct gtcgagtacg aagacaacct tcgacctcaa cgccgccgag   480
ggggaccttc agcgcaagcg gcttctggcg gctaccctcg aattctgcga ggggctcaag   540
gcgctcgggt gcccccacac ctaccacgag ttcccc                             576

<210> SEQ ID NO 26
<211> LENGTH: 600
<212> TYPE: DNA
<213> ORGANISM: Alexandrium catenella

<400> SEQUENCE: 26
ggttcctcct cctgtacata aacgcccacg actgcgtgca gacggccgcc aggctctgca    60
agaagggcgc caccgtggtg cgcctgaagc acaacgacac ggaacagccc gagcacatgc   120
tctcgtcgat cccgcagggg gccgacatca cctacgtgtg cgacggcgtg tactccacgg   180
acgaagagct cgccgacttg cccgccatat gtgcttgttt gaggccgcgc ggggccaaga   240
tactcgtaga cgactcgcat ggctgcggcg ttcttggccg caaccccaac tcggagcaac   300
ccctcgggta tggtggcggc ggcgtcatcg agtacttcgg gctggactac gcggagaaca   360
acatcatcta cgccgggcag ctgagcaagg cgttcaattc gcccggcgga ttcgtcagct   420
gtgcgcgcga accgacgag aatttcggcg ttctgaactt ggccaagaac tcgaacacac   480
tcgtgttcac agggccgatc tgtactgccg gcctgtcgag tgcgaagacg accttcgacc   540
tcaacgccgc cgaggggggac cttcagcgca agcggcttct ggcggctacc ctcgaattct   600

<210> SEQ ID NO 27
<211> LENGTH: 653
<212> TYPE: DNA
<213> ORGANISM: Alexandrium tamarense

<400> SEQUENCE: 27
ccagcctcgc gggcgagagc gggttcctcc tcctggacat aaacgcccac gactgcgtgc    60
agacggccgc caggctctgc aagaagggcg tcaccgtggt gcgcctgaag cacaacgaca   120
cggagcagct ggagcgcatg ctctcctcga tcccgcaggg ggccgacatc acctacgtgt   180
gcgacggcgt gtactccaca gacggagagc tcgccgactt gcccgccata tgtgcttgtt   240
tgaggccgcg cggggccaag atactcgtgg acgactcgca tggctgcggc gttcttggcc   300
gaaacccaga ctcggagcaa cccttcgggt atggtggcgg tggcgtcgtc gagtacttcg   360
ggctggacta cgcggagaac aacatcatct acgccgggca gctgagcaag gcgttcaact   420
cgcccggcgg attcgtcggc tgcgcgcgcg agaccgacga gaagttcggc atcctgaact   480
tggccaagaa ctcgaacaca ctcgtgttca gggccgat ctgtaccgcc ggcctgtcga   540
gtgcaaagac gaccctggac ctcaacgccg ccgagggga ccttcagcgc aggcggctcc   600
tggcggcgac ccctcgagtt ctgcgagggg ctcaaggcgc tcgggtgccc cca           653
```

<210> SEQ ID NO 28
<211> LENGTH: 639
<212> TYPE: DNA
<213> ORGANISM: Alexandrium tamarense

<400> SEQUENCE: 28

| | | | | | |
|---|---|---|---|---|---|
| ctggacataa | acgcccacga | ctgcgtgcag | acggccgcca | ggctctgcaa | gaagggtcaa | 60 |
| ccgtggtgcg | cctgaagcac | aacgacacgg | agcagctgga | gcgcatgctc | tcctcgatcc | 120 |
| cgcaggggc | cgacatcacc | tacgtgtgcg | acggcgtgta | ctccacagac | ggagagctcg | 180 |
| ccgacttgcc | cgccatatgt | gcttgtttga | ggccgcgcgg | ggccaagata | ctcgtggacg | 240 |
| actcgcatgg | ctgcggcgtt | cttggccgaa | acccagactc | ggagcaaccc | ttcgggtatg | 300 |
| gtggcggtgg | cgtcgtcgag | tacttcgggc | tggactacgc | ggagaacaac | atcatctacg | 360 |
| ccgggcagct | gagcaaggcg | ttcaactcgc | ccggcggatt | cgtcggctgc | gcgcgcgaga | 420 |
| ccgacgttta | agttcggcat | cctgaacttg | gccaagaact | cgaacacact | cgtgttcaca | 480 |
| gggccgatct | gtaccgccgg | cctgtcgagt | gcaaagacga | ccctggacct | caacgccgcc | 540 |
| gaggggggacc | ttcagcgcag | gcggctcctg | gcggcgaccc | tcgagttctg | cgaggggctc | 600 |
| agggcgctcg | ggtgccccca | cacctaccac | ggcttcccc | | | 639 |

<210> SEQ ID NO 29
<211> LENGTH: 671
<212> TYPE: DNA
<213> ORGANISM: Alexandrium tamarense

<400> SEQUENCE: 29

| | | | | | |
|---|---|---|---|---|---|
| ccagcctcgc | gggcgagagc | gggttcctcc | tcctggacat | aaacgcccac | gactgcgtgc | 60 |
| agacggccgc | caggctctgc | aagaagggcg | tcaccgtggt | gcgcctgaag | cacaacgaca | 120 |
| cggagcagct | ggagcgcatg | ctctcctcga | tcccgcaggg | ggccgacatc | acctacgtgt | 180 |
| gcgacggcgt | gtactccaca | gacggagagc | tcgccgactt | gcccgccata | tgtgcttgtt | 240 |
| tgaggccgcg | cggggccaag | atactcgtgg | acgactcgca | tggctgcggc | gttcttggcc | 300 |
| gaaacccaaa | ctcggagcaa | cccttcaggt | atggtggcgg | tggcgtcgtc | gagtacttcg | 360 |
| ggctggacta | cgcggagaac | aacatcatct | acgccgggca | gctgagcaag | gcgttcaact | 420 |
| cgcccggcgg | attcgtcggc | tgcgcgcgcg | agaccgacga | gaagttcggc | atcctgaact | 480 |
| tggccaagaa | ctagaacaca | ctcgtgttca | cagggccgat | ctgtaccgcc | ggcctgtcga | 540 |
| gtgcaaagac | gaccctggac | ctcaacgccg | ccgaggggga | ccttcagcgc | aggcggctcc | 600 |
| tggcggcgac | cctcgagttc | tgcgaggggc | tcagggcgct | cgggtgcccc | cacacctacc | 660 |
| acggcttccc | c | | | | | 671 |

<210> SEQ ID NO 30
<211> LENGTH: 624
<212> TYPE: DNA
<213> ORGANISM: Alexandrium minutum

<400> SEQUENCE: 30

| | | | | | |
|---|---|---|---|---|---|
| tcctcctgga | cataaacgcc | cacgactgcg | tgcagacggc | agccaggctc | tgcaagaagg | 60 |
| gagtcaccgt | cgtgcgcctg | aagcacaacg | acacggagca | gctcgagcgc | gtgctctcgt | 120 |
| cgatcccgga | gggggccgac | atcacctacg | tgtgcgacgg | cgtctactcc | acggacggag | 180 |
| agctcgccga | cttgcccgcc | atatgtgctt | gtttgaggcc | gcgcggggcc | aagatactcg | 240 |
| tggacgactc | gcacggttgc | ggcgttcttg | gccgcaaccc | cgactcggag | caacccttcg | 300 |

```
gatatggcgg cggcggcgtc gtcaagtact tcgggctgga ctacgcggag aacaacatca    360
tctacgccgg gcagctgagc aaggcgttca attcgcccgg cggattcgtg ggctgcgcac    420
gcgagaccga cgagaagttc ggcattctga acttggccaa gaactcgaac acgctcgtgt    480
tcacagggcc gatctgtact gccggcctgt cgagtgcgaa gacgaccctc gacctcaact    540
ttgccgaggg ggaccgtcag cgcaagcggc ttcttgaggc gaccctggaa tttgcgaggg    600
gctcaaggcg ctcgggtgcc ccca                                           624

<210> SEQ ID NO 31
<211> LENGTH: 671
<212> TYPE: DNA
<213> ORGANISM: Gymnodinium catenatum

<400> SEQUENCE: 31
cggccctcgt aggcgagaat ggattccttc tcttggacat aaatgcccac gattgtgtgc     60
agacagctgc caggctttgc aagaaaggca ccaccaccgt acgcttgaag cacaatgacg    120
cagagcagct cgagcgcgta cttgcgtcga tcccagaggg ggccgacatc acctacgtgt    180
gcgacggtgt gtactccacg gacggtgaag tcgctgactt gcccgccata tgtgcttgtt    240
tgaggccgcg cggggccaag atactcgttg acgactcgca tggctgcggc gttcttggcc    300
gcaatcccga ctcggagcag ccctacgggt atggcggcgg cggcgtcgtc aagtacttcg    360
ggctggatta tgcggagaac aacatcatct acgccgggca gttgagcaag gcgttcaatt    420
cacccggcgg attcgtcggt tgcgcacgtg agaccgacga gaattcggc  attctgagct    480 tggccaagaa ttcgaacacg ctcgtgttca cggggccgat ttgtactgcc ggcctatcga    540
gtgcgaagac aaccctcgac ctcaacgccg ccgaggggga ccttcagcgc aagcggcttc    600
tggaggcgac cctcagattt tgtgaggggc tcaaggcgct cgggtgcccc cacacttatc    660
atgggttccc c                                                         671

<210> SEQ ID NO 32
<211> LENGTH: 546
<212> TYPE: DNA
<213> ORGANISM: Alexandrium minutum

<400> SEQUENCE: 32
tgcagcgttg ctactcctac tacgtcccga cgtcctacgc cccactgctg gacaggtacc     60
acagcatcat cttcgagaat cccgggtggg ggttcgccgg cgccggcggg gactcgcagg    120
agcaggaggt ccacgtccac aggacgctga acgtggtggg cagcggggcg cagcaccaga    180
cgctcttcac ggacctcgtg cggctcgtgg actcggtctt cgcgggcggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgctcacga    360
tggtcggcat cgacttcaac aaagactctc gggtggcgac ggagctcaac ctgagcaggc    420
acgcggtccc gcacctggtg ctgttcgggg acgtcggcaa gcccgccgac atcatggagc    480
tccacgggcg gaaggggtg  gacccgagca ggtccctcca cgtgcgctcc ttcctagacc    540
acgacc                                                               546

<210> SEQ ID NO 33
<211> LENGTH: 546
<212> TYPE: DNA
<213> ORGANISM: Alexandrium minutum
```

<400> SEQUENCE: 33

```
tgcagcgatg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac ggacctcgtg cggctcgtgg actcggtctt cgcgggcggg gacttcgcgt   240
cgcagccggc gttcgtcgtg gacacggggt gcggcgacgg ccgcttgctc aggcgcatct   300
acgagcacgt gaagagcaac acgccgcgcg ggaaggcgct cgccgagcac ccgctcacga   360
tggtcggcgt cgacttcaac aaggactctc gggtggcgac ggagctcaac ctgagcaggc   420
acgcggtccc gcacctggtg ctgttcgggg acgtcggcaa gcccgccgac atcatggagc   480
tcctcgggcg aagggggtg gacccgagca ggtccctcca cgtgcgctcc ttcctggacc   540
acgacc                                                              546
```

<210> SEQ ID NO 34
<211> LENGTH: 546
<212> TYPE: DNA
<213> ORGANISM: Alexandrium minutum

<400> SEQUENCE: 34

```
tgcagcgatg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac ggacctcgtg cggctcgtgg actcggtctt cgcgggcggg gacttcgcgt   240
cgcagccggc gttcgtcgtg gacacggggt gcggcgacgg ccgcttgctc aggcgcatct   300
acgagcacgt gaagagcaac acgccgcgcg ggaaggcgct cgccgagcac ccgctcacga   360
tggtcggcgt cgacttcaac aaggactctc gggtggcgac ggagctcaac ctgagcaggc   420
acgcggtccc gcacctggtg ctgttcgggg acgtcggcaa gcccgccgac atcatggagc   480
ccctcgggcg aagggggtg gacccgagca ggtccctcca cgtgcgctcc ttcctagacc   540
ccgacc                                                              546
```

<210> SEQ ID NO 35
<211> LENGTH: 546
<212> TYPE: DNA
<213> ORGANISM: Alexandrium minutum

<400> SEQUENCE: 35

```
tgcagcgctg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac gggcctcgtg cggctcgtgg actcggtttt cgcgggcggg gacttcgcgt   240
cgcagccggc gttcgtcgtg gacacggggt gcggcgacgg ccgcttgctc aggcgcatct   300
acgagcacgt gaggagcaac acgccgcgcg ggaaggcgct cgccgagcac ccgctcacga   360
tggtcggcgt cgacttcaac aaggactctc gggtggcgac ggagctcaac ctgagctggc   420
acgcggtccc gcacctggtg ctgttcgggg acgtcggcaa gcccgccgac atcatggagc   480
tcctcgggcg aagggggtg gacccgagca ggtccctcca cgtgcgctcc ttcctggacc   540
acgacc                                                              546
```

<210> SEQ ID NO 36
<211> LENGTH: 546
<212> TYPE: DNA
<213> ORGANISM: Alexandrium minutum

<400> SEQUENCE: 36

| | | | | |
|---|---|---|---|---|
| tgcagcgatg ctactcctac tacgtcccga cgtcctacgc cccactgctg gacaggtacc | 60 |
| acagcatcat cttcgagaat cccgggtggg ggttcgccgg cgccggcggg gactcgcagg | 120 |
| agcaggaggt ccacgtccac aggacgctga acgtggtggg cagcggggcg cagcaccaga | 180 |
| cgctcttcac ggacctcgtg cggctcgtgg actcggtctt cgcgggcggg gacttcgcgt | 240 |
| cgcagccggc gttcgtcgtg gacacggggt gcggcgacgg ccgcttgctc aggcgcatct | 300 |
| acgagcacgt gaagagcaac acgccgcgcg ggaaggcgct cgccgagcac ccgctcacga | 360 |
| tggtcggcgt cgacttcaac aaggactctc gggtggcgac ggagctcaac ctgagcaggc | 420 |
| acgcggtccc gcacctggtg ctgttcgggg acgtcggcaa gcccgccgac atcatggagc | 480 |
| tcctcgggcg aaggggggtg gacccgagca ggtccctcca cgtgcgctcc ttcctagacc | 540 |
| acgacc | 546 |

<210> SEQ ID NO 37
<211> LENGTH: 545
<212> TYPE: DNA
<213> ORGANISM: Alexandrium minutum

<400> SEQUENCE: 37

| | | | | |
|---|---|---|---|---|
| gcagcgatgc tactcctact acgtcccgac gtcccacgcc ccactgctgg acaggtacca | 60 |
| cagcatcatc ttcgagaatc ccgggtgggg gttcgccggc gccggcgggg actcgcagga | 120 |
| gcaggaggtc cacgtccaca ggacgctgaa cgtggtgggc agcggggcgc agcaccagac | 180 |
| gctcttcacg gacctcgtgc ggctcgtgga ctcggtcttc gcgggcgggg acttcgcgtc | 240 |
| gcagccggcg ttcgtcgtgg acacggggtg cggcgacggc cgcttgctca ggcgcatcta | 300 |
| cgagcacgtg aagagcaaca cgccgcgcgg gaaggcgctc gccgagcacc cgctcacgat | 360 |
| ggccggcgtc gacttcaaca aggactctcg ggtggcgacg gagctcaacc tgagcaggca | 420 |
| cgcggtcccg cacctggtgc tgttcgggga cgtcggcaag cccgccgaca tcatggagct | 480 |
| cctcgggcgg aaggggtgg acccgagcag gtccctccac gtgcgctcct tcctggacca | 540 |
| cgacc | 545 |

<210> SEQ ID NO 38
<211> LENGTH: 546
<212> TYPE: DNA
<213> ORGANISM: Alexandrium minutum

<400> SEQUENCE: 38

| | | | | |
|---|---|---|---|---|
| tgcagcgatg ctactcctac tacgtcccga cgtcctacgc cccactgctg gacaggtacc | 60 |
| acagcatcat cttcgagaat cccgggtggg ggttcgccgg cgccggcggg gactcgcagg | 120 |
| agcaggaggt ccacgtccac aggacgctga acgtggtggg cagcggggcg cagcaccaga | 180 |
| cgctcttcac ggacctcatg cggctcgtgg actcggtcct cgcgggcggg gacttcgcgt | 240 |
| cgcagccggc gttcgtcgtg gacacggggt gcggcgacgg ccgcttgctc aggcgcatct | 300 |
| acgagcacgt gaagagcaac acgccgcgcg ggaaggcgct cgccgagcac ccgctcacga | 360 |
| tggtcggcgt cgacttcaac aaggactctc gggtggcgac ggagctcaac ctgagcaggc | 420 |
| acgcggtccc gcacctggtg ctgttcgggg acgtcggcaa gcccgccgac atcatggagc | 480 | tcctcgggcg aaggggggtg acccgagca ggtccctcca cgtgcgctcc ttcctggacc    540 acgacc                                                              546

<210> SEQ ID NO 39
<211> LENGTH: 546
<212> TYPE: DNA
<213> ORGANISM: Alexandrium minutum

<400> SEQUENCE: 39
tgcagcgatg ctattcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac ggacctcgtg cggctcgtgg actcggtctt cgcggcggg gacttcgcgt    240 cgcagccggc gttcgtcgtg gacacggggt gcggcgacgg ccgcttgctc aggcgcatct   300
acgagcacgt gaagagcaac acgccgcgcg ggaaggcgct cgccgagcac ccgctcacga   360
tggtcggcgt cgacttcaac gaggactctc gggtggcgac ggagctcaac ctgagcaggc   420
acgcggtccc gcacctggtg ctgttcgggg acgtcggcaa gcccgccgac atcatggagc   480
tcctcgggcg aaggggggtg acccgagca ggtccctcca cgtgcgctcc ttcctggacc   540
acgacc                                                              546

<210> SEQ ID NO 40
<211> LENGTH: 546
<212> TYPE: DNA
<213> ORGANISM: Alexandrium minutum

<400> SEQUENCE: 40
tgcagcgatg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac ggacctcgtg cggctcgtgg actcggtctt cgcgggcggg gacttcgcgt   240
cgcagccggc gttcgtcgtg gacacggggt gcggcgacgg ccgcttgctc aggcgcatct   300
acgagcacgt gaagagcaac acgccgcgcg ggaaggcgct cgccgagcac ccgctcacga   360
tggtcggcgt cgacttcaac aaggactctc gggtggcgac ggagctcaac ctgagcaggc   420
acgcggtccc gcacctggtg ctgttcgggg acgtcggcaa gcccgccgac atcatggagc   480
tcctcgggcg aaggggggtg acccgagca ggtccctcca cgtgcgctcc ttcctggacc   540
acgacc                                                              546

<210> SEQ ID NO 41
<211> LENGTH: 546
<212> TYPE: DNA
<213> ORGANISM: Alexandrium minutum

<400> SEQUENCE: 41
tgcagcgatg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac ggacctcgtg cggctcgtgg actcggtctt cgcgggcggg gacttcgcgt   240
cgcagccggc gttcgtcgtg gacacggggt gcggcgacgg tcgcttgctc aggcgcatct   300
acgagcacgt gaagagcaac acgccgcgcg ggaaggcgct cgccgagcac ccgctcacga   360

```
tggtcggcgt cgacttcaac aaggactctc gggtggcgac ggagctcaac ctgagcaggc    420
acgcggtccc gcacctggtg ctgttcgggg acgtcggcaa gcccgccgac atcatggagc    480
tcctcgggcg aaggggggtg gacccgagca ggtccctcca cgtgcgctcc ttcctagacc    540
acgacc                                                               546
```

<210> SEQ ID NO 42
<211> LENGTH: 546
<212> TYPE: DNA
<213> ORGANISM: Alexandrium minutum

<400> SEQUENCE: 42

```
tgcagcgatg ctactcctac tacgtcccga cgtcctacgc cccactgctg gacaggtacc     60
acagcatcat cttcgagaat cccgggtggg ggttcgccgg cgccggcggg gactcgcagg    120
agcaggaggt ccacgtccac aggacgctga acgtggtggg cagcggggcg cagcgccaga    180
cgctcttcac ggacctcgtg cggctcgtgg actcggtctt cgcggcgggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgctcacga    360
tggtcggcgt cgacttcaac aaggactctc gggtggcgac ggagctcgac ctgagcaggc    420
acgcggtccc gcacctggtg ctgttcgggg acgtcggcaa gcccgccggc atcatggagc    480
tcctcgggcg aaggggggtg gacccgagca ggtccctcca cgtgcgctcc ttcctggacc    540
acgacc                                                               546
```

<210> SEQ ID NO 43
<211> LENGTH: 546
<212> TYPE: DNA
<213> ORGANISM: Alexandrium minutum

<400> SEQUENCE: 43

```
tgcagcgatg ctactcctac tacgtcccga cgtcctacgc cccactgctg gacaggtacc     60
acagcatcat cttcgagaat cccgggtggg ggttcgctgg cgccggcggg gactcgcagg    120
agcaggaggt ccacgtccac aggacgctga acgtggtggg cagcggggcg cagcaccaga    180
cgctcttcac ggacctcgtg cggctcgtgg actcggtctt cgcggcgggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgctcacga    360
tggtcggcgt cgacttcaac aaggactctc gggtggcgac ggagctcaac ctgagcaggc    420
acgcggtccc gcacctggtg ctgttcgggg acgtcggcaa gcccgccgac atcatggagc    480
tcctcgggcg aaggggggtg gacccgagca ggtccctcca cgtgcgctcc ttcctggacc    540
acgacc                                                               546
```

<210> SEQ ID NO 44
<211> LENGTH: 546
<212> TYPE: DNA
<213> ORGANISM: Alexandrium catenella

<400> SEQUENCE: 44

```
tgcagcgctg ctactcctac tacgtcccag tgtcgtacgc accactgatg gcccagatct     60
caccgatcct ctttgatgat gcgggctggg ggttcactga cgcggggaca gactccttcg    120
acgtggagga gcatgttgac agaatcttga atgtcgttgg cagtggtgcg caacaccgga    180
```

```
ccctctttaa ggatctgatg cgacacatca gtgccgtgtt caagggcgag gcatttccct    240
cgcagccaaa ttttgttgtg gacactggct gtggcgacgg gagcctgctc atacacgtct    300
acgagcacat caaggagcac acgccccggg ggaaagtgct cgacgagttc cctctgacga    360
tggtcggcgt ggacctcaac gaggagccgc gagtgacgac ggccgtgaat ctgagcaagc    420
agggcgtccc gcacgtggtc atctccggcg acgtgggcaa gcccgcggag atcatggccg    480
cgctgaagaa gaagaaggtg gacccatcga ggacgcttca tgtccgctcc ttcctagacc    540
acgtcc                                                               546

<210> SEQ ID NO 45
<211> LENGTH: 546
<212> TYPE: DNA
<213> ORGANISM: Alexandrium catenella

<400> SEQUENCE: 45
tgcagcgatg ctactcctac tacgtcccga cctcctacgc cccactgctg gacaggtacc     60
accgcatcct cttcragaat cccggctggg ggttcgccgg cgccggccgg gactcgcagg    120
arcaggaggt ccacgtccac cggacgctga acgtggtggg cagcggggcg cagcaccaga    180
cgctcttcac ggatctcgtg cggctgattg actcggtctt cgcgggcggg gacttcgcgg    240
cgcagccggc gttcgtcgtg gacacggggt gcggcgacgg ccgcttgctc aggcgcatct    300
acgagcacgt gaagagcaac acgccgcgcg ggaaggcgct cggcgagcac ccgctcacga    360
tggtcggcgt cgacttcaac aaggactctc gggtggccac ggagctcaac ctgagcaggc    420
acgcggtccc gcacctggtg ctgttcgggg acgtcggcaa gcccgccgac atcatggagc    480
tcctcgggcg gaggggggtg gacccgagca ggtccctcca cgtgcgctcc ttcctggacc    540
acgacc                                                               546

<210> SEQ ID NO 46
<211> LENGTH: 546
<212> TYPE: DNA
<213> ORGANISM: Alexandrium catenella

<400> SEQUENCE: 46
tgcagcgatg ctactcctac tacgtcccga cctcctacgc cccactgctg gacaggtacc     60
accgcatcct cttcgagaat cccggctggg ggttcgccgg cgccggccgg gactcgcagg    120
agcaggaggt ccacgtccac cggacgctga acgtggtggg cagcggggcg cagcaccaga    180
cgctcttcac ggatctcgtg cggctgattg actcggtctt cgcgggcggg gacttcgcgg    240
cgcagccggc gttcgtcgtg gacacggggt gcggcgacgg ccgcttgctc aggcgcatct    300
atgagcacgt gaagagcaac acgccgcgcg ggaaggcgct cggcgagcac ccgctcacga    360
tggtcggcgt cgacttcaac aaggactctc gggtggccac ggagctcaac ctgagcaggc    420
acgcggtccc gcacctggtg ctgttcgggg acgtcggcaa gcccgccgac atcatggagc    480
tcctcgggcg gaggggggtg gacccgagca ggtccctcca cgtgcgctcc ttcctagacc    540
acgacc                                                               546

<210> SEQ ID NO 47
<211> LENGTH: 546
<212> TYPE: DNA
<213> ORGANISM: Alexandrium catenella

<400> SEQUENCE: 47
tgcagcgatg ctactcctac tacgtcccga cctcctacgc cccactgctg gacaggtacc     60
```

```
accgcatcct cttcgagaat cccggctggg ggttcgccgg cgccggccgg gactcgcagg    120
agcaggaggt ccacgtccac cggacgctga acgtggtggg cagcggggcg cagcaccaga    180
cgctcttcac ggatctcgtg cggctgattg actcggtctt cgcgggcggg gacttcgcgg    240
cgcagccggc gttcgtcgtg gacacagggg tgcggcgacgg ccgcttgctc aggcgcatct    300
acgagcacgt gaagagcaac acgccgcgcg ggaaggcgct cggcgagcac ccgctcacga    360
tggtcggcgt cgacttcaac aaggactctc gggtggccac ggagctcaac ctgagcaggc    420
acgcggtccc gcacctggtg ctgttcgggg acgtcggcaa gcccgccgac atcatggagc    480
tcctcgggcg gagggggggtg gacccgagca ggtccctcca cgtgcgctcc ttcctggacc    540
acgacc                                                                546
```

```
<210> SEQ ID NO 48
<211> LENGTH: 546
<212> TYPE: DNA
<213> ORGANISM: Alexandrium catenella

<400> SEQUENCE: 48
tgcagcgatg ctactcctac tacgtcccga cctcctacgc cccactgctg gacaggtacc     60
accgcatcct cttcgagaat cccggctggg ggttcgccgg cgccggccgg gactcgcagg    120
agcaggaggt ccacgtccac cggacgctga acgtggtggg cagcggggcg cagcaccaga    180
cgctcttcac ggatctcgtg cggctgattg actcggtctt cgcgggcggg gacttcgcgg    240
cgcagccggc gttcgtcgtg gacacagggt gcggcgacgg ccgcttgctc aggcgcatct    300
acgagcacgt gaagagcaac acgccgcgcg ggaaggcgct cggcgagcac ccgctcacga    360
tggtcggcgt cgacttcaac aaggactctc gggtggccac ggagctcaac ctgagcaggc    420
acgcggtccc gcacctggtg ctgttcgggg acgtcggcaa gcccgccgac atcatggagc    480
tcctcgggcg gagggggggtg gacccgagca ggtccctcca cgtgcgctcc ttcctagacc    540
acgacc                                                                546
```

```
<210> SEQ ID NO 49
<211> LENGTH: 546
<212> TYPE: DNA
<213> ORGANISM: Alexandrium tamarense

<400> SEQUENCE: 49
tgcagcgatg ctactcctac tacgtcccga cgtcctacgc cccgctgctg gacaggtacc     60
acagcatcct cttcgataat cccggctggg ggttcgccgg tgccggccgg gactcgcagg    120
agcaggagat ccacgtccac cggacgctga acgtggtggg cagcggggcg cagcaccaga    180
cgctcttcac ggacctcgtg cggctcattg actcggtctt cgcgggcggg gacttcgcgt    240
cgcagccggc gctcgtcgtg gacacggggt gtggcgactg ccgcttgctc aggcgcatct    300
acgagcacgt gaagagcaac acgccgcgcg ggaaggcgct cgccgagcac ccgctcacga    360
tggtcggcat agacttcaac aaggactctc gggtggcgac ggagctcaac ctgagcaggc    420
acgcggtccc gcacctggtt ctgttcgggg acgtcggcaa gcccgccgac atcatggaga    480
tcctcgggcg gaagggggtg gacccgagca ggtccctcca cgtgcgctcc ttcctggacc    540
acgacc                                                                546
```

```
<210> SEQ ID NO 50
<211> LENGTH: 546
<212> TYPE: DNA
```

<213> ORGANISM: Alexandrium tamarense

<400> SEQUENCE: 50

| | | | | | |
|---|---|---|---|---|---|
| tgcagcgatg | ctactcctac | tacgtcccga | cgtcctacgc | cccgctgctg | gacaggtacc | 60 |
| acagcatcct | cttcgataat | cccggctggg | ggttcgccgg | tgccggccgg | gactcgcagg | 120 |
| agcaggagat | ccacgtccac | cggacgctga | acgtggtggg | cagcggggcg | cagcaccaga | 180 |
| cgctcttcac | agacctcgtg | cggctcattg | actcggtctt | cgcggcggg | gacttcgcgt | 240 |
| cgcagccggc | gttcgtcgtg | gacacggggt | gtggcgactg | ccgcttgctc | aggcgcatct | 300 |
| acgagcacgt | gaagagcaac | acgccgcgcg | ggaaggcgct | cgccgagcac | ccgctcacga | 360 |
| tggtcggcat | agacttcaac | aaggactctc | gggtggcgac | ggagctcaac | ctgagcaggc | 420 |
| acgcggtccc | gcacctggtt | ctgttcgggg | acgtcggcaa | gcccgccgac | atcatggaga | 480 |
| tcctcgggcg | gaaggggtg | gacccgagca | ggtccctcca | cgtgcgctcc | ttcctagacc | 540 |
| acgacc | | | | | | 546 |

<210> SEQ ID NO 51
<211> LENGTH: 546
<212> TYPE: DNA
<213> ORGANISM: Alexandrium tamarense

<400> SEQUENCE: 51

| | | | | | |
|---|---|---|---|---|---|
| tgcagcgatg | ctactcctac | tacgtcccac | tgtcgtacgc | acctctgatg | gcccagatct | 60 |
| cgccgatcct | gtttgatgat | gcggactggg | ggttcgcgga | cgcggggaca | gactccttcg | 120 |
| acgtggagga | gcatgttgac | agaatcttga | atgttgttgg | cagtggtgcg | caacaccgga | 180 |
| ccctctttaa | ggatctgatg | cgacacatca | gtgccgtgtt | caagggcgag | gcatttgcct | 240 |
| tgcagccaaa | tttcgttgtg | gacactggct | gtggcgacgg | gggcctgctc | atgcatatct | 300 |
| atgaacatat | caaacagcac | acgccccggg | ggaaaatgct | cgatgagttc | cctctgacaa | 360 |
| tggtcggcgt | tgacctcaat | gaggagccgc | gagtgacaac | agccgtgaat | ctgagcaagc | 420 |
| agggcgtccc | gcacgtggtc | atctccggcg | acgtgggtag | gcccgcggag | ataattgccg | 480 |
| cgctgaagaa | gaagaaggtg | gacccgtcga | ggacgcttca | cgtccgctcc | ttcctggacc | 540 |
| acgacc | | | | | | 546 |

<210> SEQ ID NO 52
<211> LENGTH: 546
<212> TYPE: DNA
<213> ORGANISM: Alexandrium tamarense

<400> SEQUENCE: 52

| | | | | | |
|---|---|---|---|---|---|
| tgcagcgatg | ctactcctac | tacgtcccga | cgtcctacgc | cccactgctg | gacaggtacc | 60 |
| acagcatcct | cttcgagaat | cccggctggg | ggttcgctgg | tgccggccgg | gactcgcagg | 120 |
| agcaggaggt | ccacgtccac | cggacgctga | acgtggtggg | cagcggggcg | cagcaccaga | 180 |
| cgctcttcac | ggacctcgtg | cggctcattg | actcggtctt | cgcggcggg | gacttcgcat | 240 |
| cgcagccggc | gttcatcgtg | gacacggggt | gcggcgacgg | ccgcttgctc | aggcgcatct | 300 |
| acgagcacgt | gaagagcaac | acgccgcgcg | ggaaggcgct | cgccgagcac | ccgctcacga | 360 |
| tggtcggcgt | cgacttcaac | aaggactctc | gggtggcgac | ggagctcaac | ctgagcaggc | 420 |
| acgcggtccc | gcacctggtg | ctcttcgggg | acgtcggcga | gcccgccgac | atcatggaga | 480 |
| ccctcgggcg | gaatggggtg | gacccgagca | ggtccctcca | cgtgcgctcc | ttcctagacc | 540 |
| acgacc | | | | | | 546 |

<210> SEQ ID NO 53
<211> LENGTH: 546
<212> TYPE: DNA
<213> ORGANISM: Alexandrium tamarense

<400> SEQUENCE: 53

| | | | | | |
|---|---|---|---|---|---|
| tgcagcgatg | ctactcctac | tacgtcccac | tgtcgtacgc | accactgatg | gcccagatct | 60 |
| caccgatcct | gtttgatgat | gcgggctggg | ggttcactga | cgcggggaca | gactcctttg | 120 |
| acgtggagga | gcatgttgac | agaattttga | atgttgttgg | cagtggtgcg | caacaccgga | 180 |
| ccctatttaa | ggatctgatg | cgacacatca | gtgccgtgtt | caaggccgag | gcatttgcct | 240 |
| tgcagccaaa | ttttgttgtg | gacactggct | gtggcgacgg | gagcctgctc | atacatatct | 300 |
| atgaacacat | caagcagcac | acgccccggg | ggaaagtgct | cgatgagttc | cctctaacga | 360 |
| tggtcggcgt | tgacctcaat | gaggagccgc | gagtgacaac | agccgtgaat | ctgagcaagc | 420 |
| agggcgtccc | gcacgtggtc | atctccggcg | acgtgggtaa | gcccgcggag | ataatggccg | 480 |
| cgctgaagaa | gaagaaggtg | gacccgtcga | ggacgcttca | tgtccgctcc | ttcctagacc | 540 |
| acgacc | | | | | | 546 |

<210> SEQ ID NO 54
<211> LENGTH: 546
<212> TYPE: DNA
<213> ORGANISM: Alexandrium tamarense

<400> SEQUENCE: 54

| | | | | | |
|---|---|---|---|---|---|
| tgcagcgatg | ctactcctac | tacgtcccga | cgtcctacgc | cccactgctg | gacaggtacc | 60 |
| acagcatcct | cttcgagaat | cccggctggg | ggttcgctgg | tgccggccgg | gactcgcagg | 120 |
| agcaggaggt | ccacgtccac | cggacgctga | acgtggtggg | cagcggggcg | cagcaccaga | 180 |
| cgctcttcac | ggacctcgtg | cggctcattg | actcggtctt | cgcgggcggg | gacttcgcat | 240 |
| cgcagccggc | gttcatcgtg | gacacggggt | gcggcgacgg | ccgcttgctc | aggcgcatct | 300 |
| acgagcacgt | gaaagagcaac | acgccgcgcg | ggaaggcgct | cgccgagcac | ccgctcacga | 360 |
| tggtcggcgt | cgacttcaac | aaggactctc | ggatggcggc | ggagctcaac | ctgagcaggc | 420 |
| acgcggtccc | gcacctggtg | ctcttcgggg | acgtcggcaa | gcccgccgac | atcatggaga | 480 |
| ccctcgggcg | gaatggggtg | gacccgagca | ggtccctcca | cgtgcgctcc | ttcctggacc | 540 |
| acgacc | | | | | | 546 |

<210> SEQ ID NO 55
<211> LENGTH: 546
<212> TYPE: DNA
<213> ORGANISM: Alexandrium tamarense

<400> SEQUENCE: 55

| | | | | | |
|---|---|---|---|---|---|
| tgcagcgatg | ctactcctac | tacgtcccga | cgtcctacgc | cccactgctg | gacaggtacc | 60 |
| acagcatcct | cttcgagaat | cccggctggg | ggttcgctgg | tgccggccgg | gactcgcagg | 120 |
| agcaggaggt | ccacgtccac | cggacgctga | acgtggtggg | cagcggggcg | cagcaccaga | 180 |
| cgctcttcac | ggacctcgtg | cggctcattg | actcggtctt | cgcgggcggg | gacttcgcat | 240 |
| cgcagccggc | gttcatcgtg | gacacggggt | gcggcgacgg | ccgcttgctc | aggcgcatct | 300 |
| acgagcacgt | gaatagcaac | acgccgcgcg | ggaaggcgct | cgccgagcac | ccgctcacga | 360 |
| tggtcggcgt | cgacttcaac | aaggactctc | gggtggcgac | ggagctcaac | ctgagcaggc | 420 |

```
acgcggtccc gcacctggtg ctcttcgggg acgtcggcaa gcccgccgac atcatggaga      480
ccctcgggcg aatggggtg  gacccgagca ggtccctcca cgtgcgctcc ttcctagacc      540
acgacc                                                                 546

<210> SEQ ID NO 56
<211> LENGTH: 546
<212> TYPE: DNA
<213> ORGANISM: Alexandrium tamarense

<400> SEQUENCE: 56
tgcagcgatg ctactcctac tacgtcccga cgtcctacgc cccactgctg gacaggtacc       60
acagcatcct cttcgagaat cccggctggg ggttcgctgg tgccggccgg gactcgcagg      120
agcaggaggt ccacgtccac cggacgctga acgtggtggg cagcggggcg cagcaccaga      180
cgctcttcac ggacctcgtg cggctcattg actcggtctt cgcgggcggg gacttcgcat      240
cgcagccggc gttcatcgtg gacacgggt  gcggcgacgg ccgcttgctc aggcgcatct      300
acgagcacgt gaagagcaac tcgccgcgcg ggaaggcgct cgccgagcac ccgctcacga      360
tggtcggcgt cgacttcaac aaggactctc gggtggcggc ggagctcaac ctgagcaggc      420
acgcggtccc gcacctggtg ctcttcgggg acgtcggcaa gcccgccgac atcatggaga      480
ccctcgggcg aatggggtg  gacccgagca ggtccctcca cgtgcgctcc ttcctggacc      540
acgacc                                                                 546

<210> SEQ ID NO 57
<211> LENGTH: 549
<212> TYPE: DNA
<213> ORGANISM: Alexandrium fundyense

<400> SEQUENCE: 57
tgcagcgatg ctactcctac tacgtcccac tgtcgtacgc accgctgatg gcccagatct       60
cgccgatcct gtttgatgat gcgggctggg ggttcactga cgcggggaca gactccttcg      120
acgacgtgga ggagcatgtt gacagaatct tgaatgttgt tggcagtggt gcgcaacacc      180
ggaccctctt taaggatatg atgcgacaca tcagtaccgt gttcaagggc gaggcatttg      240
ccttgcagcc aagtttcgct gtggacactg gctgtggcga cgggagcctg ctcatacata      300
tctatgaaca tatcaaacag cacacacccc ggggaaagt  gcttgatcag ttccctctga      360
cgatggtcgg cgttgacctc aatgaggatc cgcgagtgac aacagctgtg aatctgagca      420
agcagggcgt cccgcacgtg gtcatctctg gcgatgtggg taagcctgcg agatacttg       480 ccgcgctgaa gaagaagaag gtggacgcgt cgaggacgct tcatgtccgc tccttcctgg      540
accacgacc                                                              549

<210> SEQ ID NO 58
<211> LENGTH: 487
<212> TYPE: DNA
<213> ORGANISM: Alexandrium fundyense

<400> SEQUENCE: 58
tgcagcgatg ctactcctac tacgtcccac tgtcgtacgc accgctgatg gcccagatct       60
cgccgatcct gtttgatgat gcgggctggg ggttcactga cgcggggaca gactccttcg      120
acgacgtgga ggagcatgtt gacagaatct tgaatgttgt tggcagtggt gcgcaacacc      180
ggaccctctt taaggatatg atgcgacaca tcagtaccgt gttcaagggc gaggcatttg      240
ccttgcagcc aagtttcgtt gtggacactg gctgtggcga cgggagcctg ctcatacata      300
```

```
tctatgaaca tatcaaacag cacacacccc gggggaaagt gcttgatcag ttccctctga    360
cgatggtcgg cgttgacctc aatgaggatc cgcgagtgac aacagctgtg aatctgagca    420
agcagggcgt cccgcacgtg gtcatctctg gcgatgtggg taagcctgcg agatacttg     480 ccgcgct                                                              487

<210> SEQ ID NO 59
<211> LENGTH: 546
<212> TYPE: DNA
<213> ORGANISM: Alexandrium fundyense

<400> SEQUENCE: 59
tgcagcgatg ctactcctac tacgtcccga cgtcctacgc cccactgctg gacaggtacc     60
acagcatcct cttcgagaat cccggctggg ggttcgccgg tgccagccgg gactcgcagg    120
agcaggagat ccacgtccac cggacgctga acgtggtggg cagcggggcg cagcaccaga    180
cgctcttcac ggacctcgtg cggctcattg actcggtctt cgcggcggg gacttcgcgt     240 cgcagccggc gttcgtcgtg gacacggggt gcggcgacgg ccgcttgctc aggcgcatct    300
acgagcacgt gaagagcaac acgccgcgcg ggaaggcgct cgccgagcac cgctcacga    360 tggtcggcgt cgacttcaac aaggactctc gggtggcgac ggagctcaac ctgagcaggc    420
acgcggtccc gcacctggtg ctgttcgggg acgtcggcaa gccggccgac atcatggagc    480
tcctcggacg aggggggtg gacccgagca ggtccctcca cgtgcgctcc ttcctagacc     540
acgacc                                                               546

<210> SEQ ID NO 60
<211> LENGTH: 545
<212> TYPE: DNA
<213> ORGANISM: Alexandrium fundyense

<400> SEQUENCE: 60
gcagcgctgc tactcctact acgtcccgac gtcctacgcc ccaatgctgg acaggtacca     60
cagtatcctc ttcgagaatc ccggctgggg gttcgccggt gccggccggg actcgcagga    120
gcaggagatc cacgtccacc ggacgctgaa cgtggtgggg agcggggcgc agcaccagac    180
gctcttcacg gacctcgtgc ggctcattga ctcggtcttc gcgggcgggg acttcgcgtc    240
gcagccggct ttcgtcgtgg acacggggtg cggcgacggc cgcttgctca ggcgcatcta    300
cgagcacgtg aagagcaaca cgccgcgcgg gaaggcgctc gccgagcacc gctcacgat    360 ggtcggcgtc gacttcaaca aggactctcg ggtggcgacg gagctcaacc tgagcaggca    420
cgcggtcccg cacctggtgc tgttcgggga cgtcggcaag ccggccgaca tcatggagct    480
cctcggacgg aggggggtgg acccgagcag gtccctccac gtgcgctcct tcctagacca    540
cgacc                                                                545

<210> SEQ ID NO 61
<211> LENGTH: 546
<212> TYPE: DNA
<213> ORGANISM: Alexandrium fundyense

<400> SEQUENCE: 61
tgcagcgatg ctactcctac tacgtcccga cgtcctacgc cccactgctg gacaggtacc     60
acagcatcct cttcgagaat cccggctggg ggttcgccgg tgccggccgg gactcgcagg    120
agcaggagat ccacgtccac cggacgctga acgtggtggg cagcggggcg cagcaccaga    180
```

```
cgctcttcac ggacctcgtg cggctcattg actcggtctt cgcgggcggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgctcacga    360
tggtcggcgt cgacttcaac aaggactctc gggtggcgac ggagctcaac ctgagcaggc    420
acgcggtccc gcacctggtg ctgttcgggg acgtcggcaa gcccgccgac atcatggaga    480
tcctcgggcg gaacggggtg gacccgagca ggtccctcca cgtgcgctcc ttcctggacc    540
acgacc                                                               546
```

<210> SEQ ID NO 62
<211> LENGTH: 546
<212> TYPE: DNA
<213> ORGANISM: Alexandrium fundyense

<400> SEQUENCE: 62

```
tgcagcgatg ctactcctac tacgtcccga cgtcctacgc cccactgctg gacaggtacc     60
acagcatcct cttcgagaat cccggctggg ggttcgccgg tgccggccgg gactcgcagg    120
agcaagagat ccacgtccac cggacgctga acgtggtggg cagcggggcg cagcaccaga    180
cgctcttcac ggacctcgtg cggctcattg actcggtctt cgcgggcggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagtac ccgctcacga    360
tggtcggcgt cgacttcaac aaggactctc gggtggcgac ggagctcaac ctgagcaggc    420
acgcggtccc gcacctggtg ctgttcgggg acgtcggcaa gccggccgac atcatggaga    480
tcctcgggcg gaacggggtg gatccgagca ggtccctcca cgtgcgctcc ttcctggacc    540
acgacc                                                               546
```

<210> SEQ ID NO 63
<211> LENGTH: 546
<212> TYPE: DNA
<213> ORGANISM: Alexandrium fundyense

<400> SEQUENCE: 63

```
tgcagcgctg ctactcctac tacgtcccga cgtcctacgc cccactgctg gacaggtacc     60
acagcatcct cttcgagaat cccggctggg ggttcgccgg tgccggccgg gactcgcagg    120
agcaggagat ccacgtccac cggacgctga acgtggtggg cagcggggcg cagcaccaga    180
cgctcttcac ggacctcgtg cggctcattg actcggtctt cgcgggcggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgatcacga    360
tggtcggcgt cgacttcaac aaggactctc gggtggcgac ggagctcaac ctgagcaggc    420
acgcggtccc gcacctggtg ctgttcgggg acgtcggcaa gccggccgac atcatggaga    480
tcctcgggcg gaacggggtg gacccgagca ggtccctcca cgtgcgctcc ttcctagacc    540
acgacc                                                               546
```

<210> SEQ ID NO 64
<211> LENGTH: 546
<212> TYPE: DNA
<213> ORGANISM: Alexandrium fundyense

<400> SEQUENCE: 64

```
tgcagcgatg ctactcctac tacgtcccga cgtcctacgc cccactgctg gacaggtacc     60
```

```
acagcatcct cttcgagaat ctcggctggg ggttcgccgg tgccggtcgg gactcgcagg    120
agcaggagat ccacgtccac cggacgctga acgtggtggg cagcggggcg cagcaccaga    180
cgctcttcac ggacctcgtg cggctcattg actcggtctt cgcgggcggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgctcacga    360
tggtcggcgt cgacttcaac aaggactctc gggtggcgac ggagctcaac ctgagcaggc    420
acgcggtccc gcacctggtg ctgttctggg acgtcggcaa gcccgccgac atcatggaga    480
tcctcgggcg aacggggtg  gacccgagca ggtccctcca cgtgcgctcc ttcctggacc    540
acgacc                                                               546
```

<210> SEQ ID NO 65
<211> LENGTH: 545
<212> TYPE: DNA
<213> ORGANISM: Alexandrium fundyense

<400> SEQUENCE: 65

```
gcagcgatgc tactcctact acgtcccgac gtcctacgcc ccactgctgg acaggtacca     60
cagcatcctc ttcgagaatc ccggctgggg gttcgccggt gccggccggg actcgcagga    120
gcaggagatc cacgtccacc ggacgctgaa cgtggtgggc agcggggcgc agcaccagac    180
gctcttcacg gacctcgtgc ggctcattga ctcggtcttc gcgggcgggg acttcgcgtc    240
gcagccggcg ttcgtcgtgg acacggggtg cggcgacggc cgcttgctca ggcacatcta    300
cgagcacgtg aagagcaaca cgccgcgcgg gaaggcgctc gccgagcacc cactcacgat    360
ggtcggcgtc gacttcaaca aggactctcg ggtggcgacg gagctcaacc tgagcaggca    420
cgcggtcccg cacctggtgc tgttcgggga cgtcggcaag cccgccgaca tcatggagct    480
cctcggacgg aggggggtgg acccgagcag gtccctccac gtgcgctcct tcctggacca    540
cgacc                                                                545
```

<210> SEQ ID NO 66
<211> LENGTH: 546
<212> TYPE: DNA
<213> ORGANISM: Alexandrium fundyense

<400> SEQUENCE: 66

```
tgcagcgatg ctacttctac tacgtcccga cgtcctacgc cccactgctg acaggtacc      60 acagcatcct cttcgagaat cccggctggg ggttcgccgg tgccggccgg gactcgcagg    120
agcaggagat ccacgtccac cggacgctga acgtggtggg cagcggggcg cagcaccaga    180
cgctcttcac ggacctcgtg cggctcattg actcggtctt cgcgggcggg gacttcgcgt    240
cgcagccggc gttcgtcgtg gacacggggt gcggcgacgg ccgcttgctc aggcgcatct    300
acgagcacgt gaagagcaac acgccgcgcg ggaaggcgct cgccgagcac ccgctcacga    360
tggtcggcgt cgacttcaac aaggaccctc gggtggcgac ggagctcaac ctgagcaggc    420
acgcggtccc gcacctggtg ctgttcggag acgtcggcaa gcccgccgac atcatggaga    480
tcctcggacg gagcggggtg gacccgagca ggtccctcca cgtgcgctcc ttcctggacc    540
acgacc                                                               546
```

<210> SEQ ID NO 67
<211> LENGTH: 545
<212> TYPE: DNA

<213> ORGANISM: Alexandrium fundyense

<400> SEQUENCE: 67

| | | | | | |
|---|---|---|---|---|---|
| tgcagcgatg | ctactcctac | tacgtcccga | cgtcctacgc | cccactgctg | gacaggtacc | 60 |
| acagcatcct | cttcgagaat | cccggctggg | ggttcgccgg | tgccggccgg | gactcgcagg | 120 |
| agcaggagat | ccacgtccac | cggacgctga | acgtggtggg | cagcggggcg | cagcaccaga | 180 |
| cgctcttcac | ggacctcgtg | cggctcattg | actcggtctt | cgcggggggg | gacttcgcgt | 240 |
| cgcagccggc | gttcgtcgtg | gacacggggt | gcggcgacgg | ccgcttgctc | aggcgcatct | 300 |
| acgagcacgt | gaagagcaac | acgccgcgcg | ggaaggcgct | cgccgagcac | ccgctcacga | 360 |
| tggtcggcgt | cgacttcaac | aaggactctc | gggtggcgat | ggagctcaac | ctgagcaggc | 420 |
| acgcggtccc | gcacctggtg | ctgttcgggg | acgtcggcaa | gccggccgac | atcatggagc | 480 |
| tcctcggacg | gagggggggtg | gacccgagca | ggtccctcca | cgtgcgctcc | ttccagacca | 540 |
| cgacc | | | | | 545 |

<210> SEQ ID NO 68
<211> LENGTH: 546
<212> TYPE: DNA
<213> ORGANISM: Alexandrium minutum

<400> SEQUENCE: 68

| | | | | | |
|---|---|---|---|---|---|
| tgcagcgatg | ctactcctac | tacgtcccga | cgtcctacgc | cccactgctg | gacaggtacc | 60 |
| acagcatcct | cttcgagaat | cccggctggg | ggttcgccgg | tgccggccgg | gactcgcagg | 120 |
| agcaggaggt | ccacgtccac | cggacgctga | acgtggtggg | cagcggggcg | cagcaccaga | 180 |
| cgctcttcac | ggacctcgtg | cggctcattg | actcggtctt | cgcgggcggg | gacttcgcat | 240 |
| cgcagccggc | gttcatcgtg | gacacggggt | gcggcgacgg | ccgcttgctc | aggcgcatct | 300 |
| acgagcacgt | gaagagcaac | acgccgcgcg | ggaaggcgct | caccgagcac | ccgctcacga | 360 |
| tggtcggcgt | cgacttcaac | aaggactctc | gggtggcgac | ggagctcaac | ctgagcaggc | 420 |
| acgcggtccc | gcacctggtg | ctcttcgggg | acgtcggcaa | gccgccgac | atcatggaga | 480 |
| ccctcgggcg | gaatggggtg | gacccgagca | ggtccctcca | cgtgcgctcc | ttcctggacc | 540 |
| acgacc | | | | | 546 |

<210> SEQ ID NO 69
<211> LENGTH: 546
<212> TYPE: DNA
<213> ORGANISM: Alexandrium minutum

<400> SEQUENCE: 69

| | | | | | |
|---|---|---|---|---|---|
| tgcagcgatg | ctactcctac | tacgtcccga | cgtcctacgc | cccactgctg | gacaggcacc | 60 |
| acagcatcat | cttcgagaat | cccggtgggg | ggttcgccgg | cgccggcggg | gactcgcagg | 120 |
| agcaggaggt | ccacgtccac | aggacgctga | acgcggtggg | cagcggggcg | cagcaccaga | 180 |
| cgctcttcac | ggacctcgtg | cggctcgtgg | actcggtctt | cgcgggcggg | gacttcgcgt | 240 |
| cgcagccggc | gttcgtcgtg | gacacggggt | gcggcgacgg | ccgcttgctc | aggcgcatct | 300 |
| acgagcacgt | gaagagcaac | acgccgcgcg | ggaaggcgct | cgccgagcac | ccgctcacga | 360 |
| tggtcggcgt | cgacttcaac | aaggactctc | gggtggcgac | ggagctcaac | ctgagcaggc | 420 |
| acgcggtccc | gcacctggtg | ctgttcgggg | acgtcggcaa | gccgccgac | atcatggagc | 480 |
| tcctcgggcg | gaagggggtg | gacccgagca | ggtccctcca | cgtgcgctcc | ttcctagacc | 540 |
| acgacc | | | | | 546 |

<210> SEQ ID NO 70
<211> LENGTH: 546
<212> TYPE: DNA
<213> ORGANISM: Alexandrium minutum

<400> SEQUENCE: 70

```
tgcagcgatg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga acgtggtggg cagcggggcg cagcaccaga   180
cgctcttcac ggacctcgtg cggctcgtgg actcggtctt cgcgggcggg gacttcgcgt   240
cgcagccggc gttcgtcgtg gacacggggt gcggcgacgg ccgcttgctc aggcgcatct   300
acgagcacgt gaagagcaac tcgccgcgcg ggaaggcgct cgccgagcac ccgctcacga   360
tggtcggcgt cgacttcaac aaggactctc gggtggcgac ggagctcaac ctgagcaggc   420
acgcggtccc gcacctggtg ccgttcgggg acgtcggcaa gcccgccgac atcacggagc   480
tcctcgggcg gaaggggggtg gacccgagca ggtccctcca cgtgcgctcc ttcctggacc   540
acgacc                                                              546
```

<210> SEQ ID NO 71
<211> LENGTH: 545
<212> TYPE: DNA
<213> ORGANISM: Alexandrium minutum

<400> SEQUENCE: 71

```
tgcagcgatg ctactcctac tacgtcccga cgtcctacgc cccactgctg gacaggtacc    60
acagcatcat cttcgagaat cccgggtggg ggttcgccgg cgccggcggg gactcgcagg   120
agcaggaggt ccacgtccac aggacgctga gcgtggtggg cagcggggcg cagcaccaga   180
cgctcttcac ggacctcgtg cggctcgtgg actcggtctt cgcgggcggg gacttcgcgt   240
cgcagccggc gttcgtcgtg gacacggggt gcggcgacgg ccgcttgctc aggcgcatct   300
acgagcacgt gaagagcaac acgccgcgcg ggaaggcgct cgccgagcac ccgctcacga   360
tggtcggcgt cgacttcaac aaggactctc gggtgcgacg gagctcaacc tgagcaggca   420
cgcggtcccg cacctggtgc tgttcgggga cgtcggcaag cccgccgaca tcatggagct   480
cctcgggcgg aaggggtggg acccgagcag gtccctccac gtgcgctcct tcctggacca   540
cgacc                                                               545
```

<210> SEQ ID NO 72
<211> LENGTH: 545
<212> TYPE: DNA
<213> ORGANISM: Alexandrium minutum

<400> SEQUENCE: 72

```
tgcagcgatg ctactcctac tacgtcccga cgtcctacgc cccactgctg gacaggtacc    60
acagcatcat cttcgagaat cccgggtggg agttcgccgg cgccggcggg gactcgcagg   120
agcaggaggt ccacgtccac aggacgctga acgtggtggg cagcggggcg cagcaccaga   180
cgctcttcat ggacctcgtg cggctcgtgg actcggtctt cgcgggcggg gacttcgcgt   240
cgcagccggc gttcgtcgtg gacacggggt gcggcgacgg ccgcttgctc aggcgcatct   300
acgagcacgt gaagagcaac acgccgcgcg ggaaggcgct cgccgagcac ccgctcacga   360
tggtcggcgt cgacttcaac aaggactctc gggtggcgac ggagctcaac ctgagcaggc   420
```

```
acgcggtccc gcacctggtg ctgttcgggg acgtcggcaa gcccgccgac atcatggagc    480
tcctcgggcg aggggggtgg acccgagcag gtccctccac gtgcgctcct tcctggacca    540
cgacc                                                                545

<210> SEQ ID NO 73
<211> LENGTH: 546
<212> TYPE: DNA
<213> ORGANISM: Alexandrium fundyense

<400> SEQUENCE: 73
tgcagcgctg ctactcctac tacgtcccga cgtcctacgc cccactgctg gacaggtacc     60
acagcatcct cttcgagaat cccggctggg ggttcgccgg tgccggccgg gactcgcagg    120
agcaggagat ccacgtccac cggacgctga acgtggtggg cagcggggcg cagcaccaga    180
cgctcttcac ggacctcgtg cggctcattg actcggtctt cgcgggcggg gacttcgcgt    240
cgcagccggt gttcgtcgtg gacacggggt gcggcgacgg ccgcttgctc aggcgcatct    300
acgagcacgt gaagagcaat acgccgcgcg ggaaggcgct cgcctagcac ccgctcatga    360
tggtcggcgt cgacttcaac aaggactctc gggtggcgac ggagctcaac ctgagcaggc    420
acgcggtccc gcacctggtg ctgttcgggg acgtcggcaa gcccgccgac atcatggaga    480
tccttgggcg aaggggggtg gacccgagca ggtccctcca ggtgcgctcc ttcctggacc    540
acgacc                                                              546

<210> SEQ ID NO 74
<400> SEQUENCE: 74

000

<210> SEQ ID NO 75
<211> LENGTH: 670
<212> TYPE: DNA
<213> ORGANISM: Alexandrium minutum

<400> SEQUENCE: 75
cgagcctggc gggcgagagc gggttcctcc tcctggacat caacgcccac gactgcgtgc     60
agacggccgc caggctctgc aagaagggag tcaccgtcgt gcgcctgaag cacaacgaca    120
cggagcagct cgagcgcgtg ctctcgtcga tcccggaagg ggccgacatc acctacgtgt    180
gcgacggcgt ctactccacg gacggagagc tcgccgactt gcccgccata tgtgcttgtt    240
tgaggccgcg cggggccaag atactcgtgg acgactcgca cggttgcggc gttcttggcc    300
gcaaccccga ctcggagcaa cccttcggat atggcggcgg cggcgtcgtc aagtacttcg    360
ggctggacta cgcggagaac aacatcatct acgccgggca gctgagcaag gcgttcaatt    420
cgcccggcag attcgtgggc tgcgcacgcg agaccgacga gaagttcggc atcctgaact    480
tggccaagaa ctcgaacatg ctcgtgttca caggccgat ctgtactgcc ggcctgtcga    540
gtgcgaagac gaccctcgac ctcaactttg ccgaggggga ccgtcagcgc aagcggcttc    600
ttcaggcgac cctcgaattt tgcgaggggc tcaaggcgct cgggtgcccc cacacctacc    660
acgggttccc                                                          670

<210> SEQ ID NO 76
<211> LENGTH: 670
<212> TYPE: DNA
<213> ORGANISM: Alexandrium minutum
```

<400> SEQUENCE: 76

```
cgagcctggc gggcgagagc ttgttcctcc tcctggacat aaacgcccac gactgcgtgc    60
agacggcagc caggctctgc aagaagggag tcaccgtcgt gcgcctgaag cacaacgaca   120
cggagcagct cgagcgcgtg ctctcgtcga tcccggaggg ggccgacatc acctacgtgt   180
gcgacggcgt ctactccacg gacggagagc tcgccgactt gcccgccata tgtgcttgtt   240
tgaggccgcg cggggccaag atactcgtgg acgactcgca cggttgcggc gttcttggcc   300
gcaaccccga ctcggagcaa cccttcggat atggcggcgg cggcgtcgtc aagtacttcg   360
ggctggacta cgcggagaac aacatcatct acgccgggca gctgagcaag gcgttcaatt   420
cgcccggcgg attcgtgggc tgcgcacgcg agaccgacga gaagttcggc attctgaact   480
tggccaagaa ctcgaacacg ctcgtgttca cagggccgat ctgtactgcc ggcctgtcga   540
gtgcgaagac gacccgcgac ctcaactttg ccgaggggga ccgtcagcgc aagcggcttc   600
ttgaggcgac cctggaattt tgcgaggggc tcaaggcgct cgggtgcccc cacacctacc   660
acgggttccc                                                          670
```

<210> SEQ ID NO 77
<211> LENGTH: 670
<212> TYPE: DNA
<213> ORGANISM: Alexandrium minutum

<400> SEQUENCE: 77

```
cgagcctggc gggcgagagc gggttcctcc tcctggacat aaacgcccac gactgcgtgc    60
agacggcagc caggctctgc aagaagggag tcaccgtcgt gcgcctgaag cacaacgaca   120
cggagcagct cgagcgcgtg ctctcgtcga tcccggaggg ggccgacatc acctacgtgt   180
gcgacggcgt ctactccacg gacggagagc tcgccgactt gcccgccata tgtgcttgtt   240
tgaggccgcg cggggccaag atactcgtgg acgactcgca cggttgcggc gttcttggcc   300
gcaaccccga ctcggagcaa cccttcggat atggcggcgg cggcgtcgtc aagtacttcg   360
ggctggacta cgcggagaac aacatcatct acgccgggca gctgagcaag gcgttcaatt   420
cgcccggcgg attcgtgggc tgcgcacgcg agaccgacga gaagttcgrc attctgaact   480
tggccaagaa ctcgaacacg ctcgtgttca cagggccgat ctgtactgcc ggcctgtcga   540
gtgcgaagac gacccgcgac ctcractttg ccgaggggga ccgtcagcgc aagcggcttc   600
ttgaggcgac cctggaattt tgcgaggggc tcaaggcgct cgggtgcccc crcacctacc   660
acgggttccc                                                          670
```

<210> SEQ ID NO 78
<211> LENGTH: 670
<212> TYPE: DNA
<213> ORGANISM: Alexandrium minutum

<400> SEQUENCE: 78

```
cgagcctggc gggcgagagc gggttcctcc tcctggacat aaacgcccac gactgcgtgc    60
agacggcagc caggctctgc aagaagggag tcaccgtcgt gcgcctgaag cacaacgaca   120
cggagcagct cgagygcgtg ctctcgtcga tcccggaggg ggccgacatc acctacgtgt   180
gcgacggcgt ctactccacg grcggagagc tcgccgactt gcccgccata tgtgcttgtt   240
tgaggccgcg cggggccaag atactcgtgg acgactcgca cggttgcggc gttcttggcc   300
gcaaccccga ctcggagcaa cccttcggat atggcggcgg cggcgtcgtc aagtacttcg   360
ggctggacta cgcggagaac aacatcatct acgccgggca gctgagcaag gcgttcaatt   420
```

-continued

```
cgcccggcgg attcgtgggc tgcgcacgcg agaccgacga gaagttcggc attctgaact    480
tggccaagaa ctcgaacacg ctcgtgttca cagggccgat ctgtactgcc ggcctgtcga    540
gtgcgaagac gaccctcgac ctcractttg ccgaggggga ccgtcagcgc aagcggcttc    600
ttgaggcgac cctggaattt tgcgaggggc tcaaggcgct cgggtgcccc crcacctacc    660
acgggttccc                                                          670
```

<210> SEQ ID NO 79
<211> LENGTH: 670
<212> TYPE: DNA
<213> ORGANISM: Alexandrium minutum

<400> SEQUENCE: 79

```
cgagcctggc gggcgagagc gggttcctcc tcctggacat aaacgcccac gactgcgtgc     60
agacggyagc caggctctgc aagaagggag tcaccgtcgt gcgcctgaag cacaacgaca    120
cggagcagct cgagygcgtg ctctcgtcga tcccggaggg ggccgacatc acctacgtgt    180
gcgacggcgt ctactccacg grcggagagc tcgccgactt gcccgccata tgtgcttgtt    240
tgaggccgcg cggggccaag atactcgtgg acgactcgca cggttgcggc gttcttggcc    300
gcaaccccga ctcggagcaa cccttcggat atggcggcgg cggcgtcgtc aagtacttcg    360
ggctggacta cgcggagaac aacatcatct acgccgggca gctgagcaag gcgttcaatt    420
cgcccggcgg attcgtgggc tgcgcacgcg agaccgacga gaagttcggc attctgaact    480
tggccaagaa ctcgaacacg ctcgtgttca cagggccgat ctgtactgcc ggcctgtcga    540
gtgcgaagac gaccctcgac ctcaactttg ccgaggggga ccgtcagcgc aagcggcttc    600
ttgaggcgac cctggaattt tgcgaggggc tcaaggcgct cgggtgcccc cacacctacc    660
acgggttccc                                                          670
```

<210> SEQ ID NO 80
<211> LENGTH: 627
<212> TYPE: DNA
<213> ORGANISM: Alexandrium minutum

<400> SEQUENCE: 80

```
cgcccacgac tgcgtgcaga cggcagccag gctctgcaag aagggagtca ccgtcgtgcg     60
cctgaagcac aacgacacgg agcagctcga gcgcgtgctc tcgtcgatcc cggaggggac    120
cgacatcacc tacgtgtgcg acggcgtcta ctccacggac ggagagctcg ccgacttgcc    180
cgccatatgt gcttgtttga ggccgcgcgg ggccaagata ctcgtggacg actcgcacgg    240
ttgcggcgtt cttggccgca accccgactc ggagcaaccc ttcggatatg gcggcggcgg    300
cgtcgtcaag tacttcgggc tggactacgc ggagaacaac atcatctacg ccgggcagct    360
gagcaaggcg ttcaattcgc ccggcggatt cgtgggctgc gcacgcgaga ccgacgagaa    420
gttcggcatt ctgaacttgg ccaagaactc gaacacgctc gtgttcacag gccgatctg    480 tactgccggc ctgtcgggtg cgaagacgac cctcgacctc aactttgccg aggggaccg    540 tcagcgcaag cggcttcttg aggcgaccct ggaattttgc gagggctca aggcgctcgg    600 gtgcccccac acctaccacg ggttccc                                       627
```

<210> SEQ ID NO 81
<211> LENGTH: 670
<212> TYPE: DNA
<213> ORGANISM: Alexandrium minutum

<400> SEQUENCE: 81

```
cgagcctggc gggcgagagc gggttcctcc tcctggacat caacgcccac gactgcgtgc    60
agacggccgc caggctctgc aagaagggag tcaccgtcgt gcgcctgaag cacaacgaca   120
cggagcagct cgagcgcgtg ctctcgtcga tcccggaagg ggccgacatc acctacgtgt   180
gcgacggcgt ctactccacg gacggagagc tcgccgactt gcccgccata tgtgcttgtt   240
tgaggccgcg cggggccaag atactcgtgg acgactcgca cggttgcggc gttcttggcc   300
gcaaccccga ctcggagcaa cccttcggat atggcggcgg cggcgtcgtc aagtacttcg   360
ggctggacta cgcggagaac aacatcatct cgccgggca gctgagcaag gcgttcaatt   420
cgcccggcgg attcgtgggc tgcgcacgcg agaccgacga gaagttcggc atcctgaact   480
tggccaagaa ctcgaacacg ctcgtgttca cagggccgat ctgtactgcc ggcctgtcga   540
gtgcgaagac gaccctcgac ctcaactttg ccgaggggga ccgtcagcgc aagcggcttc   600
ttcaggcgac cctcgaattt tgcgaggggc tcaaggcgct cgggtgcccc cacacctacc   660
acgggttccc                                                           670
```

<210> SEQ ID NO 82
<211> LENGTH: 669
<212> TYPE: DNA
<213> ORGANISM: Alexandrium minutum

<400> SEQUENCE: 82

```
cgagcctggc gggcgagagc gggttcctcc tcctggacat caacgcccac gactgcgtgc    60
agacggccgc caggctctgc aagaagggag tcaccgtcgt gcgcctgaag cacaacgaca   120
cggagcagct cgagcgcgtg ctctcgtcga tcccggaagg ggccgacatc acctacgtgt   180
gcgacggcgt ctactccacg gacggagagc tcgccgactt gcccgccata tgtgcttgtt   240
tgaggccgcg cggggccaag atactcgtgg acgactcgca cggttgcggc gttcttggcc   300
gcaaccccga ctcggagcaa cccttcggat atggcggcgg cggcgtcgtc aagtactcgg   360
gctggactac gcggagaaca acatcatcta cgccgggcag ctgagcaagg cgttcaattc   420
gcccggcgga ttcgtgggct gcgcacgcga ccgacgag aggttcggca ttctgaactt   480
ggccaagaac tcgaacacgc tcgtgttcac agggccgatc tgtactgccg gcctgtcgag   540
tgcgaagacg accctcgacc tcaactttgc cgaggggac cgtcagcgca agcggcttct   600
tgaggcgacc ctggaatttt gcgaggggct caaggcgctc gggtgccccc acacctacca   660
cgggttccc                                                            669
```

<210> SEQ ID NO 83
<211> LENGTH: 670
<212> TYPE: DNA
<213> ORGANISM: Alexandrium minutum

<400> SEQUENCE: 83

```
agcctttgtg ggcgagagca ggttcccccg cctgtgcata aacgcctacg attgcgcgca    60
gacggccgcc aggctctgca agaagggcgc caccgtggtg cgcttgaagc acaacgacac   120
ggagcagctc gagcacatgc tctcgtcgat cctgcagggg ccgacatcac ctacgtgtgc   180
gacggcgtgt actccacgga cggagagctc gccgacttgc ccgccatatg tgttttgtgt   240
gaggccgcgt ggggccaata tactcgtaga cgactcgcat ggctgcgcg ttcttggccg   300
cgaccccgac tcggagcaac ccctcgggta tggtggcggc ggcgccgtcg agtatttcgg   360
gctgggctac gcggagaaca acatcagcta cgccgggcag ctgagcaagg cgttcaattc   420
```

```
gcccggcgga atcgtcggtt gtgcgcgcga gaccgacgag aatttcggcg ctctgaactt    480
ggccaagaac tcgagcacac tcgcgctcac agggccgatc tgtactgtcg gcctgtcgag    540
tgcgaagacg accttcgacc tcaacgccgt cgagggggac ttttcagcgc aagcggctgc    600
tggcgactac cctcgaattc tgcgaggggc tcaaggcgct cgggtgcccc cacacctacc    660
acgggttccc                                                           670
```

<210> SEQ ID NO 84
<211> LENGTH: 671
<212> TYPE: DNA
<213> ORGANISM: Alexandrium minutum

<400> SEQUENCE: 84

```
cgagcctggc gggcgagagc ttgttcctcc tcctggacat aaacgcccac gactgcgtgc     60
agacggcagc caggctctgc aagaagggag tcaccgtcgt gcgcctgaag cacaacgaca    120
cggagcagct cgagcacatg ctctcgtcga tcctgcaggg ccgacatca cctacgtgtg     180 cgacggcgtg tactccacgg acggagagct cgccgacttg cccgccatat gtgttttgtg    240
tgaggccgcg tggggccaat atactcgtag acgactcgca tggctgcggc gttcttggcc    300
gcgaccccga ctcggagcaa cccctcgggt atggtggcgg cggcgccgtc gagtatttcg    360
ggctgggcta cgcggagaac aacatcagct acgccgggca gctgagcaag gcgttcaatt    420
cgcccggcgg aatcgtcggt tgtgcgcgcg agaccgacga gaatttcggc gctctgaact    480
tggccaagaa ctcgagcaca ctcgcgctca cagggccgat ctgtactgtc ggcctgtcga    540
gtgcgaagac gaccttcgac ctcaacgccg tcgaggggga cttttcagcg caagcggctg    600
ctggcgacta ccctcgaatt ctgcgagggg ctcaaggcgc tcgggtgccc ccacacctac    660
cacgggttcc c                                                         671
```

<210> SEQ ID NO 85
<211> LENGTH: 672
<212> TYPE: DNA
<213> ORGANISM: Alexandrium minutum

<400> SEQUENCE: 85

```
cgagcctttg tgggcgagag caggttcccc cgcctgtgca taaacgccta cgattgcgcg     60
cagacggccg ccaggctctg caagaagggc gccaccgtgg tgcgcttgaa gcacaacgac    120
acggagcagc tcgagcacat gctctcgtcg atcctgcagg ggccgacatc acctacgtgt    180
gcgacggcgt gtactccacg gacggagagc tcgccgactt gcccgccata tgtgttttgt    240
gtgaggccgc gtggggccaa tatactcgta gacgactcgc atggctgcgg cgttcttggc    300
cgcgactccg actcggagca acccctcggg tatggtggcg gcggcgccgt cgagtatttc    360
gggctgggct acgcggagaa caacatcagc tacgccgggc agctgagcaa ggcgttcaat    420
tcgcccggcg aatcgtcgg ttgtgcgcgc gagaccgacg agaatttcgg cgctctgaac    480
ttggccaaga actcgagcac actcgcgctc acagggccga tctgtactgt cggcctgtcg    540
agtgcgaaga cgaccttcga cctcaacgcc gtcgaggggg acttttcagc gcaagcggct    600
gctggcgact accctcgaat tctgcgaggg gctcaaggcg ctcgggtgcc cccacaccta    660
ccacgggttc cc                                                        672
```

<210> SEQ ID NO 86
<211> LENGTH: 672
<212> TYPE: DNA

<213> ORGANISM: Alexandrium minutum

<400> SEQUENCE: 86

| | | | | | |
|---|---|---|---|---|---|
| cgagcctttg | tgggcgagag | caggttcccc | cgcctgtgca | taaacgccta | cgattgcgcg | 60 |
| cagacggccg | ccaggctctg | caagaagggc | gccaccgtgg | tgcgcttgaa | gcacaacgac | 120 |
| acggagcagc | tcgagcacat | gctctcgtcg | atcctgcagg | ggccgacatc | acctacgtgt | 180 |
| gcgacggcgt | gtactccacg | gacggagagc | tcgccgactt | gcccgccata | tgtgttttgt | 240 |
| gtgaggccgc | gtggggccaa | tatactcgta | gacgactcgc | atggctgcgg | cgttcttggc | 300 |
| cgcgaccccg | actcggagca | acccctcggg | tatggtggcg | gcggcgccgt | cgagtatttc | 360 |
| gggctgggct | acgcggagaa | caacatcagc | tacgccgggc | agctgagcaa | ggcgttcaat | 420 |
| tcgcccggcg | gaatcgtcgg | ttgtgcgcgc | gagaccgacg | agaatttcgg | cgctctgaac | 480 |
| ttggccaaga | actcgagcac | actcgcgctc | acaggccga | tctgtactgt | cggcctgtcg | 540 |
| agtgcgaaga | cgaccttcga | cctcaacgcc | gtcgagggg | acttttcagc | gcaagcggct | 600 |
| gctggcgact | accctcgaat | tctgcgaggg | gctcaaggcg | ctcgggtgcc | cccacaccta | 660 |
| ccacgggttc | cc | | | | | 672 |

<210> SEQ ID NO 87
<211> LENGTH: 672
<212> TYPE: DNA
<213> ORGANISM: Alexandrium minutum

<400> SEQUENCE: 87

| | | | | | |
|---|---|---|---|---|---|
| cgagcctttg | tgggcgagag | caggttcccc | cgcctgtgca | taaacgccta | cgattgcgcg | 60 |
| cagacggccg | ccaggctctg | caagaagggc | gccaccgtgg | tgcgcttgaa | gcacaacgac | 120 |
| acggagcagc | tcgagcacat | gctctcgtcg | atcctgcagg | ggccgacatc | acctacgtgt | 180 |
| gcgacggcgt | gtactccacg | gacggagagc | tcgccgactt | gcccgccata | tgtgttttgt | 240 |
| gtgaggccgc | gtggggccaa | tatactcgta | gacgactcgc | atggctgcgg | cgttcttggc | 300 |
| cgcgactccg | actcggagca | accccctcggg | tatggtggcg | gcggcgccgt | cgagtatttc | 360 |
| gggctgggct | acgcggagaa | caacatcagc | tacgccgggc | agctgagcaa | ggcgttcaat | 420 |
| tcgcccggcg | gaatcgtcgg | ttgtgcgcgc | gagaccgacg | agaatttcgg | cgctctgaac | 480 |
| ttggccaaga | actcgagcac | actcgcgctc | acaggccga | tctgtactgt | cggcctgtcg | 540 |
| agtgcgaaga | cgaccttcga | cctcaacgcc | gtcgagggg | acttttcagc | gcaagcggct | 600 |
| gctggcgact | accctcgaat | tctgcgaggg | gctcaaggcg | ctcgggtgcc | cccacaccta | 660 |
| ccacgggttc | cc | | | | | 672 |

<210> SEQ ID NO 88
<211> LENGTH: 671
<212> TYPE: DNA
<213> ORGANISM: Alexandrium minutum

<400> SEQUENCE: 88

| | | | | | |
|---|---|---|---|---|---|
| cgagcctggc | gggcgagagc | gggttcctcc | tcctggacat | aaacgcccac | gactgcgtgc | 60 |
| agacggcagc | caggctctgc | aagaagggag | tcaccgtcgt | gcgcctgaag | cacaacgaca | 120 |
| cggagctgct | cgagcgcgtg | ctctcgtcga | tcccggaggg | ggccgacatc | acctacgcgt | 180 |
| gcgacggcgt | ctactccacg | gacggagagc | tcgccgactt | gcccgccata | tgtgcttgtt | 240 |
| tgaggccgcg | cggggccaag | atactcgtgg | acgactcgca | tggctgcggc | gttcttggcc | 300 |
| gcgaccccga | ctcggagcaa | cccctcgggt | atggtggcgg | cggcgccgtc | gagtatttcg | 360 |

```
ggctgggcta cgcggagaac aacatcagct acgccgggca gctgagcaag gcgttcaatt    420
cgcccggcgg aatcgtcggt tgtgcgcgcg agaccgacga gaatttcggc gctctgaact    480
tggccaagaa ctcgagcaca ctcgcgctca cagggccgat ctgtactgtc ggcctgtcga    540
gtgcgaagac gaccttcgac ctcaacgccg tcgaggggga cttttcagcg caagcggctg    600
ttggcgacta ccctcgaatt ctgcgagggg ctcaaggcgc tagggtgccc ccacacctac    660
cacgggttcc c                                                         671

<210> SEQ ID NO 89
<211> LENGTH: 714
<212> TYPE: DNA
<213> ORGANISM: Alexandrium minutum

<400> SEQUENCE: 89
tgctcaacat gggagtcatc ccgagcctgg cgggcgagag cttgttcctc ctcctggaca     60
taaacgccca cgactgcgtg cagacggcag ccaggctctg caagaaggga gtcaccgtcg    120
tgcgcctgaa gcacaacgac acggagcagc tcgagcgcgt gctctcgtcg atcccggagg    180
gggccgacat cacctacgtg tgcgacggcg tctactccac ggacggagag ctcgccgact    240
tgcccgccat atgtgctcgt ttggggccgc gcggggccga gatactcgtg gacgactcgc    300
acggttgcgg cgttcttggc cgcaaccccg actcggagca accttcgga tatggcggcg     360 gcggcgtcgt ctagtacttc gggctggact acgcggagaa caacatcatc tacgccgggc    420
agctgagcaa ggcgttcaat tcgcccggcg gattcgtggg ctgcgcacgc gagaccgacg    480
agaagttcgg cattctgaac ttggccaaga actcgaacac gctcgtgttc acagggccga    540
tctgtactgc cggcctgtcg agtgcgaaga cgaccctcga cctcaacttt gccgaggggg    600
accgtcagcg caagcggctt cttgaggcga ccctggaatt ttgcgagggg ctcaaggcgc    660
tcgggtgccc ccacacctac cacgggttcc ccatcgtcaa catctactgg accc          714

<210> SEQ ID NO 90
<211> LENGTH: 714
<212> TYPE: DNA
<213> ORGANISM: Alexandrium minutum

<400> SEQUENCE: 90
tgctcaacat gggagtcatc ccgagcctgg cgggcgagag cttgttcctc ctcctggaca     60
taaacgccca cgactgcgtg cagacggcag ccaggctctg caagaaggga gtcaccgtcg    120
tgcgcctgaa gcacaacgac acggagcagc tcgagcgcgt gctctcgtcg atcccggagg    180
gggccgacat cacctacgtg tgcgacggcg tctactccac ggacggagag ctcgccgact    240
tgcccgccat atgtgctcgt ttggggccgc gcggggccga gatactcgtg gacgactcgc    300
acggttgcgg cgttcttggc cgcaaccccg actcggagca accttcgga tatggcggcg     360 gcggcgtcgt ctagtacttc gggctggact acgcggagaa caacatcatc tacgccgggc    420
agctgagcaa ggcgttcaat tcgcccggcg gattcgtggg ctgcgcacgc gagaccgacg    480
agaagttcgg cattctgaac ttggccaaga actcgaacac gctcgtgttc acagggccga    540
tctgtactgc cggcctgtcg agtgcgaaga cgaccctcga cctcaacttt gccgaggggg    600
accgtcagcg caagcggctt cttgaggcga ccctggaatt ttgcgagggg ctcaaggcgc    660
tcgggtgccc ccacacctac cacgggttcc ccatcgtcaa catctactgg accc          714

<210> SEQ ID NO 91
```

```
<211> LENGTH: 714
<212> TYPE: DNA
<213> ORGANISM: Alexandrium minutum

<400> SEQUENCE: 91
tgctcaacat gggagtcatc ccgagcctgg cgggcgagag cgggttcctc ctcctggaca      60
taaacgccca cgactgcgtg cagacggcag ccaggctctg caagaaggga gtcaccgtcg     120
tgcgcctgaa gcacaacgac acggagcagc tcgagcgcgt gctctcgtcg atcccggagg     180
gggccgacat cacctacgtg tgcgacggcg tctactccac ggacggagag ctcgccgact     240
tgcccgccat atgtgcttgt ttgaggccgc gcggggccaa gatactcgtg gacgactcgc     300
acggttgcgg cgttcttggc cgcaaccccg actcggagca acccttcgga tatggcggcg     360
gcggcatcgt caagtacttc gggctggact acgcggagaa caacatcatc tacgccgggc     420
agctgagcaa ggcgttcaat tcgcccggcg gattcgtggg ctgcgcacgc gagaccgacg     480
agaagttcgg cattctgaac ctggccaaga actcgaacac gctcgtgttc acagggccga     540
tctgtactgc cggcctgtcg agtgcgaaga cgaccctcga cctcaacttt gccgagggg      600
accgtcagcg caagcggctt cttgaggcga ccctggaatt ttgcgagggg ctcaaggcgc     660
tcgggtgccc ccacacctac cacgggttcc ccatcgtcaa catctactgg accc           714

<210> SEQ ID NO 92
<211> LENGTH: 713
<212> TYPE: DNA
<213> ORGANISM: Alexandrium minutum

<400> SEQUENCE: 92
tgctcaacat gggagtcatc ccgagcctgg cgggcgagag cttgttcctc ctcctggaca      60
taaacgccca cgactgcgtg cagacggcag ccaggctctg caagaaggag tcaccgtcgt     120
gcgcctgaag cacaacgaca cggagcagct cgagcgcgtg ctctcgtcga tcccggaggg     180
ggccgacatc acctacgtgt gcgacggcgt ctactccacg gacggagagc tcgccgactt     240
gcccgccata tgtgcttgtt tggggccgcg cggggccaag atactcgtgg acgactcgca     300
cggttgcggc gttcttggcc gcaaccccga ctcggagcaa cccttcggat atggcggcgg     360
cggcgtcgtc aagtacttcg ggctggacta cgcggagaac aacatcatct acgccgggca     420
gctgagcaag gcgttcaatt cgcccggcgg attcgtgggc tgcgcacgcg agaccgacga     480
gaagttcggc attctgaact ggccaagaa ctcgaacacg ctcgtgttca cagggccgat      540
ctgtactgcc ggcctgtcga gtgcgaagac gaccctcgac ctcaactttg ccgaggggga     600
ccgtcagcgc aagcggcttc ttgaggcgac cctggaattt tgcgaggggc tcaaggcgct     660
cgggtgcccc cacacctacc acgggttccc catcgtcaac atctactgga ccc            713

<210> SEQ ID NO 93
<211> LENGTH: 713
<212> TYPE: DNA
<213> ORGANISM: Alexandrium minutum

<400> SEQUENCE: 93
tgctcaacat gggagtcatc ccgagcctgg cgagcgagac cgggttcctc ctcctggaca      60
tcaacgccca cgactgcgtg cagacggcca ccaggctctg caagaaggga gtcaccgtcg     120
tgcgcctgaa gcacaacgac acggagcagc tcgagcgcgt gctctcgtcg atcccggagg     180
ggccgacatc gcctacgtgt gcgacggcgt ctactccacg gacggagagc tcgccgactt     240
gcccgccata tgtgcttgtt tgaggccgcg cggggccaag atactcgtgg acgactcgca     300
```

```
cggttgcggc gttcttggcc gcaaccccga ctcggagcaa cccttcggat atggcggcgg    360
cggcgtcgtc aagtacttcg ggctggacta cgcggagaac aacatcatct acgccgggca    420
gctgagcaag gcgttcaatt cgcccggcgg attcgtgggc tgcgcacgcg agaccgacga    480
gaagttcggc atcctgaact tggccaagaa ctcgaacacg ctcgtgttca ccgggccgat    540
ctgtactgcc ggcctgtcga gtgcgaagac gaccctcgac ctcaactttg ccgaggggga    600
ccgtcagcgc aagcggcttc ttcaggcgac cctcgaattt tgcgaggggc tcaaggcgct    660
cgggtgcccc cacacctacc acgggttccc catcgtcaac atctactgga ccc           713
```

<210> SEQ ID NO 94
<211> LENGTH: 670
<212> TYPE: DNA
<213> ORGANISM: Alexandrium catenella

<400> SEQUENCE: 94

```
cgagcctcgt gggcgagagc gggttcctcc tcctgtacat aaacgcccac gactgcgtgc     60
agatggccgc caggctctgc aagaagggcg ccaccgtggt gcgcctgaag cacaacgaca    120
cggaacagcc cgagcacatg ctctcgtcaa tcccgcaggg ggccgacatc acctacgtgt    180
gcgacggcgt gtactccacg gacgaagagc tcgccgactt gcccgccata tgtgcttgtt    240
tgaggccgcg cggggccaag atactcgtag acgactcgca tggctgcggc gttcttggcc    300
gcaaccccaa ctcggagcaa cccctcgggt atggtggcgg cggcgtcatc gagtacttcg    360
ggctggacta cgcggagaac aacatcatct acgccgggca gctgagcaag gcgttcaatt    420
cgcccggcgg attcgtcagc tgtgcgcgcg agaccgacga gaatttcggc gttctgcact    480
tggccaagaa ctcgaacaca ctcgtgctca cagggccgat ctgtactgcc agcctgtcga    540
gtgcgaagac gaccttcgac ctcaacgccg ccaggggga ccttcagcgc aagcggcttc    600
tggcggctac cctcgaattc tgcgaggggc tcaaggcgct cgggtgcccc cacacctacc    660
acgagttccc                                                           670
```

<210> SEQ ID NO 95
<211> LENGTH: 670
<212> TYPE: DNA
<213> ORGANISM: Alexandrium tamarense

<400> SEQUENCE: 95

```
cgagcctcgt gggcgagagc gggttcctcg tcctcgacat aaacacccac gactgcgtgc     60
agacggccgc caggctctgc aagaagggcg ccaccgtggt gcgcctgaag cacaacgaca    120
cggagcagct cgagcacatg ctctcgtcga tcccgcaggg ggccgacatc acctacgtgt    180
gcgacggcgt gtactccacg gacggagagc tcgccgactt gcccgccata tgtgcttgtt    240
tgaggccgcg cggggccaag atactcgtag acgactcgca tggctgcggc gttcttggcc    300
gcaaccccga ctcggagcaa cccctcgggt gtggtggtgg cggcgtcgtc gagtacttcg    360
ggctggatta cgcggagaac aacgacatct acgccgggca gctgagcaag gcattcaatt    420
cgcccggcgg attcgtcggc tgtgcgcgcg agacagacga gaagtgcggc attctgagct    480
tggccaagaa ctcgaacaca ctcgtgttca cagggccgat ctgtactgcc ggcctgtcga    540
gtgcaatgac gaccctcgac ctcaacgccg ccaggggga ccttcagcgc aagcggcttc    600
tggcggcgac cctcgaattc tgcgaggggc tcaaggcgct cgggtgcccc cacacctacc    660
acgggctccc                                                           670
```

<210> SEQ ID NO 96
<211> LENGTH: 670
<212> TYPE: DNA
<213> ORGANISM: Alexandrium tamarense

<400> SEQUENCE: 96

| | | | | | |
|---|---|---|---|---|---|
| cgagcctcgt | gggcgagagc | gggttcctcg | tcctcgacat | aaacacccac | gactgcgtgc | 60 |
| agacggccgc | caggctctgc | aagaagggcg | ccaccgtggt | gcgcctgaag | cacaacgaca | 120 |
| cggagcagct | cgagcacatg | ctctcgtcga | tcccgcaggg | ggccgacatc | acctacgtgt | 180 |
| gcgacggcgt | gtactccacg | gacggagagc | tcgccgactt | gcccgccata | tgtgcttgtt | 240 |
| tgaggccgcg | cggggccaag | atactcgtag | acgactcgca | tggctgcggc | gttcttggcc | 300 |
| gcaaccctga | ctcggagcaa | cccctcgggt | gtggtggtgg | cggcgtcgtc | gagtacttcg | 360 |
| ggctggatta | cgcggagaac | aacgacatct | acgccgggca | gctgagcaag | gcgttcaatt | 420 |
| cgcccggcgg | attcgtcggc | tgtgcgcgcg | agacagacga | gaagtgcggc | attctgagct | 480 |
| tggccaagaa | ctcgaacaca | ctcgtgttca | cagggccgat | ctgtactgcc | ggcctgtcga | 540 |
| gtgcaatgac | gaccctcgac | ctcaacgccg | ccgaggggga | ccttcagcgc | aagcggcttc | 600 |
| tggcggcgac | cctcgaattc | tgcgaggggc | tcaaggcgct | cgggtgcccc | cacacctacc | 660 |
| acgggctccc | | | | | | 670 |

<210> SEQ ID NO 97
<211> LENGTH: 670
<212> TYPE: DNA
<213> ORGANISM: Alexandrium tamarense

<400> SEQUENCE: 97

| | | | | | |
|---|---|---|---|---|---|
| ccagcctcgc | gggcgagagc | gggttcctcc | tcctggacat | aaacgcccac | ggctgcgtgc | 60 |
| agacggccgc | caggctctgc | aagaatggcg | tcaccgtggt | gcgcctgaag | cacaacgaca | 120 |
| cggagcagct | ggagcgcatg | ctctcctcga | tcccgcaggg | ggccgacatc | acctacgtgt | 180 |
| gcgacggcgt | atactccaca | gacggagagc | tcgccgactt | gcccgccata | tgtgcttgtt | 240 |
| tgaggccgcg | cggggccaag | atactcgtgg | acgactcgca | tggctgcggc | gttcttggcc | 300 |
| gaaacccaga | ctcggagcaa | cccttcgggt | atggtggcgg | tggcgtcgtc | gagtacttcg | 360 |
| ggctggacta | cgcggagaac | aacatcatct | acgccgggca | gctgagcaag | gcgttcaact | 420 |
| tgcccggcgg | attcgtcggc | tgcgcgcgcg | agaccgacga | gaagttcggc | atcctgaact | 480 |
| tggccaagaa | ctcgaacaca | ctcgtgttca | cagggccgat | ctgtaccgcc | ggcctgtcga | 540 |
| gtgcaaagac | gaccctggac | ctcaacgccg | ccgaggggga | ccttcagcgc | aggcggctcc | 600 |
| tggcggcgac | cctcgagttc | tgcgaggggc | tcagggcgct | cgggtgcccc | cacacctacc | 660 |
| acggcttccc | | | | | | 670 |

<210> SEQ ID NO 98
<211> LENGTH: 713
<212> TYPE: DNA
<213> ORGANISM: Alexandrium tamarense

<400> SEQUENCE: 98

| | | | | | |
|---|---|---|---|---|---|
| tgctcaacat | gggagtcatc | cccagcctcg | cgggcgagag | cgggttcctc | ctcctggaca | 60 |
| taaacgccca | cgactgcgtg | cagacggccg | ccaggctctg | caagaagggc | gtcaccgtgg | 120 |
| tgcgcctgaa | gcacaacgac | acggagcagc | tggagcgcat | gctctcctcg | atcccgcagg | 180 |
| gggccgacat | cacccacgtg | tgcgacggcg | tgtactccac | agacggaggg | ctcgccgact | 240 |

```
tgcccgccat atgtgcttgt ttgaggccgc gcgggaccaa gatactcgtg gacgactcgc      300
atggctgcgg cgttcttggc cgaaacccag actcggagca acccttcggg tatggtggcg      360
gtgcgtcgtc gagtacttcg ggctggacta cgcggagaac aacatcatct acgccgggca      420
gctgagcaag gcgttcaact cgcccggcgg attcgtcggc tgcgcgcgcg agaccgacga      480
gaagttcggc atcctgaact tggccaagaa ctcgaacacg ctcgtgttca cagggccgat      540
ctgtaccgcc ggcctgtcga gtgcaaagac gaccctggac ctcaacgccg ccagggggga      600
ccttcagcgc aggcggctcc tggcggcgac cctcgagttc tgcgaggggc tcagggcgct      660
cgggtgcccc cacacctacc acggcttccc catcgtcaac atctactgga ccc             713
```

<210> SEQ ID NO 99
<211> LENGTH: 713
<212> TYPE: DNA
<213> ORGANISM: Alexandrium tamarense
<400> SEQUENCE: 99

```
tgctcaacat gggagtcatc cccagcctcg cgggcgggag cgggttcctc ctcctggaca       60
taaacgccca cgactgcgtg cagacggccg ccaggctctg caagaagggc gtcaccgtgt      120
gcgcctgaag cacaacgaca cggagcagct ggagcgcatg ctctcctcga tcccgcaggg      180
ggccgacatc acctacgtgt gcgacggcgt gtactccaca gacggagagc tcgccgactt      240
gcccgccata tgtgcttgtt tgaggccgcg cggggccaag atactcgtgg acgactcgca      300
tggctgcggc gttcttggcc gaaacccaga ctcggagcaa cccttcgggt atggtggtgg      360
tggcgtcgtc gagtacttcg ggctggacta cgcggagaac aacatcatct acgccgggca      420
gctgagcaag gcgttcaact cgcccggcgg attcgtcggc tgcgcgcgcg agaccgacga      480
gaagttcggc atcctgaact tggccaagaa ctcgaacaca ctcgtgttca cagggccgat      540
ctgtaccgcc ggcctgtcga gtgcaaagac gaccctggac ctcaacgccg ccagggggga      600
ccttcagcgc aggcggctcc tggcggcgac cctcgagttc tgcgaggggc tcagggcgct      660
cgggtgcccc cacacctacc acggcttccc catcgtcaac atctactgga ccc             713
```

<210> SEQ ID NO 100
<211> LENGTH: 713
<212> TYPE: DNA
<213> ORGANISM: Alexandrium tamarense
<400> SEQUENCE: 100

```
tgctcaacat gggagtcatc cccagcctcg cgggcgggag cgggttcctc ctcctggaca       60
taaacgccca cgactgcgtg cagacggccg ccaggctctg caagaagggc gtcaccgtgt      120
gcgcctgaag cacaacgaca cggagcagct ggagcgcatg ctctcctcga tcccgcaggg      180
ggccgacatc acctacgtgt gcgacggcgt gtactccaca gacggagagc tcgccgactt      240
gcccgccata tgtgcttgtt tgaggccgcg cggggccaag atactcgtgg acgactcgca      300
tggctgcggc gttcttggcc gaaacccaga ctcggagcaa cccttcgggt atggtggtgg      360
tggcgtcgtc gagtacttcg ggctggacta cgcggagaac aacatcatct acgccgggca      420
gctgagcaag gcgttcaact cgcccggcgg attcgtcggc tgcgcgcgcg agaccgacga      480
gaagttcggc atcctgaact tggccaagaa ctcgaacaca ctcgtgttca cagggccgat      540
ctgtaccgcc ggcctgtcga gtgcaaagac gaccctggac ctcaacgccg ccagggggga      600
ccttcagcgc aggcggctcc tggcggcgac cctcgagttc tgcgaggggc tcagggcgct      660
```

```
cgggtgcccc cacacctacc acggcttccc catcgtcaac atctactgga ccc        713
```

<210> SEQ ID NO 101
<211> LENGTH: 714
<212> TYPE: DNA
<213> ORGANISM: Alexandrium tamarense

<400> SEQUENCE: 101

```
tgctcaacat gggagtcatc cccagccccg cgggcgagag cgggttcctc ctcctggaca   60
taaacgccca cgactgcgtg cagacggccg ccaggctctg caagaagggc gtcaccgtgg  120
tgcgcctgaa gcacaacgac acggagcagc tggagcgcat gctctcctcg atcccgcagg  180
gggccgacat cacctacgtg tgcgacggcg tgtactccac agacggagag ctcgccgact  240
tgcccgccat atgtgattgt ttgaggccgc gcggggccaa gatactcgtg gacgactcgc  300
atggctgcgg cgttcttggc cgaaacccag actcggagca accttcggg tatggtggcg  360
gtggcgtcgt cgagtacttc gggctggact acgcggagaa caacatcatc tacgccgggc  420
agctgagcaa ggcgttcaac tcgcccgcg gattcgtcgg ctgcgcgcgc gagaccgacg  480
agaagttcgg catcctgaac ttggccaaga actcgaacac actcgtgttc acagggccga  540
tctgtaccgc cggcctgtcg agtgcaaaga cgaccctgga cctcaacgcc gcgaggggg  600
accttcagcg caggcggctc ctggcggcga ccctcgagtt ctgcgagggg ctcagggcgc  660
tcgggtgccc ccacacctac cacggcttcc ccatcgtcaa catctactgg accc         714
```

<210> SEQ ID NO 102
<211> LENGTH: 667
<212> TYPE: DNA
<213> ORGANISM: Alexandrium fundyense

<400> SEQUENCE: 102

```
cgagcctcgt gggcgagagc gggttcctcc tcctgtacat aaacgcccac gtctgcgtgc   60
agacggccgc caggctctgc aagaagggcg ccaccgtggt gcgcctgaag cacaacgaca  120
cggaacagcc cgagcacatg ctctcgtcga tcccgcaggg ggccgacatc acctacgtgt  180
gcgacgtact ccacggacga agagctcgcc gacttgcccg ccatatgtgc ttgtttgagg  240
ccgcgcgggg ccaagatact cgtagacgac tcgcatggct gcggcgttct tggccgcaac  300
cccaactcgg agcaacccct cgggtatggt ggcggcggcg tcatcgagta cttcgggctg  360
gactacgcgg agaacaccat catatacgcc gggcagctga gcaaggcgtt caattcgccc  420
ggcggattcg tcagctgtgc gcgcgcgaga ccgacgagaa tttcggcgtt atgaacttgg  480
ccaagaactc gaacacactc gtgttcacag gccgatctg tactgccggc ctgtcgagtg  540
cgaagacgac cttcgacctc aacgccgccg agggggacct tcagcgcaag cggcttctgg  600
cggctaccct cgaattctgc gagggctca aggcgctcgg gtgccccac acctaccacg  660
ggttccc                                                           667
```

<210> SEQ ID NO 103
<211> LENGTH: 670
<212> TYPE: DNA
<213> ORGANISM: Alexandrium fundyense

<400> SEQUENCE: 103

```
cgagcctcgt gggcgagagc gggttcctcc tcctgtacat aaacgcccac gactgcgtgc   60
agacggccgc caggctctgc aagaagggtg ccaccgtggt gcgcctgaag cacaacgaca  120
cggaacagcc cgagcacatg ctctcgtcga tcccgcaggg ggccgacatc acctacgtgt  180
```

```
gcgacggcgt gtactccacg gacgaagagc tcgccgactt gcccgccata tgtgcttgtg    240
tgaggccgcg cggggccaag atactcgtag acgactcgca tggttgcggc gttcttggcc    300
gcaaccccaa ctcggagcaa ccccgcgggt atggtggtgg cggcgtcatg gagtacttcg    360
ggctggacta cgcggagaac aacatcatct atgccgggca gctgagcaag gcgttcaatt    420
cgcccggcgg attcgtcagc tgtgcgcgcg agaccgacga gaattgcggc gttctgaact    480
tggccaagaa ctcgaacaca ctcgtgttca cagggccgat ctgtattgcc ggcctgtcga    540
gtgcgaagac gaccttcgac ctctacgccg ccgaggggg ccttcagcgc aagcggcttc     600
tggcggctac cctcgaattc tgcgagggc tcaaggcgct cgggtgcccc cacacctacc     660
acgggttccc                                                          670

<210> SEQ ID NO 104
<211> LENGTH: 670
<212> TYPE: DNA
<213> ORGANISM: Alexandrium fundyense

<400> SEQUENCE: 104
cgagcctcgt gggcgagagc gggttcctcc tcctggacat aaacgcccac gactgcgtgc     60
agacggccgc caggctctgc aagaagggcg ccaccgtggt gcgcctgaag cacaacgacg    120
cggagcagct cgagcacatg ctctcgtcga tcccgcaggg ggccgacatc acctacgtgt    180
gcgacggcgt gtactccacg gacggagagc tcgccgactt gcccgccata tgtgcttgtt    240
tgaggccgcg cggggccaag atactcgtag acgactcgca tggctgcggc gttcttgacc    300
gcaaccccga ctcggagcaa cccttcgggt atggtggcgg cggcgtcgtc gagtacttcg    360
ggctggacta cgcggagaac aacatcatct acgccgggca gctgagcaag gcgttcaatt    420
cgcccggcgg attcgtcggc tgtgcgcgcg agaccgacga gaagttcggc attctgaact    480
tggccaagaa ctcaaacaca ctcgtgttca cagggccgat ctgtactgcc ggcctgtcga    540
gtgcgatgac gaccctcgac ctcaacgccg ccgagggga ccttcagcgc aagcggcttc     600
tggcggcgac cctcgaattc tgcgagggc tcaaggcgct cgggtgcccc cacacctacc     660
acgggttccc                                                          670

<210> SEQ ID NO 105
<211> LENGTH: 667
<212> TYPE: DNA
<213> ORGANISM: Alexandrium fundyense

<400> SEQUENCE: 105
cgagcctcgt gggcgagagc gggttcctcc tcctgtacaa aaatgcccac gactgcgtgc     60
agacggccgc caggctctgc aagaagggag ccaccgtggt gcgcctgaag cacaacgaca    120
cggaacagcc cgagcacata ctctcgtcga tcccgcaggg gggcgacatc acctacatgt    180
gcgacggcgt gtactccacg gacagagagc tcgccgactt gcccgccata tgtgcttgtt    240
tgaggccgcg tggggccaag atactcgtag acgactcgca tggctgcggc tttcttggcc    300 gcaccccga ctcggagcaa cccctcgggt atggtggcgg cgtcgtcaag tacttcgggc    360
tggactacgc ggagaacaac atcaactacg ccgggcatct gagcaaggcg ttcaattcgc    420
ccggcggatt cgtcggctgt gcgcgcgaga ccgacgataa tttcggcgtt ctgaacttgg    480
ccaagaactc gaccacactc gcgctcacag ggccgatctg tactgccggc ctgtagagtg    540
cgaagacgac cttcgacctc aacgccgccg agggggacct tcagcgcaag cggcttctgg    600
```

```
cggctaccct cgaattctgc gaggggctca aggcgctcgg gtgaccccac acctaccacg    660
ggttccc                                                              667

<210> SEQ ID NO 106
<211> LENGTH: 670
<212> TYPE: DNA
<213> ORGANISM: Alexandrium fundyense

<400> SEQUENCE: 106
cgagcctcgt gggcgagagc aggttcctcc tcctgtacat aaacgcccac gactgcgtgc     60
agacagccgc caggctctgc aagaagggcg ccaccgtggt gcgcctgaag cacaacgaca    120
cggagcagct cgagcacata ctctcgtcga tcccgcaggg ggccgacatc acctacgtgt    180
gcgacggcgt gtactccacg gacggagagc tcgccgactt gcccgccata tgtgcttgtt    240
tgaggccgcg cggggccaag atactcgtag acgactcgca tggctgcggc gttcttggcc    300
gcaaccccga ctcggagcaa cccctcgggt atggtggcgg cggcgtcgtc gagtacttcg    360
ggctggacta cgcggagaac aacatcatct acgccggca gctgagcaag gcgttcaatt     420
cgcccggcgg attcgtcggc tgtgcgcgcg agaccgacga gaagttcggc attctgaact    480
tggccaagaa ctcaaacaca ctcgtgttca cagggccgat ctgtactgcc ggcctgtcga    540
gtgcgaagac gaccttcgac ctcaacgccg ccgaggggga ccttcagcgc aagcggcttc    600
tggcggcgac cctcgaattc tgcgaggggc tcaaggcgct cgggtgcccc cacacctacc    660
acgggttccc                                                           670

<210> SEQ ID NO 107
<211> LENGTH: 668
<212> TYPE: DNA
<213> ORGANISM: Alexandrium fundyense

<400> SEQUENCE: 107
cgggcctcgt gggcgagagc gggttcctcc tcctgtacat aaacgcccac gactgcgtgc     60
agacggccgc caggctctgc aagaagggcg ccaccgtggt gcgcctgaag cacaacgaca    120
cggaacagcc cgagcacatg ctctcgtcga tcccgcaggg gccgacatca cctacgtgtg    180
cgacggcgtg tactccacgg acgaagagct cgccggcttg cccgccatat gtgcttgttt    240
gaggccgcgc ggggccaaga tactcgtaga cgactcgcat ggctgcggcg ttcttggccg    300
caaccccaac tcggagcaac ccctcgggta tggtggcggc ggcgtcatcg agtacttcgg    360
gctggactac gcggagaaca acatcatcta cgccggcag ctgagcaagg cgttcaattc     420
gcccggcgga ttcgtcagct gtgcgcgcga gaccgacgag aatttcggcg ttctgaactt    480
ggccaagaac tcgaacacac tcgtgctcac agggccgatc tgtactgccg gcctgtcgag    540
tgcgaagacg accttcgacc tcaacgccgc cgaggggac cttcagcgca agcggcttct     600
ggcggcgacc ctcgaattct gcgaggggct caaggcgctc gggtgcccca cacctaccac    660
gggttccc                                                             668

<210> SEQ ID NO 108
<211> LENGTH: 673
<212> TYPE: DNA
<213> ORGANISM: Alexandrium fundyense

<400> SEQUENCE: 108
cgaggcacgt gggcgagagc gggttcctcc tcctgtacat aaacgcccac gactgcgtgc     60
agacggccgc caggctctgc aagacgggcg ccaccgtggt gcgcctgaag cacaacgaca    120
```

```
cggagcagct cgagcacatg ctctcgccga tcctgcaggg gggggcgaca tcacctacat    180
gtgcgacggc gtgtactcca cggacggaga gctcgccaac ttgcccgcca tatgtgcttg    240
tttgaggccg cgtggggcca acatacgcgt agacgactcg catggttgcg gcgctcttgg    300
ccgcaacccc gactcggagc aacccctcgg gtatggtggc ggcggcggcg ccgagtactt    360
cgggctggac tacgcggaga acaacatcat ctacgccggg cagttgagca aggcgttcaa    420
ttcgcccggc ggattcgtct tttgtgcgcg cgagaccgac gcgaagtttg gcttttctga    480
acttggccaa gagctcgaac ccactcgtgc tcacagggcc gatctgtcct gccggcctgt    540
cgagtgcgaa gaccttcgac ctcaacgccg ccgagggg gaccttcag cgcaagcggc       600 ttctggcggc gaccctcgaa ttctgcgagg ggttcaaggc gctcggtgc ccccacacct     660 accacgggtt ccc                                                       673
```

<210> SEQ ID NO 109
<211> LENGTH: 669
<212> TYPE: DNA
<213> ORGANISM: Alexandrium fundyense

<400> SEQUENCE: 109

```
cgagcctcgt gggcgagagc gggttcctcc tcctgtacat aaacgcccac gactgcgtgc    60
agacggccgc caggctctgc aagaagggcg ccaccgtggt gcgcctgaag cacaacgaca   120
cggaacagcc cgagcacatg ctctcgtcga tcccgcaggg ggccgacatc acctacgtgt   180 gtgacgcgt gtactccacg gacgaagagc tcgccgactt gcccgccata tgtgcttgtt    240
tgaggccgcg cgggccaata tactcgtaga cgactcgcat ggctgcggcg ttcttggccg   300
caaccccaac tcggagcaac ccctcgggta tggtggcggc ggcgtcatcg agtacttcgg   360
gctggactac gcggagaaca acatcatcta cgccgggcag ctgagcaagg cattcaattc    420
gcccggcgga ttcgtcagct gtgcgcgcga gaccgacgag aatttcggcg ttctgaactt    480
ggccaagaac tcgaacacac tcgtgttcac agggccgatc tgtactgctg gcctgtcgag   540
tgcgaagacg accttcgacc tcagcgccgc cgaggggac cttcagcgca agcggcttct     600
ggcggctacc ctcgaattct gcgaggggct caaggcgctc ggtgccccc acacctacca    660 cgggttccc                                                           669
```

<210> SEQ ID NO 110
<211> LENGTH: 673
<212> TYPE: DNA
<213> ORGANISM: Alexandrium fundyense

<400> SEQUENCE: 110

```
cgaggctcgt gggcgagagc gggttcctcc tcctgtacat aaacgcccac gactgcgtgc    60
agacggccgc caggctctgc aagacgggcg ccaccgtggt gcgcctgaag caca

```
cgagtgcgaa gacgaccttc gacctcaacg ccgccgaggg ggaccttcag cgcaagcggc    600
ttctggcggc gaccctcgaa ttctgcgagg ggttcaaggc gctcgggtgc ccccacacct    660
accacgggtt ccc                                                      673

<210> SEQ ID NO 111
<211> LENGTH: 668
<212> TYPE: DNA
<213> ORGANISM: Alexandrium fundyense

<400> SEQUENCE: 111
cgagcctcgt gggcgagagc aggttcctcc tcctgtacat aaacgcccac gactgcgtgc     60
agacagccgc caggctctgc aagaagggcg ccaccgtggt gcgcctgaag cacaacgaca    120
cggagcagct cgagcacatg ctctcgtcga tcccgcaggg gccgacatca cctacgtgtg    180
cgacggcgcg tactccacgg acagagagct cgccgacttg cccgccatat gtgcttgttt    240
gaggccgcgc ggggccaaga tactcgtaga cgactcgcat ggctgcggcg ttcttggccg    300
caaccccgac tcggagcaac ccctcaagta tggtggcggc gtcgtcgtcg agtacttcgg    360
gctggactac gcagagaaca acatcatcta cgccgggcag ctgatcaagg cgttcaattc    420
gcccggcgga ttcgtcggct gtgcgcgcga gaccgacgag aatttaggcg ttctgagctt    480
ggccaagaac tcgaacacac tcgggttcac agggccgatc tgtactgcca gcctgtcgag    540
tgcgaagacg accttcgacc tcaacgccgc caaggggggac cttcagcgca gcggcttct    600 ggcggctacc ctcgaattct gcgaggggtt caggcgctcg ggtgccccca cacctaccat    660
gggttccc                                                            668

<210> SEQ ID NO 112
<211> LENGTH: 668
<212> TYPE: DNA
<213> ORGANISM: Alexandrium minutum

<400> SEQUENCE: 112
agcctggcgg gcgagagcgg gttcctcctc ctggacatca cgcccacga ctgcgtgcag     60 acggccgcca ggctctgcaa gaagggagtc accgtcgtgc gcctgaagca caacgacacg    120
gagcagctcg agcgcgtgct ctcgtcgatc ccggaagggg ccgacatcac ctacgtgtgc    180 gacgcgtct actccacggg cggagagctc gccgacttgc ccgccatatg tgcttgtttg    240
aggccgcgcg gggccaagat actcgtggac gactcgcacg gttgcggcgt tcttggccgc    300
aaccccgact cggagcaacc cttcggatat ggcggcggcg cgtcgtcaa gtacttcggg    360 ctggactacg cggagaacaa catcatctac gccgggcagc tgagcaaggc gttcaattcg    420
cccggcggat tcgtgggctg cgcacgcgag accgacgaga agttcggcat cctgaacttg    480
gccaagaact cgaacacgct cgtgttcaca gggccgatct gtactgccgg cctgtcgagt    540
gcgaagacga ccctcgacct caactttgcc gaggggggacc gtcagcgcaa gcggcttctt    600
caggcgaccc tcgaattttg cgaggggctc aaggcgctcg ggtgccccca cacctaccac    660
gggttccc                                                            668

<210> SEQ ID NO 113
<211> LENGTH: 670
<212> TYPE: DNA
<213> ORGANISM: Alexandrium minutum

<400> SEQUENCE: 113
cgagcctggc gggcgagagc gggttcctcc tcctggacat aaacgcccac gactgcgtgc     60
```

```
agacggcagc caggctctgc aagaagggag tcaccgtcgt gcgcctgaag cacaacgaca    120
cggagcagct cgagcgcgtg ctctcgtcga tcccggaggg ggccgacatc acctacgtgt    180
gcgacggcgt ctactccacg gacggagagc tcgccgactt gcccgcccta tgtgcttgtt    240
tgaggccgcg cggggccaag atactcgtgg acgactcgca cggttgcggc gttcttggcc    300
gcaaccccga ctcggagcaa cccttcggat atggcggcgg cggcgtcgtc aagtacttcg    360
ggctggacta cgcggagaac aacatcatct acgccgggca gctgagcaag gcgttcaatt    420
cgcccggcgg attcgtgggc tgcgcacgcg agaccgacga gaagttcggc attctgaact    480
tggccaagaa ctcgaacacg ctcgtgttca cagggccgat ctgtactacc ggcctgtcga    540
gtgcgaagac gaccctcgac ctcaactttg ccgagggga ccgtcagcgc aagcggcttc    600
ttgaggcgac cctggaattt tgcgaggggc tcaaggcgct cgggtgcccc cacacctacc    660
acgggttccc                                                            670
```

```
<210> SEQ ID NO 114
<211> LENGTH: 711
<212> TYPE: DNA
<213> ORGANISM: Alexandrium minutum

<400> SEQUENCE: 114
tgctcaacat gggagtcatc ccgagcctgg cgggcgagag cgggctcctc ctcctggaca     60
taaacgccca cgactgcgtg cagacggcgg ccaggctctg taagaaggga gtcaccgtcg    120
tgcgcctgaa gcacaacgac acggagcagc tcgagcgcgt gctctcgtcg atcccggagg    180
gggccgacat cacctacgtg tgcgacggcg tctactccac ggacggagag ctcgccgact    240
tgcccgccat atgtgcttgt ttgaggccgc gcggggccaa gatactcgtg gacgactcgc    300
acggttgcgg cgttcttggc cgcaaccccg actcggagca accccttcgga tatggcggcg    360 gcgtcgtcaa gtacttcggg ctggactacg cggagaacaa catcatctac gccgggcagc    420
tgagcaaggc gttcaattcg cccggcggat tcgtgggctg cgcacgcgag accgacgaga    480
agttcggcat tctgaacttg gccaagaact cgaacacgct cgtgttcaca gggccgatct    540
gtactgccgg cctgtcgagt gcgaagacga ccctcgacct caactttgcc gagggggacc    600
gtcagcgtaa gcggcttctt gaggcgaccc tggaattttg cgaggggctc aaggcgctcg    660
ggtgccccca cacctaccac gggttcccca tcgtcaacat ctactggacc c             711
```

```
<210> SEQ ID NO 115
<211> LENGTH: 714
<212> TYPE: DNA
<213> ORGANISM: Alexandrium minutum

<400> SEQUENCE: 115
tgctcaacat gggagtcatc ccgagcctgg cgggcgagag cgggttcctc ccctggaca     60 tcaacgccca cgactgcgtg cagacggccg ccaggctctg caagaaggga gtcaccgtcg    120
tgcgcctgaa gcacaacgac acggagcagc tcgagcgcgt gctctcgtcg atcccggaag    180
gggccgacat cacctacgtg tgcgacggcg tctaccccac ggacggagag ctcgccgact    240
tgcccgccat atgtgcttgt ttgaggccgc gcggggccaa gatactcgtg gacgactcgc    300
acggttgcgg cgttcttggc cgcaaccccg actcggagca accccttcgga tatggcggcg    360 gcggcgtcgt caagtacttc gggctggact acgcggagaa caacatcatc tacgccgggc    420
agctgagcaa ggcgttcaat tcgcccggcg gattcgtggg ctgcgcacgc gagaccgacg    480
```

```
agaagttcgg catcctgaac ttggccaaga actcgaacac gctcgtgttc acagggccga    540
tctgtactgc cggcctgtcg agtgcgaaga cgaccctcga cctcaactt t gccgaggggg   600 accgtcagcg caagcggctt cttcaggcga ccctcgaatt ttgcgagggg ctcaaggcgc    660
tcgggtgccc ccacacctac cacgggttcc ccatcgtcaa catctactgg accc          714

<210> SEQ ID NO 116
<211> LENGTH: 714
<212> TYPE: DNA
<213> ORGANISM: Alexandrium minutum

<400> SEQUENCE: 116
tgctcaacat gggagtcatc ccgagcctgg cgggcgggag cgggttcctc ctcctggaca     60
taaacgccca cgactgcgtg cagacggcag ccaggctctg caagaaggga gtcaccgtcg    120
tgcgcctgaa gcacaacgac acggagcagc tcgagcgcgt gctctcgtcg atcccggagg    180
gggccgacat cacctacgtg tgcgacggc t ctactccac ggacggagag ctcgccgacc    240
tgcccgccat atgtgcttgt ttgaggccgc gcggggccaa gatactcgtg gacgactcgc    300
acggttgcgg cgttcttggc cgcaaccccg actcggagca accttcgga tatggcggcg     360 gcggcgtcgt caagtacttc gggctggact acgcggagaa caacatcatc tacgccgggc    420
agctgagcaa ggcgttcaat tcgccggcg gattcgtggg ctgcgcacgc gagaccgacg    480
agaagttcgg cattctgaac ttggccaaga actcgaacac gctcgtgttc acagggccga    540
tctgtactgc cggcctgtcg agtgcgaaga cgaccctcga cctcaactt t gccgaggggg   600 accgtcagcg caagcggctt cttgaggcga ccctggaatt ttgcgagggg ctcaaggcgc    660
tcgggtgccc ccacacctac cacgggttcc ccatcgtcaa catctactgg accc          714

<210> SEQ ID NO 117
<211> LENGTH: 663
<212> TYPE: DNA
<213> ORGANISM: Alexandrium fundyense

<400> SEQUENCE: 117
gagcctcgtg ggcgagagcg ggttcctcct cctggacata cacgcccacg actgcgtgca     60
gacggccgcc aggctctgca aacagggtgc caccgtggtg cgcctgaggc gcaacgacac    120
ggagcagctc gagcacatgc tctcgtcgac cccgcagggg ccgacatcac ctacgtgtgc    180
gacggcgtgt actccacgga cggagagctc gccgacttgc ccgccatatg tgcttgtttg    240
aggccgcacg gggccaatat actcgtagac gactcgcatg gttgcggcgt tcttggccgc    300
aaccccgact cggagcaacc cctcgggtat ggtgcggcg t cgtctagta cttcgggctg    360 ggctacgcgg agcgcaacat catctacgcc tggcagttga gcaaggcgtt caattcgccc    420
ggcggattcg ccggctgtac cggagaccga cgataagttc ggcgttctga gcttggccaa    480
gcactcgaac acactcgtgt gcacagggcc gatctgtact gccggcctgc cgagtgcgaa    540
gacgaccttc gacctcaacg ccgccgaggg ggaccttcag cgcaagcggc ttctggcggt    600 gacccctcgga ttctgcgagg ggctcaaggc gctcgggtgc ccccacacct accacgggct    660
ccc                                                                   663

<210> SEQ ID NO 118
<211> LENGTH: 671
<212> TYPE: DNA
<213> ORGANISM: Alexandrium fundyense

<400> SEQUENCE: 118
```

```
cgagcctttg tgggcgagag caggttcctc ctcctggaca taaacgccca cgactgcgtg    60
cagacggccg ccaggctctg caagaagggc gccaccgtgg tgcgcctgag cacaacgac    120 gcggagcagc tcgagcacat gctctcgtcg atcccgcagg gggccgacat cacctacgtg   180
tgcgacggcg tgtactccac ggacggagag ctcgccgact gcccgccat atgtgcttgt    240 ttgaggccgc gcggggccaa gatactcgta gacgactcgc atggctgcgg cgttcttggc   300
cgcaaccccg actcggagca acccttcggg tatggtggcg gcggcgtcgt cgagtacttc   360
gggctggact acgcggagaa caacatcatc tacgccgggc agctgagcaa ggcgttcaat   420
tcgcccggcg gattcgtcgg ctgtgcgcgc gagaccgacg agaagttcgg cattctgaac   480
ttggccaaga actcaaacac actcgcgttc acagggccga tctgtactgc cggcctgtcg   540
agtgcgatga cgaccctcga cctcaacgcc gccgaggggg accttcagcg caagcggctt   600
ctggaggcgg ccctcgaatt ctgcgagggg ctcaaggcgc tcgggtgccc ccacacctac   660
cacgggttcc c                                                        671

<210> SEQ ID NO 119
<211> LENGTH: 669
<212> TYPE: DNA
<213> ORGANISM: Alexandrium fundyense

<400> SEQUENCE: 119
cgagcctcgt gggcgagagc gggttcctcc tcctgtacat aaacgcccgc gactgcgcgc    60
agacggccgc caggctctgc aagaagggtg ccaccgtggt gcgcctgaag cacaacgaca   120
cgctacagcc cgagcgcatg ctctcgtcga tcccgcaggg gccgacatca cctacgtgtg   180
cgacggcgtg tactccacgg acgaagagct cgccgacttg cccgccatat gtgcttgttt   240
gaggccgcgc ggggccaaga tactcgtaga cgactcgcat ggctgcggcg ttcttggccg   300
caaccccaac tcggagcaac ccctcgggta tggtggcggc ggcgtcatcg agtacttcgg   360
gctggactac gcggagaacg acatcatcta cgccgggcag ctgagcaagg cgttcaattc   420
gcccggcgga ttcgtcagtt gtgcgcgcga gaccgacgct aatttcgcg ttctgaactt    480 ggccaagaac tcgaacacac tcgtgttcac agggccgatc tgtactgccg gcctgtcgag   540
tgcgaagacg accttcgacc tcaacgccgc cgaggggggac cttcagcgca agcggcttct   600
ggcggctacc ctcgaattct gcgaggggct caaggcgctc gggtgccccc acacctacca   660
cgggttccc                                                          669

<210> SEQ ID NO 120
<211> LENGTH: 669
<212> TYPE: DNA
<213> ORGANISM: Alexandrium fundyense

<400> SEQUENCE: 120
cgagcctcgt gggcgagagc aggttcctcc tcctgtacat caacgcccac gactgcgtgc    60
agacagccgc caggctctgc aagaagggcg ccaccgtggt gcgcctgaag cacaacgaca   120
cggagcagct cgagcacatg ctctcgtcga tcccgcaggg ggccgacatc acctacgtgt   180
gcgacggcgc gtactccaca gacagagagc tcgccgactt gcccgccata tgtgcttgtt   240
tgaggccgcg cggggccaag atactcgtag acgactcgca tggctgcggc gttcttggcc   300
gcaaccccga ctcggagcaa cccctcaagt atggtgcgg cggcgtcgtc gagtacttcg     360
ggctggacta cgcagagaac aacatcatct acgccgggca gctgagcaag gcgttcaatt   420
```

```
cgcccggcgg attcgtcggc tgtgcgcgcg agaccgacga gaatttcggc gttctgaact        480
tggccaagaa ctcgaacaca ctcgggttca cagggccgat ctgtactgcc ggcctgtgga        540
gtgcgaagac gaccttcgac ctcaacgccg ccaagggggga ccttcagcgc aagcggcttc       600
tggcggctac cctcgaattc gcgagggggc tcaggcgctc gggtgccccc acacctacca       660
cgggttccc                                                                669

<210> SEQ ID NO 121
<211> LENGTH: 668
<212> TYPE: DNA
<213> ORGANISM: Alexandrium fundyense

<400> SEQUENCE: 121
cgggcctcgt gggcgagagc gggttcctcc tcctgtacat aaacgcccac gactgcgtgc         60
agacggccgc caggctctgc aagaagggcg ccaccgtggt gcgcctgaag cacaacgaca        120
cggaacagcc cgagcacatg ctctcgtcga cccgcaggg gccgacatca cctacgtgtg         180
cgacggcgtg tactccacgg acgaagagct cgccggcttg cccgccatat gtgcttgttt        240
gaggccgcgc ggggccaaga tactcgtaga cgactcgcat ggctgcggcg ttcttggccg        300
caaccccaac tcggagcaac ccctcgggta tggtggcggc ggcgtcatcg agtacttcgg        360
gctggactac gcggagaaca acatcatcta cgccgggcag ctgagcaagg cgttcaattc        420
gcccggcgga ttcgtcagct gtgcgcgcga gaccgacga aatttcggcg ttctgaactt        480
ggccaagaac tcgaacacac tcgtgctcac agggccgatc tgtactgccg gcctgtcgag        540
tgcgaagacg accttcgacc tcaacgccgc cgaggggggac cttcagcgca agcggcttct       600
ggcggcgacc ctcgaattct gcgagggggct caaggcgctc gggtgcccca cacctaccac       660
gggttccc                                                                668

<210> SEQ ID NO 122
<211> LENGTH: 1428
<212> TYPE: DNA
<213> ORGANISM: Alexandrium fundyense

<400> SEQUENCE: 122
tccgtagcca ttttggctca agagttggat cccaagctgc tcttccgcag ccaggcggcc         60
ggcgcacccg ctcccgccga tcggtccgcc tctgctcccg ttcctcccaa gccaagcgca        120
tgccgcagct tctgagcacc cctgtagcac cggacagcgc tggatcttgt gagagcgtcg        180
cgggggacag gcacggggcc tccggacgca acgagctcga ggaggcttcc gccaagtcga        240
acatccacgg cctcgacctc ggcaccgatg ccttcatgct ggcgcacggg tggacttgcg        300
ggcccttgct cctggaattt gttgcgagct tcctgcagcc cctgcagcgg cagcccatga        360
ccgccgagca gctcgccgcg gagacaaacg caggggaagg gcccgtggcg atcactctgc        420
ggacaatggc catcctcggg tacttggacc tggaccctga gaccgatgtg tatgccgtgg        480
tccccgggcc gggattcagg cgctcgccgc gctcctccgg ctagcggcgc ccaccagcgc        540
ggccttgcga agcatctacc agcacgccca gccgccgttc aggggtgccct catccgaggc       600 ggcgcactgc ttgcggattt gggcggagca ccagcccacc tggagaaggg cggcttgcaa       660
gcggctggcc ctcctgctcg acgggccgt cctcgtcccg ctgttgacct cgatcacata        720
ctttgcgagg tgggacgagg aggggctgga ttccggcaag gagggcgcct ggaccgcct        780 cgacttcagc aaggccaatg ccgcggcaag ggcggccctc gggggcatct tcggcgagtt        840
gggcgtgggc acagtggacg gcaagggcac cgtgaccttg accgcggagg gctcgctcgc        900
```

```
cctgcagcgt agctactcct actacgtccc gacgtcctac gccccactgc tggacaggta    960
ccacagcatc ctcttcgaga atcccggctg gggattcgcc ggtgccggcc gggactcgca   1020
ggagcaggag atccacgtcc accggacgct gaacgtggtg ggcagcgggg cgcagcacca   1080
gacgctcttc acggacctcg tgcggctcat tgactcggtc ttcgcgggcg gggacttcgc   1140
gtcgcagccg gcgttcgtcg tggacacggg gtgcggcgac ggccgcttgc tcaggcgcat   1200
ctacgagcac gtgaagagca acacgccgcg cgggaaggtg ctcgccgagc acccgatcac   1260
gatggtcggc gtcgacttca acaaggactc tcgggtggcg acggagctca acctgagcag   1320
gcacgcggtc ccgcacctgg tgctgttcgg ggacgtcggc aagccggccg acatcatgga   1380
gatcctcggg cggaacgggg tggacccgag caggtccctc cacgtgcg              1428
```

<210> SEQ ID NO 123
<211> LENGTH: 925
<212> TYPE: DNA
<213> ORGANISM: Alexandrium fundyense

<400> SEQUENCE: 123

```
tccgtagcca ttttggctca agagttggat cccaagctgc tcttccgcag ccaggcggcc     60
ggcgcacccg ctcccgccga tcggtccgcc tctgctcccg ttcctcccaa gccaagcgca    120
tgccgcagct tctgagcacc cctgtagcac cggacagcgc tggatcttgt gagagcgtcg    180
cgggggacag gcacggggcc tccggacgca acgagctcga ggaggcttcc gccaagtcga    240
acatccacgg cctcgacctc ggcaccgatg ccttcatgct ggcgcacggg tggacttgcg    300
ggcccttgct cctggaattt gttgcgagct tcctgcagcc cctgcagcgg cagcccatga    360
ccgccgagca gctcgccgcg gagacaaacg caggggaagg gcccgtggcg atcactctgc    420
ggacaatggc catcctcggg tacttggacc tggaccctga ccgatgtg tatgccgtgg      480 tccccgggcc gggattcagg cgctcgccgc gctcctccgg ctagcggcgc ccaccagcgc    540
ggccttgcga agcatctacc agcacgccca gccgccgttc agggtgccct catccgaggc    600
ggcgcactgc ttgcggattt gggcggagca ccagcccacc tggagaaggg cggcttgcaa    660
gcggctggcc ctcctgctcg acggggccgt cctcgtcccg ctgttgacct cgatcacata    720
ctttgcgagg tgggacgagg aggggctgga ttccggcaag gagggcgcct tggaccgcct    780
cgacttcagc aaggccaatg ccgcggcaag ggcggccctc gggggcatct tcggcgagtt    840
gggcgtgggc acagtggacg gcgagggcac cgtgaccttg accgcggagg gctcgttcgc    900
cctgcagcgt agctactcct actac                                          925
```

<210> SEQ ID NO 124

<400> SEQUENCE: 124

000

<210> SEQ ID NO 125
<211> LENGTH: 1450
<212> TYPE: DNA
<213> ORGANISM: Alexandrium fundyense

<400> SEQUENCE: 125

```
accgtagcca ttttagctca agagttggat cccaagctgc tcttccgcag ccaggcggcc     60
ggcgcacccg ctcccgctga tcggtccgcc tctgctcccg ttcctcccaa gccaagcgca    120
tgccgcagct tctgagcacc cttgtagcac cggacagcgc tggatcttgt gagagcgtcg    180
```

-continued

```
cggggggacag ccacggggcc tccggacgca acgagctcga ggaggcttcc gccaagtcga       240
acatccacgg cctcgacctc ggcaccgatg ccttcatgct ggtgcacggg tggacttgcg       300
ggcccttgct cctggagttt gttgcgagct tcctgcagcc cttgcagcgg cagcccatga       360
ccgccgagca gctcgccgcg gagacaaacg cggggggaagg gcccgtggcg atcactctgc     420
ggacaatggc catcctcggg tacttggacc tggaccctga gaccgatgtg tttgccgtgg       480
tccccgggcc ggggattcag gcgctcactg cgctcctccg gccagcggcg cccaccagcg       540
cggccttgca aagcatctac cagcacgccc agccgccgtt cagggtgccc tcatccgagg       600
cggcgcactg cttgcggatt tgggcggagc accggcccac ctggagaagg gcggcttgca       660
agcggctggc cctcctgctc gacggggccg tcctcgtccc gttgttgacc tcgatcacat       720
actttgcgag gtgggacgag gaggggctgg attccggcaa ggtgggggcc ttggaccgcc       780
tcgacttcag caaggccaat gccgcggcaa gggcggccct cggtggcatc ttcggcgagt       840
tgggcgtggg cacagtggac ggcgagggca ccgtgacctt gaccgcggag ggctcgttcg       900
ccctgcagcg ttgctactcc tactacgtcc cgacgtccta cgccccaatg ctggacaggt       960
accacagcat cctcttcgag aatcccggct ggggggttcgc cggtgccggc cgggactcgc     1020
aggagcagga gatccacgtc caccggacgc tgaacgtggt gggcagcggg gcgcagcacc     1080
agacgctctt cacggacctc gtgcggctca ttgactcggt cttcgcgggc ggggacttcg     1140
cgtcgcagcc ggcgttcgtc gtggacacgg ggtgcggcga cggccgcttg ctcaggcgca     1200
tctacgagca cgtgaagagc aacacgccgc gcgggaaggc gctcgccgag cacccgctca     1260
tgatggtcgg cgtcgacttc aacaaggact ctcgggtggc gacggagctc aacctgagca     1320
ggcacgcggt cccgcacctg gtgctgttcg gggacgtcgg caagcccgcc gacatcatgg     1380
agatcctcgg gcggaagggg gtggacccga gcaggtccct ccgcgtgcgc tccttcctgg     1440
accacgacca                                                             1450
```

<210> SEQ ID NO 126
<211> LENGTH: 1449
<212> TYPE: DNA
<213> ORGANISM: Alexandrium fundyense

<400> SEQUENCE: 126

```
accgtagcca tttttggctca agagttggat cccaagctgc tcttccgcag ccaggcagcc       60
ggcacacccg ctcccgccga tcggtccgcc tctgctcccg ttcctcccaa gccaagcgca     120
tgccgcagct tctgagcacc cttgtagcac cggacagcgc tggatcttgt gagagcgtcg     180 cggggggacag gcacggggcc tccggacgca acgagctcga ggaggcttcc gccaagtcga     240
acatccacgg cctcgacctc ggcaccgatg ccttcatgct ggtgcacggg tggacttgcg     300
ggcccttgct cctggagttt gttgcgaact tcctgcagcc cttgcagcag cagcccatga     360
ccgccgagca gctcgccgcg gagacaaacg cggggggaagg gcccgtggcg atcactctgc     420
ggacaatggc catcctcggg tacttggacc tggaccctga gaccgatgtg tataccgtgg     480
tccccgggcc ggggattgag gcgctcgccg cgctcctccg gccagcggcg cccaccggcg     540
cggccttgca aagcatctac cagcacgccc agccgccgtt cagggtgccc tcatccgagg     600
cggcgcactg cttgcggatt tgggcggagc accggcccac ctggagaagg gcggcttgca     660
agcggctggc cctcctgctc gacggggccg tcctcgtccc gttgttgacc tcgatcacat     720
actttgcgag gtgggacgag gaggggctgg attccggcaa ggagggcgcc ttggaccgcc     780
```

```
tcgacttcag caaggccaat gccgcggcaa gggcggccct cggggcatc ttcggcgagt    840 tgggcgtggg cacagtggac ggcgagggca ccgtgacctt gaccgcggag ggctcgttcg    900
ccctgcagcg ttgctactcc tactacgtcc cgacgtccta cgccccattg ctggacaggt    960
accacagcat cctctttgag aatcccggct ggggttcgc cagtgccggc cgggactcgc   1020
aggagcagga gatccacgtc caccggacgc tgaacgtggt gggcagcggg gcgcagcacc   1080
agacgctctt cacggacctc gtgcggctca ttgactcggt cttcgcgggc ggggactttg   1140
cgtcgcagcc cgcgttcgtc gtggacacgg ggtgcggcga cggccgcttg ctcaggcgca   1200
tctacgagca cgtgaagagc aacccgccgc gcgggaaggc gctcgccgag cacccgctca   1260
cgatggtcgg cgtcgacttc aacaaggact ctcgggtggc gacggagctc aacctgagca   1320
ggcacgcagt cccgcacctg gtgctgttcg gggacgtcgg caagcccgcc gacatcatgg   1380
agatcctcgg gcggaagggg gtggacccga gcaggtccct ccacgtgcgc tccttcctag   1440
accacgacc                                                          1449
```

<210> SEQ ID NO 127
<211> LENGTH: 1449
<212> TYPE: DNA
<213> ORGANISM: Alexandrium fundyense

<400> SEQUENCE: 127

```
accgtagcca ttttggctca agagttggat cccaagctgc tcttccgcag ccaggcggcc     60
ggcgcacccg ctcccgccga tcggtccgcc tctgctcccg ttcctcccaa gccaagcgca    120
tgccgcagct tctgagcacc cttgtagcac cggacagcgc tggatcttgt gagagcgtcg    180
cgggggacag gcacggggcc tccggacgca acgagctcga ggaggcttcc gccaagtcga    240
acatccacgg cctcgacctc ggcaccgatg ccttcatgtt ggtgcacggg tggacttgcg    300
ggcccttgct cctggagttt gttgcgaact tcctgcagcc cttgcagcgg cagcccatga    360
ccgccgagca gctcgccgcg gagacaaacg cggggaagg gcccgtggcg atcactctgc    420
ggacaatggc catcctcggg tgcttggacc tggaccctga gaccgatgtg tataccgtga    480
tccccgggcc ggggattgag gcgctcgccg cgctcctccg gccagcggcg cccaccagcg    540
cggccttgca aagcatctac cagcacgccc agccgccgtt cagggtgccc tcatccgagg    600
cggcgcactg cttgcggatt tgggcggagc accggcccac ctggagaagg gcggcttgca    660
agcggctggc cctcctgctc gacggggccg tcctcgtccc gttgttgacc tcgatcacat    720
actttgcgag gtgggacgag gaggggctgg attccggcaa ggagggcgcc ttggaccgcc    780
tcgacttcag caaggccaat gccgcggcaa gggcggccct cggggcatc ttcggcgagt    840 tgggcgtggg cacagtggac ggcgagggca ccgtgtcctt gaccgcggag ggctcgttcg    900
ccctgcagcg ttgctactcc tactacgtcc cgacgtccaa cgccccattg ctggacaggt    960
accacagcat cctctttgag aatcccggct ggggttcgc cggtgccggc cgggactcgc   1020
aggagcagga gatccacgtc caccggacgc tgaacgtggt gggcggcggg gcgcagcacc   1080
agacgctctt cacggacctc gtgcggctca ttgacccggt cttcgcgggc ggggactttg   1140
cgtcgcagcc ggcgttcgtc gtggacacgg ggtgcggcga cggccgcttg ctcaggcgca   1200
tctacgagca cgtgaagagc aacacgccgc gcgggaaggc gctcgccgag cacccgctca   1260
cgatggtcgg cgtcgacttc aacaaggact ctcgggtggc gacggagctc aacctgagca   1320
ggcacgcagt cccgcacctg gtgctgttcg gggacgtcgg caagcccgcc gacatcatgg   1380
agatcctcgg gcggaagggg gtggacccga gcaggtccct ccacgtgcgc tccttcctgg   1440
``` accacgacc                                                                    1449

<210> SEQ ID NO 128
<211> LENGTH: 882
<212> TYPE: DNA
<213> ORGANISM: Alexandrium fundyense

<400> SEQUENCE: 128
ttccgcagcc aggcggccgg cgcacccgct cccgccgatc ggtccgcctc tgctcccgtt    60
cttccaagcc aagcgcatgc cgcagcttct gagcacccct gtagcaccgg acagcgctgg   120
atcttgtgag agcgtcgcgg gggacaggca cggggcctcc ggacgcaacg agctcgagga   180
ggcttccgcc aagtcgaaca tccacggcct cgacctcggc accgatgcct tcatgctggc   240
gcacgggtgg acttgcgggc ccttgctcct ggagtttgtt gcgagcttcc tacagcccct   300
gcagcggcag cccatgaccg ccgagcagct cgccgcggag acaaacgcgg gggaagggcc   360
cgtggcgatc actctgcgga caatggccat cctcgggtac ttggacctgg accctgagac   420
cgatgtgtat gccgtggtcc ccgggccggg gattcaggcg ctcgccgcgc tcctccggcc   480
agcggcgccc accagcgcgg ccttgcgaag catctaccag cacgcccagc cgccgttcag   540
ggtgccctca tccgaggcgg cgcactgctt gcggatttgg gcggagcacc ggcccacctg   600
gagaagggcg gcttgcaagc ggctggccct cctgctcgac ggggccgtcc tcgtcccgct   660
gttgacctcg atcacatact ttgcgaggtg ggacgaggag gggctggatt ccggcaagga   720
gggcgccttg gaccgcctcg acttcagcaa ggccaatgcc gcggcaaggg cggccctcgg   780
gggcatcttc ggcgagttgg gcgtgggcac agtggacggc gagggcaccg tgaccttgac   840
cgcggagggc tcgttcgccc tgcagcgtcg ctactcctac ta                      882

<210> SEQ ID NO 129
<211> LENGTH: 815
<212> TYPE: DNA
<213> ORGANISM: Alexandrium fundyense

<400> SEQUENCE: 129
ccaagcgcat gccgcagctt ctgagcaccc ttgtagcacc ggacagcgct ggatcttgtg    60
agagcgtcgc gggggacagg cacggggcct ccggacgcaa cgagctcgag gaggcttccg   120
ccaagtcgaa catccacggc ctcgacctcg caccgatgc cttcatgctg gcgcacgggt   180
ggacttgcgg gcccttgctc ctggagtttg ttgcgagctt cctgcagccc ttgcagcggc   240
agcccatgac cgccgagcag ctcgccgcgg agacaaacgc gggggagggg cccgtggcga   300
tcactctgcg gacaatggcc atcctcgggt acttggacct ggaccctgag accgatgtgt   360
atgccgtggt ccccgggccg gggattgagg cgctcgccgc gctcctccgg ccagcggcgc   420
ccaccagcgc ggccttgcga agcatctacc agcacgccca gccgccgttc agggtgccct   480
catccgaggc ggcgcactgc ttgcggattt gggcggagca ccggtccacc tggagaaggg   540
cggcttgcaa gcggctggcc ctcctgctcg acggggccgt cctcgtcccg ttgttgacct   600
cgatcacata ctttgcgagg tgggacgagg aggggctgga ttccggcaag gagggcgcct   660
tggaccgcct cgacttcagc aaggccaatg ccgcggcaag gcggccctc ggggcatct   720 tcggcgagtt aggcgtgggc acagtggacg gcgagggcac cgtgaccttg accgcggagg   780
gctcgttcgc cctgcagcgt cgctactcct actac                              815

<210> SEQ ID NO 130

```
<211> LENGTH: 480
<212> TYPE: DNA
<213> ORGANISM: Alexandrium fundyense

<400> SEQUENCE: 130
caatggccat cctcgggtac ttggacctgg accctgagac cgatgtgtat accgtggtcc    60
ccgggccggg gattgaggcg ctcgccgcgc tcctccggcc agcggcgccc accagcgcgg   120
ccttgcaaag catctaccag cacgcccagc cgccgttcag ggtgccctca tccgaggcgg   180
cgcactgctt gcggatttgg gcggagcacc ggcccacctg gagaagggcg gcttgcaagc   240
ggctggccct cctgctcgac ggggccgtcc tcgtcccgct gttgacctcg atcacatact   300
ttgcggggtg ggacgaggag gggctggatt ccggcaagga gggcgccttg gaccgcctcg   360
acttcagcaa ggccaatgcc gcggcaaggg cggccctcgg gggcatcttc ggcgagttgg   420
gcgtgggcac agtggacggc gagggcaccg tgaccttgac cgcggagggc tcgttcaccc   480

<210> SEQ ID NO 131
<211> LENGTH: 451
<212> TYPE: DNA
<213> ORGANISM: Alexandrium fundyense

<400> SEQUENCE: 131
gaccctgaga ccgatgtgta tgccgtggtc cccgggccgg ggattgaggc gttcgccgcg    60
ctcctccggc cagcggcgcc caccagcgcg gccttgcgaa gcatctacca gcacgcccag   120
ccgccgttca gggtgccctc atccgaggcg gcgcactgct tgcggatttg gcggagcac   180
cggcccacct ggagaacggc ggcttgcaag cggctggccc tcctgctcga cggggccgtc   240
ctcgtcccgt tgttgacctc gatcacatac tttgcgaggt gggacgagga ggggctggat   300
tccggcaagg agggcgcctt ggaccgcctc gacttcagca aggccaatgc cgcggcaagg   360
gcggccctcg ggggcgtctt cggcgagttg ggcgtgggca cagtggacgg cgagggcacc   420
gtgaccttga ccgcggaggg ctcgttcgcc c                                  451

<210> SEQ ID NO 132
<211> LENGTH: 397
<212> TYPE: DNA
<213> ORGANISM: Alexandrium fundyense

<400> SEQUENCE: 132
gccgcgctcc tccggccagc ggcgcccacc agcgcggcct tgcgaagcat ctaccagcac    60
gcccagccgc cgttcagggt gccctcatcc gaggcggcgc actgcttgcg gatttgggcg   120
gagcaccggc ccacctggag aacggcggct tgcaagcggc tggccctcct gctcgacggg   180
gccgtcctcg tcccgttgtt gacctcgatc acatactttg cgaggtggga cgaggagggg   240
ctggattccg gcaaggaggg cgccttggac cgcctcgact tcagcaaggc caatgccgcg   300
gcaagggcgg ccctcggggg catcttcggc gagttgggcg tgggcacagt ggacggcgag   360
ggcaccgtga ccttgaccgc ggagggctcg ttcgccc                            397

<210> SEQ ID NO 133
<211> LENGTH: 234
<212> TYPE: DNA
<213> ORGANISM: Alexandrium fundyense

<400> SEQUENCE: 133
ccctcctgct cgacggggcc gtcctcgtcc cgttgttgac ctcgatcaca tactttgcga    60
ggtgggacga ggaggggctg gattccggca aggagggcgc cttggaccgc ctcgacttca   120
```

```
gcaaggccaa tgccgcggca agggcggccc tcggggggcat cttcggcgag ttgggcgtgg      180
gcacagtgga cggcgagggc accgtgacct tgaccgcgga gggctcgttc gccc            234
```

<210> SEQ ID NO 134
<211> LENGTH: 254
<212> TYPE: DNA
<213> ORGANISM: Alexandrium fundyense

<400> SEQUENCE: 134

```
tcctgctcga cggggccgtc ctcgtcccgt tgttgacctc gatcacatac tttgcgaggt      60
gggacgagga ggggctggat ccggcaagg agggcgcctt ggaccgcctc gacttcagca       120
aggccaatgc cgcagcaagg gcggccctcg ggggcatctt cggcgagttg ggcgtgggca     180
cagtggacgg cgagggcacc gtgaccttga ccgcggaggg ctcgttcgcc ctgcagcgtc      240
gctactccta ctac                                                       254
```

<210> SEQ ID NO 135
<211> LENGTH: 561
<212> TYPE: DNA
<213> ORGANISM: Alexandrium fundyense

<400> SEQUENCE: 135

```
caccgtgacc ttgaccgcgg agggctcgtt cgccctgcag cgtcgctact cctactacat      60
cccgacgtcc tacgccccac tgctggacag gtaccacagc atcctcttcg agaatcccgg     120 ctggggttc gccggtgccg ccgggactc gcaggagcag gagatccacg tccaccggac       180
actgaacgtg gtgggcagcg gtgcgcagca ccagacgctc ttcacggacc tcgtgcggct     240
cattgactcg gtcttcgcgg gtggggactt cgcgtcgcag ccggcgttcg tcgtggacac     300
ggggtgcggc gacggccgct tgctcaggcg catctacgag cacgtgaaga gcaacacgcc    360
gcgcgggaag cgctcgccg agcaccgct cacgatggtc ggcgtcgact tcaacaagga     420
ctctcgggtg gcgacggagc tcaacctgag caggcacgcg gttccgcacc tggtgctgtt     480 cggggggcgtc ggcaagccgg ccgacatcat ggagatcctc gggcggaacg gggtggaccc   540
gagcaggtcc ctccacgtgc g                                               561
```

<210> SEQ ID NO 136
<211> LENGTH: 553
<212> TYPE: DNA
<213> ORGANISM: Alexandrium fundyense

<400> SEQUENCE: 136

```
ccttgaccgc ggagggctcg ttcgccctgc agcgtcgcta ctcctactac atcccgacgt      60
cctacgcccc actgctggac aggtaccaca gcatcctctt cgagaatccc ggctgggggt   120
tcgccggtgc cggccgggac tcgcaggagc aggagatcca cgtccaccgg acgctgaacg   180
tggtgggcag cggggcgcag caccagacgc tcttcacgga cctcgtgcgg ctcattgact    240
cggtcttcgc gggcggggac ttcgcgtcgc agccggcgtt cgtcgtggac acggggtgcg    300
gcgacggccg cttgctcagg cgcatctacg agcacgtgaa gagcaacacg ccgcgcggga   360
aggcgctcgc cgagcacccg ctcacgatgg tcggcgtcga cttcaacaag gactctcggg   420
tggcgacgga gctcaacctg agcaggcacg cggtcccgca cctggtgctg ttcggggacg    480
tcggcaagcc cgccgacatc atggagctcc tcggacggag ggggtggac ccgagcaggt    540 ccctccacgt gcg                                                        553
```

<210> SEQ ID NO 137
<211> LENGTH: 1880
<212> TYPE: DNA
<213> ORGANISM: Alexandrium fundyense

<400> SEQUENCE: 137

```
tgagcaggca cgcagtcctg cacctggtgc tgttcgggga cgtcggcaag cccgccgaca    60
tcatggagat cctcgggcgg aacggggtgg acccgagcag gtccctccac gtgcgctcct   120
tcctggacca cgaccggccg tacgtccccc cggcccgcga gatggacccg acagcgcggg   180
ccgggaggtt cgcgaggctg cagctgccgg actgcgccca cctcgacggc gagggcaagc   240
ggatcgcgcc gagcgagatg ttcgcctcgc tggtggagca cttccagcgc tggggcggcg   300
ccctgcaggg ctcgttcggc ctctgcatgc tggaggtcat gatgctggac gtgccgacga   360
cgagggcgtc cctgaacgat tgcgtctcgc tccacttcga cctcgtgcag tgcctctccc   420
ggcagtacat ggtgtcgccg gcggccttcg ccttgggcct ggccatggcc ggcctcctgc   480
ccgggagcta cgagggcgtc cagacccacc cggcgcgggg gcggtactgc cgcgtgatga   540
gccagcacct cgtgcgccgg ccgtaccaga tccgcctcgc cgaggtcggt gacctgccga   600
ggctcgcgcg cctggaggag ctggcgtggg gccgccttgg cgccacgccc gaggtcctgc   660
ggaggcgcct ggagacgtct ccgaccacgt gcctggccgt cgagatggac cagctggtcg   720
tggccgtgct ctacacgcag cgggtggaca cgccgatgt ggtggaccag cagaagttca   780
tgcaggtctc cgactcgcac agcccgagcg gccgcgtcat gcagctcatc gcgatctgct   840
ccgacccggc cgccaagcac ctgggcgtcg cggcggacct gctcgccttc gcgctccacc   900
tggcccgcct cagcccggac gtggacagcg tcatcggggt gacgcgctgc aaaaacttcg   960
agacgttcgc cgggtcgatg cggactacg tggacgagca catcgccggc accgcgtag  1020
atcccatcat cggcctccac accggcaacg gagctcgggt agtccgcctc gtgcgcggct  1080
tcaggccgga ggacgtgggc aaccgcgggg acggcgtgct catacagtac gacacgagca  1140
agctcggcgc ggcaaccggc gagcgcgcgg ccccggtgt cgggcctgct gcggcacccc  1200
cccccgggcc ggctcccgcg ccatgcccca cggactacga gcaccacgag gctcttgtcc  1260
tggccgctct gggcagcctg atgctgaaga acggcggcac cgaggcggcg gccgcgggca  1320
gcgccgacgt cagatttgtg gacatggacc tcctggactc cctcaacttc accgacttcg  1380
caggccagct ggacgccgcg ctccccgtgc ccgtctccgt cgggctgctc ttcgaggcgt  1440
ccacgcccag gaagctggcc gcgcacctcc accgcgagat gcagcggctg gccggccagg  1500
cggacggggg gccgcgcctc ggccccgtac cggccgccgc cgccgcgccg ccgcccgctg  1560
cggccaggga ggaggccgcg gaggctccgc tggcctcctt cgactcggtg tgcaccaagc  1620
tcgagggggtg ctccgcgctg gtcgacggct gctggtgcat cgacgtggcg aactgcagct  1680
acctcggctt ccagtggcgg gacgagatcg ccgatggcgt ggaccgggac gtgcgcactt  1740
ggggcgtcca ccccccgtgg accaggctcg tctcgtctcc gaagctgtac gacgacgtcg  1800
aggcgcgctg ttgcgagctg accggcatct ggaagtgcgt tctgtacccg agcgttacca  1860
tgctcaacat gggagtcatc                                             1880
```

<210> SEQ ID NO 138
<211> LENGTH: 2570
<212> TYPE: DNA
<213> ORGANISM: Alexandrium fundyense

<400> SEQUENCE: 138

```
tgagcaggca cgcagtcccg cacctggtgc tgttcgggga cgtcggcaag cccgccgaca    60
tcatggagat cctcgggcgg aacggggtgg acccgagcag gtccctccac gtgcgctcct   120
tcctggacca cgaccggccg tacgtccccc cggcccgcga gatggacccg gacagcgcgg   180
ccgggaggtt cgcgaggctg cagctgtcgg actgcgccca cctcgacggc gagggcaagc   240
ggatcgcgcc gagcgagatg ttcgcctcgc tggtggagca cttccagcgc tggggcggcg   300
ccctgcaggg ctcgttcggc ctctgcatgc tggaggtcat gatgctggac gtgccgacga   360
cgagggcgtc cctgaacgat tgcgtctcgc tccacttcga cctcgtgcag tgcctctccc   420
ggcagtacat ggtgtcgccg gcggccttcg ccttgggcct ggccatggcc ggcctcctgc   480
ccgggagcta cgagggcgtc cagacccacc cggcgcgggg gcggtactgc cgcgtgatga   540
gccagcacct cgtgcgccgg ccgtaccaga tccgcctcgc cgaggtcggt gacctgccga   600
ggctcgcgcg cctggaggag ctggcgtggg gccgccttgg cgccacgccc gaggtcctgc   660
ggaggcgcct ggagacgtct ccgaccacgt gcctggccgt cgagatggac cagctggtcg   720
tggccgtgct ctacacgcag cgggtggaca cgccgatgt ggtggaccag cagaagttca    780
tgcaggtctc cgactcgcac agcccgagcg gccgcgtcat gcagctcatc gcgatctgct   840
ccgacccggc cgccaagcac ctgggcgtcg cggcggacct gctcgccttc gcgctccacc   900
tggcccgcct cagcccggac gtggacagcg tcgtcggggt gacgcgctgc caaaacttcg   960
agacgttcgc cgggtcgatg cgggactacg tggacgagca catcgccggc acccgcgtag  1020
atcccatcat cggcctccac accggcaacg gagctcgggt agtccgcctc gtgcgcggct  1080
tcaggccgga ggacgtgggc aaccgcgggg acggcgtgct catacagtac gacacgagca  1140
agctcggcgc ggcaaccggc gagcgcgcgg ccccggtgt caggcctgct gcggcacccc   1200
cccccgggcc ggctcccgcg ccatgcccca cggactacga gcaccacgag gctcttgtcc  1260
tggccgctct gggcagcctg atgctgaaga acgcggcac cgaggcggcg gccgcgggca   1320
gcgccgacgt cagatttgtg gacatggacc tcctggactc cctcaacttc accgacttcg  1380
caggccagct ggacgccgcg ctccccgtgc ccgtctccgt cgggctgctc ttcgaggcgt  1440
ccacgcccag gaagctggcc gcgcacctcc accgcgagat gcagcggctg gccggccagg  1500
cggacggggg ggccgcgcct cggccccgta ccggccgccg ccgccgcgcc gccgcccgct  1560
gcggccaggg aggaggccgc ggaggctccg ctggcctcct tcgactcggt gtgcaccaag  1620
ctcgaggggt gctccgcgct ggtcgacggc tgctggtgca tcgacgtggc gaactgcagc  1680
tacctcggct tccagtggcg ggacgagatc gccgatggcg tggaccggga cgtgcgcact  1740
tggggcgtcc acccccgtg gaccaggctc gtctcgtctc cgaagctgta cgacgacgtc   1800
gaggcgcgct gttgcgagct gaccggcatc tggaagtgcg ttctgtaccc gagcgttacc  1860
atgctcaaca tgggagtcat cccgagcctc gtgggcgaga gcgggttcct cctcctggac  1920
ataaacgccc acgactgcgt gcagacggcc gccaggctct gcaagaaggg cgccaccgtg  1980
gtgcgcctga ggcacaacga cgcggagcag ctcgagcaca tgctctcgtc gatcccgcag  2040
ggggccgaca tcacctacgt gtgcgacggc gtgtactcca cggacggaga gctcgccgac  2100
ttgcccgcca tatgtgcttg tctgaggccg cgcggggcca agatactcgt agacgactcg  2160
catggctgcg gcgttcttgg ccgcaacccc gactcggagc aacccttcgg gtatggtggc  2220
ggcggcgtcg tcgagtactt cgggctggac tacgcggaga caacatcat ctacgccggg   2280
cagctgagca aggcgttcaa ttcgcccggc ggattcgtcg gctgtgcgcg cgagaccgac  2340
```

```
gagaagttcg gcattctgaa cttggccaag aactcgagca cactcgtgtt cacagggccg    2400
atctgtactg ccggcctgtc gagtgcgatg acgaccctcg acctcaacgc cgccgagggg    2460
gaccttcagc gcaagcgact tctggcggcg accctcgaat tctgtgaggg gctcaaggcg    2520
ctcgggtgcc cccacaccta ccacgggttc cccatcgtca acatctactg               2570
```

<210> SEQ ID NO 139

<400> SEQUENCE: 139

000

<210> SEQ ID NO 140
<211> LENGTH: 2574
<212> TYPE: DNA
<213> ORGANISM: Alexandrium fundyense

<400> SEQUENCE: 140

```
tgagcaggca cgcagtcccg cacctggtgc tgttcgggga cgtcggcaag cccgccgaca      60
tcatggagat cctcgggcgg aaggggggtgg acccgagcag gtccctccac gtgcgctcct    120
tcctggacca cgaccggccg tacgtccccc cggcccgcga gatggacccg gacagcgcgg    180
ccgggaggtt cgcgaggctg cagctgtcgg actgcgccca cctcgacggc gagggcaagc    240
ggatcgcgcc gagcgagatg ttcgcctcgc tggtggagca cttccagcgc tggggcggcg    300
ccctgcaggg ctcgttcggc ctctgcatgc tggaggtcat gatgctggac gtgccgacga    360
cgagggcgtc cctgaacgat tgcgtgtcgc tccacttcga cgtcgtgcag tgcctctccc    420
ggcagtacat ggtgtcgccg gcggccttcg ccttgggcct ggccatggcc ggcctcctgc    480 ccggagcta cgagggcgtc cagacccacc cggcgcgggg gcgtactgc cgcgtgatga    540 gccagcacct cgtgcgccgg ccgtaccaga tccgcctcgc cgaggtcggt gacctgccga    600
ggctcgcgcg cctggaggag ctggcgtggg gccgcctcgg cgccacgccg gaggtcctgc    660
ggaggcgcct ggagacgtct ccgaccacgt gcctggccgt cgagatggac cagctggtcg    720
tggccgtgct ctacacgcag cggtggaca gcgccgatgt ggtggaccag cagaagttca    780
tgcaggtctc cgactggcac agcccgagcg ccgcatcat gcagctcatc gcgatctgct    840
ccgacccggc cgccaagcac ctgggcgtcg cggcggacct gctcgccttc gcgctccacc    900
tggcccgcct cagcccggac gtggacgcg tcatcgggt gacgcgctgt caaaacttcg    960
agacattcgc cgggtcgatg cgggactacg tggacgagca catcgccggc acccgcgtag   1020
atcccatcat cggcctccac accggcaacg gagctcgggt agtccgcctc gtgcacggct   1080
tcaggccgga ggacgtgggc aaccgcgggg acggcgtgct catacagtac gacacgagcc   1140
agctcggcgc ggcaaccggc gagcgggcgg cccccgcgct cgggcctgct gcggcgcccc   1200
cccccgggcc ggctcccgcg ccatgcccca cggactacga gcaccacgag gctcttgtcc   1260
tggccgctct gggcagcctg atgctgcaga acggcggcac cgaggcggcg gccgcggca   1320 gcgccgacgt cagatttgtg gacatggacc tcctggactc cctcaacttc accgacttcg   1380
caggccagct ggatgccgca ctcccccgtgc ccgtctccgt cgggctgctc ttcgaggcgt   1440
ccacgcccag gaagctggcc gcgcacctcc accgcgagat gcagcggctg gccggccagg   1500
cggacggggg gccgcgcctc ggccccgcac cggccgccgc cgccgcgccg ccgccgctg   1560 cggccaggga ggaggccgcg gaggctccgc tggcctcctt cgactcggtg tgcaccaagc   1620 tcgagggggtg ctccgcgctg gtcgacggct gctggtgcat cgacgtggcg aactgcagct   1680
```

| | |
|---|---:|
| acctcggctt ccagtggcgg gacgagatcg ccgagggcgt ggaccgggac gtgcgcactt | 1740 |
| ggggcgtcca cccccatgg accaggctcg tctcgtctcc gaagctgtac gacgacgtcg | 1800 |
| aggcgcgctg ttgcgagctg accggcatct ggaagtgcgt tctgtacccg agcgttacca | 1860 |
| tgctcaacat gggagtcatc ccgagcctcg tgggcgagag cggttcctc ctcctggaca | 1920 |
| tcaacgccca cgactgtgtg cagacggccg ccaggctctg caagaagggc gccaccgtgg | 1980 |
| tgcgcctgaa gcacaacgac acggagcagc tcgagcacat gctctcgtcg atcccgcagg | 2040 |
| gggccgacat cacctacgtg tgcgacggcg tgtactccac ggacggagag ctcgctgact | 2100 |
| tgcccgccat atgtgcttgt ttgaggccac gcggggccaa gatactcgta gacgactcgc | 2160 |
| atggctgcgg cgttcttggc cgcaaccccg actcggaaca acccttcggg tatggtggcg | 2220 |
| gcggcgtcgt cgagtacttc gggctggact acgcggagaa caacatcatc tatgccgggc | 2280 |
| agctgagcaa ggcgttcaat tcgcccggcg gattcgtcgg ctgtgcgcgc gagaccgacg | 2340 |
| agaagttcgg cattctgaac ttggccaaga actcgaacac actcgtgttc acagggccga | 2400 |
| tctgtactgc cggcctgtcg agtgcgaaga cgaccctcga cctcaacgcc gccgagggg | 2460 |
| accttcagcg caagcggctt ctggcggcga ccctcgaatt ctgcgagggg ctcaaggcgc | 2520 |
| ttgggtgtcc ccacacctac cacgggttcc ccatcgtcaa catctactgg accc | 2574 |

<210> SEQ ID NO 141
<211> LENGTH: 1881
<212> TYPE: DNA
<213> ORGANISM: Alexandrium fundyense

<400> SEQUENCE: 141

| | |
|---|---:|
| ggatgactcc catgttgagc atggtaacgc tcgggtacag aacgcacttc cagatgccgg | 60 |
| tcagctcgca acagcgcgcc tcgacgtcgt cgtacagctt cggagacgag acgagcctgg | 120 |
| tccacggggg gtggacgccc caagtgcgca cgtcccggtc cacgccatcg gcgatctcct | 180 |
| cccgccactg gaagccgagg tagctgcagt tcgccacgtc gatgcaccag cagccgtcga | 240 |
| ccagcgcgga gcacccctcg agcttggtgc acaccgagtc gaaggaggcc agcggagcct | 300 |
| ccgcggcctc ctccctggcc gcagcgggcg gggcgcggc ggcggcggcc ggtacggggc | 360 |
| cgaggcgcgg cccccccgtcc gcctggccgg ccagccactg catctcgcgg tggaggtgcg | 420 |
| cggccagctt cctgggcgtg gacgcctcga agagcagccc gacggagacg ggcacgggga | 480 |
| gcgcggcgtc cagctggcct gtgaagtcgg tgaagttgag ggagtccagg aggcccatgt | 540 |
| ccacaaatct gacgtcggcg ctgcccgcgg ccgccgcctc ggtgccgccg ttcttcagca | 600 |
| tcaggctgcc cagagcggcc aggacaagag cctcgtggtg ctcgtagtcc gtggggcatg | 660 |
| gcgcgggagc cggccggggg ggggcgccg cagcaggccc gacgccgggg gccgcgcgct | 720 |
| cgccggttgc gcgccgtgc ttgctcgtgt cgtactgtat gagcacgccg tccccgcggt | 780 |
| tgcccacgtc ctccggcctg aagccgcgca cgaggcggac tacccgagct ccgttgccgg | 840 |
| tgtggaggcc gatgatggga tctacgcggg tgccggcgat gtgctcgtcc acgtagtccc | 900 |
| gcatcgaccc ggcgaacgtc tcgaagtttt ggcagcgcgt caccccgatg acgctgtcca | 960 |
| cgtccgggct gaggcgggcc aggtggagcg cgaaggcgag caggtccgcc gcgacgccca | 1020 |
| ggtgcttggc ggccgggtcg gagcagatcg cgatgagctg catgatgcgg ccgctcgggc | 1080 |
| tgtgccagtc ggagacctgc atgaacttct gctggtccac cccatcgcg ctgtccaccc | 1140 |
| gctgcgtgta gagcacggcc acgaccagct ggtccatctc gacggccagg cacgtggtcg | 1200 |
| gagacgtctc caggcgcctc cgcaggacct ccggcgtggc gccgaggcgg ccccacgcca | 1260 |

```
gctcctccag gcgcgcgagc ctcggcaggt caccgacctc ggcgaggcgg atctggtacg      1320
gccggcgcac gaggtgctgg ctcatcacgc ggcagtaccg ccccgcgcc gggtgggtct       1380 ggacgccctc gtagctcccg ggcaggaggc cggccatggc caggcccaag gcgaaggccg      1440
ccggcgacac catgtactgc cgggagaggc actcacgag gccgaagtgg agtgagacgc       1500
aatcgttcag ggacgccctc gtcgtcggca cgtccagcat catgacctcc agcatgcaga      1560
ggccgaacga gccctgcagg gcgccgcccc agcgctggaa gtgctccacc agcgaggcga     1620
acatctcgct cggcgcgatc cgcttgccct cgccgtcgag gtgggcgcag tccgacagct     1680
gcagcctcgc aaacctcccg gccgcgctgt ccgggtccat ctcgcgggcc ggagggacgt     1740
acggccggtc gcggtccagg aaggagcgca cgtggaggga cctgctcggg tccaccccgt    1800
tccgcccgag gatctccatg atgtcggccg gcttgccgac gtccccgaac agcaccaggt    1860
gcgggactgc gtgcctgctc a                                              1881
```

<210> SEQ ID NO 142
<211> LENGTH: 2575
<212> TYPE: DNA
<213> ORGANISM: Alexandrium fundyense

<400> SEQUENCE: 142

```
gggtccagta gatgttgacg atggggaacc cgtggtaggt gtgggggcac ccaagcgcct       60
tgagcccctc gcagaattcg agggtcgccg ccagaagcca cttgcgctga aggtccccct      120
cggcggcgtt gaggtcgagg gtcgtcttcg cactcgacag gccggcagta cagatcggcc      180
ctgtgaacac gagtgtgttc gagttcttgg ccaagttcag aatgccgaac ttctcgtcgg      240
tctcgcgcgc acagccgacg aatccgccgg gcgaattgaa cgccttgctc agctgcccgg      300
catagatgat gttgttctcc gcgtagtcca gcccgaagta ctcgacgacg ccgccgccac      360
catacccgaa gggttgctcc gagtcggggt tgcggccaag aacgccgcag ccatgcgagt      420
cgtctacgag tatcttggcc ccgcgtggcc tcaaacaagc acatatggcg ggcaagtcag      480
cgagctctcc gtccgtggag tacacgccgt cgcacacgta ggtgatgtcg gcccctgcg      540 ggatcgacga gagcatgtgc tcgagctgct ccgtgtcgtt gtgcttcagg cgcaccacgg      600
tggcgccctt cttgcagagc ctggcggccg tctgcacaca gtcgtgggcg ttgatgtcca      660
ggaggaggaa cccgctctcg cccacgaggc tcgggatgac tcccatgttg agcatggtaa      720
cgctcgggta cagaacgcac ttccagatac cggtcagctc gcaacagcgc gcctcgacgt      780
cgtcgtacag cttcggagac gagacgagcc tggtccatgg ggggtggacg ccccaagtgc      840
gcacgtcccg gtccacgccc tcggcgatct cgtcccgcca ctggaagccg aggtagctgc      900
agttcgccac gtcgatgcac cagcagccgt cgaccagcgc ggagcacccc tcgagcttgg      960
tgcacaccga gtcgaaggag gccagcggag cctccgcggc ctcctcccct ggccgcagcg     1020 gcggcggcg cggcggcggc ggccggtgcg gggccgaggc gcggcccccc gtccgcctgg     1080
ccggccagcc gctgcatctc gcggtggagg tgcgcggcca gcctcctggg cgtggacgcc     1140
tcgaagagca gcccgacgga gacgggcacg gggagtgcgg catccagctg gcctgcgaag     1200
tcgatgaagt tgagggagtc caggaggtcc atgtccacaa atctgacgtc ggcgctgccc    1260
gcggccgccg cctcggtgcc gccgttctgc agcatcaggc tgcccagagc ggcaggaca     1320 agagcctcgt ggtgctcgta gtccgtgggg catggcgcgg gagccggccc ggggggggc     1380 gccgcagcag gcccgacgcc gggggccgcc cgctcgccga ttgccgcgcc gagctggctc     1440
```

```
gtgtcgtact gtatgagcac gccgtccccg cggttgccca cgtcctccgg cctgaagccg    1500
tgcacgaggc ggactacccg agctccattg ccggtgtgga ggccgatgat gggatctacg    1560
cgggtgccgg cgatgtgctc gtccacgtag tcccgcatcg acccggcgaa tgtctcgaag    1620
ttttggcagc gcgtcacccc gatgacgctg tccacgtccg ggctgaggcg ggccaggtgg    1680
agcgcgaagg cgagcaggtc cgccgcgacg cccaggtgct ggcggccgg  gtcggagcag    1740 atcgcgatga gctgcatgat gcggccgctc gggctgtgcc agtcggagac ctgcatgaac    1800
ttctgctggt ccaccacatc ggcgcagtcc gcccgctgcg tgtagagcac ggccacgacc    1860
agctggtcca tctcgacggc caggcacgtg gtcggagacg tctccaggcg cctccgcagg    1920
acctccggcg tggcgccgag gcggccccac gccagctcct ccaggcgcgc gagcctcggc    1980
aggtcaccga cctcggcgag gcggatctgg tacggccggc gcacgaggtg ctggctcatc    2040
acgcggcagt accgccccccg cgccgggtgg gtctggacgc cctcgtagct cccgggcagg    2100
aggccggcca tggccaggcc caaggcgaag gccgccggcg acaccatgta ctgccgggtg    2160
aggcactgca cgacgtcgaa gtggagcgac acgcaatcgt tcaggacgc  ccccgtcgtc    2220 ggcacgtcca gcatcatgac ctccagcatg cagaggccga acgagccctg cagggcgccg    2280
ccccagcgct ggaagtgctc caccagcgag gcgaacatct cgctcggcgc gatccgcttg    2340
ccctcgccgt cgaggtgggc gcagtccgac agctgcagcc tcgcgaacct cccggccgcg    2400
ctgtccgggt ccatctcgcg ggccgggggg acgtacggcc ggtcgtggtc caggaaggag    2460
cgcacgtgga gggacctgct cgggtccacc cccttccgcc cgaggatctc catgatgtcg    2520
gcgggcttgc cgacgtcccc gaacagcacc aggtgcagga ctgcgtgcct gctca        2575
```

<210> SEQ ID NO 143
<211> LENGTH: 1209
<212> TYPE: DNA
<213> ORGANISM: Alexandrium fundyense
<220> FEATURE:
<221> NAME/KEY: misc_feature
<222> LOCATION: (314)..(314)
<223> OTHER INFORMATION: n is a, c, g, or t

<400> SEQUENCE: 143

```
catggacctc ctggactccc tcaacttcac cgacttcgca ggccagctgg acgccgcgct      60
ccccgtgccc gtctccgtcg ggctgctctt cgaggcgtcc acgcccagga agctggccgc     120
gcacctccac cgcgagatgc agcggctggc cggccaggcg gacgggggc  cgcgcctcgg     180 ccccgcaccg gccgccgccg ccgcgccgcc cccgctgcg  gccagggagg aggcgcgga     240 ggctccgctg gcctcctttg actcggtgtg caccaagctc gagggtgct  ccgcgctggt     300 cgacggctgc tggngcatcg acgtggcgaa ctgcagctac ctcggcttcc agtggcggga     360
cgagatcgcc gagggcgtgg accgggacgt gcgcacttgg ggcgtccacc ccgtggac      420 caggctcgtc tcgtctccga agctgtacga cgacgtcgag gcgcgctgtt gcagctgac     480 cggcatctgg aagtgcgttc tgtacccgag cgttaccatg ctcaacatgg gagtcatccc     540
gagcctcgtg ggcgagagcg ggttcctcct cctggacata aacgcccacg actgcgtgca     600 gacgccgcc  aggctctgca agaagggcgc caccgtggtg cgcctgaggc acaacgacgc     660
ggagcagctc gagcacatgc tctcgtcgat cccgcagggg gccgacatca cctacgtgtg     720
cgacggcgtg tactccacgg acggagagct cgccgacttg cccgccatat gtgcttgttt     780
gaggccgcgc ggggccaaga tactcgtaga cgactcgcat ggctgcggcg ttcttggccg     840
caaccccgac tcggagcaac ccttcgggta tggtggcggc ggcgtcgtcg agtacttcgg     900
```

```
gctggactac gcggagaaca acatcatcta cgccgggcag ctgagcaagg cgttcaattc      960
gcccggcgga ttcgtcggct gtgcgcgcga gaccgacgag aagttcggca ttctgaactt     1020
ggccaagaac tcgaacacac tcgtgttcac agggccgatc tgtactgccg gcctgtcgag     1080
tgcgaagacg accctcgacc tcaacgccgc cgaggggggac cttcagcgca agcggcttct     1140
ggcggcgacc ctcgaattct gcgaggggct caaggcgctc gggtgccccc acacctacca     1200
cgggttccc                                                              1209

<210> SEQ ID NO 144
<211> LENGTH: 1208
<212> TYPE: DNA
<213> ORGANISM: Alexandrium fundyense

<400> SEQUENCE: 144
catggacctc ctggactccc tcaacttcac cgacttcgca ggccagctgg acgccgcgct       60
ccccgtgccc gtctccgtcg ggctgctctt cgaggcgtcc acgcccagga agctggccgc      120
gcacctccac cgtgagatgc agcggctggc cggccaggcg acgggggcc gcgcctcggc       180 cccgcaccgg ccgccgccgc cgcgccgccg cccgctgcgg ccaggagga ggccgcggag       240 gctccgctgg cctcctttga ctcggtgtgc accaagctcg aggggtgctc cgcgctggtc      300
ggcggctgct ggagcatcga cgtggcgaac tgcagctacc tcggcttcca gtggcgggac      360
gagatcgccg agggcgtggc ccgggacgtg cgcacttggg gcgtccaccc ccgtggacc       420 aggctcgtct cgtctccgaa gctgtacgac gacgtcgagg cgcgctgttg cgagctgacc      480
ggcatctgga agtgcgttct gtacccgagc gttaccatgc tcaacatggg agtcatcccg      540
agcctcgtgg gcgagagcgg gttcctcctc ctggacataa acgcgcacga ctgcgtgtag      600
acggccgcca ggctctgcaa gaagggcgcc accgtggtgc gcctgaggca caacgacgcg      660
gagcagctcg agcacatgct ctcgacgatc ccgcagggg ccgacatcac ctacgtgtgc       720
gacggcgtgt actccacgga cggagagctc gccgacttgc ccgccatatg tgcttgtttg      780
aggccgcgcg gggccaagat actcgtagac gactcgcatg gctgcggcgt tcttggccgc      840
aaccccgact cggagcaacc cttcgggtat ggtggcggcg cgtcgtcga gtacttcggg       900 ctggactacg cggagaacaa catcatctac gccgggcagc tgagcaaggc gttcaattcg      960
cccggcggat tcgtcggcgg tgcgcgcgag accgacgaga gtttggcat tctgaacttg       1020 gccaagaact cgaacacact cgtgttcgca gggccgatct gtactgccgg cctgtcgagt     1080
gcgaagacga ccctcgacct caacgccgcc gaggggggacc ttcagcgcaa gcggcttctg     1140
gcggcgaccc tcgaattctg cgaggggctc aaggcgctcg ggtgcccccca cacctaccac     1200 gggttccc                                                               1208

<210> SEQ ID NO 145
<211> LENGTH: 1209
<212> TYPE: DNA
<213> ORGANISM: Alexandrium fundyense

<400> SEQUENCE: 145
catggacctc ctggactccc tcaacttcac cgacttcgca ggccagctgg atgccgcact       60
ccccgtgccc gtctccgtcg ggctgctctt cgaggcgtcc acgcccagga agctggccgc      120
gcacctccac cgtgagatgc agcggctggc cggccaggcg acgggggcc gcgcctcgg        180 ctccgcaccg gccgccgccg ccgcgccgcc gcccgctgcg gccagggagg aggccgcgga      240
```

```
ggctccgctg gcctccttcg actcggtgtg caccaagctc gagggtgct ccgcgctggt      300 cgacggctgc tggtgcatcg acgtggcgaa ctgcagctac ctcggcttcc cgtggcggga      360
cgagatcgcc gagggcgtgg accgggacgt gcgcacttgg ggcgtccacc ccccatggac      420
caggctcgtc tcgtctccga agctgtacga cgacgtcgag gcgcgctgtt gcagctgac      480 cggcatctgg aagtgcgttc tgtacccgag cgttaccatg ctcaacatgg gagtcatccc      540
gagcctcgtg ggcgagagcg ggttcctcct cctggacatc aacgcccacg actgtgtgca      600
gacggccgcc aggctctgca agaagggcac caccgtggtg cgcctgaagc acaacgacac      660
ggagcagctc gagcacatgc tctcgtagat cccgcagggg gccgacatca cctacgtgtg      720
cgacggcgtg tactccacgg acggagagct cgctgacttg cccgccatat gtgcttgttt      780
gaggccacgc ggggccaaga tactcgtaga cgactcgcat ggctgcggcg ttcttggccg      840
caaccccgac tcggagcaac cctccgggta tggtggcggc ggcgtcgtcg agtacttcgg      900
gctggactac gcggagaaca acatcatcta tgccgggcag ctgagcaagg cgttcaattc      960
gcccggcgga ttcgtcggct gtgcgcgcga gaccgacgag aagttcggca ttctgaactt     1020
ggccaagaac tcgaacacac tcgtgttcac agggccgatc tgtactgccg gcctgtcgag     1080
tgcgaagacc accctcgacc tcaacgccgc cgaggggggac cttcagcgca gcggcttct     1140 ggcggcgacc ctcgaattct gcgagggct caaggcgctt gggtgccccc acacctacca     1200
cgggttccc                                                             1209

<210> SEQ ID NO 146
<211> LENGTH: 1207
<212> TYPE: DNA
<213> ORGANISM: Alexandrium fundyense

<400> SEQUENCE: 146
catggacctc ctggactccc tcaacttcac cgacttcgca ggtcagctgg acgccgcgct       60
ccccgtgccc gtctccgtcg ggctgctctt cgaggcgtcc acgcccagga agctggccgc      120
gcacctccac cgcgagatgc agcggctggc cggccaggcg acgggggggc gcgcgcctcgg     180 ccccgcaccg gccgccgccg ccgcgccgcc gcccgctgcg gccagggagg aggccgcgga      240
ggctccgctg gcctcctttg actcagtgtg cgccaagctc gagggtgct ccgcgctggt       300 cgacggctgc tggcgcatcg acgtggcgaa ctgcagctac ctcggcttcc agtggcggga      360
cgagatcgcc gatggcgtgg accgggacgt gcgcacttgg ggcgtccacc ccccgtggac      420
caggctcgtc tcgtccccga agctgtacga cgacgtcgag gcgcgctgtt gcagctgac      480 cggcatctgg gagtgcgttc tgtacccgag cgttaccatg ctcaacatgg gagtcatccc      540
gagcctcgtg ggcgagagcg ggttcctcct cctgacataa acgcccacga ctgcgtgcag      600
acggccgcca ggctctgcaa gaagggcgcc accgtggtgc gcctgaggca acgacgcg       660 gagcagctcg agcacatgct ctcgtcgatc ccgcaggggg ccgacatcac ctacgtgtgc      720
gacggcgtgt actccacgga cggagagctc gccgacttgc ccgccatatg tgcttgtctg      780
aggccgcgcg ggccgagat actcgtagac gactcgcatg gctgcggcgt tcttggccgc      840
aaccccgact cggagcaacc ttcgggtat ggtggcggcg cgtcgtcga gtacttcggg       900 ctggactacg cggagaacaa catcatctac gccgggcagc tgagcaaggc gttcaattcg      960
cccggcggat tcgtcggctg tgcgcgcgag accgacgaga agttcggcat tctgaacttg     1020
gccaagaact cgaacacact cgtgttcaca gggccgatct gtactgccgg cctgtcgagt     1080
gcgatgacga ccctcgacct caacgccgcc gaggggacct tcagcgcaag cggcttctgg     1140
```

```
tggcgaccct cgaattctgt gaggggctca aggcgctcgg gtgcccccac acctaccacg   1200
ggttccc                                                             1207

<210> SEQ ID NO 147
<211> LENGTH: 873
<212> TYPE: DNA
<213> ORGANISM: Alexandrium fundyense

<400> SEQUENCE: 147
ggacgagatc gccgatggcg tggaccggga cgtgcgcact tggggcgtcc acccccgtg    60 gaccaggctc gtctcgtctc cgaagctgta cgacgacgtc gaggcgcgct gttgcgagct   120
gaccggcatc tggaagtgcg ttctgtaccc gagcgttacc atgctcaaca tgggagtcat   180
cccgagcctc gtgggcgaga gcggggttcct cctcctggac ataaacgccc acgactgcgt   240
gcagacggcc gccaggctct gcaagaaggg cgccaccgtg gtgcgcctga ggcacaacga   300
cgcggagcag ctcgagcaca tgctctcgtc gatcccgcag gggccgacat cacctacgtg   360
tgcgacggcg tgtactccac ggacggagag ctcgccgact agcccaccat atgtgcttgt   420
ctgaggccgc gtgggccaa gatacccgta cgactcgc atggctgcgg cgttcttggc    480
cgcaaccccg actcggagca acccttcggg tatggtggcg gcggcgtcgt cgagtacttc   540
gggctggact acgcggagaa caacatcatc tacgccgggc agctgagcaa ggcgttcaat   600
tcgcccggcg gattcgtcgg ctgtgcgcgc gagaccgacg agaagttcgg cattctgaac   660
ttggccaaga ctcgaacac actcgtgttc acagggccga tctgtactgc cagcctgtcg   720
agtgcgatga cgaccctcga cctcaacgcc gccgagggggg accttcagcg caagcggctt   780
ctggcggcga ccctcgaatt ctgtgagggg ctcaaggcgc tcgggtgccc cacacctacc   840
acgggttccc catcgtcaac atctactgga ccc                                873

<210> SEQ ID NO 148
<211> LENGTH: 597
<212> TYPE: DNA
<213> ORGANISM: Alexandrium fundyense

<400> SEQUENCE: 148
acgagatcgc cgatggcgtg gaccgggacg tgcgcacttg gggcgtccac ccccgtgga    60 ccaggctcgt ctcgtctccg aagctgtacg acgacgtcga ggcgcgctgt tgcgagctga   120
ccggcatctg gaagtgcgtt ctgtacccga gcgttaccat gctcaacatg ggagtcatcc   180
cgagcctcgt gggcgagagc gggttcctcc tcctggacat aaacgccac gactgcgtgc   240 agacggccgc caggctctgc aagaagggcg ccaccgtggt gcgcctgagg cacaacgacg   300
cggagcagct cgagcacatg ctctcgtcga tcccgcaggg ggccgacatc acctacgtgt   360
gcgacggcgt gtactccacg gacggagagc tcgccgactt gcccgccata tgtgcttgtc   420
tgaggccgcg cggggccaag atactcgtag acgactcgca tggctgcggc gttcttggcc   480
gcaaccccga ctcggagcaa cccttcgggt atggtggcgg cggcgtcgtc gagtacttcg   540
rgctggacta cgcggagaac aacatcatct acgccgggca gctgagcaag gcgttca     597

<210> SEQ ID NO 149
<211> LENGTH: 723
<212> TYPE: DNA
<213> ORGANISM: Alexandrium fundyense

<400> SEQUENCE: 149
```

| | |
|---|---:|
| acgagatcgc cgatggcgtg gaccgggacg tgcgcacttg gggcgtccac ccccgtgga | 60 |
| ccaggctcgt ctcgtctccg aagctgtacg acgacgtcga ggcgcgctgt tgcgagctga | 120 |
| ccggcatctg gaagtgcgtt ctgtacccga gcgttaccat gctcaacatg ggagtcatcc | 180 |
| cgagcctcgt gggcgagagc gggttcctcc tcctggacat aaacgcccac gactgcgtgc | 240 |
| agacggccgc caggctctgc aagaagggcg ccaccgtggt gcgcctgagg cacaacgacg | 300 |
| cggagcagct cgagcacatg ctctcgtcga tcccgcaggg ggccgacatc acctacgtgt | 360 |
| gcgacggcgt gtactccacg gacggagagc tcgccgactt gcccgccata tgtgcttgtc | 420 |
| tgaggccgcg cggggccaag atactcgtag acgactcgca tggctgcggc gttcttggcc | 480 |
| gcaaccccga ctcggagcaa cccttcgggt atggtggcgg cggcgtcgtc gagtacttcg | 540 |
| ggctggacta cgcggagaac aacatcatct acgcccggca gctgagcaag gcgttcaatt | 600 |
| cgcccggcgg attcgtcggc tgtgcgcgcg agaccgacga gaagttcggc attctgaact | 660 |
| tggccaagaa ctcgaacaca ctcgtgttca cagggccgat ctgtactgcc ggcctgtcga | 720 |
| gta | 723 |

<210> SEQ ID NO 150
<211> LENGTH: 722
<212> TYPE: DNA
<213> ORGANISM: Alexandrium fundyense

<400> SEQUENCE: 150

| | |
|---|---:|
| acgagatcgc cgatggcgtg gaccgggacg tgcgcacttg gggcgtccac ccccgtgga | 60 |
| ccaggctcgt ctcgtctccg aagctgtacg acgacgtcgg ggcgcgctgt tgcgagctga | 120 |
| ccggcatctg gaagtgcgtt ctgtacccga gcgttaccat gctcaacatg ggagtcatcc | 180 |
| cgagcctcgt gggcgagagc gggttcctcc tcctggacat aaacgcccac gactgcgtgc | 240 |
| agacggccgc caggctctgc aagaagggcg ccaccgtggt gcgcctgagg cacaacgacg | 300 |
| cggagcagct cgagcacatg ctctcgtcga tcccgcaggg ggccgacatc acctacgtgt | 360 |
| gcgacggcgt gtattccacg gacggagagc tcgccgactt gcccgccata tgtgcttgtc | 420 |
| tgaggccgcg cggggccaag atactcgtag acgactcgca tggctgcggc gttcttggcc | 480 |
| gcaaccctg actcggagca accctccggg tatggtagcg gcggcgtcgt cgagtacttc | 540 |
| gggctggact acgcggagaa caacatcatc tacgccgggc agccgagcaa ggcgttcaat | 600 |
| tcgcccggcg gattcgtcgg ctgtgcgcgc gagaccgatg agaagttcgg cattctgaac | 660 |
| ttggccaaga actcgaacac actcgtgttc acagggccga tctgtactgc cggcctgtcg | 720 |
| ag | 722 |

<210> SEQ ID NO 151
<211> LENGTH: 721
<212> TYPE: DNA
<213> ORGANISM: Alexandrium fundyense

<400> SEQUENCE: 151

```
acgagatcgt cgatggcgtg gaccgggacg tgcgcacttg ggcgtccac cccccgtgga     60 ccaggctcgt ctcgtctccg aagctgtacg acgacgtcga ggcgcgctgt tgcgagctga   120
ccggcatctg gaagtgcgtt ctgtacccga gcgttaccat gctcaacatg ggagtcatcc   180
cgagcctcgt gggcgagagc gggttcctcc tcctggacat aaacgcccac gactgcgtgc   240
agacggccgc caggctctgc aagaagggcg ccaccgtggt gcgcctgagg cacaacgacg   300
cggagcagct cgagcacatg ctctcgtcgg tcccgcaggg ggccgacatc acctacgtgt   360
```

```
gcgacggcgt gtactccacg gacggagagc tcgccgactt gcccgccata tgtgcttgtc   420
tgaggccgcg cggggccaag atactcgtag acgactcgca tggctgcggc gttcttggcc   480
gcaaccccga ctcggagcaa cccttcgggt atggtggcgg cggcgtcgtc gagtacttcg   540
ggctggacta cgcggagaac aacatcatct acgccgggca gctgagcaag gcgttcaatt   600
cgcccggcgg attcgtcggc tgtgcgcgcg agaccgacga gaagttcggc attctgaact   660
tggccaagaa ctcaaacaca ctcgtgttca cagggccgat ctgtactgcc ggcctgtcga   720
g                                                                   721
```

<210> SEQ ID NO 152
<211> LENGTH: 872
<212> TYPE: DNA
<213> ORGANISM: Alexandrium fundyense

<400> SEQUENCE: 152

```
acgagatcgc cgatggcgtg gaccgggacg tgcgcacttg gggcgtccac cccccgtgac    60
caggctcgtc tcgtctccga agctgtacga cgacgtcgag gcgcgctgtt gcgagctgac   120
cggcatctgg aagtgcgttc tgtacccgag cgttaccatg ctcaacatgg gagtcatccc   180
gagcctcgtg ggcgagagcg ggttcctcct cctggacata aacgcccacg actgcgtgca   240 gacgccgcc aggctctgca ggaagggcgc accgtggtg cgcctgaggc acaacgacgc    300
ggagcagctc gagcacatgc tctcgtcgat cccgcagggg gccgacatca cctacgtgag   360 cgacggcgt tactccacgg acggagagct cgccgacttg cccgccatat gtgcttgtct    420
gaggccgcgc ggggccaaga tactcgtaga cgactcgcat ggctgcggcg tccttggccg   480
caaccccgac tcggagcaac ccttcgggta tggtggcggc ggcgtcgtcg agtacttcgg   540
gctggactac gcggagaaca acatcatcta cgccgggcag ctgagcaagg cgttcaattc   600
gcccggcgga ttcgtcggct gtgcgcgcga gaccgacgag aagttcggca ttctgaactt   660
ggccaagaac tcgaacacac tcgtgttcac agggccgatc tgtactgccg gcctgtcgag   720
tgcgatgacg accctcgacc tcaacgccgc cgaggggggac cttcagcgca agcggcttct   780
ggcggcgacc ctcgaattct gtgagggggct caaggcgctc gggtgccccc acacctacca   840
cgggttcccc atcgtcaaca tctactggac cc                                 872
```

<210> SEQ ID NO 153
<211> LENGTH: 873
<212> TYPE: DNA
<213> ORGANISM: Alexandrium fundyense

<400> SEQUENCE: 153

```
acgagatcgc cgatggcgtg gacctggacg tgcgcacttg gggcgtccac cccccgtgga    60
ccaggctcgt ctcgtctccg aagctgtacg acgacgtcga ggcgcgctgt tgcgagctga   120
ccggcatctg gaagtgcgtt ctgtacccga gcgttaccat gctcaacatg ggagtcatcc   180
cgagcctcgt gggcgagagc gggttcctcc tcctggacat aaacgcccac gactgcgtgc   240
agacggccgc caggctctgc aagaagggcg ccaccgtggt gtgcctgagg cacaacgacg   300
cggagcagct cgagcacatg ctctcgtcga tcccgcaggg ggccgacatc acctacgtgt   360
gcgacggcgt gtactccacg gacggagagc tcgccgactt gcccgccata tgtgcttgtc   420
tgaggccgcg cggggccaag atactcgtag acgactcgca tggctgcggc gttcttggcc   480
gcaaccccga ctcggagcaa cccttcgggt atggtggcgg cggcgtcgtc gagtacttcg   540
```

```
ggctggacta cgcggagaac aacatcatct acgccgggca gctgagcaag gcgttcaatt      600
cgcccggcgg attcgtcggc tgtgcgcgcg agaccgacga gaagttcggc attctgaact      660
tggccaagaa ctcgaacaca ctcgtgttca cagggccgat ctgtactgcc ggcctgtcaa      720
gtgcgatgac gaccctcgac ctcaacgccg ccgaggggga ccttcagcgc aagcggcttc      780
tggcggcgac cctcgaattc tgtgaggggc tcaaggcgct cgggtgcccc cacacctacc      840
acgggttccc catcgtcaac atctactgga ccc                                  873

<210> SEQ ID NO 154
<211> LENGTH: 827
<212> TYPE: DNA
<213> ORGANISM: Alexandrium fundyense

<400> SEQUENCE: 154
ccaccccccg tggaccaggc tcgtctcgtc ttcgaagctg tacgacgacg tcgaggcgcg       60
ctgttgcgag ctgaccggca tctggaagtg cgttctgtac ccgagcgtta ccatgctcaa      120
catgggagtc atcccgagcc tcgtgggcga gagcgggttc ctcctcctag acataaacgc      180
ccacgactgc gtacagacgg ccgccaggct ctgcaagaag agcgcctccg tggtgcgcct      240
gaggcacaac gacgcggagc agctcgagca catgctctcg tcgatcccgc aggggccga      300 catcacctac gtgtgcgacg gcgtgtactc cacggacgga gagctcgccg acttgcccgc      360
catatgtgct tgtctgtggc cgcgcggggc caagatactc gtagacgact cgcatggctg      420
cggcgttctt ggccgcaacc ccgactcgga gcaacccttc gggtatggtg gcggcggcgt      480
cgtcgagtac tacgggctgg actacgcgga gaacaacatc atctacgccg ggcagctgaa      540
caaggcgttc aattcgcccg gcggattcgt cggctgtgcg cgcgagaccg acgagaagtt      600
cggcattctg aacttggtca gaactcgaa cacacttgtg ttcacagggc cgatctgtac      660
tgccggcccg tcgagtgcga tgacgaccct cgacctcaac gccgccgagg ggaccctca      720 gcgcaagcgg cttctggcgg cgaccctcga attctgtgag gggctcaagg cgctcgggtg      780
cccccacacc taccacgggt tccccatcgt caacatctac tggaccc                    827

<210> SEQ ID NO 155
<211> LENGTH: 670
<212> TYPE: DNA
<213> ORGANISM: Alexandrium fundyense

<400> SEQUENCE: 155 cccccgtgg accaggctcg tctcgtctcc gaagctgtgc gacgacgtcg aggcgcgctg       60
ttgcgagctg accggcatct ggaagtgcgt tctgtacccg agcgttacca tgctcaacat      120
gggagtcatc ccgagcctcg tgggcgagag cgggttcctc ctcctgggca taaacgccca      180
cgactgcgtg cagacggccg ccaggctctg caagaagggc gccaccgtgg tgcgcctgag      240
gcacaacgac gcggagcagc tcgagcacat gctctcgtcg atcccgcagg ggccgacat      300 cacctacgtg tgcgacggtg tactccacgg acgagagct cgccgacttg cccgccatat      360
gtgcttgtct gaggccgcgc ggggccaagg tactcgtaga cgactcgcat ggctgcggcg      420
ttcttggccg caaccccgac tcggagcaac ccttcgggta tggtggcggc ggcgtcgtcg      480
agtacttcgg gctggactac gcggagaaca acatcatcta cgccgggcag ctgagcaagg      540
cgttcaattc gcccggcgga ttcgttggct gtgcgcgcga gaccgacgag aagttcggca      600
ttctgagctt ggccaagaac tcgaacacac tcgtgttcac agggccgatc tgtactgccg      660
gcctgtcgag                                                            670
```

<210> SEQ ID NO 156
<211> LENGTH: 533
<212> TYPE: DNA
<213> ORGANISM: Alexandrium fundyense

<400> SEQUENCE: 156

```
tcgaggcgct ctgttgcgag ctgaccggca tctggaagtg cgttctgtac ccgagcgtta      60
ccatgctcaa catgggagtc atcccgagcc tcgtgggcga gagcgggttc ctcctcctgg     120
acataaatgc ccacgactgt gtgcagacgg ccgccaggct ctgcaagaag ggcgccaccg     180
tggtgcgcct gaggcacaac gacgcggagc agctcgagca catgctctcg tcgatcccgc     240
aggggggccga catcacctac gtgtgcgacg cgtgtactc cacggacgga gagctcgccg      300
acttgcccgc catatgtgct tgtttgaggc cgcgcggcgc caagatactc gtagacgact     360
cgcatggctg cggcgttctt ggccgcaacc ccgactcgga gcaacccttc gggtatggtg     420
gcggcggcgt cgtcgagtac ttcgggctgg actacgcgga gaacaacatc atctacgccg     480
ggcagctgag caaggcgttc aattcgcccg gcggattcgt cggctgtgcg cgc            533
```

<210> SEQ ID NO 157
<211> LENGTH: 1414
<212> TYPE: DNA
<213> ORGANISM: Alexandrium fundyense

<400> SEQUENCE: 157

```
tgctcaacat gggagtcatc ccgagcctcg tgggcgagag cgggttcctc ctcctggaca      60
tcaacgccca cgactgtgtg cagacggccg ccaggctctg caagaagggc gccaccgtgg     120
tgcgcctgaa gcacaacgac acggagcagc tcgagcacat gctctcgtcg atcccgcagg     180
ggccgacat cacctacgtg tgcgacggcg tgtactccac ggacggagag ctcgctgact      240
tgcccgccat atgtgcttgt ttgaggccac gcggggccaa gatactcgta gacgactcgc     300
atggctgcgg cgttcttggc cgcaaccccg actcggagca accttcggg tatggtggcg      360
gcggcgtcgt cgagtacttc gggctggact acgcggagaa caacatcatc tatgccgggc     420
agctgagcaa ggcgttcaat tcgcccggcg gattcgtcgg ctgtgcgcgc gagaccgacg     480
agaagttcgg cattctgaac ttggccaaga actcgaacac actcgtgttc acagggccga     540
tctgtactgc cggcctgtcg agtgcgaaga cgaccctcga cctcaacgcc gccgagggg      600
accttcagcg caagcggctt ctggcggcga ccctcgaatt ctgcgagggg ctcaaggcgc     660
ttgggtgccc ccacacctac cacgggttcc ccatcgtcaa catctactgg accccggtcg     720
aggtgtgcgc agaggtgtac agggagctga tgagcgcgag gcagggcgcg ttccagtggg     780
gcgtcgtcac gaccccatg tggcaccca tcgccccgaa gggccacgag atgctgcgct       840
tccagttcac gtcgctccac gacgaggccg ccgtgcgcca catcctcgtg atcctcgagg     900
acctgatcaa cgcgctaccc ccctccgccg tgccgccgcg catctgatcg gccgcccgag     960
ccgcaggacc agcgccgctc atcccagggg tggtttaagg gattgtttaa tcttttcaat    1020
ctagtcagcg tgtttttaat gtgcaagcag caagggtcag gcggattctg gcttgtaca     1080
ccaagggcca ggcaggtttt ggctgccgcc gttttgatcc tgctgtgttg tcgtagcgtg    1140
caagcagcaa gggtcaggcg gattctgggc ttgtacacca agggccaggc aggttttggc    1200
tgccgccgtt tgatcctgc tgtgttgtcg tagcgtgcaa gcagcagggg tcaggcggat     1260
tttgggcttt gctgatcctg atccaaggta tgaccagcca tggcgcatca tcgcgtctaa    1320
```

| | |
|---|---|
| ggtagcgcct gtccgtgtct gccatcttag ctggtcacta ttcgcatcaa cactcgcaag | 1380 |
| gtacgcgtct gctaaaaaaa aaaaaaaaaa aaaa | 1414 |

<210> SEQ ID NO 158
<211> LENGTH: 1315
<212> TYPE: DNA
<213> ORGANISM: Alexandrium fundyense

<400> SEQUENCE: 158

| | |
|---|---|
| tgctcaacat gggagtcatc ccgagcctcg tgggcgagag cgggttcctc ctcctggaca | 60 |
| taaacgccca cgactgcgtg cagacggccg ccaggctctg caagaagggc gccaccgtgg | 120 |
| tgcgcctgag gcacaacgac gcggagcagc tcgagcacat gctctcgtcg atcccgcagg | 180 |
| gggccgacat cacctacgtg tgcgacggcg tgtactccac ggacggagag ctcgccgact | 240 |
| tgcccgccat atgtgcttgt ctgaggccgc gcggggccaa gatactcgta gacgactcgc | 300 |
| atggttgcgg cgttcttggc cgcaaccccg actcggagca accttcgggt atggtggcg | 360 |
| gcggcgtcgt cgagtacttc gggctggact acgcggagaa caacatcatc tacgccgggc | 420 |
| agctgagcaa ggcgttcaat tcgcccggcg gattcgtcgg ctgtgcgcgc gagaccgacg | 480 |
| agaagttcga cattctgaac ttggccaaga actcgaacac actcgtgttc acagggccga | 540 |
| tctgtactgc cggcctgtcg agtgcgatga cgaccctcga cctcaacgcc gccgagggg | 600 |
| accttcagcg caagcggctt ctggcggcga ccccgaatt ctgtgagggg ctcaaggcgc | 660 |
| tcgggtgccc ccacacctac cacgggttcc ccatcgtcaa catctactgg accccggtcg | 720 |
| aggtgtgcgc agaggtgtac agcgagctga tgagcgcgag gcaggcgcg ttccagctgg | 780 |
| gcgtcgtcac gaccccatg tggcacccca tcgctccgaa gggccacgag atgctgcgct | 840 |
| tccagttcac gtcgctccac gacgaggcg ccgtgcgcca catcctcgtg atcctcgagg | 900 |
| acctgatcaa gcgctacccg ccctccgccg tgccgccgcg catctgatcg gccgcccgag | 960 |
| ccgcaggacc agcgccgctc atcccagggg ttgtttaagg gattgtttaa tcttctcaat | 1020 |
| ctagtcagcg tgtttttaat gtgcaagcag caagggtcaa gcggattctg ggcttgtaca | 1080 |
| ccaagggcca gcaggtttt ggctgccgcc attttgatcc tgctgtgttg tcgtagcgtg | 1140 |
| caagcagcaa gggccaggcg gagtctgtgc ttgtacacca agggccaggc aggttttggc | 1200 |
| tgccgccgtt tttatccggc tgtgttgtgg tagcgtgcaa gcagcaaggg tcaggcggat | 1260 |
| ttggggcttt gctgatcctg atccaaggta aaaaaaaaa aaaaaaaaa aaaaa | 1315 |

<210> SEQ ID NO 159
<211> LENGTH: 1453
<212> TYPE: DNA
<213> ORGANISM: Alexandrium fundyense

<400> SEQUENCE: 159

| | |
|---|---|
| gctcaacatg ggagtcatcc cgagcctcgt gggcgagagc gggttcctcc tcctggacat | 60 |
| aaacgcccac gactgcgtgc agacggccgc caggctctgc aagaagggcg ccaccgtggt | 120 |
| gcgcctgaag cacaacgacg cggagcagct cgagcacatg ctctcgtcga tcccgcaggg | 180 |
| ggccgacatc acctacgtgt gcgacggcgt gtactccacg gacggagagc tcgccgactt | 240 |
| gcccgccata tgtgcttgtt tgaggccgcg cggggccaag atactcgtag acgactcgca | 300 |
| tggctgcggc gttcttggcc gcaaccccga ctcggagcaa ccttcgggt atggtggcgg | 360 |
| cggcgtcgtc gagtacttcg ggctggacta cgcggagaac aacatcatct acgccgggca | 420 |
| gctgagcaag gcgttcaatt cgcccggcgg attcgtcggc tgtgcgcgcg agaccgacga | 480 |

```
gaagttcggc attctgaact tggccaagaa ctcaaacaca ctcgtgttca cagggccgat    540
ctgtactgcc ggcctgtcga gtgcgatgac gaccctcgac ctcaacgccg ccaggggga    600 ccttcagcgc aagcggcttc tggcggcgac cctcgaattc tgcgaggggc tcaaggcgct    660
cgggtgcccc cacacctacc acgggttccc catcgtcaac atctactgga ccccggtcga    720
ggtgtgcgca gaggtgtaca gggagctgat gagcgcgagg cagggcgcgt tccagctggg    780
cgtcgtcacg accccatgt ggcacccat cgccccaaag gccacgaga tactgcgctt    840 ccagttcacg tcgctccacg acgaggccgc cgtgcgccac atcctcgtga tcctcgagga    900
cctgatcaag cgctacccgc cctccgccgt gccgccgcgc atctgatcgg ctgcccgagc    960
cgcaggacca gcgccgctca tcccaggggt tgtttaaggg attgttgagt cttttcaatc    1020
tagtcagcgt gttttaatg tgcaagcagc aagggtcagg cggattctgg gcttgtacac    1080
caagggccag gcaggttttg gctgccgccg ttttgatcct gctgtgttgt cgtagcgtgc    1140
aagcagcaag ggtcaggcgg agtctgggct tgtacaccaa gggccaggca ggttttggct    1200
gccgccgttt tgatcctgct gtgttgtggt agcatgcaag cagcaagggt caggcggatt    1260
ttgtggcttt gctgatcctg atccaaggta tgaccagcca tggcgcatca tcgcgtctaa    1320
tgtagcgcct gtccatgtct gccatcttag ctggtcacta tttgcatcaa cactcgcaag    1380
gtacgcgtct gctacgcaca ggtgacaatt gacattgtgg atcgagccac ggaagggaga    1440
aaaaaaaaaa aaa                                                      1453

<210> SEQ ID NO 160
<211> LENGTH: 469
<212> TYPE: DNA
<213> ORGANISM: Alexandrium fundyense

<400> SEQUENCE: 160
gctcaacatg ggagtcatcc cgagcctcgt gggcgagagc gggttcctcc tcctggacat     60
aaacgcgcac gactgcgtgc agacggccgc caggctctgc aagaagggcg ccaccgtggt    120
gcgcctgagg cacaacgacg cggagcagct cgagcacatg ctctcgtcga tcccgcaggg    180
ggccgacatc acctacgtgt gcgacggcgt gtactccacg gacggagagc tcgccgactt    240
gcccgccata tgtgcttgtt tgaggccgcg cggggccaag atactcgtag acgactcgca    300
tggctgcggc gttcttggcc gcaaccccga ctcggagcaa cccttcgggt atggtggcgg    360
cggcgtcgtc gagtacttcg gctggactac gcggagaac aacatcatct gcgccgggca    420
gctgagcaag gcgttcaatt cgcccggcgg attcgtcggc tgtgcgcgc                469

<210> SEQ ID NO 161
<211> LENGTH: 457
<212> TYPE: DNA
<213> ORGANISM: Alexandrium fundyense

<400> SEQUENCE: 161
agtcatcccg agcctcgtgg gcgagagcgg gttcctcctc ctggacataa acgcccacga     60
ctgtgtgcag acggccgcca ggctctgcaa gaagggcgcc accgtggtgc gcctgaagca    120
caacgacacg gagcagctcg agcacatgct ctcgtcgatc ccgcaggggg ccgacatcac    180
ctacgtgtgc gacggcgtgt actctacgga cggagagctc gccgacttgc ccgccatatg    240
tgcttgtttg aggccgcgcg gggccaagat actcgtagac gactcacatg gctgcggcgt    300
tcttggccgc aaccccgact cggagcaacc cttcgggtat ggtggcggcg cgtcgtcga    360
```

```
gtacttcggg ctggactacg cggagaacaa catcatctac gccgggcagc tgagcaaggc    420
gttcaattcg cccggcggat tcgtcggctg tgcgcgc                              457
```

<210> SEQ ID NO 162
<211> LENGTH: 424
<212> TYPE: DNA
<213> ORGANISM: Alexandrium fundyense

<400> SEQUENCE: 162

```
cctcctcctg dacataaacg cccacgactg cgtgcagacg gccgccaggc tctgcaagaa     60
gggcgccacc gtggtgcgcc tgaagcacaa cgacgcggag cagctcgagc acatgctctc   120
gtcgatcccg caggggccg acatcaccta cgtgtgcgac gacgtgtact ccacggacgg    180
agagctcgcc gacttgcccg ccatatgtgc ttgtttgagg ccgcgcgggg ccaagatact   240
cgtagacgac tcgcatggct gcggcgttct tggccgcaac cccgactcgg agcaacccct   300
cgggtatggt ggcggcggcg tcgtcgagta cttcgggctg gactacgcgg agaacaacat   360
catctacgcc gggcagctga gcaaggcgtt caattcgccc ggcggattcg tcggctgtgc   420
gcgc                                                                 424
```

<210> SEQ ID NO 163
<211> LENGTH: 503
<212> TYPE: DNA
<213> ORGANISM: Alexandrium fundyense

<400> SEQUENCE: 163

```
taaacgccca cgactgcgtg cagacggccg ccaggctctg caagaagggc gccaccgtgg     60
tgcgcctgag cacaacgac gcggagcagc tcgagcacat gctctcgtcg atcccgcagg    120
gggccgacat cacctacgtg tgcgacggcg tgtactccac ggacggagag ctcgccgact   180
tgcccgccat atgtgcttgt ctgaggccgc gcggggccaa gatactcgta gacgactcgc   240
atggctgcgg cgttcttggc cgcaaccccg actcggagca accttcggg tatggtggcg    300 gcggcgtcgt cgagtacttc gggctggact acgcggagaa caacatcatc tacgccgggc   360
agctgagcaa ggcgttcaat tcgccccggcg gattcgtcgg ctgtgcgcgc gagaccgacg   420
agaagttcgg cattctgaac ttggccaaga actcgaacac actcgtgttc acagggccga   480
tctgtactgc cggcctgtcg agt                                            503
```

<210> SEQ ID NO 164
<211> LENGTH: 344
<212> TYPE: DNA
<213> ORGANISM: Alexandrium fundyense

<400> SEQUENCE: 164

```
tgaggcacaa cgacgcggag cagctcgagc acatgctctc gtcgatcccg caggggccg     60 acatcaccta cgtgtgcgac ggcgtgtact ccacggacgg agagctcgcc gacttgcccg   120
ccatatgtgc ttgtttgagg ccgcgcgggg ccaagatact cgtagacgac tcgcatggct   180
gcggcgttct tggccgcaac cccgactcgg agcaaccctt cgggtatggt ggcggcggcg   240
tcgtcgagta cttcgggctg gactacgcgg agaacaacat catctacgcc gggcagctga   300
gcaaggcgtt caattcgccc ggcggattcg tcggctgtgc gcgc                     344
```

<210> SEQ ID NO 165
<211> LENGTH: 302
<212> TYPE: DNA
<213> ORGANISM: Alexandrium fundyense

<400> SEQUENCE: 165

```
cgatcccgca gggggccgac atcacctacg tgtgcgacgg cgtgtactcc acggacggag    60
agctcgccga cttgcccgcc atatgtgctt gtttgaggcc gcgcgggcc aagatactcg    120
tagacgactc gcatggctgc ggcgttcttg ccgcaaccc cgactcggag caacccttcg    180
ggtatggtgg cggcggcgtc gtcgagtact tcgggctgga ctacgcggag aacaacatca    240
tctacgccgg gcagctgagc aaggcgttca attcgcccgg cggattcgtc ggctgtgcgc    300
gc                                                                    302
```

<210> SEQ ID NO 166
<211> LENGTH: 1286
<212> TYPE: DNA
<213> ORGANISM: Alexandrium fundyense

<400> SEQUENCE: 166

```
accgtagcca ttttggctca agtgaggcct gtgcgcgcca gccaaactcg gatcattcct    60
ggccactgcg ccgccatctg tgccggcgcc ccgaccgggg gcacctcatg tccgtggagc    120
atgcgacgat cgcggacgcg gccccgaacg ggatcgacct ggcgacaaat gccttcatgc    180
tcgtccacgg ctggacggcg gcgcccctgc tcctggagct cgtggccaac ttcagcgcgc    240
ccctggaggg gcgggcccag accgcggggg agctggccgc ggagacgggc gccgaggagg    300
ggccctggc gatcctcctc cgcgcctgca gcgtcctggg ctacgtgcgc ttcgacgccc    360
agagcagggc gtactccctg gtcccggggc cggagctgga cgagctcagg accgtgctcc    420
accctgcgtc ggaggtcgcg aggggcctgc aggagctgta cagcgaggtc gccccccccct    480
tccagctgcc ctcggaggac gcggcgcggt gcctggccct ctgggaggag cagtggccct    540
cctggagcca gtgcaggagc agggccctgg gcgtcctgct ggacggcgct gtgctggcgc    600
cgctgcttgt gtccgtgacg tactcctcga ggtgggacga ggaggccag gagcacggca    660
gggataacgt catggagcgc ttcgacttca gcaagatgtt gccggcgcag cggtccgcgc    720
tcggggacat cttcgagcag ttgggcgtcg gcactatgaa cgcgaagggc gtgatcatga    780
tgtcgtcaaa gggggccatg gcgttgcagc gatgctactc ctactacgtc ccactgtcgt    840
acgcaccgct gatggcccag atctcgccga tcctgtttga tgatgcgggc tggggggttca    900
ctgacgcggg gacagactcc ttcgacgacg tggaggagca tgttgacaga atcttgaatg    960
ttgttggcag tggtgcgcaa caccggaccc tctttaagga tatgatgcga cacatcagta    1020
ccgtgttcaa gggcgaggca tttgccttgc agccaagttt cattgtggac actggctgtg    1080
gcgacgggag cctgctcata catatctatg aacatatcaa acagcacaca ccccggggga    1140
aagtgcttga tcagttccct ctgacgatgg acggcgttga ccacaatgag gatccgcgag    1200
tgacaacagc tgtgaatctg agcaagcagg gcgtcccgca cgtggtcatc tctggcgatg    1260
tgggtaagcc tgcggagata cttgcc                                         1286
```

<210> SEQ ID NO 167
<211> LENGTH: 1282
<212> TYPE: DNA
<213> ORGANISM: Alexandrium fundyense

<400> SEQUENCE: 167

```
accgtagcca ttttggctca aggcctgtgc gcgccagcca aactcggatc attcctggcc    60
actgcgccgc catccgtgcc

```
gacgatcgcg gacgcggtcc cgaacgggat cgacctggcg acaaatgcct tcatgctcgt    180
ccacggctgg acggcggcgc ccctgctcct ggagctcgtg gccaacttca gcgcgcccct    240
ggaggggcgg gcccagaccg cgggggagct ggccgcggag acgggcgccg aggaggggcc    300
cctggcgatc ctcctccgcg cctgcagcgt cctgggctac gtgcgcttcg acgcccagag    360
cagggcgtac tccctggtcc cggggccgga gctggacgag ctcaggaccg tgctccaccc    420
tgcgtcggag gtcgcgaggg gcctgcagga gctgtacagc gaggtcgccc cccccttcca    480
gctgccctcg gaggacgcgg cgcggtgcct ggccctctgg gaggagcagc ggccctcctg    540
gagccagtgc aggagcaggg ccctgggcgt cctgctggac ggcgctgtgc tggccgcgct    600
gcttgtgtcc gtgacgtact cctcgaggtg ggacgaggag ggccaggagc acggcaggga    660
taatgtcatg gagcgcttcg acttcagcaa gatgttgccg cgcagcggt ccgcgctcgg    720 ggacatcttc gagcagttgg gcgtcggcac tatgaacgcg aagggcgtga tcatgatgtc    780
gtcaaagggg gccatggtgt tgcagcgatg ctactcctac tacgtccac tgtcgtacgc     840 accgctgatg gcccagatct cgccgatcct gtttgatgat gcgggctggg ggttcactga    900
cgcggggaca gactccttcg acgacgtgga ggagcatgtt gacagaatct tgaatgttgt    960
tggcagtggt gcgcaacacc ggaccctctt taaggatatg atgcgacaca tcagtaccgt   1020
gttcaagggc gaggcatttg ccttgcagcc aagtttcgtt gtggacactg gctgtggcga   1080
cgggagcctg ctcatacata tctatgaaca tatcaaacag cacacaccc gggggaaagt   1140 gcttgatcag ttccctctga cgatggtcgg cgttgacctc aatgaggatc gcgagtgac    1200 aacagctgtg aatctgagca agcagggcgt cccgcacgtg tcatctctg gcgatgtggg    1260 taagcctgcg gagatacttg cc                                            1282
```

<210> SEQ ID NO 168
<211> LENGTH: 1267
<212> TYPE: DNA
<213> ORGANISM: Alexandrium fundyense

<400> SEQUENCE: 168

```
accgtagcca ttttggctca agccaaactc ggatcattcc tggccactgc gccgccatcc     60
gtgccggcgc cccgaccggg ggcacctcat gtccgtggag catgcgacga tcgcggacgc    120
ggtcccggac gggatcgacc tggtgacaaa tgccttcatg ctcgtccacg gctgacggc    180 ggcgcccctg ctcctggagc tcgtggccaa cttcagcgcg cccctggagg ggcgggccca    240
gaccgcgggg gagctggccg cggagacggg cgccgaggag gggcccctgg cgatcctcct    300
ccgcgcctgc agcgtcctgg gctacgtgcg cttcgacgcc cagagcaggg cgtactccct    360
ggtcccgggg ccggagctgg acgagctcag gaccgtgctc caccctgcgt cggaggtcgc    420
gaggggcctg caggagctgt acagcgaggt cgccccccccc ttccagctgc cctcggagga    480
cgcggcgcgc tgcctggccc tctgggagga gcagcggccc tcctggagcc agtgcaggag    540
cagggccctg ggcgtcctgc tggacggcgc tgtgctggcc cgctgcttg tgtccgtgac    600 gtactcctcg aggtgggacg aggagggcca ggagcacggc agggataacg tcatggagcg    660
cttcgacttc agcaagatgt tgccggcgca gcggtccgcg ctcggggaca tcttcgagca    720
gttgggcgtc ggcactatga acgcgaaggg cgtgatcatg atgtcgtcaa agggggccat    780
ggcgttgcag cgatgctact cctactacgt cccactgtcg tacgcaccgc tgatggccca    840
gatctcgccc atcctgtttg atgatgcggg ctggggttc tctgacgcgg ggacagactc    900
cttcgacgac gtggaggagc atgttgacag aatcttgaat gttgttggca gtggtgcgca    960
```

| | |
|---|---|
| acaccggacc ctctttaagg atatgatgcg acacatcagt accgtgttca agggcgaggc | 1020 |
| atttgccttg cagccaagtt tcgttgtgga cactggctgt ggcgacggga gcctgctcat | 1080 |
| acatatctat gaacatatca aacagcacac accccggggg aaagtgcttg atcagtttcc | 1140 |
| tctgacgacg tcggcgttg acctcaatga ggatccgcga gtgacaacag ctgtgaatct | 1200 |
| gagcaagcag ggcgtcccgc acgtggtcat ctctggcgat gtgggtaagc ctgcggagat | 1260 |
| acttgcc | 1267 |

<210> SEQ ID NO 169
<211> LENGTH: 1267
<212> TYPE: DNA
<213> ORGANISM: Alexandrium fundyense

<400> SEQUENCE: 169

| | |
|---|---|
| accgtagcca ttttggctca agccaaaccc ggatcattcc tggccactgc gccgccatcc | 60 |
| gtgccggcgc cccgaccggg ggcacctcat gtccgtggag catgcgacga tcgcggacgc | 120 |
| ggtcccgaac gggatcgacc tggcgacaaa tgccttcatg ctcgtccacg gctggacggc | 180 |
| ggcgcccctg ctcctggagc tcgtggccaa cttcagcgcg ccctggagg ggcgggccca | 240 |
| gaccgcgggg gagctggccg cggagacggg cgccgaggag gggcccctgg cgatcctcct | 300 |
| ccgcgcctgc agcgtcctgg gctacgtgcg cttcgacgcc cagagcaggg cgtactccct | 360 |
| ggtcccgggg ccggagctgg acgagctcag gaccgtgctc caccctgcgt cggaggtcgc | 420 |
| gaggggcctg caggagctgt acagcgaggt cgccccccc ttccagctgc cctcggagga | 480 |
| cgcggcgcgg tgcctggccc tctgggagga gcagcggccc tcctggagcc agtgcaggag | 540 |
| cagggccctg ggcgtcctgc tggacggcgc tgtgctggcg ccgctgcttg tgtccgtgac | 600 |
| gtactcctcg aggtgggacg aggagggcca ggagcacggc agggataacg tcatggagcg | 660 |
| cttcgacttc agcaagatgt tgccggcgca gcggtccgcg ctcggggaca tcttcgagca | 720 |
| gttgggcgtc ggcactatga acgcgaaggg cgtgatcatg atgtcgtcaa aggggggccat | 780 |
| ggcgttgcag cgatgctact cctactacgt cccactgtcg tacgcaccgc tgatggccca | 840 |
| gatctcgccg atcctgtttg atgatgcggg ctggggggttc actgacgcgg ggacagactc | 900 |
| cttcgacgac gtggaggagc atgttgacag aaccttgaat gttgttggca gtggtgcgca | 960 |
| acaccggacc ctctttaagg atatgatgcg acacatcagt accgtgttca agggcgaggc | 1020 |
| atttgccttg cagccaagtt tcgttgtgga cactggctgt ggcgacggga gcctgctcat | 1080 |
| acatatctat gaacatatca aacagcacac accccggggg aaagtgcttg atcagtttcc | 1140 |
| tctgacgatg tcggcgttg acctcaatga ggatccgcga gtgacaacag ctgtgaatct | 1200 |
| gagcaagcag ggcgtcccgc acgtggtcat ctctggcgat gtgggtaagc ctgcggagat | 1260 |
| acttgcc | 1267 |

<210> SEQ ID NO 170
<211> LENGTH: 1267
<212> TYPE: DNA
<213> ORGANISM: Alexandrium fundyense

<400> SEQUENCE: 170

| | |
|---|---|
| accgtagcca ttttggctca agccaaactc ggatcattcc tggccactgc gccgccatcc | 60 |
| gtgccggcgc cccgaccggg ggcacctcat gtccgtggag catgcgacga tcgcggacgc | 120 |
| ggtcccgaac gggatcgacc tggcgacaaa tgccttcatg ctcgtccacg gctggacggc | 180 |

```
ggcgcccctg ctcctggagc ttgtggccaa cttcagcgcg ccCctggagg ggcgggccca    240
gaccgcgggg gagctggccg cggagacggg cgccgaggag gggcccctgg cgatcctcct    300
ccgcgcctgc agcgtcctgg gctacgtgcg cttcgacgcc cagagcaggg cgtactccct    360
ggtcccgggg ccggagctgg acgagctcag gaccgtgctc caccctgcgt cggaggtcgc    420
gaggggcctg caggagctgt acagcgaggt cgccccCccc ttccagctgc cctcggagga    480
cgcggcgcgg tgcctggccc tctgggagga gcagcggccc tcctggagcc agtgcaggag    540
cagggccctg ggcgtcctgc tggacggcgc tgtgctggcg ccgctgcttg tgtccgtgac    600
gtactcctcg aggtgggacg aggagggcca ggagcacggc agggataacg tcatggagcg    660
cttcgacttc agcaagatgt tgccggcgca gcggtccgcg ctcggggaca tcttcgagcg    720
gttgggcgtc ggcactatga acgcgaaggg cgtgatcatg atgtcgtcaa agggggccat    780
ggcgttgcag cgatgctact cctactacgt cccactgtcg tacgcaccgc tgatgggccca    840
gatctcgccg atcctgtttg atgatgcggg ctggggttc actgacgcgg ggacagactc    900
cttcgacgac gtggaggagc atgttgacag aatcttgaat gttgttggca gtggtgcgca    960
acaccggacc ctctttaagg atatgatgcg acacatcagt accgtgttca agggcgaggc    1020
atttgccttg cagccaagtt tcgttgtgga cactggctgt ggcgacggga gcctgctcat    1080
acatatctat gaacatatca aacagcacac accccggggg aaagtgcttg atcagttccc    1140
tctgacgatg gtcggcgttg acctcaatga ggatccgcga gtgacaacag ctgtgaatct    1200
gagcaagcag ggcgtcccgc acgtggtcat ctctggcgat gtgggtaagc ctgcggagat    1260
acttgcc                                                             1267

<210> SEQ ID NO 171
<211> LENGTH: 1267
<212> TYPE: DNA
<213> ORGANISM: Alexandrium fundyense

<400> SEQUENCE: 171
accgtagcca ttttggctca agccaaactc ggatcattcc tggccactgc gccgtcatcc    60
gtgccggcgc cccgaccggg ggcacctcat gtccgtggag catgcgacga tcgcggacgc    120
ggtcccgaac gggatcgacc tggcgacaaa tgccttcatg ctcgtccacg gctggacggc    180
ggcgcccctg ctcctggagc tcgtggccaa cttcagcgcg ccCctggagg ggcgggccca    240
gaccgcgggg gagctggccg cggagacggg cgccgaggag gggcccctgg cgatcctcct    300
ccgcgcctgc agcgtcctgg gctacgtgcg cttcgacgcc cagagcaggg cgtactccct    360
ggtcccgggg ccggagctgg acgagctcag gaccgtgctc caccctgcgt cggaggtcgc    420
gaggggcctg caggagctgt acagcgaggt cgccccCccc ttccagctgc cctcggagga    480
cgcggcgcgg tgcctggccc tctgggagga gcagcggccc tcctggagcc agtgcaggag    540
cagggccctg ggcgtcctgc tggacggcgc tgtgctggcg ccgctgcttg tgtccgtgac    600
gtactcctcg aggtgggacg aggagggcca ggagcacggc agggataacg tcatggagcg    660
cttcgacttc agcaagatgt tgccggcgca gcggtccgcg ctcggggaca tcttcgagca    720
gttgggcgtc ggcactatga acgcgaaggg cgtgatcatg atgtcgtcaa agggggccat    780
ggcgttgcag cgatgctact cctactacgt cccactgtcg tacgcaccgc tgatgggccca    840
gatctcgccg atcctgtttg atgatgcggg ctggggttc actgacgcgg ggacagactc    900
cttcgacgac gtggaggagc atgttgacag aatcttgaat gttgttggca gtggtgcgca    960
acaccggacc ctctttaagg atatgatgcg acacatcagt accgtgttca agggcgaggc   1020
```

```
atttgccttg cagccaagtt tcgttgtgga cactggctgt ggcgacggga gcctgctcat    1080
acatatctat gaacatatca aacagcacac accccggggg aaagtgcttg atcagttccc    1140
tctgacgatg gtcggcgttg acctcaatga ggatccgcga gtgacaacag ctgtgaatct    1200
gagcaagcag ggcgtcccgc acgtggtcat ctctggcgat gtgggtaagc ctgcggagat    1260
acttgcc                                                              1267
```

<210> SEQ ID NO 172
<211> LENGTH: 1267
<212> TYPE: DNA
<213> ORGANISM: Alexandrium fundyense

<400> SEQUENCE: 172

```
accgtagcca ttttggctca agccaaactc ggatcattcc tggccactgc gccgccatcc     60
gtgccggcgc cccgaccggg ggcacctcat gtccgtggag catgcgacga tcgcggacgc    120
ggtcccgaac gggatcgacc tggcgacaaa tgccttcatg ctcgtccacg gctgacggc    180 ggcgcccctg ctcctggagc tcgtggccaa cttcagcgca ccctggagg ggcgggccca    240 gaccgcgggg gagctggccg cggagacggg cgccgaggag gggcccctgg cgatcctcct    300
ccgcgcctgc agcgtcctgg gctacgtgcg cttcgacgcc cagagcaggg cgtactccct    360
ggtcccgggg ccggagctgg acgagctcag gaccgtgctc caccctgcgt cggaggtcgc    420
gaggggcctg caggagctgt acagcgaggt cgcccccccc ttccagctgc cctcggagga    480
cgcggcgcgc tgcctggccc tctgggagga gcagcggccc tcctggagcc agtgcaggag    540
cagggccctg ggcgtcctgc tggacggcgc tgtgctggcg ccgctgcttg tgtccgtgac    600
gtactcctcg aggtgggacg aggagggcca ggagcacggc agggataacg tcatggagcg    660
cttcgacttc agcaagatgt tgccggcgca gcggtccgcg ctcggggaca tcttcgagca    720
gttgggcgtc ggcactatga acgcgaaggg cgtgatcatg atgtcgtcaa agggggccat    780
ggcgttgcag cgatgctact cctactacgt cccactgtcg tacgcaccgc tgatggccca    840
gatctcgccg atcctgtttg atgatgcggg ctgggggttc actgacgcgg ggacagactc    900
cttcgacgac gtggaggagc atgttgacag aatcttgaat gttgttggca gtggtgcgca    960
acaccggacc ctctttaagg atatgatgcg acacatcagt accgtgttca agggcgaggc   1020
atttgccttg cagccaagtt tcgttgtgga cactggctgt ggcgacggga gcctgctcat   1080
acatatctat gaacatatca aacagcacac accccggggg aaagtgcttg atcagttccc   1140
tctgacgatg gtcggcgttg acctcaatga ggatccgcga gtgacaacag ctgtgaatct   1200
gagcaagcag ggcgtcccgc acgtggtcat ctctggcgat gtgggtaagc ctgcggagat   1260
acttgcc                                                              1267
```

<210> SEQ ID NO 173
<211> LENGTH: 1266
<212> TYPE: DNA
<213> ORGANISM: Alexandrium fundyense

<400> SEQUENCE: 173

```
ccgtagccat tttggctcaa gccaaactcg gatcattcct ggccactgcg ccgccatccg     60
tgccggcgcc ccgaccgggg gcacctcatg tccgtggagc atgcgacgat cgcggacgcg    120
gtcccgaacg ggatcgacct ggcgacaaat gccttcatgc tcgcccacgg ctggacggcg    180
gcgcccctgc tcctggagct cgtggccaac ttcagcgcgc ccctggaggg gcgggcccag    240
```

| | |
|---|---:|
| accgcggggg agctggccgc ggagacgggc gccgaggagg ggcccctggc gatcctcctc | 300 |
| cgcgcctgca gcgtcctggg ctacgtgcgc ttcgacgccc agagcagggc gtactccctg | 360 |
| gtcccggggc cggagctgga cgagctcagg accgtgctcc accctgcgtc ggaggtcgcg | 420 |
| aggggcctgc aggagctgta cagcgaggtc gccccccccct tccagctgcc ctcggaggac | 480 |
| gcggcgcggt gcctggccct ctgggaggag cagcggccct cctggagcca gtgcaggagc | 540 |
| agggccctgg gcgtcctgct ggacggcgct gtgctggcgc cgctgcttgt gtccgtgacg | 600 |
| tactcctcga ggtgggacga ggagggccag gagcacggca gggataacgt catggagcgc | 660 |
| ttcgacttca gcaagatgtt gccggcgcag cggtccgcgc tcggggacat cttcgagcag | 720 |
| ttgggcgtcg gcactatgaa cgcgaagggc gtgatcatga tgtcgtcaaa gggggccatg | 780 |
| gcgttgcagc gatgctactc ctactacgtc ccactgtcgt acgcaccgct gatggcccag | 840 |
| atctcgccga tcctgtttga tgatgcgggc tgggggttca ctgacgcggg gacagactcc | 900 |
| ttcgacgacg tggaggagca tgttgacaga atcttgaatg ttgttggcag tggtgcgcaa | 960 |
| caccggaccc tctttaagga tatgatgcga cacatcagtg ccgtgttcaa gggcgaggca | 1020 |
| tttgccttgc agccaagttt cgttgtggac actggctgtg gcgacgggag cctgctcata | 1080 |
| catatctatg aacatatcaa acagcacaca ccccggggga aagtgcttga tcagttccct | 1140 |
| ctgacgatgg tcggcgttga cctcaatgag gatccgcgag tgacaacagc tgtgaatctg | 1200 |
| agcaagcagg gcgtcccgca cgtggtcatc tctggcgatg tgggtaagcc tgcggagata | 1260 |
| cttgcc | 1266 |

<210> SEQ ID NO 174
<211> LENGTH: 1102
<212> TYPE: DNA
<213> ORGANISM: Alexandrium fundyense

<400> SEQUENCE: 174

| | |
|---|---:|
| ccaaactcgg atcattcctg gccactgcgc cgccatccgt gccggcgccc cgaccggggg | 60 |
| cacctcatgt ccgtggagca tgcgacgatc gcggacgcgg tcccgaacgg gatcgacctg | 120 |
| gcgacaaatg ccttcatgct cgtccacggc tggacggcgg cgcccctgct cctggagctc | 180 |
| gtggccaact tcagcgcgcc cctggagggg cgggcccaga ccgcggggga gctggccgcg | 240 |
| gagacgggcg ccgaggaggg gcccctggcg atcctcctcc gcgcctgcag cgtcctgggc | 300 |
| tacgtgcgct tcgacgccca gagcagggcg tactccctgg tcccggggcc ggagctggac | 360 |
| gagctcagga ccgtgctcca ccctgcgtcg gaggtcgcga ggggcctgca ggagctgtac | 420 |
| agcgaggtcg ccccccccctt ccagctgccc tcggaggacg cggcgcggtg cctggccctc | 480 |
| tgggaggagc agcggccctc ctggagccag tgcaggagca gggccctggg cgtcctgctg | 540 |
| gacggcgctg tgctggcgcc gctgcttgtg tccgtgacgt actcctcgag gtgggacgag | 600 |
| gagggccagg agcacggcag ggataacgtc atggagcgct cgacttcag caagatgttg | 660 |
| ccggcgcagc ggtccgcgct cggggacatc ttcgagcagt tgggcgtcgg cactatgaac | 720 |
| gcgaagggcg tgatcatgat gtcgtcaaag ggggccatgg cgttgcagcg atgctactcc | 780 |
| tactacgtcc cactgtcgta cgcaccgctg atggcccaga tctcgccgat cctgtttgat | 840 |
| gatgcgggct gggggttcac tgacgcgggg acagactcct tcgacgacgt ggaggagcat | 900 |
| gttgacagaa tcttgaatgt tgttggcagt ggtgcgcaac accggaccct ctttaaggat | 960 |
| atgatgcgac acatcagtac cgtgttcaag ggcgaggcat ttgccttgca accaagtttc | 1020 |
| gttgtggaca ctggctgtgg cgacgggagc ctgctcatac atatctatga acatatcaaa | 1080 |

```
cagcacacac cccgggggaa ag                                           1102
```

<210> SEQ ID NO 175
<211> LENGTH: 1001
<212> TYPE: DNA
<213> ORGANISM: Alexandrium fundyense

<400> SEQUENCE: 175

```
gagacgggcg ccgaggaggg ccctggcgat cctcctccgc gcctgcagcg tctgggctac     60
gtgcgcttcg acgcccagag cagggcgtac tccctggtcc ggggccgga gctggacgag     120
ctcaggaccg tgctccaccc tgcgtcggag gtcgcgaggg gctgcaggag ctgtacagcg    180
aggtcgcccc ccccttccag ctgccctcgg aggacgcggc gcggtgcctg gccctctggg    240
aggagcagcg gccctcctgg agccagtgca ggagcagggc cctgggcgtc ctgctggacg    300
gcgctgtgct ggcgccgctg cttgtgtccg tgacgtactc ctcgaggtgg gacgaggagg    360
gccaggagca cggcagggat aacgtcatgg agcgcttcga cttcagcaag atgttgccgg    420
cgcagcggtc cgcgctcggg gacatcttcg agcagttggg cgtcggcact atgaacgcga    480
agggcgtgat catgatgtcg tcaaagggg ccatggcgtt acagcgatgc tactcctact    540
acgtcccact gtcgtacgca ccgctgatgg cccagatctc gccgatcctg tttgatgatg    600
cgggctgggg gttcactgac gcggggacag actccttcga cgacgtggag gagcatgttg    660
acagaatctt gaatgttgtt ggcagtggtg cgcaacaccg gaccctcttt aaggatatga    720
tgcgacacat cagtaccgtg ttcaagggcg aggcatttgc cttgcagcca agtttcgttg    780
tggacactgg ctgtggcgac gggagcctgc tcatacatat ctatgaacat atcaaacagc    840
acacaccccg ggggaaagtg cttgatcagt tccctctgac gatggtcggc gttgacctca    900
atgaggatcc gcgagtgaca acagctgtga atctgagcaa gcagggcgtc ccgcacgtgg    960
tcatctctgg cgatgtgggt aagcctgcgg agatacttgc c                       1001
```

<210> SEQ ID NO 176
<211> LENGTH: 713
<212> TYPE: DNA
<213> ORGANISM: Alexandrium fundyense

<400> SEQUENCE: 176

```
gtgcaggagc agggccctgg gcgtcctgct ggacggcgct gtgctggcgc cgctgcttgt     60
gtccgtgacg tactcctcga ggtaggacga ggagggccag gagcacggca gggataacgt    120
catggagcgc ttcgacttca gcaagatgtt gccggcgcag cggtccgcgc tcggggacat    180
cttcgagcag ttgggcgtcg gcactatgaa cgcgaagggc gtgatcatga tgtcgtcaaa    240
gggggccatg gcgttgcagc gatgctactc ctactacgtc ccactgtcgt acgcaccgct    300
gatggcccag atctcgccga tcctgtttga tgatgcgggc tggggttca ctgacgcggg    360
gacagactcc ttcgacgacg tggaggagca tgttgacaga tcttgaatg ttgttggcag    420
tggtgcgcaa caccggaccc tctttaagga tatgatgcga cacatcagta ccgtgttcaa    480
gggcgaggca tttgccttgc agccaagttt cgttgtggac actgactgtg gcgacgggag    540
cctgctcata catatctatg aacatatcaa acagcacaca ccccggggga aagtgcttga    600
tcagttccct ctgacgatgg tcggcgttga cctcaatgag gatccgcgag tgcaacagc    660
tgtgaatctg agcaagcagg gcgtcccgca cgtggtcatc tctggcgatg tgg          713
```

<210> SEQ ID NO 177

<211> LENGTH: 2369
<212> TYPE: DNA
<213> ORGANISM: Alexandrium fundyense

<400> SEQUENCE: 177

```
tgcagcgatg ctactcctac tacgtcccac tgtcgtacgc accgctgatg gcccagatct     60
cgccgatcct gtttgatgat gcgggctggg ggttcactga cgcggggaca gactccttcg    120
acgacgtgga ggagcatgtt gacagaatct tgaatgttgt tggcagtggt gcgcaacacc    180
ggaccctctt taaggatatg atgcgacaca tcagtaccgt gttcaagggc gaggcatttg    240
ccttgcagcc aagtttcgtt gtgggcactg gctgtggtga cggagcctg ctcatacata    300
tctatgaaca tatcaaacag cacacacccc ggggaaagt gcttgatcag ttccctctga    360
cgatggtcgg cgttgacctc aatgaggatc cgcgagtgac aacagctgtg aatctgagca    420
agcagggcgt cccgcacgtg gtcatctctg gcgatgtggg taagcctgcg agatacttg    480
ccgcgctgaa gaagaagaag gtggacgcgt cgaggacgct tcatgtccgc tccttcctag    540
accacgaccg tacttacatc ccaccggtca tgagaataga ggaagagagc agcacagcca    600
ggtttgcccg cactcagatg gcagactttg tgcatctgga caagcgtgga agcccatca    660
cggctctgga gctgttttgca tccctggtgg aacattttga agatgggct gatgcgctgg    720
aggtctcctt cggactgtgt gtgctggagg ttatgatgct ggatgtgccc acgacgcagc    780
gctggttcaa cgactgcgtg tccttccctc tggacttcgt ccagtgtctt tcgcggcagt    840
acatggtatc ggcggcggca tttacaatgg gagctgccat ggcgggcctc ctgcctgcgg    900
acttccgcgc cgtggagacg tatcctgagc atgggaggta caaccgaatg ttgagccagc    960
acctggtcaa gaggccgttc aggctgcgcc ttgcagaggt tgccgacctc cagagcctcg   1020
ttcatgtcga gagctggca tggcccaagc agatgcaggg aagcctggag gtgctccgca   1080
gacgactgga ggcgtccccc accaccaacc tggtctgcga gctggagggc agggtcgttg   1140
ccgtgcttta catgcaacgg atcgagagtc ttgccgtcct cgatgggtg cagttcatgg   1200
acgtatcgtc tgcgcactcc cccaggggtc gtctgctgca gctcatctcg atagcggtcc   1260
atccggactt tgcaggcatg aatctgggcc gcgagctgaa ggagtttggc cttcacttgg   1320
ctcggttgga cagcaccatc gagagggtca tcggtgtcac aaggtgcagc aaggagtttc   1380
ggcagtacga tggcccatg agtgagtacg tcaatgcgca cttctctggg gcccggaccg   1440
acagcacgct ggacttccac tcctccgccg gagcgcagtt cgtccgcttg gtggagggct   1500
tccgccccga ggacaccgac aacgcggca caggagtggg catcgcctac gacatcagga   1560
gggctctgcc cagggaggcg gctgcgggcg cgccccgag caggccgccg ccgaggacga   1620
aggtccctc gctgcagctg gtccaggacg tcatgaccag catcggctac cccccaacc   1680
tcaatgacct caccaagggc ttcttcgact acggcatgga ctccctggag ctcgtccgca   1740
tccgaacaa gctgagcctc gccctgcaga cggagctccc cgcgacgctg ctcctcgact   1800
tccccaccgt gcacgacctc gtggagcggc tggaccagga ccgggccccc gagtccgatg   1860
aggaggagga ggtgcgggag gaggccaagg ccacggccag agccccggcc aaggccaagg   1920
ccctggccaa tggcggcgag gcgacccagc gcttcgggcc ctcggagatc atcagcgtgc   1980
agaagcgctg cctcaacgtc tacgcccagc ccatctacca gaagcggttc acggacatgg   2040
ccaagaagtg cttcccggac atgctcaagt acatcctcgc catagagtcc atcctggtcg   2100
aggtcgaggg gccggtcctg caggagttcc agctgatcca agatctcgag tacaagtcgg   2160
tccagagagg ccgcgagaat ttgatgtact acatgtcaag ctattggctg gcccacccag   2220
```

```
agatacgcga tcagagccag cagttactcc tcctcacgct gcaggaccag tgctggggca    2280
ataaccactt gtaggctggc gctccgcggg cacctcgaat ctgcggagcc acatacgaga    2340
gtctcagtgc gaaaaaaaaa aaaaaaaaa                                      2369
```

<210> SEQ ID NO 178
<211> LENGTH: 2374
<212> TYPE: DNA
<213> ORGANISM: Alexandrium fundyense

<400> SEQUENCE: 178

```
tgcagcgatg ctactcctac tacgtcccac tgtcgtacgc accgctgatg gcccagatct      60
cgccgatcct gtttgatgat gcgggctggg ggttcactga cgcggggaca gactccttcg     120
acgacgtgga ggagcatgtt gacagaatct gaatgttgt tggcagtggc gcgcaacacc      180
ggaccctctt taaggatatg atgcgacaca tcagtaccgt gttcaagggc gaggtatttg     240
ccttgcagcc aagtttcgtt gtggacactg gctgtggcga cgggagcctg ctcatacata     300
tctatgaaca tatcaaacag cacacacccc ggggaaagt gcttgatcag ttccctctga      360
cgatggtcgg cgttgacctc aatgaggatc cgcgagtgac aacagctgtg aatctgagca     420
agcagggcgt cccgcacgtg gtcatctctg gcgatgtggg taagcctgcg agatacttg      480 ccgcgctgaa gaagaagaag gtggacgcgt cgaggacgct tcatgtccgc tccttcctag     540
accacgaccg tacttacatc ccaccggtca tgagaataga ggaagagagc agcacagcca     600
ggtttgcccg cactcagatg gcagactttg tgcatctgga caagcgtgga aagcccatca     660
cggctctgga gctgttttgca tccctggtgg aacattttga aagatgggct gatgcgctgg    720
aggtctcctt cggactgtgt gtgctggagg ttatgatgct ggatgtgccc acgacgcagc     780
gctggttcaa cgactgcgtg tccttccctc tggacttcgt ccagtgtctt tcgcggcagt    840
acatggtatc ggcggcggca tttacaatgg gagctgccat ggcgggcctc ctgcctgcgg     900
acttccgcgc cgtggagacg tatcctgagc atgggaggta caaccgaatg ttgagccagc     960
acctggtcaa gaggccgttc aggctgcgcc ttgcagaggt tgccgacctc cagagcctcg    1020
ttcatgtcga agagctggca tggcccaagc agatgcaggg aagcctggag gtgctccgca    1080
gacgactgga ggcgtccccc accaccaacc tggtctgcga gctggagggc agggtcgttg    1140 ccgtgctttta catgcaacgg atcgagagtc ttgccgtcct cgatggggtg cagttcatgg    1200
acgtatcgtc tgcgcactcc cccaggggtc gtctgctgca gctcatctcg atagcggtcc    1260
atccggactt tgcaggcatg aatctgggcc gcgagctgaa ggagtttggc cttcacttgg    1320
ctcggttgga cagcaccatc gagagggtca tcggtgtcac aaggtgcagc aaggagtttc    1380
ggcagtacga tggcccccatg agtgagtacg tcaatgcgca cttctctggg gcccggaccg    1440
acagcacgct ggacttccac tcctccgccg gagcgcagtt cgtccgcttg gtggagggct    1500
tccgccccga ggacaccgac aacgcgcgca caggagtggt catcgcctac gacatcagga    1560
gggctctgcc cagggaggcg gctgcgggcg cgccccgag caggccgccg ccgaggacga     1620
aggtcccctc gctgcagctg gtccaggacg tcatgaccag catcggctac ccccccaacc     1680
tcaatgacct caccaagggc ttcttcgact acggcatgga ctccctggag ctcgtccgca     1740
tccggaacaa gctgagcctc gccctgcaga cggagctccc cgcgacgctg ctcctcgact     1800
tccccaccgt gcacgacctc gtggagcggc tggaccagga ccgggccccc gagtccgatg    1860
aggaggagga ggtgcgggag gaggccaagg ccacggccag agccccggcc aaggccaagg    1920
```

| | |
|---|---:|
| ccctggccaa gggcggcgag gcgacccagc gcttcgggcc ctcggagatc atcagcgtgc | 1980 |
| agaagcgctg cctcaacgtc tacgcccagc ccatctacca gaagcggttc acggacatgg | 2040 |
| ccaagaagtg cttcccggac atgctcaagt acatcctcgc catagagtcc atcctggtcg | 2100 |
| aggtcgaggg gccggtcctg caggagttcc agctgatcca agatctcgag tacaagtcgg | 2160 |
| tccagagagg ccgcgagaat tgatgtact acatgtcaag ctattggctg gcccacccag | 2220 |
| agatacgcga tcagagccag cagttactcc tcctcacgct gcaggaccag tgctggggca | 2280 |
| ataaccactt gtaggctggc gctccgcggg cacctcgaat ctgcggagcc acatacgaga | 2340 |
| gtctcagtgc gaaaaaaaaa aaaaaaaaaa aaaa | 2374 |

<210> SEQ ID NO 179
<211> LENGTH: 2365
<212> TYPE: DNA
<213> ORGANISM: Alexandrium fundyense

<400> SEQUENCE: 179

| | |
|---|---:|
| tgcagcgatg ctactcctac tacgtcccac tgtcgtacgc accgctgatg gcccagatct | 60 |
| cgccgatcct gtttgatgat gcgggctggg ggttcactga cgcggggaca gactccttcg | 120 |
| acgacgtgga ggagcatgtt gacagaatct tgaatgttgt tggcagtggt gcgcaacacc | 180 |
| ggaccctctt taaggatatg atgcgacaca tcagtaccgt gttcaagggc gaggcatttg | 240 |
| ccttgcagcc aagtttcgtt gtggacactg gctgtggcga cgggagcctg ctcatacata | 300 |
| tctatgaaca tatcaaacag cacacacccc gggggaaagt gcttgatcag ttccctctga | 360 |
| cgatggtcgg cgttgacctc aatgaggatc cgcgagtgac aacagctgtg aatctgagca | 420 |
| agcagggcgt cccgcacgtg gtcatctctg gcgatgtggg taagcctgcg gagatacttg | 480 |
| ccgcgctgaa gaagaagaag gtggacgcgt cgaggacgct tcatgtccgc tccttcctag | 540 |
| accacgaccg tacttacatc ccaccggtca tgagaataga ggaagagagc agcacagcca | 600 |
| ggtttgcccg cactcagatg gcagactttg tgcatctgga caagcgtgga aagcccatca | 660 |
| cggctctgga gctgtttgca tccctggtgg aacattttga agatgggct gatgcgctgg | 720 |
| aggtctcctt cggactgtgt gtgctggagg ttatgatgct ggatgtgccc acgacgcagc | 780 |
| gctggttcaa cgactgcgtg tccttccctc tggacttcgt ccagtgtctt tcgcggcagt | 840 |
| acatggtatc ggcggcggca tttacaatgg gagctgccat ggcgggcctc ctgcctgcgg | 900 |
| acttccgcgc cgtggagacg tatcctgagc atgggaggta caaccgaatg ttgagccagc | 960 |
| acctggtcaa gaggccgttc aggctgcgcc ttgcagaggt tgccgacctc cagagcctcg | 1020 |
| ttcatgtcga agagctggca tggcccaagc agatgcaggg aagcctggag gtgctccgca | 1080 |
| gacgactgga ggcgtccccc accaccaacc tggtctgcga gctggagggc agggtcgttg | 1140 |
| ccgtgcttta catgcaacgg atcgagagtc ttgccgtcct cgatggggtg cagttcatgg | 1200 |
| acgtatcgtc tgcgcactcc cccagggtc gtctgctgca gctcatctcg atagcggtcc | 1260 |
| atccggactt tgcaggcatg aatctgggcc gcgagctgaa ggagtttggc cttcacttgg | 1320 |
| ctcggttgga cagcaccatc gagagggtca tcggtgtcac aaggtgcagc aaggagtttc | 1380 |
| ggcagtacga tggcccccatg agtgagtacg tcaatgcgca cttctctggg gcccggaccg | 1440 |
| acagcacgct ggacttccac tcctccgccg gagcgcagtt cgtccgcttg gtggagggct | 1500 |
| tccgccccga ggacaccgac aacgcgggca caggagtggt catcgcctac gacatcagga | 1560 |
| gggctctgcc cagggaggcg gctgcgggcg cgccccgag caggccgccg ccgaggacga | 1620 |
| aggtccccctc gctgcagctg gtccaggacg tcatgaccag catcggctac ccccccaacc | 1680 |

```
tcaatgacct caccaagggc ttcttcgact acggcatgga ctccctggag ctcgtccgca    1740
tccggaacaa gctgagcctc gccctgcaga cggagctccc cgcgacgctg ctcctcgact    1800
tccccaccgt gcacgacctc gtggagcggc tggaccagga ccgggccccc gagtccgatg    1860
aggaggagga ggtgcgggag gaggccaagg ccacggccag agccccggcc aaggccaagg    1920
ccctggccaa gggcggcgag gcgacccagc gcttcgggcc ctcggagatc atcagcgtgc    1980
agaagcgctg cctcaacgtc tacgcccagc ccatctacca gaagcggttc acggacatgg    2040
ccaagaagtg ctcccccggac atgctcaagt acatcctcgc catagagtcc atcctggtcg    2100
aggtcgaggg gccggtcctg caggagttcc agctgatcca agatctcgag tacaagtcgg    2160
tccagagagg ccgcgagaat ttgatgtact acatgtcaag ctattggctg cccacccag    2220 agatacgcga tcagagccag cagttactcc tcctcgcgct gcaggaccag tgctggggca    2280
ataaccactt gtaggctggc gctccgcggg cacctcgaat ctgcggagcc acatacgaga    2340
gtctcagtgc gaaaaaaaaa aaaaa                                          2365

<210> SEQ ID NO 180
<211> LENGTH: 900
<212> TYPE: DNA
<213> ORGANISM: Alexandrium fundyense

<400> SEQUENCE: 180
tgcagcgatg ctactcctac tacgtcccac tgtcgtacgc accgctgatg gcccagatct     60
cgccgatcct gtttgatgat gcgggctggg ggttcactga cgcggggaca gactccttcg    120
acgacgtgga ggagcatgtt gacagaatct tgaatgttgt tggcagtggt gcgcaacacc    180
ggaccctctt taaggatatg atgcgacaca tcagtaccgt gttcaagggc gaggcatttg    240
ccttgcagcc aagtttcgtt gtggacactg gctgtggcga cgggagcctg ctcatacata    300
tctatgaaca tatcaaacag cacacacccc gggggaaagt gcttgatcag ttccctctga    360
cgatggtcgg tgttgacctc aatgaggatc cgcgagtgac aacagctgtg aatctgagca    420
agcagggcgt cccgcacgtg gtcatctctg gcgatgtggg taagcctgcg agatacttg     480 ccgcgctgaa gaagaagaag gtggacgcgt cgaggacgct tcatgtccgc tccttcctag    540
accacgaccg tacttacatc ccaccggtca tgagaataga ggaagagagc agcacagcca    600
ggtttgcccg cactcagatg gcagactttg tgcatctgga caagcgtgga aagcccatca    660
cggctctgga gctgtttgca tccctggtgg aacattttga aagatgggct gatgcgctgg    720
aggtctcctt cggactgtgt gtgctggagg ttatgatgct ggatgtgccc acgacgcagc    780
gctggttcaa cgactgcgtg tccttccctc tggacttcgt ccagtgtctt tcgcggcagt    840
acatggtatc ggcggcggca tttacaatgg gagctgccat ggcgggcctc ctgcctgcgg    900

<210> SEQ ID NO 181
<211> LENGTH: 488
<212> TYPE: DNA
<213> ORGANISM: Alexandrium fundyense

<400> SEQUENCE: 181
tgcagcgatg ctactcctac tacgtcccac tgtcgtacgc accgctgatg gcccagatct     60
cgccgatcct gtttgatgat gcgggctggg ggttcactga cgcggggaca gactccttcg    120
acgacgtgga ggagcatgtt gacagaatct tgaatgttgt tggcagtggt gcgcaacacc    180
ggaccctctt taaggatatg atgcgacaca tcagtaccgt gttcaagggc gaggcatttg    240
```

| | |
|---|---|
| ccttgcagcc aagtttcgtt gtggacactg gctgtggcga cgggagcctg ctcatacata | 300 |
| tctatgaaca tatcaaacag cacacacccc gggggaaagt gcttgatcag ttccctctga | 360 |
| cgatggtcgg cgttgacctc aatgaggatc cgcgagtgac aacagctgtg aatctgagca | 420 |
| agcagggcgt cccgcacgtg gtcatctctg gcgatgtggg taagcctgcg agatacttg | 480 |
| ccgcgctg | 488 |

<210> SEQ ID NO 182
<211> LENGTH: 486
<212> TYPE: DNA
<213> ORGANISM: Alexandrium fundyense

<400> SEQUENCE: 182

| | |
|---|---|
| tgcagcgatg ctactcctac tacgtcccac tgtcgtacgc accgctgatg gcccagatct | 60 |
| cgccgatcct gtttgatgat gcgggctggg ggttcactga cgcggggaca gactccttcg | 120 |
| acgacgtgga ggagcatgtt gacagaatct tgaatgttgt tggcagtggt gcgcaacacc | 180 |
| ggaccctctt taaggatatg atgcgacaca tcagtaccgt gttcaagggc gaggcatttg | 240 |
| ccttgcagcc aagtttcgtt gtggacactg gctgtggcga cgggagcctg ctcatacata | 300 |
| tctatgaaca tatcaaacag cacacacccc gggggaaagt gcttgatcag ttccctctga | 360 |
| cgatggtcgg tgttgacctc aatgaggatc cgcgagtgac aacagctgtg aatctgagca | 420 |
| agcagggcgt cccgcacgtg gtcatctctg gcgatgtggg taagcctgcg agatacttg | 480 |
| ccgcgc | 486 |

<210> SEQ ID NO 183
<211> LENGTH: 365
<212> TYPE: DNA
<213> ORGANISM: Alexandrium fundyense

<400> SEQUENCE: 183

| | |
|---|---|
| cactgacgcg gggacagact ccttcgacga cgtggaggag catgttgaca gaatcttgaa | 60 |
| tgttgttggc agtggtgcgc aacaccggac cctctttaag gatatgatgc gacacatcag | 120 |
| taccgtgttc aagggcgagg catttgcctt gcagccaagt tcgttgtgg acactggctg | 180 |
| tggcgacggg agcctgctca tacatatcta tgaacatatc aaacagcaca caccccgggg | 240 |
| gaaagtgctt gatcagttcc ctctgacgat ggtcggcgtt gacctcaatg aggatccgcg | 300 |
| agtgacaaca gctgtgaatc tgagcaagca gggcgtcccg cacgtggtca tctctggcga | 360 |
| tgtgg | 365 |

<210> SEQ ID NO 184
<211> LENGTH: 2244
<212> TYPE: DNA
<213> ORGANISM: Alexandrium fundyense

<400> SEQUENCE: 184

| | |
|---|---|
| cgtggaggag catgttgaca gaatcttgaa tgttgttggc agtggtgcgc acaccggac | 60 |
| cctctttaag gatatgatgc gacgcatcag taccgtgttc aagggcgagg catttgcctt | 120 |
| gcagccaagt ttcgttgtgg acactggctg tggcgacggg agcctgctca tacatatcta | 180 |
| tgaacatatc aaacagcaca caccccgggg gaaagtgctt gatcagttcc ctctgacgat | 240 |
| ggtcggcgtt gacctcaatg aggatccgcg agtgacaaca gctgtgaatc tgagcaagca | 300 |
| gggcgtcccg cacgtggtca tctctggcga tgtgggtaag cctgcggaga tacttgccgc | 360 |
| gctgaagaag aagaaggtgg acgcgtcgag gaagcttcat gtccgctcct tcctagacca | 420 |

```
cgaccgtact tacatcccac cggtcatgag aatagaggaa gagagcagca cagccaggtt    480
tgcccgcact cagatggcag actttgtgca tctggacaag cgtggaaagc ccatcacggc    540
tctggagctg tttgcatccc tggtggaaca ttttgaaaga tgggctgatg cgctggaggt    600
ctccttcgga ctgtgtgtgc tggaggttat gatgctggat gtgccacga cgcagcgctg    660 gttcaacgac tgcgtgtcct tccctctgga cttcgtccag tgtctttcgc ggcagtacat    720
ggtatcggcg gcggcattta caatgggagc tgccatggcg ggcctcctgc ctgcggactt    780
ccgcgccgtg gagacgtatc ctgagcatgg gaggtacaac gaatgttga ccagcacct    840 ggtcaagagg ccgttcaggc tgcgccttgc agaggttgcc gacctccaga gcctcgttca    900
tgtcgaagag ctggcatggc ccaagcagat tcagggaagc ctggaggtgc tccgcagacg    960
actggaggcg tcccccacca ccaacctggt ctgcgagctg gagggcaggg tcgttgccgt    1020
gctttacatg caacggatcg agagtcttgc cgtcctcgat ggggtgcagt tcatggacgt    1080
atcgtctgcg cactccccca ggggtcgtct gctgcagctc atctcgatag cggtccatcc    1140
ggactttgca ggcatgaatc tgggccgcga gctgaaggag tttggccttc acttggctcg    1200
gttggacagc accatcgaga gggtcatcgg tgtcacaagg tgcagcaagg agtttcggca    1260
gtacgatggc cccatgagtg agtacgtcaa tgcgcacttc tctggggccc ggaccgacag    1320
cacgctggac ttccactcct ccgccggagc gcagttcgtc cgcttggtgg agggcttccg    1380
ccccgaggac accgacaacg gcggcacagg agtggtcatc gcctacgaca tcaggagggc    1440
tctgcccagg gaggcggctg cgggcgcgcc cccgagcagg ccgccgccga ggacgaaggt    1500
cccctcgctg cagctggtcc aggacgtcat gaccagcatc ggctacccc ccaacctcaa    1560 tgacctcacc aagggcttct tcgactacgg catggactcc ctggagctcg tccgcatccg    1620
gaacaagctg agcctcgccc tgcagacgga gctccccgcg acgctgctcc tcgacttccc    1680
caccgtgcac gacctcgtgg agcggctgga ccaggaccgg gccccgagt ccgatgagga    1740 ggaggaggtg cgggaggagg ccaaggccac ggccagagcc ccggccaagg ccaaggccct    1800
ggccaagggc ggcgaggcga cccagcgctt cgggccctcg gagatcatca gcgtgcagaa    1860
gcgctgcctc aacgtctacg cccagcccat ctaccagaag cggttcacgg acatggccaa    1920
gaagtgcttc ccggacatgc tcaagtacat cctcgccata gagtccatcc tggtcgaggt    1980
cgaggggccg gtcctgcagg agttccagct gatccaagat ctcgagtaca agtcggtcca    2040
gagaggccgc gagaatttga tgtactacat gtcaagctat tggctggccc acccagagat    2100
acgcgatcag agccagcagt tactcctcct cacgctgcag gaccaatgct ggggcaataa    2160
ccacttgtag gctggcgctc cgcgggcacc tcgaatctgc ggagccacat acgagagtct    2220
cagtgcgaaa gttcatgaaa aaaa                                          2244
```

<210> SEQ ID NO 185
<211> LENGTH: 2243
<212> TYPE: DNA
<213> ORGANISM: Alexandrium fundyense

<400> SEQUENCE: 185

```
cgtggaggag catgttgaca gaatcttgaa tgttgttggc agtggtgcgc aacaccggac     60
cctctttaag gatatgatgc gacacatcag taccgtgttc aagggcgagg catttgcctt    120
gcagccaagt ttcgttgtgg acactggctg tggcgacggg agcctgctca tacatatcta    180
tgaacatatc aaacagcaca caccccgggg gaaagtgctt gatcagttcc ctctgacgat    240
```

```
ggtcggcgtt gacctcaatg aggatccgcg agtgacaaca gctgtgaatc tgagcaagca      300
gggcgtcccg cacgtggtca tctctggcga tgtgggtaag cctgcggaga tacttgccgc      360
gctgaagaag aagaaggtgg acgcgtcgag gacgcttcat gtccgctcct tcctagacca      420
cgaccgtact tacatcccac cggtcatgag aatagaggaa gagagcagca cagccaggtt      480
tgcccgcact cagatggcag actttgtgca tctggacaag cgtggaaagc ccatcacggc      540
tctggagctg tttgcatccc tggtggaaca ttttgaaaga tgggctgatg cgctggaggt      600
ctccttcgga ctgtgtgtgc tggaggttat gatgctggat gtgcccacga cgcagcgctg      660
gttcaacgac tgcgtgtcct tccctctgga cttcgtccag tgtctttcgc ggcagtacat      720
ggtatcggcg gcggcattta caatgggagc tgccatggcg ggcctcctgc ctgcggactt      780
ccgcgccgtg gagacgtatc ctgagcatgg gaggtacaac cgaatgttga gccagcacct      840
ggtcaagagg ccgttcaggc tgcgccttgc agaggttgcc gacctccaga gcctcgttca      900
tgtcgaagag ctggcatggc ccaagcagat gcagggaagc ctggaggtgc tccgcagacg      960
actggaggcg tcccccacca ccaacctggt ctgcgagctg gagggcaggg tcgttgccgt     1020
gctttacatg caacggatcg agagtcttgc cgtcctcgat ggggtgcagt tcatggacgt     1080
atcgtctgcg cactccccca ggggtcgtct gctgcagctc atctcgatag cggtccatcc     1140
ggactttgca ggcatgaatc tgggccgcga gctgtaggag tttggccttc acttggctcg     1200
gttggacagc accatcgaga gggtcatcgg tgtcacaagg tgcagcaagg agtttcggca     1260
gtacgatggc cccatgagtg agtacgtcaa tgcgcacttc tctggggccc ggaccgacag     1320
cacgctggac ttccactcct ccgccggagc gcagttcgtc cgcttggtgg agggcttccg     1380
ccccgaggac accgacaacg gcggcacagg agtggtcatc gcctacgaca tcaggagggc     1440
tctgcccagg gaggcggctg cgggcgcgcc cccgagcagg ccgccgccga ggacgaaggt     1500
cccctcgctg cagctggtcc aggacgtcat gaccagcatc ggctacccc ccaacctcaa     1560 tgacctcacc aagggcttct tcgactacg catggactcc ctggagctcg tccgcatccg     1620
gaacaagctg agcctcgccc tgcagacgga gctccccgcg acgctgctcc tcgacttccc     1680
caccgtgcac gacctcgtgg agcggctgga ccaggaccgg gcccccgagt ccgatgagga     1740
ggaggaggtg cgggaggagg ccaaggccac ggccagagcc ccggccaagg ccaaggccct     1800
ggccaagggc ggcgaggcga cccagcgctt cgggcccctcg agatcatca gcgtgcagaa     1860 gcgctgcctc aacgtctacg cccagcccat ctaccagaag cggttcacgg acatggccaa     1920
gaagtgcttc ccggacatgc tcaagtacat cctcgcccata gagtccatcc tggtcgaggt     1980
cgaggggccg gtcctgcagg agttccagct gatccaagat ctcgagtaca agtcggtcca     2040
gagaggccgc gagaatttga tgtactacat gtcaagctat tggctggccc acccagagat     2100
acgcgatcag agccagcagt tactcctcct cacgctgcag gaccagtgct ggggcaataa     2160
ccacttgtag gctggcgctc cgcgggcacc tcgaatctgc ggagccacat acgagagtct     2220
cagtgcgaaa aaaaaaaaaa aaa                                             2243

<210> SEQ ID NO 186
<211> LENGTH: 2238
<212> TYPE: DNA
<213> ORGANISM: Alexandrium fundyense

<400> SEQUENCE: 186
cgtggaggag catgttgaca gaatcttgaa tgttgttggc agtggtgcgc aacaccggac       60
cctctttaag gatatgatgc gacacatcag taccgtgttc aagggcgagg cgtttgcctt      120
```

-continued

```
gcagccaagt tcgttgtgg acactggctg tggcgacggg agcctgctca tacatatcta      180
tgaacatatc aaacagcaca cacccgggg gaaagtgctt gatcagttcc ctctgacgat      240
ggtcggcgtt gacctcaatg aggatccgcg agtgacaaca gctgtgaatc tgagcaagca      300
gggcgtcccg cacgtggtca tctctggcga tgtgggtaag cctgcggaga tacttgccgc      360
gctgaagaag aagaaggtgg acgcgtcgag gacgcttcat gtccgcccct cctagacca      420 cgaccgtact tacatcccac cggtcatgag aatagaggaa gagagcagca cagccaggtt      480
tgcccgcact cagatggcag actttgtgca tctggacaag cgtggaaagc ccatcacggc      540
tctggagctg tttgcatccc tggtggaaca ttttgaaaga tgggctgatg cgctggaggt      600
ctccttcgga ctgtgtgtgc tggaggttat gatgctggat gtgcccacga cgcagcgctg      660
gttcaacgac tgcgtgtcct ccctctgga cttcgtccag tgtctttcgc ggcagtacat      720
ggtatcggcg gcggcattta caatgggagc tgccatggcg ggcctcctgc ctgcggactt      780
ccgcgccgtg gagacgtatc ctgagcatgg gaggtacaac cgaatgttga ccagcacct      840 ggtcaagagg ccgttcaggc tgcgccttgc agaggttgcc gacctccaga gcctcgttca      900
tgtcgaagag ctggcatggc ccaagcagat gcagggaagc ctggaggtgc tccgcagacg      960
actggaggcg tcccccacca ccaacctggt ctgcgagctg gagggcaggg tcgttgccgt     1020
gctttacatg caacggatcg agagtcttgc cgtcctcgat ggggtgcagt tcatggacgt     1080
atcgtctgcg cactccccca ggggtcgtct gctgcagctc atctcgatag cggtccatcc     1140
ggactttgca ggcatgaatc tgggccgcga gctgaaggag tttggccttc acttggctcg     1200
gttggacagc accatcgaga gggtcatcgg tgtcacaagg tgcagcaagg agtttcggca     1260
gtacgatggc cccatgagtg agtacgtcaa tgcgcacttc tctggggccc ggaccgacag     1320
cacgctggac ttccactcct ccgccggagc gcagttcgtc cgcttggtgg agggcttccg     1380
ccccgaggac accgacaacg gcggcacagg agtggtcatc gcctacgaca tcaggagggc     1440
tctgcccagg gaggtggctg cgggcgcgcc cccgagcagg ccgccgccga ggacgaaggt     1500
cccctcgctg cagctggtcc aggacgtcat gaccagcatc ggctaccccc ccaacctcaa     1560
tgacctcacc aagggcttct tcgactacg catggactcc ctggagcccg tccgcatccg     1620
gaacaagctg agcctcgccc tgcagacgga gctccccgcg acgctgctcc tcgacttccc     1680
caccgtgcac gacctcgtgg agcggctgga ccaggaccgg gcccccgagt ccgatgagga     1740
ggaggaggtg cgggaggagg ccaaggccac ggccagagcc ccggccaagg ccaaggccct     1800
ggccaagggc ggcgaggcga cccagcgctt cgggtcctcg gagatcatca gcgtgcagaa     1860
gcgctgcctc aacgtctacg cccagcccat ctaccagaag cggttcacgg acatggccaa     1920
gaagtgcttc ccggacatgc tcaagtacat cctcgccata gagtccatcc tggtcgaggt     1980
cgaggggccg gtcctgcagg agttccagtt gatccaagat ctcgagtaca agtcggtcca     2040
gagaggccgc gagaatttga tgtactacat gtcaagccat ggctggccc acccagagat     2100 acgcgatcag agccagcagt tactcctcct cacgctgcag accagtgctg ggcaataac      2160 cacttgtagg ctggcgctcc gcgggcacct cgaatctgcg gagccacata cgagagtctc     2220
agtgcgaaaa aaaaaaaa                                                   2238
```

<210> SEQ ID NO 187
<211> LENGTH: 295
<212> TYPE: DNA
<213> ORGANISM: Alexandrium fundyense

<400> SEQUENCE: 187

```
cgtggaggag catgttgaca gaatcttgaa tgttgttggc agtggtgcgc aacaccggac      60
cctctttaag gatatgatgc gacacatcag taccgtgttc aagggcgagg catttgcctt     120
gcagccaatt ttcgttgtgg acactggctg tggcgacggg agcctgctca tacatatcta     180
tgaacatatc aaacagcaca caccccgggg gaaagtgctt gatcagttcc ctctgacgat     240
ggtcggcgtt gacctcaatg aggatccgcg agtgacaaca gctgtgaatc taagc          295
```

<210> SEQ ID NO 188
<211> LENGTH: 315
<212> TYPE: DNA
<213> ORGANISM: Alexandrium fundyense

<400> SEQUENCE: 188

```
gaatcttgaa tgttgttggc agtggtgcgc aacaccggac cctctttaag gatatgatgc      60
gacacatcag taccgtgttc aagggcgggg catttgcctt gcagccaagt ttcgttgtgg     120
acactggctg tggcgacggg agcctgctca tacatatcta tgaacatatc aaacagcaca     180
caccccgggg gaaagtgctt gatcagttcc ctctgacgat ggtcggcgtt gacctcaatg     240
aggatccgcg ggtgacaaca gctgtgaatc tgagcaagca gggcgtcccg cacgtggtca     300
tctctggcga tgtgg                                                      315
```

<210> SEQ ID NO 189
<211> LENGTH: 293
<212> TYPE: DNA
<213> ORGANISM: Alexandrium fundyense

<400> SEQUENCE: 189

```
tggtgcgcaa caccggaccc tctttaagga tatgatgcga cacatcagta ccgtgttcaa      60
gggcgaggca tttgccttgc agccaagttt cgttgtggac actggctgtg gcgacgggag     120
cctgctcata catatctatg aacatatcaa acagcacaca ccccggggga agtgcttga      180
tcagttccct ctgacgatgg tcggcgttga cctcaatgag gatccgcgag tgacaacagc     240
tgtgaatctg agcaagcagg gcgtcccgca cgtggtcatc tctggcgatg tgg            293
```

<210> SEQ ID NO 190
<211> LENGTH: 293
<212> TYPE: DNA
<213> ORGANISM: Alexandrium fundyense

<400> SEQUENCE: 190

```
tggtgcgcaa caccggaccc tctttaagga tatgatgcga cacatcagta ccgtgttcaa      60
gggcgaggca tttgccttgc agccaagttt cgttgtggac actggctgtg gcgacgggag     120
cctgctcata catatctatg aacatatcaa acagcacaca ccccggggga aagtgcttga     180
tcagttccct ctgacgatgg tcggcgttga cctcaatgag gatccgcgag tgacaacggc     240
tgtggatctg agcaagcagg gcgtcccgca cgtggtcatc tctggcgatg tgg            293
```

<210> SEQ ID NO 191
<211> LENGTH: 282
<212> TYPE: DNA
<213> ORGANISM: Alexandrium fundyense

<400> SEQUENCE: 191

```
accggaccct ctttaaggat atgatgcgac acatcagtac cgtgttcaag gcgaggcat      60
ttgccttgca gccaagtttc gttgtggaca ctagctgtgg cgacgggagc ctgctcatac     120
```

```
atatctatga acatatcaaa cagcacacac cccgggggaa agtgcttgat cagttccctc    180
tgacgatggt cgacgttgac ctcaatgagg atccgcgagt gacaacagct gtgaatctga    240
gcaagcaggg cgtcccgcac gtggtcatct ctggcgatgt gg                      282

<210> SEQ ID NO 192
<211> LENGTH: 961
<212> TYPE: DNA
<213> ORGANISM: Alexandrium fundyense

<400> SEQUENCE: 192
gagtgagtac gtcaatgcgc acttctctgg ggcccggacc gacagcacgc tggacttcca     60
ctcctccgcc ggagcgcagt tcttccgctt ggtggagggc ttccgccccg aggacaccga    120
caacggcggc acaggagtgg tcatcgccta cgacatcagg agggctctgc ccagggaggc    180
ggctgcgggc gcgcccccga gcaggccgcc gccgaggacg aaggtcccct cgctgcagct    240
ggtccaggac gtcatgacca gcatcggcta cccccccaac ctcaatgacc tcaccaaggg    300
cttcttcgac tacggcatgg actccctgga gctcgtccgc atccggaaca agctgagcct    360
cgccctgcag acggagctcc ccgcgacgct gctcctcgac ttccccaccg tgcacgacct    420
cgtggagcgg ctggaccagg accgggcccc cgagtccgat gaggaggagg aggtacggga    480
ggaggccaag gccacggcca gaccccggc caaggcaag gccctggcca agggcggcga    540
ggcgacccag cgcttcgggc cctcggagat catcagcgtg cagaagcgct gcctcaacgt    600
ctacgcccag cccatctacc agaagcggtt cacggacatg ccaagaagt gcttcccgga    660 catgctcaag tacatcctcg ccatagagtc catcctggtc gaggtcgagg ggccggtcct    720
gcaggagttc cagctgatcc aagatctcga gtacaagtcg gtccagagag gccgcgagaa    780
tttgatgtac tacatgtcaa gctattggct ggccccaccca gagatacgcg atcagagcca    840
gcagttactc ctcctcacgc tgcagaccag tgctggggcc ataaccactt gtaggctggc    900
gctccgcggg cacctcgaat ctgcggagcc acatacgaga gtctcagtgc gaaaaaaaaa    960
a                                                                    961

<210> SEQ ID NO 193
<211> LENGTH: 975
<212> TYPE: DNA
<213> ORGANISM: Alexandrium fundyense

<400> SEQUENCE: 193
agtgagtacg tcaatgcgca cttctctggg gcccggaccg acagcacgct ggacttccac     60
tcctccgccg gagcgcagtt cgtccgcttg gtggagggct tccgccccga ggacaccgac    120
aacggcggca caggagtggt catcgcctac gacatcagga gggctctgcc cagggaggcg    180
gctgcgggcg cgcccccgag caggccgccg ccgaggacga aggtcccctc gctgcagctg    240
gtccaggacg tcatgaccag catcggctac ccccccaacc tcaatgacct caccaagggc    300
ttcttcgact acggcatgga ctccctggag ctcgtccgca tccggaacaa gctgagcctc    360
gccctgcaga cggagctccc cgcgacgctg ctcctcgact tccccaccgt gcacgacctc    420
gtggagcggc tggaccagga ccgggccccc gagtccgatg aggaggagga ggtgcgggag    480
gaggccaagg ccacggccag agccccggcc aaggccaagg ccctggccaa gggcggcgag    540
gcgacccagc gcttcgggcc ctcggagatc atcagcgtgc agaagcgctg cctcaacgtc    600
tacgcccagc ccatctacca gaagcggttc acggacatgc caagaagtg cttcccggac    660
```

```
atgctcaagt acatcctcgc catagagtcc atcctggtcg aggtcgaggg gccggtcctg    720
caggagttcc agctgatcca agatctcgag tacaagtcgg tccagagagg ccgcgagaat    780
ttgatgtact acatgtcaag ctattggctg gcccacccag agatacgcga tcagagccag    840
cagttactcc tcctcacgct gcaggaccag tgctggggca ataaccactt gtaggctggc    900
gctccgcggg cacctcgaat ctgcggagcc acatacgaga gtcccagtgc gaaaaaaaca    960
caaaaaaaaa aaaaa                                                    975
```

<210> SEQ ID NO 194
<211> LENGTH: 966
<212> TYPE: DNA
<213> ORGANISM: Alexandrium fundyense

<400> SEQUENCE: 194

```
agtgagtacg tcaatgcgca cttctctggg gcccggaccg acagcacgct ggacttccac     60
tcctccgccg gagcgcagtt cgtccgcttg gtgagggct tccgcccga ggacaccgac      120 aacggcggca caggagtggt catcgcctac gacatcagga gggctctgcc cagggaggcg    180
gctgcgggcg cgcccccgag caggccgccg ccgaggacga aggtcccctc gctgcagctg    240
gtccaggacg tcatgaccag catcggctac cccccccaacc tcaatgacct caccaagggc    300
ttcttcgact acggcatgga ctccctggag ctcgtccgca tctggaacaa gctgagcctc    360
gccctgcaga cggagctccc cgcgacgctg ctcctcgact cccccaccgt gcacgacctc    420
gtggagcggc tggaccagga ccgggccccc gagtccgatg aggaggagga ggtgcgggag    480
gaggccaagg ccacgccag agccccgccc aaggccaagg ccctggccaa gggcggcgag    540
gcgacccagc gcttcgggcc ctcggagatc atcagcgtgc agaagcgctg cctcaacgtc    600
tacgcccagc ccatctacca gaagcggttc acggacatgg ccaagaagtg cttcccggac    660
atgctcaagt acatcctcgc catagagtcc atcctggtcg aggtcgaggg gccggtcctg    720
caggagttcc agctgatcca agatctcgag tacaagtcgg tccagagagg ccgcgagaat    780
ttgatgtact acatgtcaag ctattggctg gcccacccag agatacgcga tcagagccag    840
cagttactcc tcctcacgct gcagaccagt gctggggcaa taaccacttg taggctggcg    900
ctccgcgggc acctcgaatc tgcggagcca catacgagag tctcagtgcg aaaaaaaaaa    960
aaaaaa                                                              966
```

<210> SEQ ID NO 195
<211> LENGTH: 350
<212> TYPE: DNA
<213> ORGANISM: Alexandrium fundyense

<400> SEQUENCE: 195

```
gcggttcacg gacatggcca agaagtgctt cccggacatg ctcaagtaca tcctcgccat     60
agagtccatc ctggtcgagg tcgaggggcc ggtcctgcag gagttccagc tgatccaaga    120
tctcgagtac aagtcggtcc agagaggccg cgagaatttg atgtactaca tgtcaagcta    180
ttggctggcc cacccagaga tacgcgatca gagccagcag ttactcctcc tcacgctgca    240
ggaccagtgc tggggcaata accacttgta ggctggcgct ccgcgggcac ctcgaatctg    300
cggagccaca tacgagagtc tcagtgcgaa aaaaaaaaa aaaaaaaaa                 350
```

<210> SEQ ID NO 196
<211> LENGTH: 358
<212> TYPE: DNA
<213> ORGANISM: Alexandrium fundyense

<400> SEQUENCE: 196

```
gcggttcacg gacatggcca agaagtgctt cccggacatg ctcaagtaca tcctcgccat    60
agagtccatc ctggtcgagg tcgaggggcc ggtcctgcag gagttccagc tgatccaaga   120
tctcgagtac aagtcggtcc agagaggccg cgagaatttg atgtactaca tgtcaagcta   180
ttggctggcc cacccagaga tacgcgatca gagccagcag ttactcctcc tcacgctgca   240
ggaccagtgc tggggcaata accacttgta ggctggcgct ccgcgggcac ctcgaatctg   300
cggagccaca tacgagagtc ccagtgcgaa aaaaaaaaaa aaaaaaaaaa aaaaaaa      358
```

<210> SEQ ID NO 197
<211> LENGTH: 344
<212> TYPE: DNA
<213> ORGANISM: Alexandrium fundyense

<400> SEQUENCE: 197

```
gcggttcacg gacatggcca agaagtgctt cccggacatg ctcaagtaca tcctcgccat    60
agagtccatc ctggtcgagg tcgaggggcc ggtcctgcag gagttccagc tgatccaaga   120
tctcgagtac aagtcggtcc agagaggccg cgagaatttg atgtactaca tgtcaagcta   180
ttggctggcc cacccagaga tacgcgatca gagccagcag ttactcctcc tcacgctgca   240
ggaccagtgc tggggccata accacttgta ggctggcgct ccgcgggcac ctcgaatctg   300
cggagccaca tacgagagtc tcagtgcgaa aaaaaaaaaa aaaa                    344
```

<210> SEQ ID NO 198
<211> LENGTH: 20
<212> TYPE: DNA
<213> ORGANISM: Artificial Sequence
<220> FEATURE:
<223> OTHER INFORMATION: Primer sequence

<400> SEQUENCE: 198

```
ctgagcaagg cgttcaattc                                                20
```

<210> SEQ ID NO 199
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (8)..(8)
<223> OTHER INFORMATION: 'm'= a or c
<220> FEATURE:
<221> NAME/KEY: misc_feature
<222> LOCATION: (19)..(19)
<223> OTHER INFORMATION: 'r'= g or a

<400> SEQUENCE: 199

```
tacagatmgg ccctgtgarc                                                20
```

<210> SEQ ID NO 200
<211> LENGTH: 23
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (8)..(8)
<223> OTHER INFORMATION: 'm'= a or c

```
<400> SEQUENCE: 200
tgcagcgmtg ctactcctac tac                                          23

<210> SEQ ID NO 201
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (11)..(11)
<223> OTHER INFORMATION: 'y'= t or c

<400> SEQUENCE: 201
ggtcgtggtc yaggaaggag                                              20

<210> SEQ ID NO 202
<211> LENGTH: 22
<212> TYPE: DNA
<213> ORGANISM: Artificial Sequence
<220> FEATURE:
<223> OTHER INFORMATION: Primer sequence

<400> SEQUENCE: 202
atgctcaaca tgggagtcat cc                                           22

<210> SEQ ID NO 203
<211> LENGTH: 23
<212> TYPE: DNA
<213> ORGANISM: Artificial Sequence
<220> FEATURE:
<223> OTHER INFORMATION: Primer sequence

<400> SEQUENCE: 203
gggtccagta gatgttgacg atg                                          23

<210> SEQ ID NO 204
<211> LENGTH: 23
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (15)..(15)
<223> OTHER INFORMATION: 'k' = g or t

<400> SEQUENCE: 204
gtagtaggag tagckacgct gca                                          23

<210> SEQ ID NO 205
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (10)..(10)
<223> OTHER INFORMATION: 'r'= g or a

<400> SEQUENCE: 205
ctccttcctr gaccacgacc                                              20

<210> SEQ ID NO 206
<211> LENGTH: 22
```

```
<212> TYPE: DNA
<213> ORGANISM: Artificial Sequence
<220> FEATURE:
<223> OTHER INFORMATION: Primer sequence

<400> SEQUENCE: 206
ggatgactcc catgttgagc at                                              22

<210> SEQ ID NO 207
<211> LENGTH: 23
<212> TYPE: DNA
<213> ORGANISM: Artificial Sequence
<220> FEATURE:
<223> OTHER INFORMATION: Primer sequence

<400> SEQUENCE: 207
catcgtcaac atctactgga ccc                                             23

<210> SEQ ID NO 208
<211> LENGTH: 23
<212> TYPE: DNA
<213> ORGANISM: Artificial Sequence
<220> FEATURE:
<223> OTHER INFORMATION: Primer sequence

<400> SEQUENCE: 208
ggcaagtatc tccgcaggct tac                                             23

<210> SEQ ID NO 209
<211> LENGTH: 25
<212> TYPE: DNA
<213> ORGANISM: Artificial Sequence
<220> FEATURE:
<223> OTHER INFORMATION: Primer sequence

<400> SEQUENCE: 209
cgtggaggag catgttgaca gaatc                                           25

<210> SEQ ID NO 210
<211> LENGTH: 24
<212> TYPE: DNA
<213> ORGANISM: Artificial Sequence
<220> FEATURE:
<223> OTHER INFORMATION: Primer sequence

<400> SEQUENCE: 210
actcgacagg ccggcagtac agat                                            24

<210> SEQ ID NO 211
<211> LENGTH: 18
<212> TYPE: DNA
<213> ORGANISM: Artificial Sequence
<220> FEATURE:
<223> OTHER INFORMATION: Primer sequence

<400> SEQUENCE: 211
tgagcaggca cgcagtcc                                                   18

<210> SEQ ID NO 212
<211> LENGTH: 25
<212> TYPE: DNA
<213> ORGANISM: Artificial Sequence
<220> FEATURE:
<223> OTHER INFORMATION: Primer sequence

<400> SEQUENCE: 212
```

```
ggctcgtatg ttgtgtggaa ttgtg                                           25
```

<210> SEQ ID NO 213
<211> LENGTH: 24
<212> TYPE: DNA
<213> ORGANISM: Artificial Sequence
<220> FEATURE:
<223> OTHER INFORMATION: Primer sequence

<400> SEQUENCE: 213

```
agtcacgacg ttgtaaaacg acgg                                            24
```

<210> SEQ ID NO 214
<211> LENGTH: 10
<212> TYPE: PRT
<213> ORGANISM: Alexandrium fundyense

<400> SEQUENCE: 214

Val Asp Thr Gly Cys Gly Asp Gly Ser Leu
1               5                   10

<210> SEQ ID NO 215
<211> LENGTH: 10
<212> TYPE: PRT
<213> ORGANISM: Alexandrium fundyense

<400> SEQUENCE: 215

Val Asp Ala Ser Arg Thr Leu His Val Arg
1               5                   10

<210> SEQ ID NO 216
<211> LENGTH: 10
<212> TYPE: PRT
<213> ORGANISM: Alexandrium fundyense

<400> SEQUENCE: 216

Leu Glu Val Ser Phe Gly Leu Cys Val Leu
1               5                   10

<210> SEQ ID NO 217
<211> LENGTH: 9
<212> TYPE: PRT
<213> ORGANISM: Alexandrium fundyense

<400> SEQUENCE: 217

Val Val Asp Thr Gly Cys Gly Asp Gly
1               5

<210> SEQ ID NO 218
<211> LENGTH: 9
<212> TYPE: PRT
<213> ORGANISM: Alexandrium fundyense

<400> SEQUENCE: 218

Val Asp Pro Ser Arg Ser Leu His Val
1               5

<210> SEQ ID NO 219
<211> LENGTH: 10
<212> TYPE: PRT
<213> ORGANISM: Alexandrium fundyense

<400> SEQUENCE: 219

Leu Gln Gly Ser Phe Gly Leu Cys Met Leu
1               5                   10

```
<210> SEQ ID NO 220
<211> LENGTH: 27
<212> TYPE: DNA
<213> ORGANISM: Artificial Sequence
<220> FEATURE:
<223> OTHER INFORMATION: Primer sequence

<400> SEQUENCE: 220
ttgatcctgc cagtagtcat atgcttg                                         27

<210> SEQ ID NO 221
<211> LENGTH: 24
<212> TYPE: DNA
<213> ORGANISM: Artificial Sequence
<220> FEATURE:
<223> OTHER INFORMATION: Primer sequence

<400> SEQUENCE: 221
ccttgttacg acttctcctt cctc                                            24

<210> SEQ ID NO 222
<211> LENGTH: 20
<212> TYPE: DNA
<213> ORGANISM: Artificial Sequence
<220> FEATURE:
<223> OTHER INFORMATION: Primer sequence

<400> SEQUENCE: 222
cctcagtgag attgtagtgc                                                 20

<210> SEQ ID NO 223
<211> LENGTH: 22
<212> TYPE: DNA
<213> ORGANISM: Artificial Sequence
<220> FEATURE:
<223> OTHER INFORMATION: Primer sequence

<400> SEQUENCE: 223
gtgcaaaggt aatcaaatgt cc                                              22

<210> SEQ ID NO 224
<211> LENGTH: 769
<212> TYPE: DNA
<213> ORGANISM: Alexandrium tamarense

<400> SEQUENCE: 224
gcgggttcct cctcctgtac ataaacgccc acgactgcgt gcagacggcc gccaggctct     60
gcaagaaggg cgccaccgtg gtgcgcctga agcacaacga cacggaacag cccgagcaca    120
tgctctcgtc gatcccgcag ggggccgaca tcacctacgt gtgcgacggc gtgtactcca    180
cggacgaaga gctcgccgac ttgcccgcca tatgtgcttg tttgaggccg cgcggggcca    240
agatactcgt agacgactcg catggctgcg gcgttcttgg ccgcaacccc aactcggagc    300 aaccctcgg gtatggtggc ggcggcgtca tcgagtactt cgggctggac tacgcggaga    360
acaacatcat ctacgccggg cagctgagca aggcgttcaa ttcgcccggc ggattcgtca    420
gctgtgcgcg cgagaccgac aaaaatttcg gcgttctgaa cttggccaaa aactcgaaca    480
cactcgtgtt cacagggccg atctgtactg ccggcctgtc gagtgcgaaa caaccttcg     540 acctcaacgc cgccgagggg gaccttcaac gcaagcggct tctggcggct accctcgaaa    600
ttctgcgagg ggctcaaggc gctcgggtgc ccccacacct accacgagtg ccccatcgtc    660
```

```
aatacggggg gggaacacac aagctacgca agcgcttctg ggtgagccat aggcgctccc    720
gtggcccaca aatataacag gaaaccaccg cccacttctc tgctattca                769

<210> SEQ ID NO 225
<211> LENGTH: 558
<212> TYPE: DNA
<213> ORGANISM: Alexandrium catenella

<400> SEQUENCE: 225
ttggtcgtgg tccaggaagg agcgcacgtg gagggccttg gtagggtcca ccccctccg     60 tccgaggacc tccatgatgt cggcgggctc gccgacgtcc ccgaacagca ccaggagagg   120
gaccgcgtgc cggctcaggt tgagctccgt cgccacctcg agagtccttg ttgaagtcaa   180
cgccgaccat ggtgagcgga tgctcgctcg agcgtcctcc ccgcgcggcg tgttgctctt   240
cacgtgctcg tagatgcgcc tgagcaaacg cccgtcgccg caccccagtg tccacgacga   300
acgccggctg cgacgcgaag tccccgcccg cgaagaccga gtcaatcagc cgcacgaggt   360
ccgggaagaa cgtttggtgc tgcaccccgc tgcccaccac gttcagcgtc cggtggacgt   420
ggacctcctg ctcatgcgag tcccggccgg cgccggcgaa ccccagccg ggattctcga    480 agaggatagc ggtcaaggtg gttgtccagc attgggcgt aggaggtcgg gacgtagtag    540
gagtagcacc gctgcaaa                                                 558

<210> SEQ ID NO 226
<211> LENGTH: 773
<212> TYPE: DNA
<213> ORGANISM: Alexandrium catenella

<400> SEQUENCE: 226
cagctatgac catgattacg ccaagctatt taggtgacac tatagaatac tcaagctatg    60
catccaacgc gttgggagct ctcccatatg gtcgacctgc aggcggcacg cgaattcact   120
agtgatttgc agcgatgcta ctcctactac gtcccgacct cctacgcccc actgctggac   180
aggtaccacc gcatcctctt cgagaatccc ggctgggggt tcgccggcgc cggccgggac   240
tcgcaggagc aggaggtcca cgtccaccgg acgctgaacg tggtgggcag cggggcgcag   300
caccagacgc tcttcacgga cctcgtgcgg ctcattgact cggtcttcgc gggcggggac   360
ttcgcgtcgc agccggcgtt cgtcgtggac acggggtgcg cgacggccg cttgctcagg    420 cgcatctacg agcacgtgaa gagcaacacg ccgcgcggga aggcgctcgc cgagcacccg   480
ctcacgatgg tcgcgtcga cttcaacaag gactctcggg tggcgacgga gctcaacctg    540
agcaggcacg cggtcccgca cctggtgctg ttcggagacg tcggcaagcc cgccgacatc   600
atggagatcc tcgacggag cggggtggac ccgagcaggt ccctccacgt gcgctccttc    660
ctagaccacg accaatcgaa ttcccgcggc cgccatggcg gccgggagca tgcgacgtcg   720
ggcccaattc gccctatagt gagtcgtatt acaattcact ggccgtcgtt tta           773

<210> SEQ ID NO 227
<211> LENGTH: 555
<212> TYPE: DNA
<213> ORGANISM: Alexandrium sp.
<220> FEATURE:
<221> NAME/KEY: misc_feature
<222> LOCATION: (126)..(127)
<223> OTHER INFORMATION: 'n'= a, c, t or g

<400> SEQUENCE: 227
tttgcagcga tgctactcct actacgtccc tgcctcctac tcgccgatgc tgtcgaacct    60
```

```
gaacactatc ctccacgagg acgccggctg gggcttcgcc gacgacgggc tcgtgcgcgc    120
atgggnngcc gaggtccacg tgaaccgcac gctgaacgtc gtcggcagcg gcctgcagca    180
ccaaaagttc ttccagcacc tcgtgcagca gatcagcgcc atctttgagg gcgaggactt    240
cacctcgcag ccatcgttcg tcgtcgacac tggcagcggc gacgggactc tacttaggca    300
gatctacgag cacgtgaagt cgatgacgcc tcgaggacgt cacctgagcc agcatccgct    360
gaccatggta ggtgttgact tcagcgagga gtccagagcc gcgacctccc gcaacctgag    420
ccaccacgcc atccctcaca tggtgctctt cggggacatt ggcgagcccg cttgagatca    480
cggcgtgcgc tggcaaggaa gggtgtcgac cttgcgaagg tgctgcacgt gcgctccttc    540
ctggaccacg accca                                                    555

<210> SEQ ID NO 228
<211> LENGTH: 20
<212> TYPE: DNA
<213> ORGANISM: Artificial Sequence
<220> FEATURE:
<223> OTHER INFORMATION: Primer sequence

<400> SEQUENCE: 228
cttgcccgcc atatgtgctt                                                20

<210> SEQ ID NO 229
<211> LENGTH: 20
<212> TYPE: DNA
<213> ORGANISM: Artificial Sequence
<220> FEATURE:
<223> OTHER INFORMATION: Primer sequence

<400> SEQUENCE: 229
gcccggcgta gatgatgttg                                                20

<210> SEQ ID NO 230
<211> LENGTH: 579
<212> TYPE: DNA
<213> ORGANISM: Alexandrium minutum

<400> SEQUENCE: 230
ttccagggtc gcctcaagaa gccgcttgcg ctgacggtcc ccctcggcaa agttgaggtc     60
gagggtcgtt ttcgcactcg acaggccggc agtacagatc ggccctgtga acacgagcgt    120
gttcgagttc ttggccaagt tcagaatgcc gaacttctcg tcggtctcgc gtgcgcagcc    180
cacgaatccg ccgggcgaat tgaacgcctt gctcagctgc ccggcgtaga tgatgttgtt    240
ctccgcgtag tccagcccga agtacttgac gacgccgccg ccgccatatc gaagggttg    300 ctccgagtcg gggttgcggc caagaacgcc gcaaccgtgc gagtcgtcca cgagtatctt    360
ggccccgcgc ggcctcaaac aagcacatat ggcgggcaag tcggcgagct ctccgtccgt    420
ggagtagacg ccgtcgcaca cgtaggtgat gtcggccccc tccgggatcg acgagagcac    480
gcgctcgagc tgctccgtgt cgttgtgctt caggcgcacg acggtgactc ccttcttgca    540
gagcctggct gccgtctgca cgcagtcgtg ggcgtttat                           579

<210> SEQ ID NO 231
<211> LENGTH: 670
<212> TYPE: DNA
<213> ORGANISM: Alexandrium minutum
<220> FEATURE:
<221> NAME/KEY: misc_feature
<222> LOCATION: (557)..(557)
```

<223> OTHER INFORMATION: 's' = g or c

<400> SEQUENCE: 231

```
gggaacccgt ggtaggtgtg ggggcacccg agcgccttga gccctcgca aaattccagg      60
gtcgcctcaa gaagccgctt gcgctgacgg tccccctcgg caaagttgag gtcgagggtc     120
gtcttcgcac tcgacaggcc ggcagtacag atcggccctg tgaacacgag cgtgttcgag    180
ttcttggcca agttcagaat gccgaacttc tcgtcggtct cgcgtgcgca gcccacgaat    240
ccgccgggcg aattgaacgc cttgctcagc tgcccggcgt agatgatgtt gttctccgcg    300
tagtccagcc cgaagtactt gacgacgccg ccgccgccat atccgaaggg ttgctccgag    360
tcggggttgc ggccaagaac gccgcaaccg tgcgagtcgt ccacgagtat cttggccccg    420
cgcggcctca aacaagcaca tatggcgggc aagtcggcga gctctccgtc cgtggagtag    480
acgccgtcgc acacgtaggt gatgtcggcc ccctccggga tcgacgagag cacgcgctcg    540
agctgctccg tgtcgttgtg cttcaggcgc acgacggtga ctcccttctt gcagagsctg    600
gctgccgtct gcacgcagtc gtgggcgttt atgtccagga ggaggaaccc gctctcgccc    660
gccaggctcg                                                          670
```

<210> SEQ ID NO 232
<211> LENGTH: 632
<212> TYPE: DNA
<213> ORGANISM: Alexandrium minutum

<400> SEQUENCE: 232

```
gggaacccgt ggtaggtgtg ggggcacccg agcgccttga gccctcgca aaattccagg      60
gtcgcctcaa gaagccgctt gcgctgacgg tccccctcgg caaagttgag gtcgagggtc     120
gtcttcgcac tcgacaggcc ggcagtacag atcggccctg tgaacacgag cgtgttcgag    180
ttcttggcca agttcagaat gccgaacttc tcgtcggtct cgcgtgcgca gcccacgaat    240
ccgccgggcg aattgaacgc cttgctcagc tgcccggcgt agatgatgtt gttctccgcg    300
tagtccagcc cgaagtactt gacgacgccg ccgccgccat atccgaaggg ttgctccgag    360
tcggggttgc ggccaagaac gccgcaaccg tgcgagtcgt ccacgagtat cttggccccg    420
cgcggcctca aacaagcaca tatggcgggc aagtcggcga gctctccgtc cgtggagtag    480
acgccgtcgc acacgtaggt gatgtcggcc ccctccggga tcgacgagag cacgcgctcg    540
agctgctccg tgtcgttgtg cttcaggcgc acgacggtga ctcccttctt gcagagcctg    600
gckgccgtct gcacgcagtc gtgggcgttt at                                   632
```

<210> SEQ ID NO 233
<211> LENGTH: 670
<212> TYPE: DNA
<213> ORGANISM: Alexandrium minutum

<400> SEQUENCE: 233

```
gggaacccgt ggtaggtgtg ggggcacccg agcgccttga gccctcgca aaattccagg      60
gtcgcctcaa gaagccgctt gcgctgacgg tccccctcgg caaagttgag gtcgagggtc     120
gtcttcgcac tcgacaggcc ggcagtacag atcggccctg tgaacacgag cgtgttcgag    180
ttcttggcca agttcagaat gccgaacttc tcgtcggtct cgcgtgcgca gcccacgaat    240
ccgccgggcg aattgaacgc cttgctcagc tgcccggcgt agatgatgtt gttctccgcg    300
tagtccagcc cgaagtactt gacgacgccg ccgccgccat atccgaaggg ttgctccgag    360
tcggggttgc ggccaagaac gccgcaaccg tgcgagtcgt ccacgagtat cttggccccg    420
```

```
cgcggcctca aacaagcaca tatggcgggc aagtcggcga gctctccgtc cgtggagtag      480
acgccgtcgc acacgtaggt gatgtcggcc ccctccggga tcgacgagag cacgcgctcg      540
agctgctccg tgtcgttgtg cttcaggcgc acgacggtga ctcccttctt gcagagcctg      600
gctgccgtct gcacgcagtc gtgggcgttt atgtccagga ggaggaaccc gctctcgccc      660
gccaggctcg                                                              670
```

<210> SEQ ID NO 234
<211> LENGTH: 636
<212> TYPE: DNA
<213> ORGANISM: Alexandrium minutum

<400> SEQUENCE: 234

```
gggaacccgt ggtaggtgtg ggggcacccg agcgccttga gcccctcgca aaattccagg       60
gtcgcctcaa gaagccgctt gcgctgacgg tcccctcgg caaagttgag gtcgagggtc       120
gtcttcgcac tcgacaggcc ggcagtacag atcggcctg tgaacacgag cgtgttcgag       180
ttcttggcca agttcagaat gccgaacttc tcgtcggtct cgcgtgcgca gcccacgaat      240
ccgccgggcg aattgaacgc cttgctcagc tgcccggcgt agatgatgtt gttctccgcg      300
tagtccagcc cgaagtactt gacgacgccg ccgccgccat atccgaaggg ttgctccgag      360
tcggggttgc ggccaagaac gccgcaaccg tgcgagtcgt ccacgagtat cttgccccg      420 cgcggcctca aacaagcaca tatggcgggc aagtcggcga gctctccgtc cgtggagtag      480
acgccgtcgc acacgtaggt gatgtcggcc ccctccggga tcgacgagag cacgcgctcg      540
agctgctccg tgtcgttgtg cttcaggcgc acgacggtga ctcccttctt gcagagcctg      600
gctgccgtct gcacgcagtc gtgggcgttt atgtcc                                636
```

<210> SEQ ID NO 235
<211> LENGTH: 670
<212> TYPE: DNA
<213> ORGANISM: Alexandrium minutum

<400> SEQUENCE: 235

```
gggaacccgt ggtaggtgtg ggggcacccg agcgccttga gcccctcgca aaattccagg       60
gtcgcctcaa gaagccgctt gcgctgacgg tcccctcgg caaagttgag gtcgagggtc       120
gtcttcgcac tcgacaggcc ggcagtacag atcggcctg tgaacacgag cgtgttcgag       180
ttcttggcca agttcagaat gccgaacttc tcgtcggtct cgcgtgcgca gcccacgaat      240
ccgccgggcg aattgaacgc cttgctcagc tgcccggcgt agatgatgtt gttctccgcg      300
tagtccagcc cgaagtactt gacgacgccg ccgccgccat atccgaaggg ttgctccgag      360
tcggggttgc ggccaagaac gccgcaaccg tgcgagtcgt ccacgagtat cttgccccg      420 cgcggcctca aacaagcaca tatggcgggc aagtcggcga gctctccgtc cgtggagtag      480
acgccgtcgc acacgtaggt gatgtcggcc ccctccggga tcgacgagag cacgcgctcg      540
agctgctccg tgtcgttgtg cttcaggcgc acgacggtga ctcccttctt gcagagcctg      600
gctgccgtct gcacgcagtc gtgggcgttt atgtccagga ggaggaaccc gctctcgccc      660
gccaggctcg                                                              670
```

<210> SEQ ID NO 236
<211> LENGTH: 670
<212> TYPE: DNA
<213> ORGANISM: Alexandrium minutum

<400> SEQUENCE: 236

```
gggaacccgt ggtaggtgtg ggggcacccg agcgccttga gcccctcgca aaattcgagg        60
gtcgcmtcaa gaagccgctt gcgctgamgg tcccccctcgg craarttgag gtcgagggtc      120
gtcttcgcac tcgacaggcc ggcagtacag atcggccctg tgaacacgag cgtgttcgag      180
ttcttggcca agttcagaat gccgaacttc tcgtcggtct cgcgtgcgca rccsacgaat      240
ccgccgggcg aattgaacgc cttgctcarc tgcccggcgt agatgatgtt gttctccgcg      300
tagtccagcc cgaagtactt gacgacgccg ccgccgccat atccgaaggg ttgctccgag      360
tcggggttry ggccaagaac gccgcaaccg tgmgagtcgt ccacgagtat cttggccccg      420
cgcggcctca aacaagcaca tayggcgggc aagtcggcga gctytccstc ygtggagtag      480
acsccgtcgc acacstaggt gatgtyggcc ccctcsggga tygacgagag cacgcgctcr      540
agstgstccg tgtcgttgtg cttcaggcgc acgacggtga ckcccttctt gcagagcctg      600
gcggctgtct gcacgcagtc gtgggcgttt atgtccagga ggaggaascc gctctcgccc      660
gccaggctcg                                                             670
```

<210> SEQ ID NO 237
<211> LENGTH: 670
<212> TYPE: DNA
<213> ORGANISM: Alexandrium minutum

<400> SEQUENCE: 237

```
gggaacccgt ggtaggtgtg ggggcacccg agcgccttga gcccctcgca aaattcgagg        60
gtcgcmtcaa gaagccgctt gcgctgamgg tcccccctcgg craarttgag gtcgagggtc      120
gtcttcgcac tcgacaggcc ggcagtacag atcggccctg tgaacacgag cgtgttcgag      180
ttcttggcca agttcakaat gccgaacttc tcgtcggtct cgcgtgcgca rccsacgaat      240
ccgccgggcg aattgaacgc cttgctcarc tgcccggcgt agatgatgtt gttctccgcg      300
tagtccagcc cgaagtactt gacgacgccg ccgccgccat atccgaaggg ttgctccgag      360
tcggggttry ggccaagaac gccgcaaccg tgmgagtcgt ccacgagtat cttggccccg      420
cgcggcctca aacaagcaca tayggcgggc aagtcggcga gctctccgtc cgtggagtag      480
acsccgtcgc acacstaggt gatgtcggcc ccctcsggga tcgacgagag cacgcgctcr      540
agstgstccg tgtygttgtg cttcaggcgc acgrcggtga ckcccttctt gcagagcctg      600
gcggcygtcy gcacgcagtc gtgggcgttt atgtccagga ggaggaascc gctctcgccc      660
gccaggctcg                                                             670
```

<210> SEQ ID NO 238
<211> LENGTH: 670
<212> TYPE: DNA
<213> ORGANISM: Alexandrium minutum

<400> SEQUENCE: 238

```
gggaacccgt ggtaggtgtg ggggcacccg agcgccttga gcccctcgca aaattcsagg        60
gtcgcmtcaa gaagccgctt gcgctgamgg tcccccctcgg craarttgag gtcgagggtc      120
gtcttcgcac tcgacaggcc ggcagtacag atcggccctg tgaacacgag cgtgttcgag      180
ttcttggcca agttcagaat gccgaacttc tcgtcggtst cgcgtgcgca rccsacgaat      240
ccgccgggcg aattgaacgc cttgctcarc tgcccggcgt agatgatgtt gttctccgcg      300
tagtccagcc cgaagtactt gacgacgccg ccgccgccat atccgaaggg ttgctccgag      360
tcggggttry ggccaagaac gccgcaaccg tgagagtcgt ccacgagtat cttggccccg      420
```

```
cgcggcctca aacaagcaca tatggcgggc aagtcggcga gctctccgtc cgtggagtag      480
acgccgtcgc acacgtaggt gatgtcggcc ccctcsggga tcgacgagag cacgcgctcr      540
agctgctccg tgtcgttgtg cttcaggcgc acgacggtga ckcccttctt gcagagcctg      600
gcggctgtct gcacgcagtc gtgggcgttt atgtccagga ggaggaascc gctctcgccc      660
gccaggctcg                                                             670
```

<210> SEQ ID NO 239
<211> LENGTH: 670
<212> TYPE: DNA
<213> ORGANISM: Alexandrium minutum

<400> SEQUENCE: 239

```
gggaacccgt ggtaggtgtg ggggcacccg agcgccttga gccctcgca aaattccagg        60 gtcgcctcaa gaagccgctt gcgctgacgg tcccctcgg caaagttgag gtcgagggtc      120
gtcttcgcac tcgacaggcc ggcagtacag atcggccctg tgaacacgag cgtgttcgag      180
ttcttggcca agttcagaat gccgaacttc tcgtcggtct cgcgtgcgca gcccacgaat      240
ccgccgggcg aattgaacgc cttgctcagc tgcccggcgt agatgatgtt gttctccgcg      300
tagtccagcc cgaagtactt gacgacgccg ccgccgccat atccgaaggg ttgctccgag      360
tcggggttgc ggccaagaac gccgcaaccg tgcgagtcgt ccacgagtat cttgcccccg      420
cgcggcctca aacaagcaca tatggcgggc aagtcggcga gctctccgtc cgtggagtag      480
acgccgtcgc acacgtaggt gatgtcggcc ccctccggga tcgacgagag cacgcgctcg      540
agctgctccg tgtcgttgtg cttcaggcgc acgacggtga ctcccttctt gcagagcctg      600
gctgccgtct gcacgcagtc gtgggcgttt atgtccagga ggaggaaccc gctctcgccc      660
gccaggctcg                                                             670
```

<210> SEQ ID NO 240
<211> LENGTH: 670
<212> TYPE: DNA
<213> ORGANISM: Alexandrium catenella

<400> SEQUENCE: 240

```
gggaagccgt ggtaggtgtg ggggcacccg agcgccctga gccctcgca gaactcgagg        60 gtcgcckcca gragccgcyt gcgctgaagg tcccctcgg cggcgttgag gtccagggtc      120
gtcytygcrc tcgacaggcc ggcggtacag atcggccctg tgaacacgag ygtgttcgag      180
ttcttsgcca agttcaggat gccgaacttc tcgtcggtct cgcgcgcgca gccgacgaat      240
ccgccgggcg agttgaacgc cttgctcagc tgcccggcgt agatgatgtt gttctccgcg      300
tagtccagcc cgaagtactc gacgacgccr ccgccrccat acccgagggg ttgctccgag      360
tcwgggttkc ggccaagaac gccgcagccr tgcgagtcgt cyacgagtat cttggccccg      420
cgcggcctca aacaagcaca katggcgggc aagtcsgcga gctctccgtc ygtggagtam      480
acgccgtcgc asacgtaggt gatgtcggcc ccctgcggga tcgasgagag caygcgctcg      540
agctgctccg ygtcgttgtg cttcaggcgc acsacggtgr cgcccttctt gcagagcctg      600
gcggccgtct gcacgcagtc gtgggcgtkt atgtccasga ggaggaaccc gctctcgccc      660
gcgaggctcg                                                             670
```

<210> SEQ ID NO 241
<211> LENGTH: 670
<212> TYPE: DNA

<213> ORGANISM: Alexandrium fundyense

<400> SEQUENCE: 241

| gggaacccgt ggtaggtgtg ggggcacccg agcgccttga gccctcgca gaattcgagg | 60 |
| gtcgccgcca gaagccgctt gcgctgaagg tccccctcgg cggcgttgag gtcgagggtc | 120 |
| gtcwtcgcac tcgacaggcc ggcagtacag atcggccctg tgaacacgag tgtgttcgag | 180 |
| ttcttggcca agttcagaat gccgaacttc tcgtcggtct cgcgcgcaca gccgacgaat | 240 |
| ccgccgggcg aattgaacgc cttgctcagc tgcccggcgt agatgatgtt gttctccgcg | 300 |
| tagtccagcc cgaagtactc gacgacgccg ccgccaccat acccgaaggg ttgctccgag | 360 |
| tcggggttgc ggccaagaac gccgcagcca tgcgagtcgt ctacgagtat cttggccccg | 420 |
| cgcggcctca aacaagcaca tatggcgggc aagtcggcga gctctccgtc cgtggagtac | 480 |
| acgccgtcgc acacgtaggt gatgtcggcc ccctgcggga tcgacgagag catgtgctcg | 540 |
| agctgctccg cgtcgttgtg cytcaggcgc accacggtgg cgcccttctt gcagagcctg | 600 |
| gcggccgtct gcacgcagtc gtgggcgttt atgtccagga ggaggaaccc gctctcgccc | 660 |
| acgaggctcg | 670 |

<210> SEQ ID NO 242
<211> LENGTH: 670
<212> TYPE: DNA
<213> ORGANISM: Alexandrium fundyense

<400> SEQUENCE: 242

| gggaacccgt ggtaggtgtg ggggcacccg agcgccttga gccctcgca gaattcgagg | 60 |
| gtcgccgcca gaagccgctt gcgctgaagg tccccctcgg cggcgttgag gtcgagggtc | 120 |
| gtchtcgcac tcgacaggcc ggcagtacag atcggccctg tgaacacgag tgtgttcgag | 180 |
| ttcttggcca agttcagaat gccgaacttc tcgtcggtct cgcgcgcaca gccgacgaat | 240 |
| ccgccgggcg aattgaacgc cttgctcagc tgcccggcgt agatgatgtt gttctccgcg | 300 |
| tagtccagcc cgaagtactc gacgacgccg ccgccaccat acccgaaggg ttgctccgag | 360 |
| tcggggttgc ggccaagaac gccgcagcca tgcgagtcgt ctacgagtat cttggccccg | 420 |
| cgcggcctca aacaagcaca tatggcgggc aagtcggcga gctctccgtc cgtggagtac | 480 |
| acgccgtcgc acacgtaggt gatgtcggcc ccctgcggga tcgacgagag catgtgctcg | 540 |
| agctgctccg cgtcgttgtg cytcaggcgc accacggtgg cgcccttctt gcagagcctg | 600 |
| gcggccgtct gcacgcagtc gtgggcgttt atgtccagga ggaggaaccc gctctcgccc | 660 |
| acgaggctcg | 670 |

<210> SEQ ID NO 243
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (2)..(2)
<223> OTHER INFORMATION: 'r'= g or a

<400> SEQUENCE: 243
grctacgcgg agaacaacat        20

<210> SEQ ID NO 244
<211> LENGTH: 21

```
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (5)..(5)
<223> OTHER INFORMATION: 'y'= t or c
<220> FEATURE:
<221> NAME/KEY: misc_feature
<222> LOCATION: (12)..(12)
<223> OTHER INFORMATION: 'k'= g or t

<400> SEQUENCE: 244
cgagygtgtt ckagttcttg g                                       21

<210> SEQ ID NO 245
<211> LENGTH: 19
<212> TYPE: DNA
<213> ORGANISM: Artificial Sequence
<220> FEATURE:
<223> OTHER INFORMATION: Probe sequence
<220> FEATURE:
<221> NAME/KEY: misc_feature
<222> LOCATION: (14)..(14)
<223> OTHER INFORMATION: 's'= g or c

<400> SEQUENCE: 245
ccggcggatt cgtsrgctg                                          19

<210> SEQ ID NO 246
<211> LENGTH: 20
<212> TYPE: DNA
<213> ORGANISM: Artificial Sequence
<220> FEATURE:
<223> OTHER INFORMATION: Probe sequence
<220> FEATURE:
<221> NAME/KEY: misc_feature
<222> LOCATION: (13)..(13)
<223> OTHER INFORMATION: 'y'= t or c

<400> SEQUENCE: 246
caaggcgttc aaytcgcccg                                         20

<210> SEQ ID NO 247
<211> LENGTH: 1319
<212> TYPE: DNA
<213> ORGANISM: Alexandrium tamarense

<400> SEQUENCE: 247
tcgcgctagt cagtgtggat gacgctgcat acactgcggt gaacagatgt ccgctcaggc    60
aatcaaaatg ccgaataata gtgttcgctc gtcaaactaa agatccactg tcgattgaac   120
gcccgcttca gtgatcgcgc gagaagagtc tctgctgcag tcgtccgagc aggaagtatt   180
gagaggcgcc gaccaccaat actcaaggag gtgcgcccga tacgagatcg ggggctgtaa   240 gcggggtcc gtcaaaaagt ctacgcctat gtttgtttta ggaggatcct gcaccccgcg    300
gcctcaaaca caacaaatag gggcggcaat tggtcacttg tttgtcccgg ggtaccaccc   360
gtacctatgt agggacctcg cccccatgcg agaaaaacaa aagcattgcc tgggttttg    420 cggggggtgg ttccccgggc ccccaccggg ggccccttt tttcagaacc ccggcgggcc    480
cgttttcccc ccccttttg ggttttttttt tttttcaaaa accaatcatc ccggaaccta   540
gtgggcgaga gcgggttcct cctcctgtac ataaacgccc acgactgcgt gcagacggcc   600
gccaggctct gcaagaaggg cgccaccgtg gtgcgcctga agcacaacga cacggaacag   660
```

-continued

```
cccgagcaca tgctctcgtc gatcccgcag ggggccgaca tcacctacgt gtgcgacggc    720
gtgtactcca cggacgaaga gctcgccgac ttgcccgcca tatgtgcttg tttgaggccg    780
cgcggggcca agatactcgt agacgactcg catggctgcg gcgttcttgg ccgcaacccc    840
aactcggagc aaccccctcgg gtatggtggc ggcggcgtca tcgagtactt cgggctggac   900
tacgcggaga acaacatcat ctacgccggg cagctgagca aggcgttcaa ttcgcccggc   960
ggattcgtca gctgtgcgcg cgagaccgac aaaaatttcg gcgttctgaa cttggccaaa   1020
aactcgaaca cactcgtgtt cacagggccg atctgtactg ccggcctgtc gagtgcgaaa   1080
acaaccttcg acctcaacgc cgccgagggg gaccttcaac gcaagcggct tctggcggct   1140
accctcgaaa ttctgcgagg ggctcaaggc gctcgggtgc ccccacacct accacgagtg   1200
ccccatcgtc aatacggggg gggaacacac aagctacgca agcgcttctg ggtgagccat   1260
aggcgctccc gtggcccaca aatataacag gaaaccaccg cccacttctc tgctattca    1319
```

DETECTION OF SAXITOXIN-PRODUCING DINOFLAGELLATES

CROSS-REFERENCE TO RELATED APPLICATIONS

This application is a continuation of U.S. patent application Ser. No. 14/114,850, filed Oct. 30, 2013, which is a U.S. 371 National Phase Entry of pending International Patent Application No. PCT/AU2012/000541, International Filing Date May 16, 2012, which claims priority to U.S. Provisional Patent Application No. 61/486,633 filed on May 16, 2011, the entire contents of which are incorporated herein by cross-reference in their entireties.

TECHNICAL FIELD

The invention generally relates to the field of saxitoxins and the identification of microorganisms capable of producing them. More specifically, the invention relates to the identification of genes encoding saxitoxin in dinoflagellates, and methods for the specific detection of dinoflagellates that are producers of saxitoxins.

BACKGROUND

Saxitoxin (STX) is a potent neurotoxin that occurs in aquatic environments worldwide and has significant economic, environmental and human health impacts. Ingestion of vector species can lead to paralytic shellfish poisoning, a severe human illness that may lead to paralysis and death. An estimated 2000 cases of human paralytic shellfish poisoning, with a mortality rate of 15%, occur globally each year. The costs of monitoring and mitigation of STX have led to an annual economic loss from harmful plankton blooms calculated at US $895 million. In freshwater environments, STX is predominantly produced prokaryotic cyanobacteria. However, in marine environments eukaryotic dinoflagellates have been associated with the presence of STX. Despite the association of a number of dinoflagellate species with STX production, the genetic basis for the production of STX in these microorganisms remains elusive.

There is a need for methods to detect the presence (or absence) of STX-producing dinoflagellates in marine samples.

SUMMARY OF THE INVENTION

A number of studies have unsuccessfully attempted to identify STX pathway genes and/or enzymes in dinoflagellates by enzymatic characterisation, PCR approaches, in silico analyses of expressed sequence tag (EST) libraries, or the use of other publicly available nucleotide sequences. In addition, several previous studies have suggested that STX may not in fact be produced by dinoflagellates but instead by co-cultured bacteria.

The present inventors have determined that dinoflagellates are in fact producers of STX and have identified genes responsible for STX production in these microorganisms. The identification of genes responsible for STX production provides a basis for numerous molecular tests to detect STX-producing dinoflagellates in both freshwater and marine environments.

In a first aspect, the invention provides a method for detecting a saxitoxin-producing dinoflagellate in a sample, the method comprising:

obtaining a sample for use in the method, and
analyzing the sample for the presence of one or more of a dinoflagellate saxitoxin A polynucleotide or a polypeptide encoded by said polynucleotide,
wherein the presence of said polynucleotide or polypeptide indicates the presence of a saxitoxin-producing dinoflagellate in the sample.

In a second aspect, the invention provides a method for determining the absence of a saxitoxin-producing dinoflagellate in a sample, the method comprising:

obtaining a sample for use in the method, and
analyzing the sample for the presence of one or more of a dinoflagellate saxitoxin A polynucleotide or a polypeptide encoded by said polynucleotide,
wherein the absence of said polynucleotide or polypeptide indicates the absence of a saxitoxin-producing dinoflagellate in the sample.

In one embodiment of the first or second aspect, the polynucleotide comprises a saxitoxin A nucleotide sequence selected from those set forth in any one of SEQ ID NOS: 5-197, 224-227, 230-242 and 247 or a fragment or variant of any one of those sequences.

In one embodiment of the first or second aspect, the polynucleotide comprises a saxitoxin A1 catalytic domain sequence, a saxitoxin A4 catalytic domain sequence, or a fragment thereof.

In one embodiment of the first or second aspect, the saxitoxin A4 catalytic domain sequence or fragment thereof comprises nucleotides 3115-4121 of the polynucleotide sequence set forth in SEQ ID NO: 3, nucleotides 3597-3721 of the polynucleotide sequence set forth in SEQ ID NO: 3, or a fragment or variant of either sequence.

In one embodiment of the first or second aspect, the saxitoxin A4 catalytic domain sequence or fragment thereof consists of nucleotides 3115-4121 of the polynucleotide sequence set forth in SEQ ID NO: 3, nucleotides 3597-3721 of the polynucleotide sequence set forth in SEQ ID NO: 3, or a fragment or variant of either sequence.

In one embodiment of the first or second aspect, the saxitoxin A1 catalytic domain sequence comprises nucleotides 160-1821 of the polynucleotide sequence set forth in SEQ ID NO: 1, nucleotides 277-2022 of the polynucleotide sequence set forth in SEQ ID NO: 3, or a fragment or variant of either sequence.

In one embodiment of the first or second aspect, the saxitoxin A1 catalytic domain sequence consists of nucleotides 160-1821 of the polynucleotide sequence set forth in SEQ ID NO: 1, nucleotides 277-2022 of the polynucleotide sequence set forth in SEQ ID NO: 3, or a fragment or variant of either sequence.

In one embodiment of the first or second aspect, the analyzing comprises amplification of polynucleotides from the sample by polymerase chain reaction.

In one embodiment of the first or second aspect, the polymerase chain reaction utilises one or more primers comprising a sequence set forth in SEQ ID NO: 198 or SEQ ID NO: 199, or a fragment or variant of either sequence.

In one embodiment of the first or second aspect, the polymerase chain reaction utilises one or more primers consisting of a sequence set forth in SEQ ID NO: 198 or SEQ ID NO: 199, or a fragment or variant of either sequence.

In one embodiment of the first or second aspect, the polymerase chain reaction utilises one or more primers comprising or consisting of a sequence set forth in any one of SEQ ID NOs: 198-199, 200-211, 220-223, 228-229, and 243-244, or a fragment or variant of any one of those sequences.

In one embodiment of the first or second aspect, the polypeptide comprises a saxitoxin A amino acid sequence set forth in SEQ ID NO: 2 or SEQ ID NO: 4, or a fragment or variant of either sequence.

In one embodiment of the first or second aspect, the polypeptide consists of a saxitoxin A amino acid sequence set forth in SEQ ID NO: 2 or SEQ ID NO: 4, or a fragment or variant of either sequence.

In one embodiment of the first or second aspect, the saxitoxin-producing dinoflagellate is from the *Alexandrium*, *Pyrodinium* or *Gymnodinium* genus.

In one embodiment of the first or second aspect, the saxitoxin-producing dinoflagellate is selected from the group consisting of *A. catenella*, *A. fundyense*, *A. lusitanicum*, *A. minutum*, *A. ostenfeldii*, *A. tamarense*, *G. catenatum*, and *P. bahamense* var *compressum*.

In one embodiment of the first or second aspect, said analysing is performed using a primer pair of the eleventh or twelfth aspect.

In a third aspect, the invention provides a kit for the detection of a saxitoxin-producing dinoflagellate in a sample, the kit comprising at least one agent for detecting the presence of a dinoflagellate saxitoxin A polynucleotide or a polypeptide encoded by said polynucleotide.

In a fourth aspect, the invention provides a kit for determining the absence of a saxitoxin-producing dinoflagellate in a sample, the kit comprising at least one agent for detecting the presence of a dinoflagellate saxitoxin A polynucleotide or a polypeptide encoded by said polynucleotide.

In one embodiment of the third or fourth aspect, the agent binds specifically to a polynucleotide comprising a saxitoxin A nucleotide sequence selected from those set forth in any one of SEQ ID NOS: 5-197, 224-227, 230-242 and 247 or a fragment or variant of any one of those sequences.

In one embodiment of the third or fourth aspect, the agent binds specifically to a polynucleotide comprising a saxitoxin A1 catalytic domain sequence, a saxitoxin A4 catalytic domain sequence, or a fragment thereof.

In one embodiment of the third or fourth aspect, the saxitoxin A4 catalytic domain sequence or fragment thereof comprises nucleotides 3115-4121 of the polynucleotide sequence set forth in SEQ ID NO: 3, nucleotides 3597-3721 of the polynucleotide sequence set forth in SEQ ID NO: 3, or a fragment or variant of either sequence.

In one embodiment of the third or fourth aspect, the saxitoxin A4 catalytic domain sequence or fragment thereof consists of nucleotides 3115-4121 of the polynucleotide sequence set forth in SEQ ID NO: 3, nucleotides 3597-3721 of the polynucleotide sequence set forth in SEQ ID NO: 3, or a fragment or variant of either sequence.

In one embodiment of the third or fourth aspect, the saxitoxin A1 catalytic domain sequence comprises nucleotides 160-1821 of the polynucleotide sequence set forth in SEQ ID NO: 1, nucleotides 277-2022 of the polynucleotide sequence set forth in SEQ ID NO: 3, or a fragment or variant of either sequence.

In one embodiment of the third or fourth aspect, the saxitoxin A1 catalytic domain sequence consists of nucleotides 160-1821 of the polynucleotide sequence set forth in SEQ ID NO: 1, nucleotides 277-2022 of the polynucleotide sequence set forth in SEQ ID NO: 3, or a fragment or variant of either sequence.

In one embodiment of the third or fourth aspect, the agent is a primer, probe or antibody.

In one embodiment of the third or fourth aspect, the agent is a primer comprising a sequence set forth in SEQ ID NO: 198 or SEQ ID NO: 199, or a fragment or variant of either sequence.

In one embodiment of the third or fourth aspect, the agent is a primer consisting of a sequence set forth in SEQ ID NO: 198 or SEQ ID NO: 199, or a fragment or variant of either sequence.

In one embodiment of the third or fourth aspect, the agent is a primer comprising or consisting of a sequence set forth in any one of SEQ ID NOs: 198-199, 200-211, 220-223, 228-229, and 243-244, or a fragment or variant of any one of those sequences.

In one embodiment of the third or fourth aspect, the agent binds specifically to a saxitoxin A amino acid sequence set forth in SEQ ID NO: 2 or SEQ ID NO: 4, or a fragment or variant of either sequence.

In one embodiment of the third or fourth aspect, the kit comprises two agents, wherein the two agents are a primer pair of the eleventh or twelfth aspect.

In one embodiment of the first, second, third or fourth aspect, the sample is an environmental sample.

In one embodiment of the first, second, third or fourth aspect, the sample is a saltwater sample.

In one embodiment of the first, second, third or fourth aspect, the sample is a freshwater sample.

In one embodiment of the first, second, third or fourth aspect, the sample is a marine sample.

In a fifth aspect, the invention provides an isolated polynucleotide comprising the sequence set forth in SEQ ID NO: 1, or a variant or fragment thereof.

In one embodiment of the fifth aspect, the isolated polynucleotide consists of the sequence set forth in SEQ ID NO: 1, or a variant or fragment thereof.

In a sixth aspect, the invention provides an isolated polynucleotide comprising the sequence set forth in SEQ ID NO: 3, or a variant or fragment thereof.

In one embodiment of the sixth aspect, the isolated polynucleotide consists of the sequence set forth in SEQ ID NO: 3, or a variant or fragment thereof.

In a seventh aspect, the invention provides an isolated polynucleotide comprising the sequence set forth in any one of SEQ ID NOS: 5-197, 224-227, 230-242 and 247 or a variant or fragment of any one of those sequences.

In one embodiment of the seventh aspect, the isolated polynucleotide consists of the sequence set forth in any one of SEQ ID NOS: 5-197, 224-227, 230-242 and 247 or a variant or fragment of any one of those sequences.

In an eighth aspect, the invention provides an isolated polypeptide encoded by any one of the polynucleotides according to the fifth, sixth or seventh aspect.

In a ninth aspect, the invention provides a primer or probe that binds specifically to a polynucleotide according to the fifth, sixth or seventh aspect.

In a tenth aspect, the invention provides an antibody that binds specifically to a polypeptide according to the eighth aspect.

In an eleventh aspect, the invention provides an primer pair for detecting a saxitoxin-producing dinoflagellate in a sample, wherein said primer pair comprises a first primer comprising the polynucleotide sequence of SEQ ID NO: 198, or a fragment or variant thereof, and a second primer comprising the polynucleotide sequence of SEQ ID NO: 199, or a fragment or variant thereof.

In one embodiment of the eleventh aspect, the primer pair comprises a first primer consisting of the polynucleotide sequence of SEQ ID NO: 198, or a fragment or variant thereof, and a second primer consisting of the polynucleotide sequence of SEQ ID NO: 199, or a fragment or variant thereof.

In a twelfth aspect, the invention provides a primer pair for detecting a saxitoxin-producing dinoflagellate in a sample, wherein said primer pair comprises:

a first primer comprising or consisting of the polynucleotide sequence of SEQ ID NO: 198 and a second primer comprising or consisting of the polynucleotide sequence of SEQ ID NO: 199; or a first primer comprising or consisting of the polynucleotide sequence of SEQ ID NO: 200 and a second primer comprising or consisting of the polynucleotide sequence of SEQ ID NO: 201; or a first primer comprising or consisting of the polynucleotide sequence of SEQ ID NO: 202 and a second primer comprising or consisting of the polynucleotide sequence of SEQ ID NO: 203; or a first primer comprising or consisting of the polynucleotide sequence of SEQ ID NO: 204 and a second primer comprising or consisting of the polynucleotide sequence of SEQ ID NO: 205; or a first primer comprising or consisting of the polynucleotide sequence of SEQ ID NO: 206 and a second primer comprising or consisting of the polynucleotide sequence of SEQ ID NO: 207; or a first primer comprising or consisting of the polynucleotide sequence of SEQ ID NO: 208 and a second primer comprising or consisting of the polynucleotide sequence of SEQ ID NO: 209; or a first primer comprising or consisting of the polynucleotide sequence of SEQ ID NO: 210 and a second primer comprising or consisting of the polynucleotide sequence of SEQ ID NO: 211; or a first primer comprising or consisting of the polynucleotide sequence of SEQ ID NO: 220 and a second primer comprising or consisting of the polynucleotide sequence of SEQ ID NO: 221; or a first primer comprising or consisting of the polynucleotide sequence of SEQ ID NO: 222 and a second primer comprising or consisting of the polynucleotide sequence of SEQ ID NO: 223; or a first primer comprising or consisting of the polynucleotide sequence of SEQ ID NO: 228 and a second primer comprising or consisting of the polynucleotide sequence of SEQ ID NO: 229; or a first primer comprising or consisting of the polynucleotide sequence of SEQ ID NO: 243 and a second primer comprising or consisting of the polynucleotide sequence of SEQ ID NO: 244.

BRIEF DESCRIPTION OF THE DRAWINGS

Preferred embodiments of the present invention will now be described, by way of an example only, with reference to the accompanying drawings wherein:

FIG. 1A-B is a diagram showing the structure of sxtA in dinoflagellates and cyanobacteria. A. Transcript structure of sxtA transcripts in *A. fundyense* CCMP1719. B. Genomic sxtA structure of *C. raciborskii* T3. C. Structure of STX with bonds and molecules introduced by sxtA marked in bold.

FIG. 2 is a graph showing GC content of *A. fundyense* sxtA transcripts and of cyanobacterial sxtA genes. GC content was calculated every 10 bp with a window size of 1000 bp.

FIG. 8 is a graph showing a standard curve of the sxtA4 primer pair based on dilutions of DNA from known numbers of cells of three exponentially growing *Alexandrium catenella* strains. The assay was tested using DNA concentrations representing 30-2600 cells in the different strains.

FIG. 9A-B provides two graphs showing the abundance of sxtA4 gene copies (primary y axis) and estimates of *Alexandrium catenella* cells (secondary y axis) based on microscopic cell identifications counts and qPCR using an LSU rDNA primer pair at A. the Georges River and B. Wagonga Inlet sampling sites, during November 2010.

FIG. 12A-F shows SEM images of *Alexandrium tamarense* ATNWB01. A) Ventral view, with cell membrane intact, showing general cell size and shape, scale bar=5 µm, B) Dorsal view, with cell membrane intact, showing cell shape, scale bar=10 µm, C) Epicone in apical view, showing APC and pore on 1' plate, scale bar=5 µm, D) Hypocone in antapical view, showing plate patterns, scale bar=10 µm, E) Apical pore complex, showing shape of comma, F) Posterior sulcal plate, showing pore, scale bar=2 µm.

FIG. 13A-H shows SEM images of strains of *Alexandrium tamarense* ATCJ33, ATEB01, and ATBB01 (for comparison, taken from Hallegraeff et al 1991). A-D, ATCJ33, A) ATCJ33 showing a chain of 2 cells, and general cell size and shape, scale bar=10 µm, B) First apical plate, showing ventral pore, C) APC, showing shape of comma, D) First apical plate showing ventral pore, E, F, H ATEB01. E) ATEB01 showing general size and shape of cells, scale bar=10 µm, F) ATEB01, first apical plate showing the ventral pore, G) ATBB01 showing the ventral pore and the APC, H) ATEB01 showing the APC.

DEFINITIONS

Figure 3:
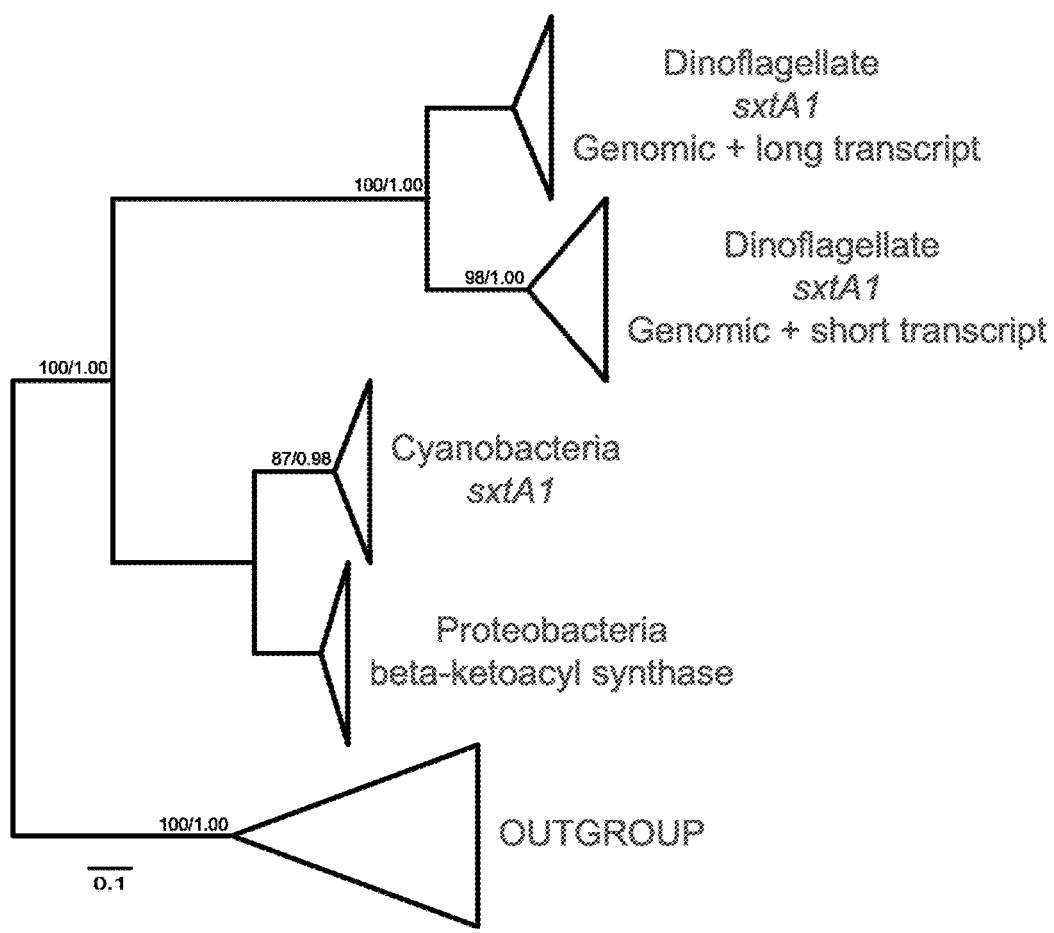
FIG. 3 shows an SxtA1 phylogenetic tree. Schematic representation, drawn to scale (for full tree see FIG. 5). Maximum likelihood topology is shown. Numbers on nodes represent bootstrap values of maximum likelihood and Bayesian analyses, respectively.

As used in this application, the singular form "a", "an" and "the" include plural references unless the context clearly dictates otherwise. For example, the term "a dinoflagellate" also includes a plurality of dinoflagellates.

As used herein, the term "comprising" means "including". Variations of the word "comprising", such as "comprise" and "comprises," have correspondingly varied meanings. Thus, for example, a polynucleotide "comprising" a sequence encoding a protein may consist exclusively of that sequence or may include one or more additional sequences.

As used herein, the term "saxitoxin" encompasses pure saxitoxin and analogs of thereof, non-limiting examples of which include neosaxitoxin (neoSTX), gonyautoxins (GTX), decarbamoylsaxitoxin (dcSTX), non-sulfated analogs, mono-sulfated analogs, di-sulfated analogs, decarbamoylated analogs and hydrophobic analogs.

Any description of prior art documents herein, or statements herein derived from or based on those documents, is not an admission that the documents or derived statements are part of the common general knowledge of the relevant art.

For the purposes of description all documents and GenBank sequences referred to herein are incorporated by reference in their entirety.

DETAILED DESCRIPTION

The present inventors have determined that dinoflagellates are producers of saxitoxin (STX) and have identified genes responsible for STX production in these microorganisms. Based on this discovery, the inventors have developed an assay capable of discerning between STX-producing dinoflagellate species and dinoflagellate species which do not produce STX.

Accordingly, certain aspects of the invention relate to the provision of STX polynucleotide and polypeptide sequences present in dinoflagellates.

Also provided are methods for the detection of STX-producing dinoflagellates in a given sample based on detecting the presence (or absence) of one or more sequences of the invention in the sample.

Also provided are kits for the detection of STX-producing dinoflagellates in a given sample comprising agent(s) for detecting the presence (or absence) of one or more sequences of the invention in the sample.

Polynucleotides and Polypeptides

Disclosed herein are dinoflagellate saxitoxin polynucleotide and polypeptide sequences ("polynucleotides of the invention" and "polypeptides of the invention", respectively). Polynucleotides of the invention may be deoxyribonucleic acids (DNA), ribonucleic acids (RNA) or complementary deoxyribonucleic acids (cDNA).

In certain embodiments, the sequences are saxitoxin A gene (sxtA) polynucleotide sequences or saxitoxin A polypeptide (STXA) sequences.

The sxtA polynucleotide sequences may comprise any one or more sxtA gene catalytic domain(s) (i.e. the sxtA1, sxtA2, sxtA3, or sxtA4 catalytic domain(s)), or fragment(s) thereof. By way of non-limiting example only, the sxtA1 sequence may be defined by nucleotides 160-1821 of the polynucleotide sequence set forth in GenBank accession number JF343238 (SEQ ID NO: 1) or nucleotides 277-2022 of the polynucleotide sequence set forth in GenBank accession number JF343239 (SEQ ID NO: 3). The sxtA2 sequence may be defined by nucleotides 1837-2415 of the polynucleotide sequence set forth in GenBank accession number JF343238 (SEQ ID NO: 1) or nucleotides 2038-2604 of the polynucleotide sequence set forth in GenBank accession number JF343239 (SEQ ID NO: 3). The sxtA3 sequence may be defined by nucleotides 2479-2694 of the polynucleotide sequence set forth in GenBank accession number JF343238 (SEQ ID NO: 1) or nucleotides 2722-2949 of the polynucleotide sequence set forth in GenBank accession number JF343239 (SEQ ID NO: 3). The sxtA4 sequence may be defined by nucleotides 3115-4121 of the polynucleotide sequence set forth in GenBank accession number JF343239 (SEQ ID NO: 3) or nucleotides 3597-3721 of the polynucleotide sequence set forth in GenBank accession number JF343239 (SEQ ID NO: 3).

Other non-limiting examples of sxtA gene polynucleotide sequences of the invention include those provided in GenBank accession numbers JF343238 and JF343239 (SEQ ID NO: 1 and SEQ ID NO: 3).

The STXA polypeptide sequences may comprise any one or more STX protein catalytic domain(s) (i.e. the STXA1, STXA2, STXA3, or STXA4 catalytic domain(s)) or fragment(s) thereof. By way of non-limiting example only, the STXA1 sequence may be defined by amino acid residues 1-554 of the polypeptide sequence set forth in GenBank accession number JF343238 (SEQ ID NO: 2) or amino acid residues 1-582 of the polypeptide sequence set forth in GenBank accession number JF343239 (SEQ ID NO: 4). The STXA2 sequence may be defined by amino acid residues 560-752 of the polypeptide sequence set forth in GenBank accession number JF343238 (SEQ ID NO: 2) or amino acid residues 588-776 of the polypeptide sequence set forth in GenBank accession number JF343239 (SEQ ID NO: 4). The STXA3 sequence may be defined by amino acid residues 774-845 of the polypeptide sequence set forth in GenBank accession number JF343238 (SEQ ID NO: 2) or amino acid residues 816-891 of the polypeptide sequence set forth in GenBank accession number JF343239 (SEQ ID NO: 4). The STXA4 sequence may be defined by amino acid residues 947-1281 of the polypeptide sequence set forth in GenBank accession number JF343239 (SEQ ID NO: 4).

Other non-limiting examples of STX polypeptide sequences of the invention include those provided in GenBank accession numbers JF343238 and JF343239 (SEQ ID NO: 2 and SEQ ID NO: 4).

Preferably, the polynucleotide and polypeptide sequences are from saxitoxin-producing dinoflagellates. For example, the polynucleotide and polypeptide sequences may be from dinoflagellates of the order Gonyaulacales or Gymnodiniales. Preferably, the dinoflagellates are of the genus *Alexandrium* (formerly *Gonyaulax*), *Pyrodinium* or *Gymnodinium*.

Non-limiting examples of preferred *Alexandrium* species include *A. catenella* (e.g. strains ACCC01, ACSH02, ACTRA02 and CCMP1493), *A. fundyense* (e.g. strains CCMP1719 and CCMP1979), *A. lusitanicum, A. minutum* (e.g. strains CCMP1888, CCMP113, ALSP01, ALSP02 and AMD16/AMAD16), *A. ostenfeldii,* and *A. tamarense* (e.g. strains CCMP1771, ATBB01, ATEB01, ATCJ33 and ATNWB01). Non-limiting examples of preferred *Gymnodinium* species include *G. catenatum* (e.g. strains GCTRA01 and CS-395). Non-limiting examples of preferred *Pyrodinium* species include *P. bahamense* var *compressum*.

Fragments of both polynucleotides of the invention and polypeptides of the invention are also provided herein.

A polynucleotide "fragment" as contemplated herein is a polynucleotide molecule that is a constituent of a polynucleotide of the invention or variant thereof. Fragments of a polynucleotide do not necessarily need to encode polypeptides which retain biological activity although this is not excluded from being the case. In certain embodiments the fragment may be useful as a hybridization probe or PCR primer. The fragment may be derived by cleaving a polynucleotide of the invention or alternatively may be synthesized by some other means, for example by chemical synthesis. A polynucleotide fragment as contemplated herein may be less than about 5000 nucleotides in length, less than about 4500 nucleotides in length, or less than about 4000, 3500, 3000, 2500, 2000, 1500, 1000, 750, 500, 400, 300, 250, 200, 150, 100, 75, 50, 25 or 15 nucleotides in length. Additionally or alternatively, a polynucleotide fragment as contemplated herein may be more than about 15 nucleotides in length, more than about 25 nucleotides in length, or more than about 50, 75, 100, 150, 200, 250, 300, 400, 500, 750, 1000, 1500, 2000, 2500, 3000, 3500 or 4000 nucleotides in length. Additionally or alternatively, a polynucleotide fragment as contemplated herein may be between about 25 and about 50 nucleotides in length, between about 25 and about 75 nucleotides in length, or between about 25 and about 100, 100 and 250, 100 and 500, 250 and 500, 100 and 1000, 500 and 2000, 1000 and 2000 nucleotides in length.

Polynucleotide fragments of the invention comprise fragments of the sxtA gene. For example, polynucleotide fragments of the invention may comprise any one or more of the sxtA1, sxtA2, sxtA3, or sxtA4 catalytic domain(s), or fragment(s) thereof. Polypeptide fragments of the invention comprise fragments of the STX protein. For example, polynucleotide fragments of the invention may comprise any one or more of the STXA1, STXA2, STXA3, or STXA4 catalytic domain(s), or fragment(s) thereof.

Specific and non-limiting examples of sxtA gene polynucleotide sequence fragments of the invention include those provided in GenBank accession numbers JF343240-JF343432 (SEQ ID NO: 5-SEQ ID NO: 197), and those set forth in SEQ ID NOs: 224-227, 230-242 and 247.

Additional specific and non-limiting examples of sxtA gene polynucleotide sequence fragments of the invention include those defined by nucleotides 3115-4121 and nucleotides 3597-3721 of the polynucleotide sequence set forth in GenBank accession number JF343238 (SEQ ID NO: 3), and fragments and variants thereof.

Specific and non-limiting examples of sxtA1 catalytic domain sequences include those set out in SEQ ID NOs: 224-227 and 247.

Specific and non-limiting examples of sxtA4 catalytic domain sequences include those set out in SEQ ID NOs: 230-242.

A polypeptide "fragment" as contemplated herein is a polypeptide molecule is a constituent of a polypeptide of the invention or variant thereof. Typically the fragment possesses qualitative biological activity in common with the polypeptide of which it is a constituent or though this is not necessarily required. A polypeptide fragment as contemplated herein may be less than about 1500 amino acid residues in length, less than about 1400 amino acid residues in length, or less than about 1300, 1200, 1100, 1000, 900, 800, 700, 600, 500, 400, 300, 250, 200, 150, 100, 75, 50, 25 or 15 amino acid residues in length. Additionally or alternatively, a polypeptide fragment as contemplated herein may be more than about 15 amino acid residues in length, more than about 25 amino acid residues in length, or more than about 50, 75, 100, 150, 200, 250, 300, 400, 500, 600, 700, 800, 900, 1000, 1100, 1200, or 1300 amino acid residues in length. Additionally or alternatively, a polypeptide fragment as contemplated herein may be between about 15 and about 25 amino acid residues in length, between about 15 and about 50 amino acid residues in length, or between about 15 and 75, 15 and 100, 15 and 150, 25 and 50, 25 and 100, 50 and 100, 50 and 150, 100 and 200, 100 and 250, 100 and 300, 100 and 500, 500 and 750, 500 and 1000, or 1000 and 1300 amino acid residues in length.

Specific and non-limiting examples of STXA polypeptide sequence fragments of the invention include those defined by amino acid residues X-Y of the polypeptide sequence set forth in GenBank accession number JF343248 (SEQ ID NO: 3), those defined by amino acid residues 947-1281 of the polypeptide sequence set forth in GenBank accession number JF343239 (SEQ ID NO: 4), and fragments and variants thereof.

Variants of polynucleotides of the invention and polypeptides of the invention, and fragments thereof, are also provided herein.

A "variant" as contemplated herein refers to a substantially similar sequence. In general, two sequences are "substantially similar" if the two sequences have a specified percentage of amino acid residues or nucleotides that are the same (percentage of "sequence identity"), over a specified region, or, when not specified, over the entire sequence. Accordingly, a "variant" of a polynucleotide and polypeptide sequence disclosed herein may share at least 40%, 45%, 50%, 55%, 60%, 65%, 70%, 75%, 80%, 83% 85%, 88%, 90%, 93%, 95%, 96%, 97%, 98% or 99% sequence identity with the reference sequence.

In general, polypeptide sequence variants possess qualitative biological activity in common. Polynucleotide sequence variants generally encode polypeptides which generally possess qualitative biological activity in common. Also included within the meaning of the term "variant" are homologues of polynucleotides of the invention and polypeptides of the invention. A polynucleotide homologue is typically from a different dinoflagellate species but sharing substantially the same biological function or activity as the corresponding polynucleotide disclosed herein. A polypeptide homologue is typically from a different dinoflagellate species but sharing substantially the same biological function or activity as the corresponding polypeptide disclosed herein. The term "variant" also includes analogues of the polypeptides of the invention. A polypeptide "analogue" is a polypeptide which is a derivative of a polypeptide of the invention, which derivative comprises addition, deletion, substitution of one or more amino acids, such that the polypeptide retains substantially the same function. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

Typically, polynucleotides of the invention and polypeptides of the invention are "isolated". It will be understood that the term "isolated" in this context means that the polynucleotide or polypeptide has been removed from or is not associated with some or all of the other components with which it would be found in its natural state. For example, an "isolated" polynucleotide may be removed from other polynucleotides of a larger polynucleotide sequence, or may be removed from natural components such as unrelated polynucleotides. Likewise, an "isolated" polypeptide may be removed from other polypeptides of a larger polypeptide sequence, or may be removed from natural components such as unrelated polypeptides. For the sake of clarity, an "isolated" polynucleotide of polypeptide also includes a polynucleotide or polypeptide which has not been taken from nature but rather has been prepared de novo, such as chemically synthesised and/or prepared by recombinant methods. As described herein an isolated polypeptide of the invention may be included as a component part of a longer polypeptide or fusion protein.

In certain embodiments, polynucleotides of the invention may be cloned into a vector. The vector may comprise, for example, a DNA, RNA or complementary DNA (cDNA) sequence. The vector may be a plasmid vector, a viral vector, or any other suitable vehicle adapted for the insertion of foreign sequences, their introduction into cells and the expression of the introduced sequences. Typically the vector is an expression vector and may include expression control and processing sequences such as a promoter, an enhancer, ribosome binding sites, polyadenylation signals and transcription termination sequences. The invention also contemplates host cells transformed by such vectors. For example, the polynucleotides of the invention may be cloned into a vector which is transformed into a bacterial host cell, for example E. coli. Methods for the construction of vectors and their transformation into host cells are generally known in the art, and described in standard texts such as, for example, Sambrook et al. (1989) Molecular Cloning: A Laboratory Manual, 2nd ed., Cold Spring Harbor Laboratory Press, Plainview, N.Y.; and Ausubel et al. (Eds) Current Protocols in Molecular Biology (2007), John Wiley and Sons, Inc.

Probes, Primers and Antibodies

Polynucleotides of the invention include derivatives and fragments thereof for use as primers and probes.

The derivatives and fragments may be in the form of oligonucleotides. Oligonucleotides are short stretches of nucleotide residues suitable for use in nucleic acid amplification reactions such as PCR, typically being at least about 5 nucleotides to about 80 nucleotides in length, more typically about 10 nucleotides in length to about 50 nucleotides in length, and even more typically about 15 nucleotides in length to about 30 nucleotides in length.

In one embodiment, the probe comprises or consists of a sequence as set forth in SEQ ID NO: 245 or SEQ ID NO: 246.

Probes are nucleotide sequences of variable length, for example between about 10 nucleotides and several thousand nucleotides, for use in detection of homologous sequences, typically by hybridization. Hybridization probes may be genomic DNA fragments, cDNA fragments, RNA fragments, or other oligonucleotides.

Methods for the design and/or production of nucleotide probes and/or primers are known in the art, and described in standard texts such as Sambrook et al. (1989) Molecular Cloning: A Laboratory Manual, 2nd ed., Cold Spring Harbor Laboratory Press, Plainview, N.Y.; and publications such as Itakura et al. (1984) Annu. Rev. Biochem. 53:323; Innis et al. (Eds) (1990) PCR Protocols: A Guide to Methods and Applications, Academic Press, New York; Innis and Gelfand, (Eds) (1995) PCR Strategies, Academic Press, New York; and Innis and Gelfand, (Eds) (1999) PCR Methods Manual, Academic Press, New York.

Polynucleotide primers and probes may be prepared, for example, by chemical synthesis techniques such as the phosphodiester and phosphotriester methods (see for example Narang et al. (1979) Meth. Enzymol. 68:90; Brown et al. (1979) Meth. Enzymol. 68:109; and U.S. Pat. No. 4,356,270), and the diethylphosphoramidite method (see Beaucage et al. (1981) Tetrahedron Letters, 22:1859-1862).

Polynucleotides of the invention, including the aforementioned probes and primers, may be labelled by incorporation of a marker to facilitate their detection. Techniques for labelling and detecting nucleic acids are described, for example, in standard texts such as Ausubel et al. (Eds) Current Protocols in Molecular Biology (2007), John Wiley and Sons, Inc. Non-limiting Examples of suitable markers include fluorescent molecules (e.g. acetylaminofluorene, 5-bromodeoxyuridine, digoxigenin, and fluorescein) and radioactive isotopes (e.g. 32P, 35S, 3H, 33P). Detection of the marker may be achieved, for example, by chemical, photochemical, immunochemical, biochemical, or spectroscopic techniques.

The probes and primers may be used, for example, to detect or isolate dinoflagellates in a sample of interest. In certain embodiments, the probes and primers may be used to detect STX-producing dinoflagellates in a sample of interest. Additionally or alternatively, the probes or primers may be used to isolate corresponding sequences in other organisms including, for example, other dinoflagellate species. Methods such as the polymerase chain reaction (PCR), hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In hybridization techniques, all or part of a known nucleotide sequence is used to generate a probe that selectively hybridizes to other corresponding nucleic acid sequences present in a given sample. The hybridization probes may be genomic DNA fragments, cDNA fragments, RNA fragments, or other oligonucleotides, and may be labelled with a detectable marker. Thus, for example, probes for hybridization can be made by labelling synthetic oligonucleotides based on the sequences of the invention. The level of homology (sequence identity) between probe and the target sequence will largely be determined by the stringency of hybridization conditions. In particular the nucleotide sequence used as a probe may hybridize to a homologue or other variant of a polynucleotide disclosed herein under conditions of low stringency, medium stringency or high stringency. There are numerous conditions and factors, well known to those skilled in the art, which may be employed to alter the stringency of hybridization such as, for example, the length and nature (DNA, RNA, base composition) of the nucleic acid to be hybridized to a specified nucleic acid; concentration of salts and other components, such as the presence or absence of formamide, dextran sulfate, polyethylene glycol etc; and altering the temperature of the hybridization and/or washing steps.

Under a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art. Known methods of PCR include, but are not limited to, methods using paired primers, nested primers, single specific primers, degenerate primers, gene-specific primers, vector-specific primers, partially-mismatched primers, and the like.

The skilled addressee will recognise that the primers described herein for use in PCR or RT-PCR may also be used as probes for the detection of dinoflagellate sxt gene sequences.

Also contemplated by the invention are antibodies which are capable of binding specifically to polypeptides of the invention. The antibodies may be used to qualitatively or quantitatively detect and analyse one or more STX polypeptides in a given sample. By “binding specifically” it will be understood that the antibody is capable of binding to the target polypeptide or fragment thereof with a higher affinity than it binds to an unrelated protein. For example, the antibody may bind to the polypeptide or fragment thereof with a binding constant in the range of at least about $10^{-4}$M to about $10^{-10}$M. Preferably the binding constant is at least about $10^{-5}$M, or at least about $10^{-6}$M. More preferably the binding constant is at least about $10^{-7}$M, at least about $10^{-8}$M, or at least about $10^{-9}$M or more. In the context of the present invention, reference to an antibody specific to an STX polypeptide of the invention includes an antibody that is specific to a fragment of the polypeptide.

Antibodies of the invention may exist in a variety of forms including, for example, as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of, but not limited to: Fv, $F_{ab}$, $F(ab)_2$, scFv (single chain Fv), dAb (single domain antibody), chimeric antibodies, bi-specific antibodies, diabodies and triabodies.

An antibody “fragment” may be produced by modification of a whole antibody or by synthesis of the desired antibody fragment. Methods of generating antibodies, including antibody fragments, are known in the art and include, for example, synthesis by recombinant DNA technology. The skilled addressee will be aware of methods of synthesising antibodies, such as those described in, for example, U.S. Pat. No. 5,296,348 and standard texts such as Ausubel et al. (Eds) *Current Protocols in Molecular Biology* (2007), John Wiley and Sons, Inc.

Preferably, antibodies are prepared from discrete regions or fragments of the STX polypeptide of interest. An antigenic portion of a polypeptide of interest may be of any appropriate length, such as from about 5 to about 15 amino acids. Preferably, an antigenic portion contains at least about 5, 6, 7, 8, 9, 10, 11, 12, 13 or 14 amino acid residues.

Antibodies that specifically bind to a polypeptide of the invention can be prepared, for example, using purified STX polypeptides of the invention, or purified sxt polynucleotide sequences of the invention that encode STX polypeptides of the invention using any suitable methods known in the art. For example, a monoclonal antibody, typically containing Fab portions, may be prepared using hybridoma technology described in Harlow and Lane (Eds) *Antibodies—A Laboratory Manual*, (1988), Cold Spring Harbor Laboratory, N.Y.; Coligan, *Current Protocols in Immunology* (1991); Goding, *Monoclonal Antibodies: Principles and Practice* (1986) 2nd ed; and Kohler & Milstein, (1975) Nature 256: 495-497. Such techniques include, but are not limited to, antibody preparation by selection of antibodies from libraries of recombinant antibodies in phage or similar vectors, as well as preparation of polyclonal and monoclonal antibodies by immunizing rabbits or mice (see, for example, Huse et al. (1989) Science 246: 1275-1281; Ward et al. (1989) Nature 341: 544-546).

It will also be understood that antibodies of the invention include humanised antibodies, chimeric antibodies and fully human antibodies. An antibody of the invention may be a bi-specific antibody, having binding specificity to more than one antigen or epitope. For example, the antibody may have specificity for one or more STX polypeptides or fragments thereof, and additionally have binding specificity for another antigen. Methods for the preparation of humanised antibodies, chimeric antibodies, fully human antibodies, and bispecific antibodies are known in the art and include, for example, those described in U.S. Pat. No. 6,995,243.

Generally, a sample potentially comprising an STX polypeptide of the invention can be contacted with an antibody that specifically binds the STX polypeptide or fragment thereof. Optionally, the antibody can be fixed to a solid support to facilitate washing and subsequent isolation of the complex, prior to contacting the antibody with a sample. Examples of solid supports include, for example, microtitre plates, beads, ticks, or microbeads. Antibodies can also be attached to a ProteinChip array or a probe substrate as described above.

Detectable labels for the identification of antibodies bound to polypeptides of the invention include, but are not limited to, fluorochromes, fluorescent dyes, radiolabels, enzymes such as horse radish peroxide, alkaline phosphatase and others commonly used in the art, and colorimetric labels including colloidal gold or coloured glass or plastic beads. Alternatively, the antibody can be detected using an indirect assay, wherein, for example, a second, labelled antibody is used to detect bound polypeptide-specific antibody.

Methods for detecting the presence of, or measuring the amount of, an antibody-marker complex include, for example, detection of fluorescence, chemiluminescence, luminescence, absorbance, birefringence, transmittance, reflectance, or refractive index such as surface plasmon resonance, ellipsometry, a resonant mirror method, a grating coupler wave guide method, or interferometry. Radio frequency methods include multipolar resonance spectroscopy. Electrochemical methods include amperometry and voltametry methods. Optical methods include imaging methods and non-imaging methods and microscopy.

Useful assays for detecting the presence of, or measuring the amount of, an antibody-marker complex include, include, for example, enzyme-linked immunosorbent assay (ELISA), a radioimmune assay (RIA), or a Western blot assay. Such methods are described in, for example, Stites & Terr, (Eds) (1991) Clinical Immunology, 7th ed; and Asai, (Ed) (1993) Methods in Cell Biology: Antibodies in Cell Biology, volume 37.

Methods for Detecting Dinoflagellates

The invention provides methods for the detection and/or isolation of polynucleotides of the invention and/or polypeptides of the invention ("methods of the invention").

In one embodiment the invention provides a method for detecting a dinoflagellate in a sample. The method comprises obtaining a sample for use in the method, and detecting the presence of a polynucleotide of the invention and/or a polypeptide of the invention, or a fragment or variant thereof in the sample. The presence of the polynucleotide, polypeptide, or variant or fragment thereof in the sample is indicative of dinoflagellates in the sample.

The present inventors have determined that the sxtA gene is present in saxitoxin-producing dinoflagellates but absent in dinoflagellates that do not produce saxitoxin. In particular, it has been identified that the detection of sxtA1 and/or sxtA4 catalytic domain(s) of the sxtA gene are indicative of saxitoxin-producing dinoflagellates.

Accordingly, in another embodiment the invention provides a method for detecting a saxitoxin-producing dinoflagellate in a sample. The method comprises obtaining a sample for use in the method, and detecting the presence of a polynucleotide of the invention and/or a polypeptide of the invention, or a fragment or variant thereof in the sample. The presence of the polynucleotide, polypeptide, or variant or fragment thereof in the sample is indicative of a saxitoxin-producing dinoflagellate in the sample.

In another embodiment the invention provides a method for determining an absence of saxitoxin-producing dinoflagellates in a sample. The method comprises obtaining a sample for use in the method, and determining an absence of a polynucleotide of the invention and/or a polypeptide of the invention, or a fragment or variant thereof in the sample. The absence of the polynucleotide, polypeptide, or variant or fragment thereof in the sample is indicative that saxitoxin-producing dinoflagellates are not present in the sample.

In the context of the methods of the invention (including those referred to in the paragraphs immediately above), the polynucleotide sequence may be a saxitoxin A gene (sxtA) sequence. The sxtA polynucleotide sequence may comprise any one or more sxtA gene catalytic domain(s) (i.e. the sxtA1, sxtA2, sxtA3, or sxtA4 catalytic domain(s)), or fragment(s) thereof. Preferably, the sxtA polynucleotide sequence comprises an sxtA1 and/or a sxtA4 domain, or fragment(s) thereof. More preferably, the sxtA polynucleotide sequence comprises an sxtA4 domain, or fragment(s) thereof. The polypeptide sequence may be saxitoxin A polypeptide (STXA) sequence.

In some embodiments, the polynucleotide sequence corresponds to a sequence provided in any one of GenBank accession numbers JF343238 and JF343239 (SEQ ID NO: 1 and SEQ ID NO: 3), or a fragment or a variant of either sequence.

In other embodiments, the polynucleotide sequence corresponds to a sequence provided in any one of GenBank accession numbers JF343240-JF343432 (SEQ ID NO: 5-SEQ ID NO: 197), or a fragment or a variant of any one of the sequences.

In other embodiments, the polynucleotide sequence comprises an sxtA1 catalytic domain sequence provided in any one of SEQ ID NOs: 224-227 and 247, or a fragment or a variant of any one of the sequences.

In other embodiments, the polynucleotide sequence comprises an sxtA4 catalytic domain sequence provided in any one of SEQ ID NOs: 230-242, or a fragment or a variant of any one of the sequences.

In other embodiments, the polynucleotide sequence may comprise nucleotides 160-1821 of the polynucleotide sequence set forth in GenBank accession number JF343238 (SEQ ID NO: 1); nucleotides 277-2022 of the polynucleotide sequence set forth in GenBank accession number JF343239 (SEQ ID NO: 3); nucleotides 1837-2415 of the polynucleotide sequence set forth in GenBank accession number JF343238 (SEQ ID NO: 1); nucleotides 2038-2604 of the polynucleotide sequence set forth in GenBank accession number JF343239 (SEQ ID NO: 3); nucleotides 2479-2694 of the polynucleotide sequence set forth in GenBank accession number JF343238 (SEQ ID NO: 1); nucleotides 2722-2949 of the polynucleotide sequence set forth in GenBank accession number JF343239 (SEQ ID NO: 3); nucleotides 3115-4121 of the polynucleotide sequence set forth in GenBank accession number JF343239 (SEQ ID NO: 3); nucleotides 3597-3721 of the polynucleotide sequence set forth in GenBank accession number JF343239 (SEQ ID NO: 3); or a fragment or a variant of any one of the sequences.

In the context of the methods of the invention (including those referred to in the paragraphs above), the polypeptide sequence may be a saxitoxin A protein (STXA) sequence. The STXA polypeptide sequence may comprise any one or more STXA protein catalytic domain(s) (i.e. the STXA1, STXA2, STXA3, or STXA4 catalytic domain(s)), or fragment(s) thereof. Preferably, the STXA polypeptide sequence comprises an STXA1 or an STXA4 domain, or fragment(s) thereof. More preferably, the STXA polypeptide sequence comprises an STXA4 domain, or fragment(s) thereof.

In some embodiments, the polypeptide sequence corresponds to a sequence provided in GenBank accession numbers JF343238 or JF343239 (SEQ ID NO: 2 and SEQ ID NO: 4), or a fragment or a variant of either sequence.

In other embodiments, the polypeptide sequence may comprise amino acid residues 1-554 of the polypeptide sequence set forth in GenBank accession number JF343238 (SEQ ID NO: 2); amino acid residues 1-582 of the polypeptide sequence set forth in GenBank accession number JF343239 (SEQ ID NO: 4); amino acid residues 560-752 of the polypeptide sequence set forth in GenBank accession number JF343238 (SEQ ID NO: 2); amino acid residues 588-776 of the polypeptide sequence set forth in GenBank accession number JF343239 (SEQ ID NO: 4); amino acid residues 774-845 of the polypeptide sequence set forth in GenBank accession number JF343238 (SEQ ID NO: 2); amino acid residues 816-891 of the polypeptide sequence set forth in GenBank accession number JF343239 (SEQ ID NO: 4); amino acid residues 947-1281 of the polypeptide sequence set forth in GenBank accession number JF343239 (SEQ ID NO: 4); or a fragment or a variant of any one of the sequences.

Dinoflagellates detected in a sample or determined to be absent from a sample using the methods of the invention may be saxitoxin-producing dinoflagellates. Without imposing any particular limitation, the dinoflagellates may be from the order Gonyaulacales or Gymnodiniales. The dinoflagellates may be from the genus *Alexandrium* (formerly *Gonyaulax*), *Pyrodinium* or *Gymnodinium*. Suitable examples of *Alexandrium* species include *A. catenella* (e.g. strains ACCC01, ACSH02, ACTRA02 and CCMP1493), *A. fundyense* (e.g. strains CCMP1719 and CCMP1979), *A. lusitanicum, A. minutum* (e.g. strains CCMP1888, CCMP113, ALSP01, ALSP02 and AMD16/AMAD16), *A. ostenfeldii* and *A. tamarense* (e.g. strains CCMP1771, ATBB01, ATEB01, ATCJ33 and ATNWB01). Suitable examples of *Gymnodinium* species include *G. catenatum* (e.g. strains GCTRA01 and CS-395). Suitable examples of *Pyrodinium* species include *P. bahamense* var *compressum*.

A sample for use in the methods of the invention may be "obtained" by any means. For example, the sample may be obtained by removing it from a naturally-occurring state (e.g. a sample from a lake, ocean or river), or, by removing it from a "non-natural" state (e.g. a culture in a laboratory setting, dam, reservoir, tank etc.).

A sample for use in the methods of the invention may be suspected of comprising one or more dinoflagellates, or one or more saxitoxin-producing dinoflagellates. The sample may be a comparative or control sample, for example, a sample comprising a known concentration or density of dinoflagellates or saxitoxin-producing dinoflagellates or a sample comprising one or more known species or strains of dinoflagellates or saxitoxin-producing dinoflagellates. The sample may be derived from any source. For example, a sample may be an environmental sample. The environmental sample may be derived from, for example, saltwater, freshwater, a river, a lake, an ocean, or coastal waters. The environmental sample may be derived from a dinoflagellate bloom. Alternatively, the sample may be derived from a laboratory source, such as a culture, or a commercial source. Alternatively, the sample may be derived from a biological source such as, for example, tissue or biological fluid. The sample may be modified from its original state, for example, by purification, dilution or the addition of any other component or components.

In certain embodiments, a sample tested using the methods of the invention may provide information regarding the presence or absence of saxitoxin in animals populating the source of the sample. For example, the sample may be tested to determine the presence or absence of saxitoxin in animal seafoods such as, for example, fish (e.g. pufferfish) and in particular shellfish (e.g. mussels, clams, oysters, scallops and the like).

Polynucleotides and polypeptides for use in methods of the invention may be isolated (i.e. extracted) from microorganisms either in mixed culture or as individual species or genus isolates. Accordingly, the microorganisms of a sample may be cultured prior to extraction or the extraction may be performed directly on a given sample. Suitable methods for the isolation (i.e. extraction) and purification of polynucleotides and polypeptides for analysis using methods of the invention are generally known in the art and are described, for example, in standard texts such as Ausubel (Eds) *Current Protocols in Molecular Biology* (2007), John Wiley and Sons, Inc; Coligan et al. (Eds) *Current Protocols in Protein Science* (2007), John Wiley and Sons, Inc; Walker, (Ed) (1988) *New Protein Techniques: Methods in Molecular Biology*, Humana Press, Clifton, N.J.; and Scopes, R. K. (1987) *Protein Purification: Principles and Practice,* 3rd. Ed., Springer-Verlag, New York, N.Y. Additional methods are described in Neilan (1995) Appl. Environ. Microbiol. 61:2286-2291. Suitable polypeptide purification techniques suitable for use in the methods of the invention include, but are not limited to, reverse-phase chromatography, hydrophobic interaction chromatography, centrifugation, gel filtration, ammonium sulfate precipitation, and ion exchange.

In alternative embodiments, methods of the invention may be performed without isolating nucleic acids and/or polypeptides from the sample.

Detecting the presence (or determining the absence) of polynucleotides of the invention and/or polypeptides of the invention in a given sample may be performed using any suitable technique. Suitable techniques may typically involve the use of a primer, probe or antibody specific for any one or more polynucleotides of the invention or any one or more polypeptides of the invention. Suitable techniques include, for example, the polymerase chain reaction (PCR) and related variations of this technique (e.g. quantitative PCR), antibody based assays such as ELISA, western blotting, flow cytometry, fluorescent microscopy, and the like. These and other suitable techniques are generally known in the art and are described, for example, in standard texts such as Coligan et al. (Eds) *Current Protocols in Protein Science* (2007), John Wiley and Sons, Inc; Walker, (Ed) (1988) *New Protein Techniques: Methods in Molecular Biology*, Humana Press, Clifton, N.J.; and Scopes (1987) *Protein Purification: Principles and Practice,* 3rd. Ed., Springer-Verlag, New York, N.Y.

In preferred embodiments, detecting the presence (or determining the absence) of polynucleotides of the invention in a given sample is achieved by amplification of nucleic acids extracted from a sample of interest by polymerase chain reaction using primers that hybridise specifically to the polynucleotide sequence, and detecting the amplified sequence. Under the PCR approach, oligonucleotide primers can be designed for use in PCR reactions to amplify polynucleotides of the invention such as, for example, RNA (e.g. mRNA), DNA and/or cDNA polynucleotides. Suitable methods of PCR include, but are not limited to, those using paired primers, nested primers, single specific primers, degenerate primers, gene-specific primers, vector-specific primers, partially-mismatched primers, and the like. Methods for designing PCR and RT-PCR primers are generally known in the art and are disclosed, for example, in standard texts such as Ausubel et al. (Eds) *Current Protocols in Molecular Biology* (2007), John Wiley and Sons, Inc; Maniatis et al. *Molecular Cloning* (1982), 280-281; Innis et al. (Eds) (1990) *PCR Protocols: A Guide to Methods and Applications* (Academic Press, New York); Innis and Gelfand, (Eds) (1995) *PCR Strategies* (Academic Press, New York); Innis and Gelfand, (Eds) (1999) *PCR Methods Manual* (Academic Press, New York); and Sambrook et al. (1989) *Molecular Cloning: A Laboratory Manual* (2nd ed., Cold Spring Harbor Laboratory Press, Plainview, N.Y.

The skilled addressee will readily appreciate that various parameters of PCR and RT-PCR procedures may be altered without affecting the ability to obtain the desired product. For example, the salt concentration may be varied or the time and/or temperature of one or more of the denaturation, annealing and extension steps may be varied. Similarly, the amount of DNA, cDNA, or RNA template may also be varied depending on the amount of nucleic acid available or the optimal amount of template required for efficient amplification. The primers for use in the methods and kits of the present invention are typically oligonucleotides typically being at least about 5 nucleotides to about 80 nucleotides in length, more typically about 10 nucleotides in length to about 50 nucleotides in length, and even more typically about 15 nucleotides in length to about 30 nucleotides in length.

The skilled addressee will recognise that primers of the invention may be useful for a number of different applications, including but not limited to, PCR, RT-PCR, and as probes for the detection of polynucleotides of the invention. Such primers can be prepared by any suitable method, including, for example, direct chemical synthesis or cloning and restriction of appropriate sequences. Not all bases in the primer need reflect the sequence of the template molecule to which the primer will hybridize. The primer need only contain sufficient complementary bases to enable the primer to hybridize to the template. A primer may also include mismatch bases at one or more positions, being bases that are not complementary to bases in the template, but rather are designed to incorporate changes into the DNA upon base extension or amplification. A primer may include additional bases, for example in the form of a restriction enzyme recognition sequence at the 5' end, to facilitate cloning of the amplified DNA.

The methods of the invention involve detecting the presence (or determining the absence) of polynucleotides of the invention and/or polypeptides of the invention in a given sample. As noted above, the sequences may comprise saxitoxin A sequences including any one or more of the saxitoxin A1, A2, A3 or A4 catalytic domain sequences (or fragment(s) thereof). Preferably, the sequence comprises the saxitoxin A1 and/or the saxitoxin A4 domain (or fragment(s) thereof). More preferably, the sequence comprises the saxitoxin A4 domain (or fragment(s) thereof).

The skilled addressee will recognise that any primer(s) capable of the amplifying a polynucleotide of the invention, any probe capable of detecting a polynucleotide of the invention, or any antibody capable of detecting a polypeptide of the invention, may be used when performing the methods of the invention. In preferred embodiments, the primers, probes and antibodies bind specifically to any one or more of the saxitoxin A sequences referred to in the preceding paragraph (i.e. paragraph directly above).

By "binding specifically" it will be understood that the primer, probe or antibody is capable of binding to the target sequence with a higher affinity than it binds to an unrelated sequence. Accordingly, when exposed to a plurality of different but equally accessible sequences as potential binding partners, the primer, probe or antibody specific for a target sequence will selectively bind to the target sequence and other alternative potential binding partners will remain substantially unbound by the primer, probe or antibody. In general, a primer, probe or antibody specific for a target sequence will preferentially bind to the target sequence at least 10-fold, preferably 50-fold, more preferably 100-fold, and most preferably greater than 100-fold more frequently than to other potential sequences that are not target sequences. A primer, probe or antibody specific for a target sequence may be capable of binding to non-target sequences at a weak, yet detectable level. This is commonly known as background binding and is readily discernible from specific binding, for example, by use of an appropriate control.

In preferred embodiments, the primers, probes or antibodies bind specifically to a saxitoxin A1 or A4 catalytic domain polynucleotide or polypeptide sequence, or a fragment thereof. More preferably the primers, probes or antibodies bind specifically to a saxitoxin A4 catalytic domain polynucleotide or polypeptide sequence, or a fragment thereof.

Suitable primers and probes may bind specifically to any fragment of a saxitoxin A1 catalytic domain polynucleotide sequence. Suitable antibodies may bind specifically to a fragment of a saxitoxin A1 catalytic domain polypeptide sequence encoded by such polynucleotide sequences.

Suitable primers and probes may bind specifically to any fragment of a saxitoxin A4 catalytic domain polynucleotide sequence. By way of non-limiting example only, suitable primers and probes may bind specifically to a fragment of the saxitoxin A4 catalytic domain polynucleotide sequence defined by nucleotides 3115-4121 of the polynucleotide sequence set forth in GenBank accession number JF343239 (SEQ ID NO: 3). Suitable antibodies may bind specifically to a fragment of a saxitoxin A4 catalytic domain polypeptide sequence encoded by such polynucleotide sequences.

In some embodiments, the methods of the invention may involve detecting the presence (or determining the absence) of polynucleotides of the invention in a sample using PCR amplification. Suitable oligonucleotide primer pairs for the PCR amplification of saxitoxin A polynucleotide sequences may be capable of amplifying any one or more catalytic domain(s) of the sxt gene, or fragments(s) thereof. Preferably, the primers amplify a sequence comprising a saxitoxin A4 catalytic domain polynucleotide sequence, or a fragment thereof. By way of non-limiting example only, a suitable primer pair for this purpose may comprise a first primer comprising the polynucleotide sequence of SEQ ID NO: 198, or a fragment or variant thereof, and/or a second primer comprising the polynucleotide sequence of SEQ ID NO: 199, or a fragment or variant thereof. Other non-limiting examples of suitable primer pairs include those set forth in SEQ ID NOs: 200-211, 220-223, 228-229, and 243-244 (including fragments and variants of these primer pair sequences).

The skilled addressee will recognise that the exemplified primers are not intended to limit the region of the saxitoxin A gene amplified or the methods of the invention in general. The skilled addressee will also recognise that the invention is not limited to the use of the specific primers exemplified, and alternative primer sequences may also be used, provided the primers are designed appropriately so as to enable the amplification of saxitoxin polynucleotide sequences, preferably saxitoxin A polynucleotide sequences, and more preferably saxitoxin A1 and/or A4 domain polynucleotide sequences.

In other embodiments, the methods of the invention may involve detecting the presence (or determining the absence) of polynucleotides of the invention in a sample by the use of suitable probes. Probes of the invention are based on sxt polynucleotide sequences of the invention. Probes are nucleotide sequences of variable length, for example between about 10 nucleotides and several thousand nucleotides, for use in detection of homologous sequences, typically by hybridization. Hybridization probes of the invention may be genomic DNA fragments, cDNA fragments, RNA fragments, or other oligonucleotides. Probes of the invention may be labelled by incorporation of a marker to facilitate their detection. Examples of suitable markers include fluorescent molecules (e.g. acetylaminofluorene, 5-bromodeoxyuridine, digoxigenin, fluorescein) and radioactive isotopes (e.g. $^{32}P$, $^{35}S$, $^{3}H$, $^{33}P$). Detection of the marker may be achieved, for example, by chemical, photochemical, immunochemical, biochemical, or spectroscopic techniques. Methods for the design and/or production of nucleotide probes are generally known in the art, and are described, for example, in standard texts such as Robinson et al. (Eds) *Current Protocols in Cytometry* (2007), John Wiley and Sons, Inc; Ausubel et al. (Eds) *Current Protocols in Molecular Biology* (2007), John Wiley and Sons, Inc; Sambrook et al. (1989) *Molecular Cloning: A Laboratory Manual* (2nd ed., Cold Spring Harbor Laboratory Press, Plainview, N.Y.; and Maniatis et al. (1982) *Molecular Cloning*, 280-281.

In other embodiments, the methods of the invention may involve detecting the presence (or determining the absence) of polypeptides of the invention in a sample using antibodies. The antibodies may be used to qualitatively or quantitatively detect and analyse one or more STX polypeptides of the invention in a given sample. The antibodies may be conjugated to a fluorochrome allowing detection, for example, by flow cytometry, immunohistochemisty or other means known in the art. Alternatively, the antibody may be bound to a substrate allowing colorimetric or chemiluminescent detection. The invention also contemplates the use of secondary antibodies capable of binding to one or more antibodies capable of binding specifically to a polypeptide of the invention.

Kits for Detecting Dinoflagellates

The invention also provides kits for the detection and/or isolation of polynucleotides of the invention and/or polypeptides of the invention ("kits of the invention").

In certain embodiments the kits are used for detecting a dinoflagellate in a sample.

In other embodiments the kits are used for detecting a saxitoxin-producing dinoflagellate in a sample.

In other embodiments the kits are used for determining an absence of saxitoxin-producing dinoflagellates in a sample.

In general, the kits of the invention comprise at least one agent for detecting the presence of one or more polynucleotides of the invention and/or one or more polypeptides of the invention, and/or variants or fragments thereof (see description in the section above entitled "Polynucleotides and polypeptides"). Any agent suitable for this purpose may be included in the kits. Non-limiting examples of suitable agents include primers, probes and antibodies such as those described above in the sections entitled "Probes, primers and antibodies" and "Methods for detecting dinoflagellates".

In preferred embodiments, the kits are for use in the methods of the invention (see description in the section above entitled "Methods for detecting dinoflagellates").

In some embodiments the invention provides a kit for the detection of a dinoflagellate in a sample, the kit comprising at least one agent for detecting in the sample the presence of one or more polynucleotides of the invention, and/or one or more polypeptides of the invention, and/or a variant or fragment of either. Preferably, the dinoflagellate is a saxitoxin-producing dinoflagellate.

In other embodiments the invention provides a kit for determining the absence of a dinoflagellate in a sample, the kit comprising at least one agent for determining in the sample the absence of one or more polynucleotides of the invention, and/or one or more polypeptides of the invention, and/or a variant or fragment of either. Preferably, the dinoflagellate is a saxitoxin-producing dinoflagellate.

In general, kits of the invention may comprise any number of additional components. By way of non-limiting example the additional components may include components for collecting and/or storing samples, reagents for cell culture, reference samples, buffers, labels, and/or written instructions for performing method(s) of the invention.

Dinoflagellates detected in a sample or determined to be absent from a sample using kits of the invention may be saxitoxin-producing dinoflagellates. Without imposing any particular limitation, the dinoflagellates may be from the order Gonyaulacales or Gymnodiniales. The dinoflagellates may be from the genus *Alexandrium* (formerly *Gonyaulax*), *Pyrodinium* or *Gymnodinium*. Suitable examples of *Alexandrium* species include *A. catenella* (e.g. strains ACCC01, ACSH02, ACTRA02 and CCMP1493), *A. fundyense* (e.g. strains CCMP1719 and CCMP1979), *A. lusitanicum, A. minutum* (e.g. strains CCMP1888, CCMP113, ALSP01, ALSP02 and AMD16/AMAD16), *A. ostenfeldii* and *A. tamarense* (e.g. strains CCMP1771, ATBB01, ATEB01, ATCJ33 and ATNWB01). Suitable examples of *Gymnodinium* species include *G. catenatum* (e.g. strains GCTRA01 and CS-395). Suitable examples of *Pyrodinium* species include *P. bahamense* var *compressum*.

It will be appreciated by persons skilled in the art that numerous variations and/or modifications may be made to the invention as described in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting Example 1: Identification of Nuclear-Encoded Genes for the Neurotoxin Saxitoxin in Dinoflagellates Materials and Methods Culturing and Toxin Measurements Saxitoxin-producing and non-producing dinoflagellate cultures were obtained from various culture collections (Table 1).

TABLE 1

List of dinoflagellate strains used in this study, their production of STX and whether sxtA1 and sxtA4 fragments were amplified from their genomic DNA.

| Order | Genus | Species | Strain | STX | PCR sxtA1 | PCR sxtA4 |
|---|---|---|---|---|---|---|
| Gonyaulacales | Alexandrium | affine | CCMP112 | n.d. | n.d. | n.d. |
| | | affine | AABB01/01 | n.d. | n.d. | n.d. |
| | | affine | AABB01/02 | n.d. | n.d. | n.d. |
| | | andersonii | CCMP1597 | n.d. | n.d. | n.d. |
| | | andersonii | CCMP2222 | n.d. | n.d. | n.d. |
| | | catenella | ACCC01 | yes | yes | yes |
| | | catenella | ACSH02 | yes | yes | yes |
| | | catenella | ACTRA02 | yes | yes | yes |
| | | catenella | CCMP1493 | yes | yes | yes |
| | | fundyense | CCMP1719 | yes | yes | yes |
| | | fundyense | CCMP1979 | yes | yes | yes |

TABLE 1-continued

List of dinoflagellate strains used in this study, their production of STX and whether sxtA1 and sxtA4 fragments were amplified from their genomic DNA.

| Order | Genus | Species | Strain | STX | PCR sxtA1 | PCR sxtA4 |
|---|---|---|---|---|---|---|
| | | minutum | CCMP1888 | yes | yes | yes |
| | | minutum | CCMP113 | yes | yes | yes |
| | | minutum | ALSP01 | yes | yes | yes |
| | | minutum | ALSP02 | yes | yes | yes |
| | | minutum | AMD16 | yes | yes | yes |
| | | tamarense | CCMP1771 | n.d. | yes | yes |
| | | tamarense | ATBB01 | n.d. | yes | yes |
| | | tamarense | ATEB01 | n.d. | yes | yes |
| | | tamarense | ATCJ33 | n.d. | yes | yes |
| | | tamarense | ATNWB01 | yes | yes | yes |
| | Gambierdiscus | australes | CAWD148 | * | n.d. | n.d. |
| | Ostreopsis | ovata | CAWD174 | * | n.d. | n.d. |
| | | siamensis | CAWD96 | * | n.d. | n.d. |
| Gymnodiniales | Amphidinium | massarti | CS-259 | * | n.d. | n.d. |
| | Gymnodinium | catenatum | GCTRA01 | yes | yes | yes |
| | | catenatum | CS-395 | yes | yes | yes |
| Prorocentrales | Prorocentrum | lima | CS-869 | * | n.d. | n.d. | n.d. not detected,
* species never reported to synthesize STX

Cultures were maintained in GSe (see method in Doblin et al. (1999), Growth and biomass stimulation of the toxic dinoflagellate *Gymnodinium catenatum* (Graham) by dissolved organic substances. J Exp Mar Biol Ecol 236: 33-47) or L1 media (see method in Guillard and Hargraves (1993) *Stichochrysis immobilis* is a diatom, not a chrysophyte. Phycologia 32, 234-236) at 16-20° C., under a 12/12 light cycle, and a photon irradiance of ~100 micromoles of photons $m^{-2}s^{-1}$. Toxicity of strains was determined using HPLC or LCMS. The detection limit of the HPLC method ranged from about 0.07 μg STXeq/100 g for C1 and C3 to 4.1 μg STXeq/100 g for GTX1. The detection limit for the LCMS method ranged from about 0.1 pg/cell for NEO and STX to 0.5 pg/cell for C1 and C2.

RNA and DNA Extraction

To isolate total RNA for the 454-library construction (see below), cultures of *Alexandrium fundyense* Balech CCMP1719 and *Alexandrium minutum* Halim CCMP113 were harvested in exponential phase through centrifugation (1 min, 1000×g, 12° C.). Cells were washed with PBS, exposed to bead-beating on dry ice with the Fast Prep bead-beater from Medinor (20 s, speed 4) using 1.4 mm beads (Medinor) and total RNA was extracted with the ChargeSwitch® Total RNA Cell kit (Invitrogen) according to the manufacturers' protocol.

For RACE analyses, polyA-enriched mRNA was isolated using the Dynabeads DIRECT kit (Invitrogen). Cells were harvested by centrifugation (2 min, 4° C., 16000×g), were washed twice with PBS, the lysis/binding buffer was added, and this was homogenised using the bead-beater (20 s, step 4). After centrifugation (1 min, 4° C., 16000×g), the clear homogenate was transferred to the Dynabeads mix and the mRNA isolated according to protocol. Finally, mRNA was treated with TURBO™ DNase (Ambion) according to the protocol supplied.

Genomic DNA was isolated from all dinoflagellate strains listed in Table 1 by either using the Genomic DNA plant ChargeSwitch® kit (Invitrogen) according to the manufacturer's protocol, or by the CTAB method.

Quality and quantity of RNA and DNA were determined using a Nanodrop spectrophotometer (ThermoScientific), by amplifying control dinoflagellate genes (cytochrome b, actin) and/or by visualizing them on an ethidium bromide stained agarose gel.

cDNA Library Construction, 454 Sequencing, Assembly and Analyses

Normalized polyA-enriched cDNA libraries with 454 adapters attached at each end were constructed commercially by Vertis Biotechnologie AG. Half a plate each of *A. fundyense* CCMP 1719 and *A. minutum* CCMP113 libraries were sequenced using Roche 454 sequencing TITAN technology at the Norwegian High-Throughput Sequencing Centre. Only 454 reads that possessed at least one cDNA adaptor were considered further. Adaptors and, where present, full and partial dinoflagellate spliced-leader (SL) sequences were removed prior to assembly using an in-house PERL script which is now integrated in the bioinformatic tool CLOTU. Reads were assembled using the software program Mira v3.0.5 with the main switches 'denovo', 'est', 'accurate' and '454'.

To identify putative sxt gene sequences within the two 454 libraries, custom BLAST searches were performed at the freely available online data portal 'Bioportal'. Two strategies were used: the cyanobacterial sxt genes were queried either against the assembled *Alexandrium* datasets or the unassembled 454 read datasets. All hits with an e-value <0.1 were extracted and the sequence with the lowest e-value for each gene was blasted against the non-redundant protein database at NCBI.

For sxtA, all retrieved sequences were re-assembled in the software program CLC Bio Main Workbench, using a minimum overlap of 10 bp and low or high alignment stringency. Resulting contig sequences were blasted against the non-redundant and EST databases at NCBI using algorithms blastn, blastx and tblastx. The structure of sxtA transcripts was determined by aligning their translated sequence to sxtA from cyanobacteria, as well as by conserved domains searches. Catalytic and substrate-binding residues of sxtA from cyanobacteria were previously determined. The transcripts were searched for the presence possible signal peptides and corresponding cleavage sites using the neural networks and hidden Markov models implemented in SignalP 3.0 and the 3-layer approach of Signal-3L. Transmembrane helices were explored using TMHMM server 2.0 and hydrophobicy profiles with Kyte-Doolittle plots.

RACE Analyses

Primers were designed in conserved regions of the contigs with high similarity to sxtA using Primer3 software (Table 2).

(BD Biosciences), 0.2 mM dNTPs, 0.5 μM of each forward and reverse primer (Table 2), DMSO (10% final concentration) and 0.25 units 50×BD Advantage 2 Polymerase Mix (BD Biosciences). If not stated otherwise, PCRs were amplified as follows: 94° C.—2.5 min; 5×(94° C.—30 s; 68° C.—variable); 5×(94° C.—30 s; 66° C.—30 s; 68° C.—vari-

TABLE 2

Primers used in PCR and sequencing

| Name | Sequence 5'-3' | Orientation | Description |
|---|---|---|---|
| sxt001 | TGCAGCGMTGCTACTCCTACTAC (SEQ ID NO: 200) | Forward | binds within sxtA1, designed on 454 reads |
| sxt002 | GGTCGTGGTCYAGGAAGGAG (SEQ ID NO: 201) | Reverse | binds within sxtA1, designed on 454 reads |
| sxt007 | ATGCTCAACATGGGAGTCATCC (SEQ ID NO: 202) | Forward | binds within sxtA4, designed on 454 reads |
| sxt008 | GGGTCCAGTAGATGTTGACGATG (SEQ ID NO: 203) | Reverse | binds within sxtA, designed on 454 reads |

Additional primers used for RACE analyses and sequencing

| sxt013 | GTAGTAGGAGTAGCKACGCTGCA (SEQ ID NO: 204) | Reverse | reverse complement of sxt001 |
| sxt014 | CTCCTTCCTRGACCACGACC (SEQ ID NO: 205) | Forward | reverse complement of sxt002 |
| sxt015 | GGATGACTCCCATGTTGAGCAT (SEQ ID NO: 206) | Reverse | reverse complement of sxt007 |
| sxt016 | CATCGTCAACATCTACTGGACCC (SEQ ID NO: 207) | Forward | reverse complement of sxt008 |
| sxt019 | GGCAAGTATCTCCGCAGGCTTAC (SEQ ID NO: 208) | Reverse | binds within sxtA1, upstream of sxt002 |
| sxt020 | CGTGGAGGAGCATGTTGACAGAATC (SEQ ID NO: 209) | Forward | binds within sxtA1, downstream of sxt001 |
| sxt026 | ACTCGACAGGCCGGCAGTACAGAT (SEQ ID NO: 210) | Reverse | binds with sxtA4, upstream of sxt008 |
| sxt040 | TGAGCAGGCACGCAGTCC (SEQ ID NO: 211) | Forward | binds within sxtA1 on the long transcript |

Primers to amplify clones directly

| TopoF | GGCTCGTATGTTGTGTGGAATTGTG (SEQ ID NO: 212) | Forward | binds within pCR ® 2.1-TOPO ® vector |
| TopoR | AGTCACGACGTTGTAAAACGACGG (SEQ ID NO: 213) | Reverse | binds within pCR ® 2.1-TOPO ® vector |

First-strand cDNA was synthesized with ~95 ng polyA-enriched mRNA using the adaptor primer AP according to the manufacturer's instructions for transcripts with high GC content (3'RACE System, Invitrogen). Following RNase H treatment, the RACE product was 1:10 diluted and used as template for PCR. To amplify the 5'end of the transcript, three different protocols were used. First, the method of Zhang (Zhang et al. (2007) Spliced leader RNA trans-splicing in dinoflagellates. Proc Natl Acad Sci USA 104: 4618-4623) was used with slight modifications: the 3'RACE library described above was amplified with the primers AUAP (adapter primer supplied with the kit) and dinoSL to enrich for full transcripts (PCR program: 94° C.—60 s; 30×(94° C.—30 s, 68° C.—5 min); 68° C.—10 min; 8° C.—hold; PCR chemistry see below). The PCR product was 1:10 diluted and used as template in nested PCRs, which were amplified using the dinoSL primer as forward and several different internal reverse primers (Table 2). Further, these experiments used the two kits 5'RACE System (Invitrogen) and the GeneRacer kit (Invitrogen), using the provided 5'Adapter primers and several different internal reverse primers (Table 2). All products were cloned and sequenced as described below.

PCR and Sequencing

All PCR reactions were carried out in 25 μl volumes containing template, 1 unit 10×BD Advantage 2 PCR buffer able); 25×(94° C.—30 s; 64° C.—30 s; 68° C.—variable); 68° C.—10 min; 8° C.—hold. PCR products were visualized on 1% ethidium bromide stained agarose gels, cut out and cleaned with the Wizard® SV Gel and PCR Clean-up System (Promega) and cloned with the TOPO TA® cloning kit according to the manufacturer's instructions (Invitrogen; pCR®2.1-TOPO® vector; One Shot® Mach1™ T1 Phage-Resistant Chemically Competent E. coli cells). Individual colonies were directly added to 25 μl PCR reactions containing 1 unit 10× standard PCR buffer (Qiagen), 0.4 μM primer TopoF and TopoR (Table 2), 0.2 mM dNTPs, and 1 unit HotStarTaq (Qiagen). Cycling conditions were 95° C.—15 min, 30×(94° C.—30 s; 60° C.—30 s; 72° C.—90 s), 72° C.—5 min, 8° C.—hold. PCR products were diluted and Sanger sequenced directly from both sides using the primers M13F and M13R supplied with the cloning kit.

SxtA1 and sxtA4 Genomic Amplification

All dinoflagellate strains (Table 1) were tested for the presence of putative sxtA1 and sxtA4 genes. PCRs were run using gDNA according to the protocol described above. The sxtA1 fragment was amplified with primers sxt001 & sxt002 (~550 bp) and the sxtA4 fragment with the primers sxt007 & sxt008 (~750 bp) (Table 2).

Phylogenetic Analyses

Dinoflagellate nucleotide sequences were aligned manually using MacClade v4.07 (see Maddison and Maddison (1992) MacClade. 3 ed: Sinauer Associates) considering the coding sequence in the correct reading frame before being translated to the corresponding amino-acid sequence. The dinoflagellate amino acid sequences were subsequently aligned, using MAFFTv6 L-INS-I model to the orthologous sxt sequences for cyanobacteria, in addition to a selection of closely related NCBI nr Blastp hits, constituting the outgroup. Resulting alignments were checked manually and poorly aligned positions excluded using MacClade v4.07 (see Maddison and Maddison (1992) supra).

ProtTest v2.4 (see Abascal et al. (2005) ProtTest: selection of best-fit models of protein evolution. Bioinformatics 21: 2104-2105) determined WAG as the optimal evolutionary model for all inferred alignments. Maximum Likelihood (ML) analyses were performed with RAxML-VI-HPCv7.2.6, PROTCATWAG model with 25 rate categories (see Stamatakis (2006) RAxML-VI-HPC: Maximum likelihood-based phylogenetic analyses with thousands of taxa and mixed models. Bioinformatics 22: 2688-2690). The most likely topology was established from 100 separate searches and bootstrap analyses were performed with 100 pseudo-replicates. Bayesian inferences were performed using Phylobayes v3.2e (see Lartillot and Philippe (2004) A Bayesian mixture model for across-site heterogeneities in the amino-acid replacement process. Mol Biol Evol 21: 1095-1109; and Lartillot and Philippe (2006) Computing Bayes factors using thermodynamic integration. Syst Biol 55: 195-207) under the same substitution model with a free number of mixing categories and a discrete across site variation under 4 categories. Trees were inferred when the largest maximum difference between the bipartitions (chains) was <0.1. All model estimation and phylogenetic analyses were done on the freely available 'Bioportal'.

Copy Number Determination

Triplicate 200 ml batch cultures of *Alexandrium catenella* strain ACSH02 were grown as previously described, and abundance was counted every three days using a Sedgewick-Rafter chamber and inverted light microscope (Leica Microsystems). Ten ml samples for gDNA extraction were taken in early exponential, late exponential and stationary phase.

Primers suitable for qPCR were designed based on conserved regions in an alignment of *A. fundyense* and *A. minutum* 454 reads covering the sxtA4 region using Primer 3 software amplifying a 161 bp product. qPCR cycles were carried out on a Rotor Gene 3000 (Corbett Life Science) using SYBR Green PCR Master Mix (Invitrogen). qPCR assays were performed in a final volume of 25 µl volume consisting of 12.5 µl SYBR Green PCR master mix, 1 µl of template DNA, 1 µl of each primer pair, 1 µl of BSA and 8.5 µl of MilliQ water. qPCR assays were performed in triplicate with the following protocol: 95° C. for 10 s, and 35 cycles of 95° C. for 15 s and 60° C. for 30 s. Melting curve analysis was performed at the end of each program to confirm amplification specificity, and select PCR products were sequenced. The standard curve was constructed from a 10-fold dilution series of a known concentration of fresh PCR product, ranging from $2-2\times10^{-5}$ ng. The molecules of PCR product were determined: $(A\times6.022\times10^{23})\times(660\times B)^{-1}$ with A: concentration of PCR product, $6.022\times10^{23}$: Avogadro's number, 660: average molecular weight per base pair and B: length of PCR product. The number of molecules in the unknown samples were determined and divided by the known number of cells in the qPCR template to obtain copy number per cell. The detection limit was around 5000 copies of the gene sequence (i.e. ~20-30 cells per assay, each with ~200 copies of the sequence). However, the analyses were run with 10-100-fold this number of cells, and thus not run at or close to the detection limit.

Results

Identification of Sxt Sequences in the Transcriptome of *A. minutum* and *A. fundyense* 454 sequencing resulted in 589,410 raw reads for *A. minutum* and 701,870 raw reads for *A. fundyense* (SRA028427.1: samples SRS151150.1 and SRS151148.1, respectively). After quality control, the reads were assembled into 44,697 contigs and 539 singletons for *A. minutum* and 51,861 contigs and 163 singletons for *A. fundyense*. The contig lengths and GC contents were similar for both libraries: the mean sequence lengths (±SD) of 669 bp (±360) and 678 bp (±361) and a GC content of 59% and 58% were calculated for *A. minutum* and *A. fundyense*, respectively.

Searching the unassembled 454 cDNA library reads with the cyanobacterial sxtA gene resulted in 94 hits for *A. fundyense* and 88 hits for *A. minutum*, respectively. The same search on the assembled datasets returned 10 contigs from the *A. fundyense* and 9 from the *A. minutum* library. After pooling of all sequences and re-assembly, two contigs showed a high similarity to sxtA from cyanobacteria: one to the domain sxtA1 (contig length=1450 bp, GC=60.1%, bit score=213, e-value=$5e^{-61}$) and the other to sxtA4 (contig length=1059 bp, GC=65%, bit score=195, e-value=$1e^{-47}$). Both contigs contained sequences from both *Alexandrium* libraries, but neither contained a full ORF, a dinoflagellate spliced leader sequence or a polyA-tail. The two contigs were used to design sxtA1 and sxtA4 primers for genomic amplification, RACE analyses and sequencing.

The results of the in silico search for the remaining core sxt genes are summarized in Table 3.

TABLE 3

Blast analyses of the core sxt genes from *C. raciborskii* T3 against the assembled *A. fundyense* and *A. minutum* 454 libraries; given are: the number of contigs with an E-value ≤0.1 present in each library; the top blastX hit, its accession number, taxonomy, score and E-value when the top contig is blasted against the non-redundant protein database of NCBI, as well as the closest hit to sxt genes from cyanobacteria from the same analysis.

| 454 library | Number of contigs | Top score/ E-value | Uppermost blastX hit of top contig against NCBI nr-database | Accession | Taxonomy | Uppermost blastX score/ E-value | Top sxt hit score/ E-value |
|---|---|---|---|---|---|---|---|
| sxtA |  |  |  |  |  |  |  |
| *A. fundyense* | 10 | 105/2e−51 | polyketide synthase [*Myxococcus xanthus* DK 1622] | YP_63211 | Bacteria; Prote obacteria | 183/5e−44 | 182/7e−44 |
| *A. minutum* | 9 | 108/3e−61 | SxtA [*Lyngbya wollei*] | ACG63826 | Bacteria; Cyanobacteria | 236/2e−65 | 236/2e−65 |
| sxtB |  |  |  |  |  |  |  |
| *A. fundyense* | 1 | 46/7e−11 | cytidine deaminase [*Plesiocystis pacifica* SIR-1] | ZP_01910517 | Bacteria; Proteobacteria | 91/9e−27 | 67/1e−11 |
| *A. minutum* | 1 | 35/0.094 | none |  |  |  |  |

TABLE 3-continued

Blast analyses of the core sxt genes from C. raciborskii T3 against the assembled A. fundyense and A. minutum 454 libraries; given are: the number of contigs with an E-value ≤0.1 present in each library; the top blastX hit, its accession number, taxonomy, score and E-value when the top contig is blasted against the non-redundant protein database of NCBI, as well as the closest hit to sxt genes from cyanobacteria from the same analysis.

| 454 library | Number of contigs | Top score/ E-value | Uppermost blastX hit of top contig against NCBI nr-database | Accession | Taxonomy | Uppermost blastX score/ E-value | Top sxt hit score/ E-value |
|---|---|---|---|---|---|---|---|
| sxtF/sxtM | | | | | | | |
| A. fundyense | 4 | 51/4e−06 | putative efflux protein, MATE [*Polysphondylium pallidum* PN500] | EFA81712 | Eukaryota; Amoebozoa | 136/2e−30 | 62/5e−08 |
| A. minutum | 1 | 34/0.01 | putative efflux protein, MATE [*Arabidopsis lyrata* subsp. *lyrata*] | XP_002873960 | Eukaryota; Viridiplantae | 78/8e−23 | none |
| sxtG | | | | | | | |
| A. fundyense | 9 | 57/2e−27 | glycine amidinotransferase [*Amycolatopsis mediterranei* U32] | YP_003768377 | Bacteria; Actinobacteria | 163/3e−38 | 140/2e−31 |
| A. minutum | 7 | 55/2e−25 | glycine amidinotransferase [*Amycolatopsis mediterranei* U32] | YP_003768377 | Bacteria; Actinobacteria | 143/2e−32 | 117/1e−24 |
| sxtH/sxtT | | | | | | | |
| A. fundyense | 7 | 43/2e−12 | Rieske (2Fe—2S) region [*Anabaena variabilis* ATCC 29413] | YP_321575 | Bacteria; Cyanobacteria | 197/6e−86 | 80/1e−12 |
| A. minutum | 6 | 41/5e−06 | Rieske (2Fe—2S) region [*Anabaena variabilis* ATCC 29413] | YP_321575 | Bacteria; Cyanobacteria | 119/5e−38 | 60/2e−07 |
| sxtI | | | | | | | |
| A. fundyense | 3 | 68/1e−13 | Carbamoyltransferase [*Nocardiopsis dassonvillei* DSM 43111] | YP_003679504 | Bacteria; Actinobacteria | 131/9e−29 | 89/9e−16 |
| A. minutum | 1 | 67/1e−13 | carbamoyl transferase [*Streptomyces griseoflavus* Tu4000] | ZP_05536710 | Bacteria; Actinobacteria | 132/6e−29 | 91/1e−16 |
| sxtR | | | | | | | |
| A. fundyense | 3 | 36/0.063 | atp-citrate synthase [*Ectocarpus siliculosus*] | CBJ30109 | Eukaryota; stramenopiles | 349/8e−96 | none |
| A. minutum | 1 | 38/0.015 | atp-citrate synthase [*Ectocarpus siliculosus*] | CBJ30109 | Eukaryota; stramenopiles | 516/1e−144 | none |
| sxtS | | | | | | | |
| A. minutum | 1 | 36/0.05 | hypothetical protein [*Perkinsus marinus* ATCC 50983] | XP_002767298 | Eukaryota; Alveolata | 91/4e−34 | none |
| sxtU | | | | | | | |
| A. fundyense | 33 | 83/2e−16 | predicted protein [*Chlamydomonas reinhardtii*] | XP_001689640 | Eukaryota; Viridiplantae | 214/4e−54 | 107/8e−22 |
| A. minutum | 27 | 84/2e−16 | hypothetical protein [*Schizophyllum commune* H4-8] | XP_003034688 | Eukaryota; Fungi | 116/1e−24 | 797/2e−13 |

Apart from sxtA, contigs with a good alignment score (bit score >55) and a highly significant e-value ($<e^{-20}$) were recovered for the amidinotransferase gene sxtG in both libraries. Re-blasting the contigs with the lowest e-values against the NCBI nr protein database showed that the most similar gene was an actinobacterial glycine aminotransferase, while the similarity to sxtG from cyanobacteria was less but still highly significant (Table 3). For the core biosynthesis genes sxtB, sxtF/M, sxtH/T, sxtI, sxtR and sxtU, contigs with an e-value ≤0.1 were recovered from both *Alexandrium* libraries, while sxtS only had a hit in the *A. minutum* library (Table 3). No matches were recovered for sxtC, sxtD and sxtE in either of the libraries. SxtC and sxtE are unknown proteins and sxtD is a sterol desaturase-like protein. It is possible that dinoflagellate proteins with no similarity to the cyanobacterial genes carry out their function. Alternatively, these genes were not present in the dataset generated. While the dataset is comprehensive, it is not complete. For example, some regions of the sxtA transcripts were also not recovered in the 454 dataset, but only obtained through RACE analyses (see above). Re-blasting against NCBI nr protein database retrieved hits to proteins for sxtB (*A. fundyense* only), sxtF/M, sxtH/T, sxtI, and sxtU that are similar to those encoded in the corresponding cyanobacterial sxt genes. The actual sequence similarity was less conserved and no significant hits between the *Alexandrium* contigs and the cyanobacterial sxt genes were observed.

Transcript Structure of sxtA in *A. fundyense*

The RACE experiments resulted in two different sxtA-like transcript families. Both had dinoflagellate spliced-leader sequences at the 5'end and polyA-tails at the 3'end, but they differed in sequence, length, and in the number of sxt domains they encode. The shorter transcripts encode the domains sxtA1, sxtA2 and sxtA3, while the longer transcripts encodes all four sxtA domains, which are also encoded by the cyanobacterial sxtA gene (FIG. 1).

The consensus sequence of the shorter transcripts was 3136 bp excluding polyA-tail. Eight clones with SL-leader were sequenced, and three different 5'UTRs were uncovered. The sequences were almost identical; however, one clone had a 15 bp and another had a 19 bp insert exactly following the SL-sequence. The two sequence inserts were, apart from the length, identical. The nine 3'UTR that were sequenced were almost identical and the polyA-tail started at the same position in each clone. The domain structure of this shorter sxtA transcript was as follows: Amino acid residues 1-27 encode a signal peptide. Residues 28-531 correspond to sxtA1, which contains three conserved motifs (I: VDTGCGDGSL (SEQ ID NO: 214), II: VDASRTLHVR (SEQ ID NO: 215), III: LEVSFGLCVL (SEQ ID NO: 216)). Residues 535-729 correspond to sxtA2 with the catalytic domains 557-W, 648-T, 663-H, 711-R; while sxtA3, the final domain of the short transcript, corresponds to residues 750-822 with the phosphopantetheinyl attachment site 783-DSL-785.

The consensus sequence of the longer sxtA transcript was 4613 bp (majority rule, longest 3'UTR, without polyA-tail, FIG. 1). Five clones with SL-sequences were characterized. One of those had a slightly divergent SL-sequence with an A at position 15 instead of the usual G. All 5'UTRs were 97 bp long (excluding SL sequence) and almost identical in sequence. Each of the four 3'clones sequenced had a different length (342, 407, 446 and 492 bp). The domain structure of the longer sxtA transcript was as follows: Amino acid residues 1-25 encode a signal peptide. Residues 26-530 correspond to domain sxtA1 with the three conserved motifs: I: VVDTGCGDG (SEQ ID NO: 217), II: VDPSRSLHV (SEQ ID NO: 218) and III: LQGSFGLCML (SEQ ID NO: 219); residues 535-724 correspond to domain sxtA2, with the catalytic residues 556-W, 661-T, 693-H, 708-R; sxtA3 corresponds to the residues 763-539 where 799-DSL-801 is the phosphopantetheinyl attachment site; finally, domain sxtA4 corresponds to residues 894-1272.

The GC content of the two *Alexandrium* sxtA transcripts was consistently higher than the cyanobacteria sxtA genes (FIG. 2). The GC contents were 69% (long transcript), 62% (short transcript) and 43% (all cyanobacteria sxtA genes).

All algorithms predicted the presence of signal peptides (SP) and corresponding cleavage sites for both transcripts. However, transmembrane helices that may indicate class I transit peptides in dinoflagellates were not predicted. Neither of the transcripts matched the criteria for class II and class III transit peptides.

The Genbank accession numbers are JF343238 for the short and JF343239 for the long sxtA transcripts (majority rule consensus sequences), and JF343357-JF343432 for the remaining cloned RACE sequences of *A. fundyense* CCMP 1719.

Phylogeny of Dinoflagellate sxtA1 and sxtA4 Sequences

The sxtA1 and sxtA4 primers designed in this study (Table 2) amplified single bands of ~550 bp (sxtA1) and ~750 bp (sxtA4) length in 18 *Alexandrium* strains comprising five species and two *Gymnodinium catenatum* strains, which had a range of toxicities (Table 1). No sxtA1 or sxtA4 PCR products were amplified for five non-STX-producing *Alexandrium affine* and *Alexandrium andersonii* strains, nor for non-STX-producing dinoflagellate strains of the genera *Gambierdicus, Ostreopsis, Prorocentrum, Amphidinium* (Table 1). These PCR-based results are generally in agreement with the toxin measurements. However, sxtA1 and sxtA4 fragments were amplified from the genomic DNA of four *A. tamarense* strains (ATCJ33, ATEB01, CCMP1771, ATBB01) in which no STX were detected (Table 1).

Figure 5:
FIG. 5 shows an SxtA1 phylogenetic tree. Maximum likelihood topology is shown. Numbers on nodes represent bootstrap values of maximum likelihood and Bayesian analyses, respectively. Sequences in bold are transcript-derived sequences; either generated using RACE or are contigs from 454 read assembly.

The phylogenetic analyses of sxtA1 (FIG. 3; FIG. 5) show that all sxtA1 sequences formed one fully supported cluster, divided into two sub-clusters. Some clones of the same strain were identical, however, slightly different clones were observed for most strains. These different clones were distributed throughout the phylogeny, generally without species- or strain-related patterns. Only sequences from *G. catenatum* formed a tight branch within one of the sub-clusters. The closest relatives to the dinoflagellate cluster were the cyanobacterial sxtA genes and proteobacterial polyketide synthases (FIG. 3; FIG. 5).

Figure 4A:
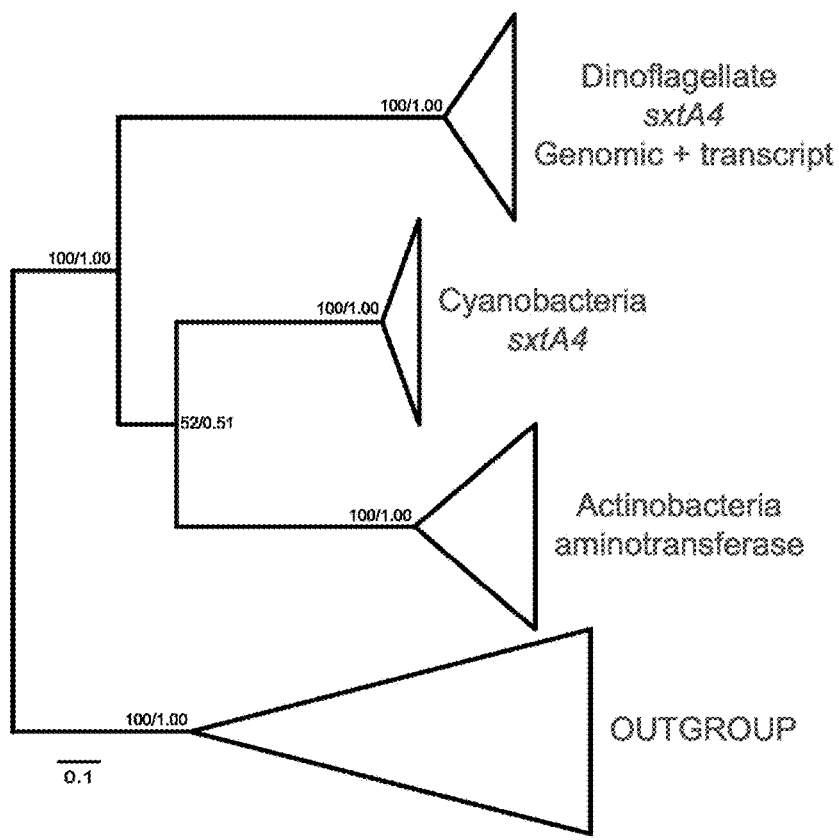
FIG. 4A shows an SxtA4 phylogenetic tree. Schematic representation of phylogenetic tree, drawn to scale (for full tree see FIG. 6). Maximum likelihood topology is shown. Numbers on nodes represent bootstrap values of maximum likelihood and Bayesian analyses, respectively.
Figure 6:
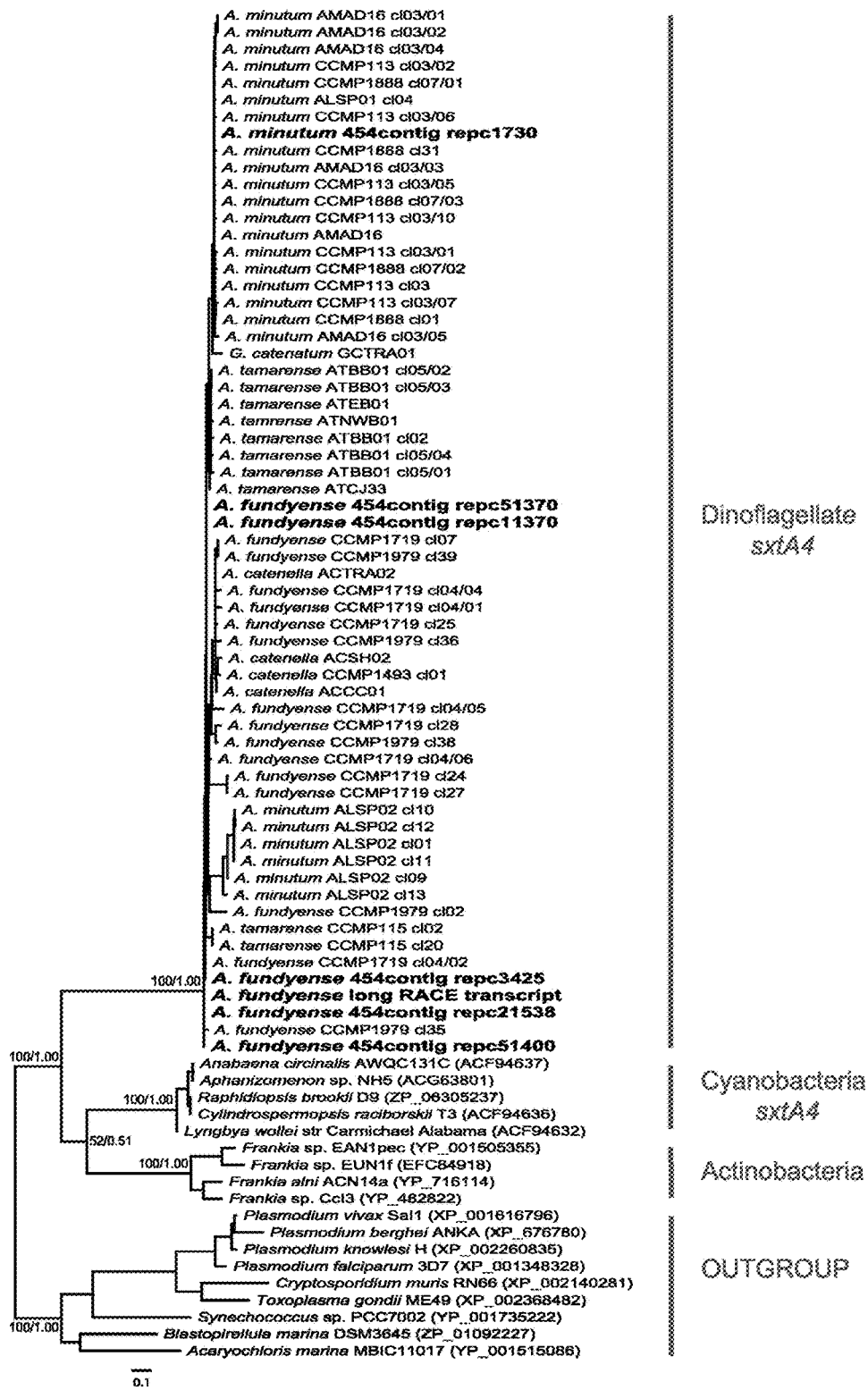
FIG. 6 shows an SxtA4 phylogenetic tree. Maximum likelihood topology is shown. Numbers on nodes represent bootstrap values of maximum likelihood and Bayesian analyses, respectively. Sequences in bold are transcript-derived sequences; either generated using RACE or are contigs from 454 read assembly.
Figure 7A:
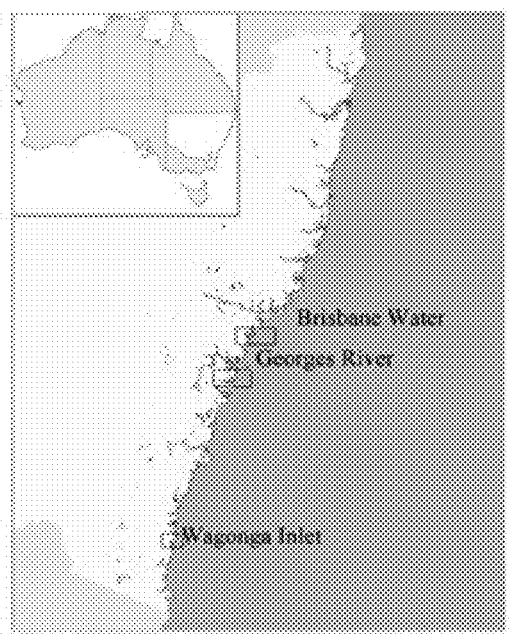
FIG. 7A-D is a map showing Phytoplankton and *S. glomerata* sampling sites referred to Example 2. A. New South Wales, Australia, and the three estuaries in which blooms were sampled: B. Brisbane Water, C. the Georges River and D. Wagonga Inlet. Scale bar in D represents 1 km in inset maps B, C and D.
Figure 7B:
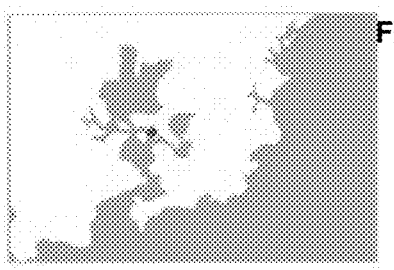
Figure 7C:
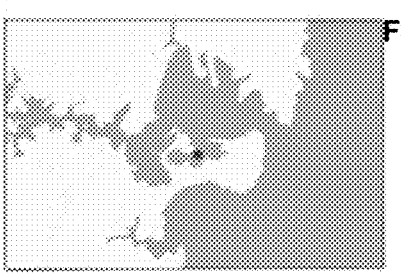
Figure 7D:
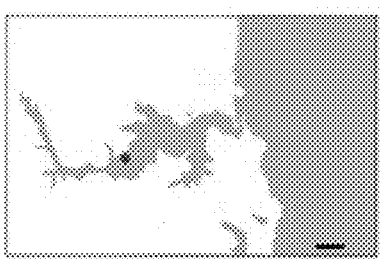

All sxtA4 sequences formed one well-supported cluster, with clones from the same strain distributed throughout (FIG. 4A; FIG. 6). The cyanobacterial sxtA genes and actinobacterial aminotransferases formed the closest sister clades.

The Genbank accession numbers for the genomic sxtA1 and sxtA4 fragments are JF343240-JF343356.

Copy Number and Polymorphisms of sxtA4

Figure 4B:
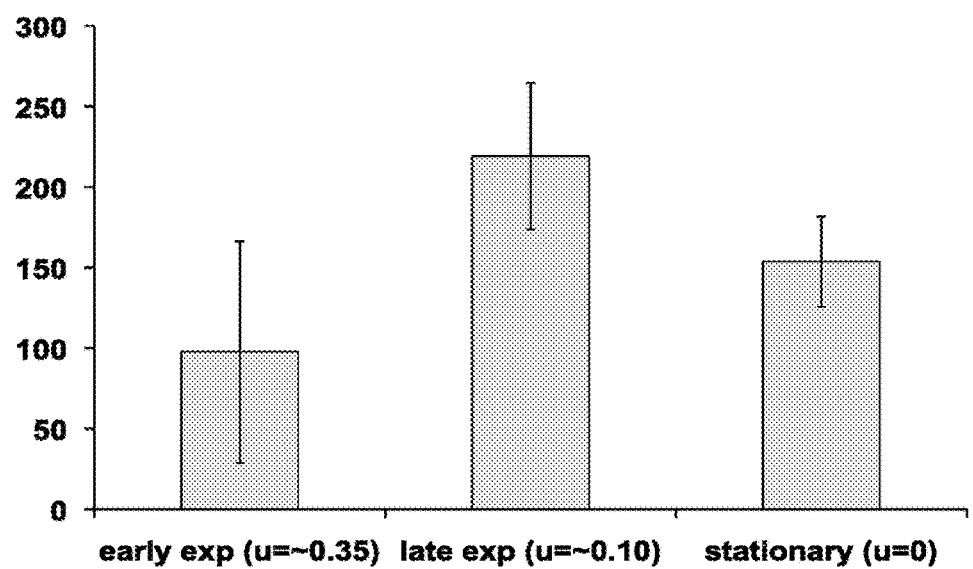
FIG. 4B is a graph showing the genomic copy number of sxtA4 in *A. catenella* ACSH02 at three different time-points during the growth cycle.

Between 100-240 genomic copies of sxtA4 in *A. catenella* were found in triplicate batch cultures of ACSH02 collected at three time points with different growth rates, based on the qPCR assay (FIG. 4B).

Analysis of a 987 bp contig, which covered the sxtA4 domain and was based on *A. fundyense* 454 reads revealed at least 20 single nucleotide polymorphisms (SNPs), 15 of which were silent. SNPs were defined as a base pair change that occurred in at least two of the reads. Homopolymer stretches and indels were ignored.

Discussion

Sxt Genes are Encoded in Dinoflagellate Genomes

The dinoflagellate genome is unusually large [1.5-200 pg DNA cell-1; 52] and highly divergent. Recent estimates predict that dinoflagellate genomes contain between 38,000 and almost 90,000 protein-encoding genes, which correspond to 1.5-4.5 the number of genes encoded in the human genome. The results of sequencing >1.2 million ESTs in this study demonstrate that close homologues of the genes involved in STX biosynthesis in cyanobacteria are also present in STX-producing dinoflagellates (Table 3). To further confirm their dinoflagellate origins sxtA was investigated being the unique starting gene of the biosynthesis pathway. The transcriptome of *A. fundyense* CCMP 1719 contained two different transcript families that had the same domain architecture as sxtA in cyanobacteria. The two transcript families varied in length, sequence, and the number of catalytic domains they encode. The longer transcripts contained all four domains present in the known cyanobacterial sxtA genes, however, the shorter transcripts lacked the terminal aminotransferase domain (FIG. 1). In contrast to bacterial transcripts, both transcript families possessed eukaryotic polyA-tails at the 3'end and dinoflagellate spliced-leader sequences at the 5'end. Hence, these results clearly show that at least sxtA, and possibly other sxt genes, are encoded in the nuclear genome of dinoflagellates and that STX-synthesis in dinoflagellates does not originate from co-cultured bacteria. These bacteria may still, however, play an important role in modulating STX biosynthesis in dinoflagellates.

The signal peptides identified in both transcripts indicate a specific targeting of both Sxt products. Many genes in the nuclear genomes of dinoflagellates are plastid-derived and their products targeted to the plastid. These proteins are translated in the cytosol and then transported to the plastid through the plastid membranes. In peridinin-containing dinoflagellates like *Alexandrium*, this process requires the presence of signal and transfer peptide motifs. Both sxtA transcripts are predicted to contain signal peptides, but transfer-peptide structures were not identified. Thus, it seems that both sxtA proteins are targeted out of the cytosol, but the region of target need to be experimentally investigated.

The dinoflagellate sxtA transcripts did not only differ from the cyanobacterial counterparts by the presence of signal peptides, SL sequences and polyA-tails, but also in their GC content. The *A. fundyense* ESTs had a considerably higher GC content (FIG. 2). Transcribed genes from *Alexandrium* species have been reported to have an average GC content >56%, while filamentous cyanobacteria, such as the STX-producing genera *Cylindrospermopsis, Anabaena, Aphanizomenon* and *Lyngbya*, have a genomic GC content around 40%. This indicates that the GC content of sxtA has diverged significantly from the progenitor sxtA possessing ancestor, in line with the rest of the genome in these microorganisms.

The involvement of the two different sxtA transcripts and their role in STX-synthesis is presently unclear, but the differences in GC content (FIG. 2) indicate that they are under different selection pressures.

The Non-Identical Copies of sxtA: Variation at the Genome and Transcriptome Level One typical feature of dinoflagellate genomes is that genes may occur in multiple copies, which may or may not be identical. This is possibly related to highly unusual genetic mechanisms such as the recycling of processed cDNAs. It appears that sxtA also occurs in multiple copies within dinoflagellate genomes. It was estimated that 100-240 copies of the sxtA4 domain were present in the genomic DNA of *A. catenella* ACSH02 (temperate Asian ribotype). The copy number differences detected throughout the cell cycle are likely related to the growth rate of the batch culture and the proportion of cells in various cell cycle phases. All genomic sxtA4 sequences from 15 different *Alexandrium* and one *G. catenatum* strains formed one well-supported phylogenetic cluster, with several slightly different clone sequences of the same strain distributed throughout the tree. SxtA1 was also found to occur in multiple, non-identical copies in all strains analysed (FIG. 5). Further, the separation of the dinoflagellate sxtA1 cluster into two sub-clades indicates that sxtA1 may be encoded by two separate gene classes, at least in some strains.

The genomic variation of sxtA is also present in the *Alexandrium* transcriptomes. Adding the transcriptome data to the sxtA1 tree showed that the upper clade corresponds to the longer sxtA transcripts, whereas the lower clade corresponds to the shorter transcripts (FIG. 3, FIG. 5). Analyses at the nucleotide level of the sxtA4 region in the transcriptome of *A. fundyense* revealed many of SNP sites, two-thirds of which were silent.

Correlation Between sxtA1, sxtA4 and Saxitoxin Production

The sxtA1 and sxtA4 genomic sequences identified during this study were present in all STX-producing dinoflagellate strains analysed, including two *G. catenatum* and 14 *Alexandrium* strains of the species *A. catenella, A. minutum, A. fundyense* and *A. tamarense*. Neither of the two sxt fragments were amplified from two *A. andersoni* and three *A. affine* strains. Homologs were also not detected in *Gambierdiscus australes, Amphidinium massartii, Prorocentrum lima, Ostreopsis siamensis* and *Ostreopsis ovata*, none of which are known to produce STX (Table 1).

Despite the very good correlation between the presence of sxtA1 and sxtA4 and STX content for most of the strains analysed, both fragments were also amplified from *A. tamarense* strains for which no STX-production was detected (Table 1). RACE analyses of *A. tamarense* strain CCMP1771 revealed that sxtA1 and sxtA4 were transcribed in this strain (data not shown). It is postulated that the amount of STX produced by *A. tamarense* is lower than the detection limit of the HPLC/MS toxin determination methods used. since a very sensitive saxiphilin assay used to investigate *A. tamarense* strain ATBB01 found it to be toxic. Transcript abundance has been suggested to be positively related to the number of gene copies present in a dinoflagellate genome. Hence, it is possible that strains with low levels of STX have fewer copies of the sxt genes compared to those with greater STX-production. If this holds true, then the presence of sxtA1 and sxtA4 would indicate toxicity and molecular methods could be developed to detect STX-producing cells in the environment.

Evolution of STX-Synthesis in Eukaryotes and its Role in the Diversification of *Alexandrium*

The cyanobacterial sxt genes are highly conserved between cyanobacteria species and the gene cluster is thought to have arisen at least 2100 million years ago. The results herein show that dinoflagellate sxtA transcripts that are phylogenetically closely related to a clade of the cyanobacteria sxtA sequences and other bacterial putative toxin-related genes (FIG. 3 & FIG. 4) also have the same domain structure as cyanobacterial sxtA genes (FIG. 1). It is proposed that this striking similarity is most likely due to a horizontal gene transfer (HGT) event between ancestral STX-producing bacteria and dinoflagellates. Within dinoflagellates, STX are produced by species of the genera *Alexandrium* and *Pyrodinium*, which belong to the family Gonyaulacaceae within the order Gonyaulacales, as well as by one species of the genus *Gymnodinium*, which belongs to the family Gymnodiniaceae in the order Gymnodiniales. Thus, these toxins are produced by two genera within one family and by a single species from a distant dinoflagellate order. This distribution of STX-synthesis within the dinoflagellates as well as the close relationship between *Alexandrium* and *Gymnodinium catenatum* sxtA sequences (FIG. 3, FIG. 4, FIG. 5, and FIG. 6), suggests that the bacteria-to-dinoflagellate HGT likely took place prior to the origin of the genera *Alexandrium* and *Pyrodinium*, and was followed by a dinoflagellate-to-dinoflagellate transfer into *G. catenatum*. The extent of eukaryote-to-eukaryote HGTs is often underestimated due to difficulties in detecting such events, however, recent work highlights the importance and prevalence of such gene transfers.

The relationship among the dinoflagellate sxtA sequences in this study was not resolved in this study, as most the internal nodes were not statistically supported (FIG. 5 and FIG. 6). Therefore, it was not possible to determine with certainty whether the evolution of the sxtA genes mirrors that of the genus *Alexandrium*, or to determine the origins of a putative HGT from *Alexandrium* into *G. catenatum*. However, the sxtA1 and sxtA4 gene copies from multiple strains of *G. catenatum, A. minutum*, and *A. catenella* tended to be clustered by species indicating that their history reflects the evolution of these species. The non-amplification of sxtA1 and sxtA4 from the non-STX-producing species *A. affine* and *A. andersoni* may indicate that the sxtA genes have either been lost from these lineages or have mutated so much, that the primers developed here were not able to amplify them.

The two *Alexandrium* EST datasets contained transcripts, which encoded homologs to the majority of core sxt genes identified from cyanobacteria (Table 3). Even though the similarity to the cyanobacterial sxt genes was often significant, it was much less than observed for sxtA. The closest hits were to other bacterial or eukaryotic genes present in the database. This indicates that different genes in the sxt pathway may have separate origins in dinoflagellates. Further work is required to elucidate the complex origins of this gene cluster and will lead to further advances regarding the genomes and molecular biology of these ancient and important microorganisms.

Example 2: Quantitative Method for Detecting and Quantifying STX Production in Dinoflagellates Materials and Methods Culture Maintenance Dinoflagellate cultures (Table 4) were maintained in GSe (Doblin et al., 1999, supra) or L1 media (Guillard &

Hargraves, 1993 supra) at 16-20° C. Light was provided by white fluorescent bulbs (Crompton Light), with photon flux of 60-100 μmol photon m$^{-2}$sec$^{-1}$ on 12/12 hour dark/light cycle. Strains used were provided by the University of Tasmania (isolated by M. de Salas) the Australian National Culture Collection of Marine Microalgae, Provasoli-Guillard Culture Collection (CCMP) and the Cawthron Institute Culture Collection.

TABLE 4

Dinoflagellate strains tested, STXs content and whether the sxtA4 qPCR primer pair resulted in a product. All samples were tested with a positive control to ensure PCR inhibitors were not present.

| Dinoflagellate | Strain number | STXs detected[1] | sxtA4 qPCR product |
|---|---|---|---|
| *Alexandrium* | | | |
| affine | CCMP112 | − | − |
| affine | CS-312/02 | − | − |
| andersonii | CCMP1597 | − | − |
| andersonii | CCMP2222 | − | − |
| catenella | ACCC01 | + | + |
| catenella | ACSH02 | + | + |
| catenella | ACTRA02 | + | + |
| fundyense | CCMP1719 | + | + |
| minutum | CCMP113 | + | + |
| minutum | CS-324 | + | + |
| tamarense | ATCJ33 | − | + |
| tamarense | ATNWB01 | + | + |
| *Gambierdiscus* | | | |
| australes | CAWD148 | − | − |
| *Ostreopsis* | | | |
| ovata | CAWD174 | − | − |
| siamensis | CAWD | − | − |
| *Amphidinium* | | | |
| massarti | CS-259 | − | − |
| *Gymnodinium* | | | |
| catenatum | GCTRA01 | + | + |
| Environmental water sample containing: *Protoceratium reticulatum* *Prorocentrum micans, Karenia* sp | | n/a | − |

*Karlodinium veneficum*

*Polarella glacialis*

*Symbiodinium* sp

DNA Extraction and PCR

Culture density was determined regularly using a Sedgewick Rafter cell (Proscitech) and an inverted light microscope (Leica Microsystems). Known numbers of cultured cells were harvested during exponential growth phase. DNA was extracted from the cell pellets using the CTAB method (see Doyle and Doyle, 1987 A rapid DNA isolation procedure for small quantities of fresh leaf tissue. Phytochem Bull 19:1-5), with an additional overnight DNA precipitation at −20° C. Quality and quantity of DNA was determined using a Nanodrop (Thermoscientific), and by amplifying a control dinoflagellate gene (cytb or SSU rRNA), according to the protocols of Lin et al. (2009), using the primer pair 4f and 6r, which amplify a 440 bp fragment, or 18S r DNA primers 18SF08 (5'-TTGATCCTGCCAGTAGTCATATGCTTG-3' (SEQ ID NO: 220)) and R0ITS (5'-CCTTGT-TACGACTTCTCCTTCCTC-3'(SEQ ID NO: 221)) that amplify ~1780 bp.

Sxt qPCR Assay Development and Copy Number Determination

An alignment of sxtA4 genomic and sequences from 9 strains of the species *Alexandrium catenella, A. tamarense, A. minutum, A. fundyense* and *Gymnodinium catenatum* (GenBank accession numbers JF343238-JF343239, JF343259-JF343265) was constructed. The degree of conservation of the gene sequences was checked for a 440 bp fraction of the sxtA4 domain and found to be 94-98% between *Alexandrium* species, and 89% between *Gymnodinium catenatum* and *Alexandrium* species. Primers specific for sxtA4 were designed using Primer3 software and a consensus sequence. The specificity of the primer sequences was then confirmed using BLAST (Basic Local Alignment Search Tool) on NCBI (National Centre for Biotechnology Information). The sequences of the primers were sxtA4F 5' CTGAGCAAGGCGTTCAATTC 3' (SEQ ID NO: 198) and sxtA4R 5' TACAGATMGGCCCTGTGARC 3' (SEQ ID NO: 199), resulting in an 125 bp product.

To determine their specificity to STX-producing, or potentially STX-producing strains, the sxtA4 primer pair was amplified from 6 species of *Alexandrium, Gymnodinium catenatum*, 3 other toxin producing species of Gonyaulacales: *Ostreopsis ovata, Gambierdiscus australes, Ostreopsis siamensis*, an additional dinoflagellate, *Amphidinium massartii*, and an environmental sample containing a mixed phytoplankton community, including 6 identified dinoflagellate species (Table 4). PCR amplification was performed in 20 μl reactions containing template, 0.5 μM of each primer, 3 mM MgCl$_2$, 1 μl BSA (NEB), and 10 μL Immomix (Bioline), containing dNTPs, Immolase Taq polymerase and reaction buffer or 20 μl containing template, 0.2 μM of each primer, 3 mM MgCl$_2$, 1 μl BSA, 2 μl MyTaq reaction buffer (Bioline) containing dNTPs, 0.2 μl MyTaq (Bioline) hot start polymerase and H$_2$O. Hot start PCRs were performed with an initial denaturing step of 95° C. for 5-10 min, and 35 cycles of 30 s at 95° C., 30 s at 55 or 60° C. (for the cytb and sxtA4 primers, respectively), 30s at 72° C. followed by a final extension step of 7 min at 72° C. The 18S fragment was amplified in 25 μL reactions containing template, 1 unit 10×BD Advantage 2 PCR buffer (BD Biosciences), 5 mM dNTPs, 0.2 μM of each primer, DMSO (10% final concentration) and 0.25 units 50×BD Advantage 2 Polymerase Mix (BD Biosciences). PCRs were amplified as follows: 94° C.—1 min; 30×(94° C.—30 s; 57° C.—30 s; 68° C.—120 s); 68° C.—10 min; 8° C.—hold. Products were analysed using 3% agarose gel electrophoresis, stained with ethidium bromide and visualized.

qPCR was also performed using a primer pair specific for the temperate Asian ribotype of *Alexandrium catenella*, found in Australian temperate waters, based on a region of the large subunit (LSU) ribosomal RNA region (Hosoi Tanabe and Sako, 2005), amplifying an 160 bp fragment, catF (5'-CCTCAGTGAGATTGTAGTGC-3' (SEQ ID NO: 222)) and catR (5'-GTGCAAAGGTAATCAAATGTCC-3' (SEQ ID NO: 223)). Assays were performed on environmental samples, and new standard curves of this LSU rRNA primer pair were constructed based on strains isolated from Australian waters by M. de Salas (UTAS): ACCC01, isolated from Cowan Creek, NSW, approximately 20 km from the Brisbane Water site and 50 km from Georges River site, ACSH02, isolated from Sydney Harbour, approximately 35 km north of the Georges River site, and ACTRA02, isolated from Tasmania, Australia.

qPCR cycling was carried out on a Rotor Gene 3000 (Corbett Life Science) using SSOFast Evagreen supermix (Biorad). qPCR assays were performed in a final volume of 20 μl consisting of 10 μl Evagreen master mix (containing DNA intercalating dye, buffer and Taq polymerase), 1 μl of template DNA, 0.5 μM of each primer, and 1 μl of BSA. qPCR assays were performed in triplicate with the following cycles: 95° C. for 10 s, and 35 replicates of 95° C. for 15 s and 60° C. for 30 s. Melting curve analysis was performed at the end of each cycle to confirm amplification specificity, and selected PCR products were sequenced.

Standard curves for both sxtA4 and LSU rRNA were constructed in two ways: (1) Using a dilution series of a known concentration of fresh PCR product, ranging from $5.7$-$5.7 \times 10^{-5}$ ng (n=6). Standard curves using PCR product were used to determine the efficiency of the assay (see method in Pfaffl, (2001) A new mathematical model for relative quantification in real-time RT-PCR Nucleic Acids Res. 2001 May 1; 29(9):e45), as well as to determine copy number. The molecules of PCR product were determined: $(A \times 6.022 \times 10^{23}) \times (660 \times B)^{-1}$ with A: concentration of PCR product, $6.022 \times 10^{23}$: Avogadro's number, 660: average molecular weight per base pair and B: length of PCR product. The number of molecules in the unknown samples were determined and divided by the known number of cells in the DNA qPCR template, to obtain copy number per cell. (2) Extracting DNA from duplicate samples of known numbers of cells of strains of *Alexandrium catenella* (ACCC01, ACSH02, ACTRA02) taken during exponential growth phase, and diluting the DNA at 50% over 3 orders of magnitude (n=6).

To estimate the environmental abundance of *A. catenella* in the samples based on the LSU rRNA assay, the equations from (2) were extrapolated and applied to the CT values measured for these samples. Because variability has been found in copy numbers of the rRNA genes among strains of some *Alexandrium* species, as well as a variability of up to a factor of 2 expected due to variability in growth and cell cycle conditions of cells, the copy number of the LSU rRNA gene region in duplicate samples of each of the 3 strains was determined. The final *A. catenella* abundances in the environmental samples were determined as the mean and standard deviation of 6 independent estimates.

Phytoplankton and Oyster Sample Collection

The phytoplankton community was sampled daily at mid-tide during the 15-20 Nov. 2010, at standard monitoring sites close to Sydney rock oyster (*Saccostrea glomerata*) farms in Wagonga Inlet, Narooma, NSW, −36′ 13″ E 150′ 6″ S and the Georges River, NSW −34′ 1″ E 151′ 8″ S (FIG. 7). Samples were also taken at Brisbane Water, NSW −33′ 28″ E 151′ 18″ S on 22 Jul. 2010 (FIG. 7).

Triplicate 4 L bottle samples were taken each day for molecular analysis. A further 500 ml bottle was taken and immediately fixed with Lugol's iodide for microscopic identification and counting. Samples were filtered using 3 μm Millipore filters and frozen at −20° C. until DNA extraction. Ten individual *S. glomerata* samples were taken from farms in the immediate vicinity of the phytoplankton sampling site on the 17 Nov. 2010 and the 19 Nov. 2010. *S. glomerata* samples were pooled for toxin testing.

To determine the specificity of the primer pair in mixed environmental samples, a phytoplankton community in which no known STX-producing species were present was sampled. 1 L of the surface community at Jervis Bay was sampled on 19 Jan. 2011, and preserved, concentrated, identified and counted species present from 500 ml, as above. Dinoflagellates present were identified as *Protoceratium reticulatum*, *Karlodinium* cf *veneficum*, *Karenia* sp., *Prorocentrum micans*, *Polarella glacialis*, *Pfiesteria shum-* *wayae*, and *Symbiodinium* sp. 500 ml of the remaining sample was filtered and performed DNA extraction and PCR as described above.

*Alexandrium* Cell Counts Using Microscopy

Phytoplankton cells in ~300 ml of the Lugol's preserved samples were concentrated by gravity assisted membrane filtration on to 5 μm cellulose ester filters (Advantec) prior to washing into 4 ml and counting. *Alexandrium* species were identified and counted using a Sedgewick Rafter cell and a Zeiss Axiolab microscope equipped with phase-contrast optics. The number of cells counted varied among samples, depending on *Alexandrium* abundance, and standard error rates were calculated using the equation: Error=2/√n, where n is the number of cells observed in the sample.

Toxin Determination in Oysters and Cultures

Shellfish samples and dinoflagellate cell pellets were tested using HPLC, according to the AOAC Official Method 2005.06 for paralytic shellfish poisoning toxins in shellfish at the Cawthron Institute, New Zealand. A matrix modifier as described in the original protocol was not used, instead used average spike recoveries for each separate compound were used. HPLC analysis was performed on a Waters Acquity UPLC system (Waters) coupled to a Waters Acquity FLR detector. Separation was achieved with a Waters Acquity C18 BEH 1.7 μm 2.1×50 mm column at 30° C., eluted at 0.2 mL min$^{-1}$. Mobile phases were 0.1 M ammonium formate (A) and 0.1 M ammonium formate in 5% acetonitrile (B), both adjusted to pH 6. The gradient consisted of 100% A for 0.5 min, a linear gradient to 80% B over 3.5 min, then returning to initial conditions over 0.1 min and held for 1.9 min. The fluorescence detector had excitation set to 340 nm and emission to 395 nm. Analytical standards for the STX analogs were obtained from the National Research Council, Canada. The detection limit of the HPLC of the cell cultures was considered to be 0.1 pg cell$^{-1}$ for NEO and STX, 0.2 pg cell$^{-1}$ for GTX1/4, GTX6 (B2) and GTX5 (B1), 0.5 pg cell$^{-1}$ for C1,2, and <0.3 pg cell$^{-1}$ for the analogs C3,4.

Results

Specificity, Sensitivity and Efficiency of the Primer Pair

The primers designed in this study were found to amplify a fragment of the correct size in all tested STX-producing dinoflagellates of the species: *Alexandrium minutum*, *A. catenella*, *A fundyense*, *A. tamarense* and *Gymnodinium catenatum* (Table 4). In addition, it amplified a fragment of the correct size from the species *A. tamarense*, strain ATCJ33, Tasmanian ribotype, which was not found to produce STXs at a level above the detection limit of the HPLC method utilised. Sequencing of the products confirmed this to be a homolog of sxtA4.

The sxtA4 primer pair did not amplify DNA from the non-STX producing related Gonyaulacalean species *Alexandrium andersonii*, *Alexandrium affine*, *Gambierdiscus australes*, *Ostreopsis ovata* or *Ostreopsis siamensis* nor from the more distantly related dinoflagellate species *Amphidinium massartii*. In addition, the sxtA4 primer pair did not amplify DNA from the phytoplankton samples, which contained a mixed planktonic community including bacteria, diatoms, picoplankton and the dinoflagellates *Protoceratium reticulatum*, *Karlodinium* cf *veneficum*, *Karenia* sp., *Prorocentrum micans*, *Polarella glacialis*, *Pfiesteria shumwayae*, and *Symbiodinium* sp. (Table 4). In contrast, DNA from all samples was amplified using the positive control primer pair to ensure the reaction template was intact and free of inhibitors.

The efficiency of the sxtA4 assay based on this primer pair was 97% as calculated using a dilution series of fresh PCR product over 6 orders of magnitude. The assay was 93-107% efficient as calculated using a duplicate 50% dilution series of gDNA from the three strains of *A. catenella* (FIG. 8). For standard curves based on both PCR product and based on gDNA, $r^2$ values of the regression equations were 0.95 or greater (FIG. 8). The assay was sensitive to DNA quantities representing ~30 to >2000 cells of the three strains of *A. catenella*. Therefore, if collection of samples was carried out following a similar protocol to that utilised, and 4 L of seawater was collected, extracted and eluted in 15 μL, of which 1 μL was assayed, then the assay would detect environmental concentrations of *A. catenella* with a lower limit of approximately 110 cells $L^{-1}$.

Copy Number of sxtA4 Genes

The copy number of sxtA4 in the 3 cultured strains of *Alexandrium catenella* had a mean of 178-280 $cell^{-1}$ (Table 5). Toxicity of these strains was 3.1-6.6 pg STX equivalent $cell^{-1}$ (Table 5). In the environmental samples, the copy number of sxtA4 was estimated to be 226 and 376 $cell^{-1}$ in the Georges River and Wagonga Inlet samples, respectively, and most variable amongst the estimates based on the Wagonga Inlet samples.

onga Inlet and Brisbane Water (48 and 145 μg STX equivalent $kg^{-1}$ of shellfish, respectively, Table 5).

Discussion

Provided

Provided herein is a new method for detecting and quantifying the potential for STX production in marine environmental samples. The assay is based on the detection of the gene sxtA that encodes a unique enzyme putatively involved in the sxt pathway. The method described detected sxtA gene in all STX-producing cultures, and did not detect it in the non STX-producing cultures or the environmental sample that did not contain known STX-producing species. However, sxtA genes were also detected in the non-producing strain of *Alexandrium tamarense*, Tasmanian ribotype, ATCJ33. As a very closely related strain of the Tasmanian ribotype of this species has been found to produce STXs (unpublished data), it is possible that the strain ATCJ33 has the potential to produce STXs under certain circumstances. The amplification of sxtA4 from the *Alexandrium* and *Gymnodinium catenatum* species and strains in this study are in line with findings in Example one above, in which approximately 550 bp and 750 bp fragments of sxtA1 and sxtA4 were amplified from the same strains tested, and no

TABLE 5

STXs present in *Alexandrium catenella* strains, in pg $cell^{-1}$ and in *Saccrostrea glomerata* from the sampling sites, in μg STX equivalents $kg^{-1}$ of shellfish, and mean copy number of sxtA4 genes in the strain or in all phytoplankton samples from that sampling site. A reading of 0 indicates levels were below the detection limit of the test. The *S. glomerata* samples were taken on 17 Nov. 2010, 19 Nov. 2010 and 22 Jul. 2010 for the Georges River, Wagonga Inlet and Brisbane Water, respectively.

|  | Total STXs | GTX-1,4 | GTX-6 | C1,2 | GTX-5 (B1) | NEO/STX | C-3,4 | B2 | sxtA4 $cell^{-1}$ +/− sd in strain or in plankton sample |
|---|---|---|---|---|---|---|---|---|---|
| cultures |  |  |  |  |  |  |  |  |  |
| ACSH02 | 5.25 | 1.75 | 0.60 | 2.40 | 0.5 | <0.1 | <0.3 | 0 | 178 +/− 49 (n = 9) |
| ACCC01 | 6.60 | 1.15 | 0 | 2.55 | 0 | 0 | 1.00 | 1.9 | 240 +/− 97 (n = 3) |
| ACTRA02 | 3.13 | 1.13 | 0 | 2.00 | 0 | 0 | 0 | 0 | 280 +/− 85 (n = 3) |
| *S. glomerata* |  |  |  |  |  |  |  |  |  |
| Georges River | 200 | 160 | trace | 30 | 10 | 0 | trace | 0 | 226 +/− 97 (n = 15) |
| Wagonga Inlet | 48 | 32 | 0 | 16 | 0 | 0 | 0 | 0 | 376 +/− 257 (n = 12) |
| Brisbane Water | 145 | 53 | 92 |  | 0 | 0 | 0 | 0 | 275 (n = 1) |

Environmental Samples sxtA4 was detected in the single Brisbane Water sample, as well as in the Georges River and Wagonga Inlet sample sets (FIG. 9). Sequencing and melt-curve analysis confirmed this to be sxtA4, with an average identity of 99% or higher to the corresponding gene from the *Alexandrium catenella* strain. A positive relationship between cell number, as estimated from microscopy, cell number as estimated from LSU rDNA, and the sxtA4 copy number was observed in both sets of environmental samples. The correlation between cell number as estimated from LSU rRNA gene qPCR and the estimated sxtA4 gene copy number was very high for the Georges River samples ($r^2=0.97$, slope=0.0059, p<0.001), and lower for the Wagonga Inlet sample ($r^2=0.70$, slope=0.001, p<0.07) (FIG. 9).

STXs in pooled *S. glomerata* samples were detected from each of these three sites, with the highest concentrations reported for the Georges River site (200 μg STX equivalent $kg^{-1}$ of shellfish) with lower levels recorded for both Wag-amplification of these fragments from the species *Alexandrium affine* and *A. andersonii* was detected.

Copy Number of sxtA4 and STXs Content

The abundance of sxtA4 was found to be relatively similar among the strains and environmental samples tested, with a range of 178-376 copies $cell^{-1}$ (Table 5). This supports results in Example one above in which 100-240 copies $cell^{-1}$ were found throughout the growth of *Alexandrium catenella* strain ACSH02 using qPCR. The total STX equivalent toxicity of the three strains of *Alexandrium catenella* was 3.1-6.6 pg STX equivalents $cell^{-1}$ (Table 5). This is within the of other STX-producing species, such as strains of *A. minutum*, *A. catenella* and *A. tamarense* (0.66-9.8 pg STX equivalents $cell^{-1}$), depending on nutrient supply and culture growth, but lower than the most toxic strains such as *Gymnodinium catenatum* (26-28 pg STX equivalent $cell^{-1}$), and *Alexandrium ostenfeldii* (up to 217 pg STX equivalent $cell^{-1}$)

sxtA4, *A. catenella* and STXs in South-Eastern Australia

*Alexandrium catenella* was sampled on three occasions in southeastern Australian estuaries throughout this study period and, in each case, sxtA4 was detected (Table 4). For the Georges River sample set, the correlation between sxtA4 copies $L^{-1}$ and cell abundance $L^{-1}$, as determined by LSU rDNA, was highly significant (FIG. 9). At the Georges River sampling site, mean abundances of 3150-26450 cells $L^{-1}$ were recorded throughout the 5 day sampling period based on the estimate of the LSU rDNA assay, and 7900-38000, based on microscope cell counts from selected days. On the final day of sampling, variability in cell counts was found amongst triplicate samples taken at the site, reflecting patchiness in the distribution of *A. catenella*. Despite this, the correlation between sxtA4 copies $L^{-1}$ and *Alexandrium catenella* cell number based on rRNA qPCR was very strong ($r^2$=0.97, slope=0.0059, p<0.001), and total STX loads in oyster samples taken during this week were 200 μg STX equivalents $kg^{-1}$ of shellfish, below the regulatory level for public health monitoring (800 μg STX equivalents $kg^{-1}$ of shellfish) but the highest of the three samples taken during this study.

At Wagonga Inlet, mean abundances of 30-288 cells $L^{-1}$ were found based on the estimate of the LSU rDNA qPCR assay and 80-540 cells $L^{-1}$ based on microscope cell counts throughout the sampling period (FIG. 9). The correlation between sxtA4 copies $L^{-1}$ and cell number, as calculated from the LSU rDNA qPCR assay, was lower than that of the Georges River samples ($r^2$=0.70, slope=0.001, p=0.07). This may reflect the fact that two of these samples contained fewer than 110 cells $L^{-1}$, and were thus at the lower limit of reliable detection of this assay. Alternatively, the lower correlation coefficient of this sampling set may be attributed to the presence of different strains of *Alexandrium catenella* which differed in copy number of sxtA.

Detection Methods for STXs and *Alexandrium* Species

Generally, the enumeration of HAB-forming phytoplankton and their toxins for industry and for biological oceanographic research relies on microscope-based counting of species and direct toxin detection methods. Quantification of STXs is generally conducted by mouse bioassay, instrumental HPLC, LC-MS or antibody-based immunoassays, such as enzyme linked immunosorbent assays (ELISA). HPLC is a time-consuming and expensive process, requiring a well-equipped analytical laboratory and pure standards of STX and its numerous analogs. While newly developed ELISA methods have overcome some of these drawbacks, they are not available for several common STX derivatives, and have problems of cross-reactivity, as toxin profiles are often quite complex.

Molecular genetic and antibody-based methods for marine phytoplankton species identification and enumeration have many advantages when compared to microscope-based counts and direct toxin detection methods: their simplicity, with a much lower requirement for training and experience compared to microscope-based taxonomic identification, cost effectiveness (qPCR reagents generally cost less than ~US $1 per sample), speed and potential for automation (up to 30 samples may be run in triplicate in under 2 hours on a standard qPCR machine using 96 well plates). Real time qPCR machines have substantially decreased in cost in recent years, and it is possible to operate them with a basic training in molecular biology techniques.

A reliable detection limit of ~110 cells $L^{-1}$ of *Alexandrium catenella* is achievable using the qPCR method reported here. Assays based on qPCR for the detection of *Alexandrium* may be more sensitive than microscopy-based methods at low cell abundances and where the species of interest may be a minor component of the phytoplankton. The Sedgewick-Rafter counting chamber method, as it is applied in the majority phytoplankton monitoring programs, is considered to have a reliable detection limit of 1000 cells $L^{-1}$. However, this is dependent on the volume of sample observed. In the present study, levels of detection down to <20 cells $L^{-1}$ were achieved using the Sedgewick-Rafter counting chamber method, by filtering the sample such that larger volumes of sample were observed. The standard error of microscope-based counts is dependent on the number of cells observed, and increases with decreasing cell number. For molecular genetic based methods, the standard error associated with cell counts is independent of the abundance of cells, for cell abundances greater than the detection threshold of the assay. Molecular genetic identification and enumeration methods have reported detection thresholds in the order of 10-100 cells $L^{-1}$ of *Alexandrium* species using qPCR and FISH probes, depending on the volume of water (typically 1-8 L) sampled using these methods. As concentrations as low as 200 cells $L^{-1}$ of *Alexandrium* species have been associated with STX uptake in shellfish, the reliable detection of species at low cell abundances is an important advantage of qPCR based enumeration methods over microscope counts as currently practiced in the majority of phytoplankton monitoring programs.

While many advantages have been noted in molecular genetic based monitoring methods, current methods have several drawbacks. qPCR for species enumeration using marker genes requires the use of multiple probes in habitats where several species of *Alexandrium*, *Pyrodinium bahamense* and *Gymnodinium catenatum* occur and produce STXs. Species not previously documented in a particular habitat are occasionally identified, and they may not be noticed if a suitable probe is not available for their identification. In addition, the enumeration of certain target species requires research to culture and determine the toxicity of local STX-producing species, as this may vary between regions. High abundances of *Alexandrium catenella* in regions in which this species generally produces STXs have not always been correlated with STXs in shellfish, suggesting that population level differences in production of STXs may occur.

A final drawback of most qPCR-based counting methods is that ribosomal RNA genes, which are commonly used for detection, as their relatively fast divergence rates allow for the design of species-specific markers, can vary significantly in copy number among strains of some species of *Alexandrium*, and in some cases, during species growth. This may be due to the presence of unstable rDNA pseudogenes in some *Alexandrium* species, and possibly the presence of extra-chromosomal rDNA molecules. The effect of this variation is to cause disparities between the estimated gene number and cell number, and consequently inconsistencies between abundance estimates based on microscopy and those based on qPCR. For this reason, in the present study, the copy number of LSU rDNA genes was determined in replicates of three strains of *A. catenella* isolated from local waters, in order to obtain a reliable estimate of cell number based on LSU rDNA copy number.

The novel method presented here relies on the direct detection of a gene (sxtA) involved in the synthesis of STXs. Therefore, it may be more closely correlated with STX production than the abundance of any particular species. In addition, it is considerably faster and cheaper to detect sxtA than the actual toxins using analytical instruments. Using the disclosed primer pair, sxtA4 was not amplified from two non-STX producing *Alexandrium* species tested but was amplified from the relatively distantly related STX-producing species *Gymnodinium catenatum*. This allows for the use of a single assay to simultaneously detect several different STX-producing genera, including potential STX producing species not previously known from a particular site. However, the assay also amplified a product from a strain of *Alexandrium tamarense* ATCJ33 that has not been found to produce STXs, mirroring findings in Example one above that this strain possessed sxtA1 and sxtA4, and showing that this assay may not, in a small percentage of cases, be indicative of the presence of STXs.

Transcription level regulation may play a relatively minor role in the expression of many dinoflagellate genes, compared to regulation in other organisms, as genes that are up-regulated have been reported to increase in transcript abundance by no more than ca. 5-fold, compared to levels during standard growth. This has led to the theory that the duplication of genomic copies of highly expressed genes in dinoflagellates may function as a means of increasing their transcription. If this were true, there may be a relationship between the copy number of sxtA cell$^{-1}$ and the quantity of STXs produced by a particular strain. In this study, the species tested had a relatively similar STXs cell quotas and no significant difference in sxtA cell$^{-1}$.

Example 3: Investigation of sxtA Sequences in Saxitoxin Producing and Non-Producing Dinoflagellate Species Aim To amplify and sequence genes involved in the synthesis of saxitoxin (STX) in dinoflagellates which are known to produce saxitoxin and those which are not known to produce STX.

Materials and Methods

Dinoflagellate strains were grown in GSe media and maintained in a culture cabinet at 18 degrees, and a 12/12 light cycle. DNA was extracted from 20 ml of exponentially growing culture by harvesting by centrifuging at 3000 g for 5 minutes, then using the CTAB method.

DNA template was PCR amplified using Advantage GC rich PCR polymerase (Clontech), which contains 10% BSA, in a Thermo Cycler with the following PCR conditions: an initial 5 minute 95° C. denaturing before 35 cycles of (1) 30 sec 94° C. denaturing, (2) 30 sec annealing (variable temperature), and (3) 1-2 minute 72° C. extension, with a final 10 minute extension at the same temperature. PCR products were gel excised using Promega Wizard SV Gel and PCR Clean-Up System (Promega), before direct sequencing with an ABI3730 DNA analyzer (Applied Biosystems) using primers as below.

| Sxt001 | F | TGCAGCGMTGCTACTCCTACTAC (SEQ ID NO: 200) | 57.1 |
| Sxt002 | R | GGTCGTGGTCYAGGAAGGAG (SEQ ID NO: 201) | 55.9 |

Species newly investigated for this study were the STX producing species: *Alexandrium tamarense*, strain CAWD121, and the non-producing species *Alexandrium* sp, strain AAKT01, *Amphidinium massartii* CS-259, *Amphidinium mootonorum* CAWD161, *Coolia monotis* CAWD98, *Gambierdiscus australes* CAWD148, *Prorocentrum lima* CAWD, *Protoceratium reticulatum* CAWD, *Gonyaulax spinifera* CAWD.

Results

An sxtA1 domain gene of the correct size was identified from the saxitoxin producing species *Alexandrium tamarense* strain CAWD121 (SEQ ID NO: 224), and the presumed saxitoxin producing species *Alexandrium catenella*, strain ACNC50 (SEQ ID NOs: 225-226 show sxtA1 domain sequences from two clones of strain ACNC50). This was found to be 99% similar to the corresponding gene from *Alexandrium catenella* strain ACSH02.

A gene for sxtA1 (SEQ ID NO: 227) was also amplified from the *Alexandrium* strain AAKT01, which has not previously been reported to produce saxitoxin.

No genes could be amplified from any of the remaining non-producing species of dinoflagellates.

Conclusion

The presence of genes putatively involved in the synthesis of saxitoxin in dinoflagellates have been confirmed in all species which produce saxitoxin. In this study, they were found in a further producing strain which has caused harmful algal blooms containing saxitoxin in New Zealand, isolated as CAWD121. In addition, one species of *Alexandrium*, strain AAKT01, closely related to species that produce saxitoxin, was found to possess the gene sxtA1. This species has not previously been reported to produce saxitoxin but is now suggested to have the potential to produce it under certain circumstances. Toxin analyses using more sensitive detection techniques may be required in order to verify this hypothesis. For example, Negri et al (2003) reported that the strain *A. tamarense*, ATBB01 showed STX activity when tested with the saxiphilin assay, but had no detectable toxins when tested with HPLC methods (see Negri, et al. (2003). "*Paralytic shellfish toxins are restricted to few species among Australia's taxonomic diversity of cultured microalgae*", J. Phycol. 39(4), 663-667.

None of the species of other dinoflagellate orders investigated in this study, not known to produce saxitoxin and not closely related to saxitoxin producing species, were found to possess the gene sxtA1.

Example 4: *Alexandrium catenella* from Opua Bay, New Zealand, as Monitored by a qPCR Assay Based on sxtA Aim To determine whether the number of copies of the gene sxtA involved in the synthesis of saxitoxin in marine dinoflagellates, is correlated with a manual count of the number of cells of *Alexandrium catenella* in marine environmental samples.

Methods

Samples were collected at Opua Bay, at the south-eastern region of Onapua Bay in Queen Charlotte Sound, South Island, New Zealand. Once a week over 4 weeks (22 Feb. 2012-13 Mar. 2012), triplicate 500 ml samples of an integrated sample from the 0-15 m depth from the water column were taken and stored at −80 degrees C. After defrosting, 200 ml of each sample was filtered through a 0.45 um Millipore filter. The filter was rinsed in ~50 ul of seawater into an eppendorf tube, vortexed and centrifuged. The pellet was extracted using the Mobio DNA soil kit, according to the manufacturer's instructions. DNA was eluted twice in 100 ul (same eluate was rinsed through filter twice). The DNA was concentrated into 20 ul of sample using a high salt/ethanol precipitation.

The sequences of the primers were sxtA4F 5'-CTGAGCAAGGCGTTCAATTC-3' (SEQ ID NO: 198) and sxtA4R 5'-TACAGATMGGCCCTGTGARC-3' (SEQ ID NO: 199), resulting in a 125 bp product.

Standard curves for sxtA4 was constructed using a dilution series of a known concentration of fresh PCR product, ranging from 5.7-5.7×10$^{-5}$ ng (n=6). Standard curves using PCR product were used to determine the efficiency of the assay, as well as to determine the number of copies. The molecules of PCR product were determined: (A×6.022× 10$^{23}$)×(660×B)$^{-1}$ with A: concentration of PCR product, 6.022×10$^{23}$: Avogadro's number, 660: average molecular weight per base pair and B: length of PCR product.

qPCR cycling was carried out on a Rotor Gene 3000 (Corbett Life Science) using SSO Fast Evagreen supermix (Biorad). qPCR assays were performed in a final volume of 20 µl consisting of 10 µl Evagreen master mix (containing DNA intercalating dye, buffer and Taq polymerase), 1 µl of template DNA, 0.5 µM of each primer, and 1 µl of BSA. qPCR assays were performed in triplicate with the following cycles: 95° C. for 10 s, and 35 replicates of 95° C. for 15 s and 60° C. for 30 s. Melting curve analysis was performed at the end of each cycle to confirm amplification specificity, and selected PCR products were sequenced.

Results

Figure 10:
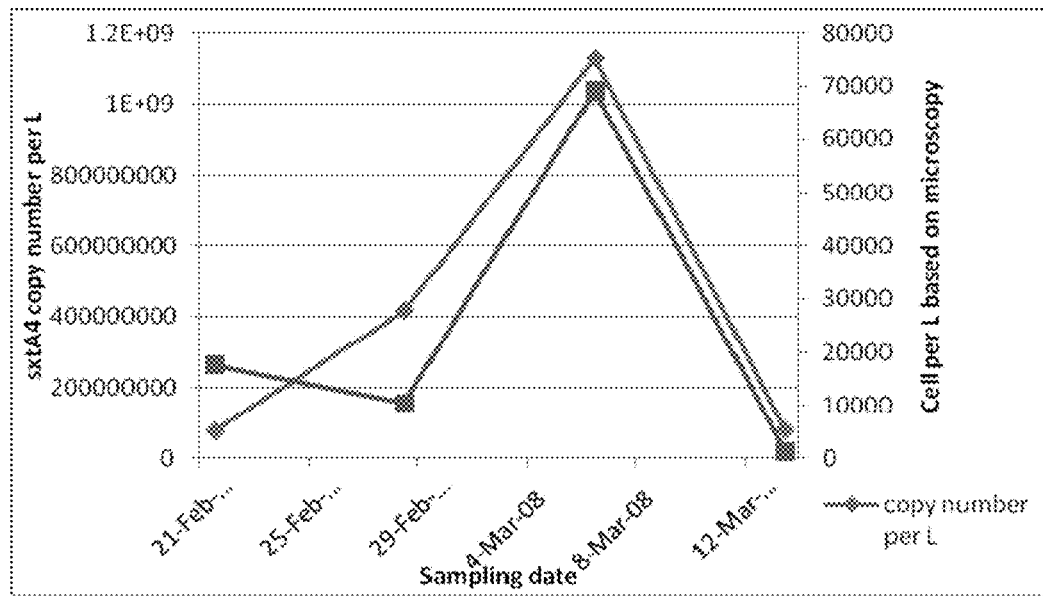
FIG. 10 provides a graph showing the number or copies of sxtA4 $L^{-1}$ and cells of *Alexandrium catenella*, as determined using a manual count under the light microscopes, each week at the sampling site.
Figure 11:
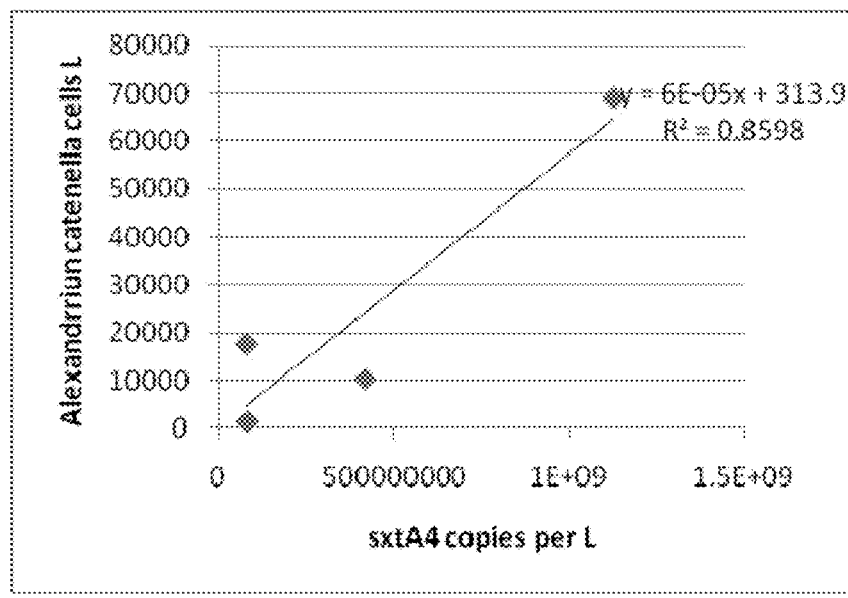
FIG. 11 provides a graph showing a regression equation between *Alexandrium catenella* cell abundance and sxtA4 copies.

The number of copies of sxtA4 L$^{-1}$ detected was found to reach a peak in the third sampling week and then drop (FIG. 10), similar to the change in abundance of *Alexandrium catenella* cells. The number of copies of sxtA4 L$^{-1}$ in the triplicate water samples was found to be significantly correlated with the mean abundance of *Alexandrium catenella* cells L$^{-1}$ (FIG. 11, R$^2$=0.86).

Conclusion

The quantitative qPCR assay based on the gene sxtA was found to be a reliable method of determining the potential for saxitoxin presence in marine environmental samples containing *Alexandrium catenella*. The abundance of copies of the gene sxtA were found to be significantly correlated with the abundance of the species *Alexandrium catenella*.

Example 5: Amplification of sxtA1 and sxtA4 Sequences and Investigation of Saxitoxin Production and sxtA in the 'Non-Toxic' *Alexandrium tamarense* Group V Clade Summary The three *Alexandrium* species *A. tamarense*. *A. fundyense* and *A. catenella* include strains that can be potent producers of the neurotoxin saxitoxin (STX) and its analogues, the causative agents of Paralytic Shellfish Poisoning (PSP). These three species are morphologically highly similar, differing from each other only in the possession of a ventral pore, or in the ability to form chains. The appropriateness of these morphological characters for species delimitation has been extensively debated. A distinctive clade of this species complex, Group V, Tasmanian clade, is found in southern Australia, and occasionally occurs in bloom proportions. This clade has been considered non-toxic, and no PSP toxins have been found in shellfish following blooms of this species. In the present study, a Tasmanian strain of *Alexandrium tamarense*, Group V was identified that produces STX and possesses the gene, sxtA that is putatively involved in STX production. The toxin profile was determined and is unusual, including a high proportion of GTX5 and a small amount of STX, and differs from that of co-occurring *A. catenella* (Group IV). A putative bloom of *A. tamarense* that occurred in October 2010, and the subsequent finding of STX in Sydney Rock Oysters (*Saccostrea glomerata*), may suggest that some naturally occurring strains of this species could produce STX.

Introduction

Three common and widespread species of the dinoflagellate genus *Alexandrium*, *A. catenella*, *A. tamarense* and *A. fundyense*, possess highly similar, sometimes overlapping morphological features (Balech, 1995; Fukuyo, 1985; Steidinger, 1990). This clade is considered to comprise a 'species complex', as it consists of five genetically distinct groups (John et al., 2003; Orr et al., 2011; Scholin et al., 1994; Lilly et al., 2007). The characteristics that are used for the identification of these species include the cell shape, shape of the apical pore complex (APC), presence (*A. tamarense*) or absence (*A. catenella/A. fundyense*) of a ventral pore on the first apical plate, and whether the cells show a tendency for chain formation (*A. catenella*) or not (*A. tamarense/A. fundyense*) (Balech, 1995). Some forms with morphologies intermediate between these three species have also been observed (Cembella et al., 1988; Gayoso and Fulco, 2006; Orlova et al., 2007; Sako et al., 1990; Orr et al., 2011).

In contrast to the information based on morphology, the many phylogenetic studies of *Alexandrium* species, based on regions of the rRNA operon, including the SSU, ITS/5.8s, and LSU genes, have clearly distinguished clades (Groups I-V) from one another (John et al., 2003; Scholin et al., 1994); (Kim and Sako, 2005; Leaw et al., 2005; Lilly et al., 2007; Montresor et al., 2004; Rogers et al., 2006; On et al., 2011). Based on a survey of dinoflagellate diversity and its relationship to rDNA sequences, Litaker et al., (2007) suggested that a conservative "species level" marker in dinoflagellates could be considered a difference of 4% (=uncorrected genetic distance of 0.04) in aligned regions of ITS1/5.8S/ITS2 rDNA. These clades of *Alexandrium tamarense/catenella/fundyense* differ from one another by 13-18% in aligned sequences of ITS1/5.85/ITS2 (Orr et al., 2011), therefore, at a level 3-4 times that in some other dinoflagellate species.

The identification of *Alexandrium tamarense/catenella/fundyense* strains to a particular genetic clade (Groups I-V) has been considered more predictive of their propensity for STX production than species identifications based on morphology (Scholin et al., 1994; John et al., 2003; Kim and Sako, 2005; Leaw et al., 2005; Montresor et al., 2004; Lilly et al., 2007; Rogers et al., 2006). All strains of Groups I and IV analysed to date produce varying quantities of STX, with diverse toxin profiles (Table 7, Anderson et al., 1994), while no strains of Group II have been reported to produce STX (John et al., 2003). The toxicity of strains of Groups III and V is unclear. They have generally been considered non-toxic (Lilly et al., 2007; Scholin et al., 1994; Genovesi et al., 2011; Bolch and de Salas, 2007; Hallegraeff et al., 1991). A single strain with a genetic sequence placing it within Group III, CCMP116, has been reported to be toxic (Penna and Magnani, 1999). While Group V strains have generally been considered non-toxic (Hallegraeff et al., 1991; Bolch and de Salas, 2007), it has been suggested that very low levels of STXs may be produced by the strain ATBB01/CS298 from Bell Bay, Tasmania (Scholin et al., 1994; Negri et al., 2003). The toxin profile was not determined.

In Australian marine waters, the *Alexandrium* species *A. catenella* and *A. minutum* produce STX, and have occurred in bloom proportions, resulting in STX uptake in shellfish (Hallegraeff et al., 1988; Hallegraeff et al., 1991; Bolch and de Salas, 2007). Of the species of the *A. tamarense* species complex, two groups have been consistently found in the region: Group V *A. tamarense* and Group IV *A. catenella* (Bolch and de Salas, 2007). No other groups of this species complex have been found, during investigations over the past 20 years (Hallegraeff et al., 1988; Hallegraeff et al., 1991; Bolch and de Salas, 2007). Several theories have been put forward as to the origins of these *A. tamarense* 'species complex' strains in Australian marine waters, including their introduction by ballast water (Group IV), or their long term presence in the region (Group V) (Bolch and de Salas, 2007).

Blooms of *A. catenella* (Group IV), *A. minutum* and the species *Gymnodinium catenatum*, have been associated with uptake of STX in shellfish vectors on multiple occasions at sites in New South Wales, South Australia, Victoria and Tasmania, Australia (reviewed in Bolch and de Salas, 2007). Potential shellfish vectors that have been investigated for the presence of STX, either experimentally or in the course of monitoring, in Australian waters are Sydney Rock Oysters (*Saccostrea glomerata*), Pacific Oysters (*Crassostrea gigas*), and Pearl Oysters *Pinctada imbricata* (Murray et al., 2009). Blooms of *A. tamarense* Group V have occurred intermittently throughout the region, but have not been reported to cause STX uptake in shellfish (Hallegraeff et al., 1991).

In the course of investigating the genetic basis of STX production, genes for the putative sxtA domains sxtA1 and sxtA4 were discovered in three strains of *A. tamarense* Group V (Stüken et al., 2011). These strains were reinvestigated to determine their genetic affinities and their potential for STX production.

This study describes the toxin profile, morphology and molecular phylogeny of a strain of *A. tamarense* that was found to produce STX. Furthermore, a finding of STX presence in samples of *S. glomerata* from New South Wales in 2010, following a putative bloom of this species is reported.

Materials and Methods
Culture Maintenance

Dinoflagellate cultures were maintained in GSe media at 18° C. Light was provided by white fluorescent bulbs (Crompton Light), with photon flux of 60-100 μmol photon m-2 sec-1 on 12/12 hour dark/light cycle. Strains used were ATCJ33, isolated from Cape Jaffa, South Australia, Australia (−36.94,139.70); ATNWB01, isolated from North West Bay, Tasmania, Australia (−43.08,147.31); and ATEB01, isolated from Emu Bay, Burnie, Tasmania, Australia (−41.05, 145.91), by M de Salas. Bulk cultures for toxin determination were inoculated on the same day in 2 L Erlenmeyer flasks and were harvested together, during late logarithmic or early stationary phase, for extraction of toxins. Cell abundance was determined by counting 1 ml subsamples using a Sedgewick Rafter counting chamber under a Leica DMIL Inverted Light microscope. Cultures were centrifuged and immediately frozen at −20° C. prior to HPLC analysis or DNA extraction. Cell pellets for HPLC analysis contained 1.25-2.25×106 cells.

LM and SEM

Cell size and shape was determined using a Leica DMIL Inverted Light Microscope with 40 or 100× magnification. For scanning electron microscopy, two methods were used, in order to either keep the cell membrane intact or to expose it. Cultures were fixed in 2% osmium tetroxide for 10 minutes, or in 4% glutaraldehyde for 1-2 hr. They were placed on a polylysine-coated cover slips or on 5 μm Millipore filters, rinsed in distilled water, and dehydrated in a series of increasing ethanol concentrations (30, 50, 70, 90, 100%), followed by critical point drying (Baltec). When completely dry, they were mounted on stubs and sputter coated with gold. They were observed using a Zeiss Ultra Plus Field Emission Scanning Electron Microscope (FESEM) at the University of Sydney (Australian Centre for Microscopy and Microanalysis) at 5-15 kV.

DNA Extraction and PCR

DNA was extracted from the cell pellets using the CTAB method, with an additional overnight DNA precipitation at −20° C. Quality and quantity of DNA was determined using a Nanodrop (Thermoscientific), and by amplifying a control dinoflagellate gene (cytb), according to the protocols of (Lin et al., 2009), using the primer pair 4f and 6r, which amplify a 440 bp fragment.

Partial sequences of the rRNA genes LSU and SSU and complete 5.8s/ITS genes were amplified using previously published primers: SS3, SS5 (Medlin et al., 1988), D1R, D3b (Scholin et al., 1994) and Alex5.8s (Orr et al., 2011). Typical cycling conditions for PCRs consisted of an initial denaturing step of 94° C. for 2 min, followed by 35 cycles of 94° C. for 20 s, 56° C. for 30 s, and 72° C. for 1 min, followed by a final extension step of 7 min. PCR products were separated by agarose gel electrophoresis and stained with Ethidium Bromide, and visualised by UV transillumination. Fragments to be sequenced were excised from the gel, DNA was purified using a Bioline gel purification kit (Bioline, USA), eluted in 2×10 μl of elution buffer, and the concentration checked by use of a Nanodrop. Approximately 40 ng of PCR product was then used for direct sequencing with the same primers used for the initial amplification of the product.

Toxin Determination

Dinoflagellate cell pellets were tested using HPLC, according to the AOAC Official Method 2005.06 for paralytic shellfish poisoning toxins in shellfish at the Cawthron Institute, New Zealand. A matrix modifier as described in the original protocol was not used; instead average spike recoveries were used for each separate compound. HPLC analysis was performed on a Waters Acquity UPLC system (Waters) coupled to a Waters Acquity FLR detector. Separation was achieved with a Waters Acquity C18 BEH 1.7 μm 2.1×50 mm column at 30° C., eluted at 0.2 mL min-1. Mobile phases were 0.1 M ammonium formate (A) and 0.1 M ammonium formate in 5% acetonitrile (B), both adjusted to pH 6. The gradient consisted of 100% A for 0.5 min, a linear gradient to 80% B over 3.5 min, then returning to initial conditions over 0.1 min and held for 1.9 min. The fluorescence detector had excitation set to 340 nm and emission to 395 nm. Analytical standards for the STX analogs were obtained from the National Research Council, Canada. The detection limit of the HPLC of the cell cultures was considered to be 0.1 pg cell-1 for NEO and STX, 0.2 pg cell-1 for GTX1/4, GTX6 (B2) and GTX5 (B1), 0.5 pg cell-1 for C1,2, and <0.3 pg cell-1 for the analogs C3,4.

Phylogenetic Analyses

New Group V *Alexandrium tamarense* sequences that were generated in this study; (1) 18S (Small Sub Unit) rDNA, (2) Internal Transcribed Region (ITS) 1 and 2 plus 5.8S rDNA, and (3) 28S (Large Sub Unit) rDNA, were concatenated to construct a 2,821 character region of the rDNA operon for strain ATNWB01 (GenBank accession numbers JQ991015, JQ991016, JQ991017). In addition, new LSU rDNA sequences were generated from strains ATCJ33 (874 bp) and ATEB01 (678 bp length, GenBank Accession numbers JQ991018 and JQ991019). This was aligned together with all orthologues from Group V sequence data in the NCBInr nucleotide database, and an *A. affine* outgroup. MAFFTv6 Q-INS-I model (Hofacker et al., 2002; Katoh and Toh, 2008; Kiryu et al., 2007), considering secondary RNA structure, was used to align the dataset (default parameters used) and the resulting alignment checked manually using MacClade v4.07 (Madison and Madison, 1992). The alignment was then inferred with Gblocks v0.91b (Castresana, 2000), under the least stringent parameters, to exclude poorly aligned positions and divergent regions from the phylogenetic inference. MODELTEST (Posada and Crandall, 1998) established the optimal model of nucleotide evolution; for all alignments GTR was preferred for both the Akaike and Bayesian information Criterion (AiC and BiC). Maximum Likelihood (ML) analyses were performed with RAxML-VI-HPC v7.2.6, GTRCAT model with 25 rate categories (Stamatakis, 2006). The most likely topology was established from 100 separate searches and bootstrap analyses were performed with 100 pseudoreplicates. Bayesian inferences were performed using Phylobayes v3.2e (Lartillot et al., 2007; Lartillot and Philippe, 2004) under the GTRCAT substitution model with a free number of mixing categories and a discrete across site variation under 4 categories. Trees were inferred when the largest maximum difference between the bipartitions (chains) was <0.1. All model estimation and phylogenetic analyses were performed on the freely available Bioportal (Kumar et al., 2009) at the University of Oslo.

Phytoplankton and Shellfish Sample Collection, Counting and Identification

Phytoplankton was collected as part of the NSW Shellfish Program fortnightly monitoring at the Hastings River, New South Wales, Australia (−31.42 E, 152.87 S) over two consecutive weeks in October and November 2010, 25 Oct. 2010 and 9 Nov. 2010. In the second week, Sydney Rock Oysters (*Saccostrea glomerata*) were collected from farms and tested using a Jellett PSP test (Jellett Rapid Testing Ltd, Canada) according to the manufacturer's instructions.

For counting of bottle samples, phytoplankton cells in 500 ml of Lugol's preserved samples were concentrated by gravity assisted membrane filtration on to 5 μm cellulose ester filters (Advantec) prior to washing into 4 ml and counting. *Alexandrium* species were identified and counted using a Sedgewick Rafter cell and a Zeiss Axiolab microscope equipped with phase-contrast optics. Species were identified by Dr S. Brett, who has identified harmful phytoplankton as part of the NSW Shellfish Program since 2003. *Alexandrium* species occur commonly in NSW waters, the most commonly identified species being *A. catenella* and *A. pseudogonyaulax*. The number of cells counted varied among samples, depending on *Alexandrium* abundance, and standard error rates were calculated using the equation: Error=$2/\sqrt{n}$, where n is the number of cells observed in the sample.

Results

Light and Scanning Electron Microscopy

Cells of ATNWB01 were rounded, 25-45 μm long (μ=34.2, n=20), 27-40 μm wide (μ=33.6, n=20) (FIG. 12, A-B). Cells were almost always single. Chains of two cells were rarely observed. The first apical plate extended to the apical pore complex and contained a small pore, the ventral pore (FIG. 12, C). The apical pore plate (Po) had a characteristic comma shape, surrounded by small marginal pores (FIG. 12E). Occasionally cells with a pore in the posterior sulcal plate were observed (FIG. 12 F). Most cells lacked a pore in the posterior sulcal plate.

Cells of the cultures ATCJ33 (FIG. 13 A-D), ATEB01 (FIG. 13, E, F, H) and ATBB01 (FIG. 13 G) had rounded cells. Cells were mostly single, occasionally in chains of 2 cells (FIG. 13 A). Cells of ATCJ33 were 23-38 μm long (μ=30.6, n=20), 23-38 μm wide (μ=29.5, n=20), cells of ATEB01 were 25-40 μm long (μ=33.5, n=20), 23-35 μm wide (μ=31.6, n=20). The first apical plate extended to the apical pore and contained a ventral pore (FIG. 13 B, D, H). The apical pore plate showed a characteristic comma shape (FIG. 13 C, G, H).

Phylogenetic Analysis

Figure 16:
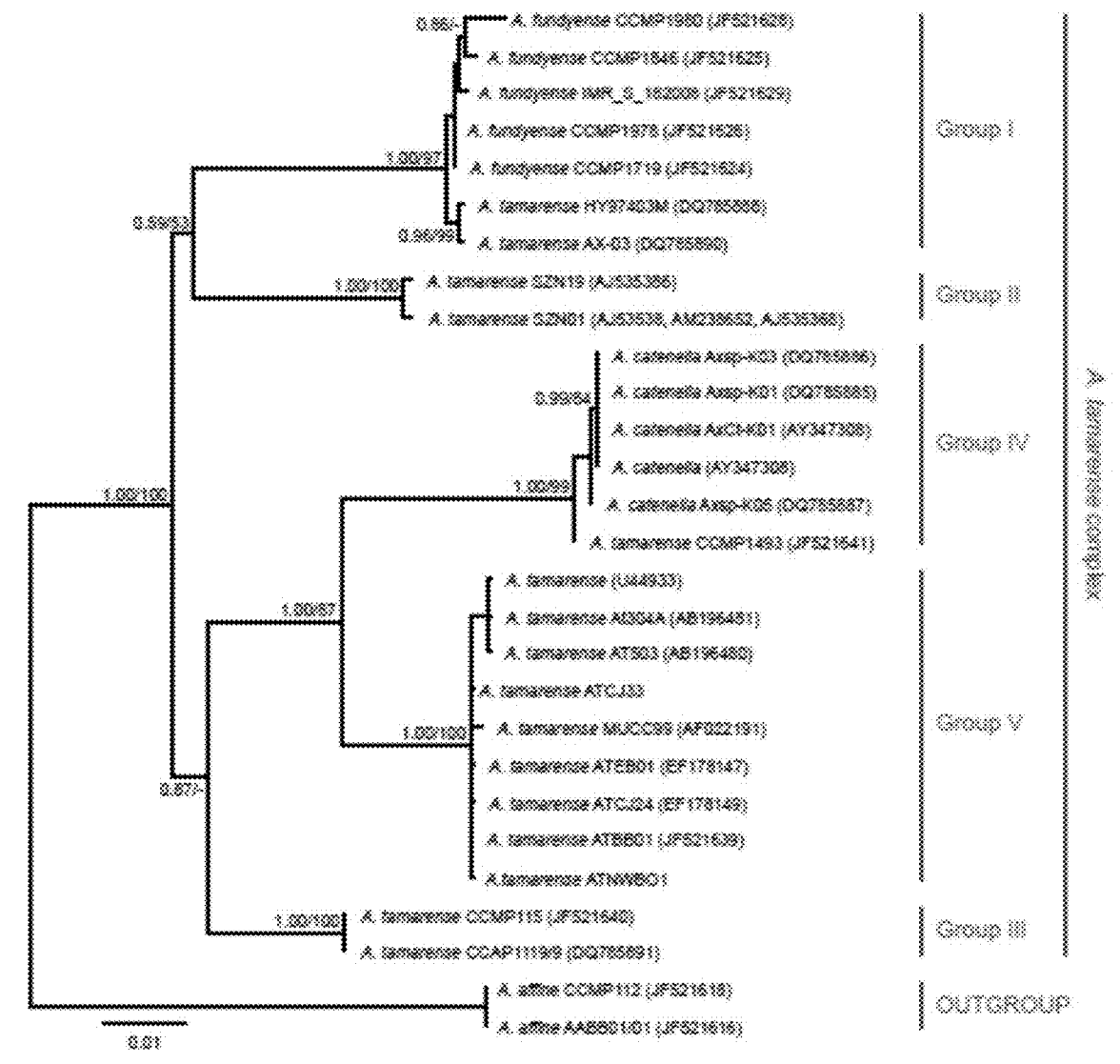
FIG. 16 shows 18S+ITS1-5.8S-ITS2+28S rDNA concatenated phylogeny of the *A. tamarense* complex (2821 characters). The tree is reconstructed with Bayesian inference (Phylobayes). Numbers on the internal nodes represent posterior probability and bootstrap values (>50%) for Phylobayes and RAxML (ordered; Phylobayes/RaxML). Black circles indicate a posterior probability value of 1.00 and bootstrap >90%.

The phylogenetic analyses including the new rDNA sequences (FIG. 14, FIG. 16), the SSU rDNA, ITS/5.8s and partial LSU rDNA sequences of the toxin producing strain ATNWB01 and the LSU sequences of the two non-toxic strains ATCJ33 and ATEB01, show that all of these form a well-supported clade (1.00/100, for PP/BS support) together with other strains of *A. tamarense* Group V. No difference could be observed in this clade based on full length rDNA, including the most variable ITS regions.

Comparison of sxtA1 and sxtA4 Domains of sxtA Genes in the Strains

The nucleotide content of sequences for the two domains of sxtA in strains of *A. tamarense* Group 5 was compared, previously sequenced (Stüken et al., 2011). A 440 bp sequence of domain sxtA4 showed that the strain ATNWB01 differed from the two other strains of Group 5 *A. tamarense* analysed, ATEB01 and ATCJ33, in only 2 nucleotides (99.5% sequence identity). In contrast, these three strains showed 89-98% sequence identity with these genes from other species of *Alexandrium* and *Gymnodinium catenatum*. In a comparison of a 450 bp region of the domain sxtA1, strain ATNWB01 differed from the other 2 strains of Group 5 by 2-2.5% (97.5-98% sequence identity), as compared to a sequence identity of 70-93% for other *Alexandrium* and *Gymnodinium catenatum* sequences of sxtA1 domain.

Toxins

Figure 15:
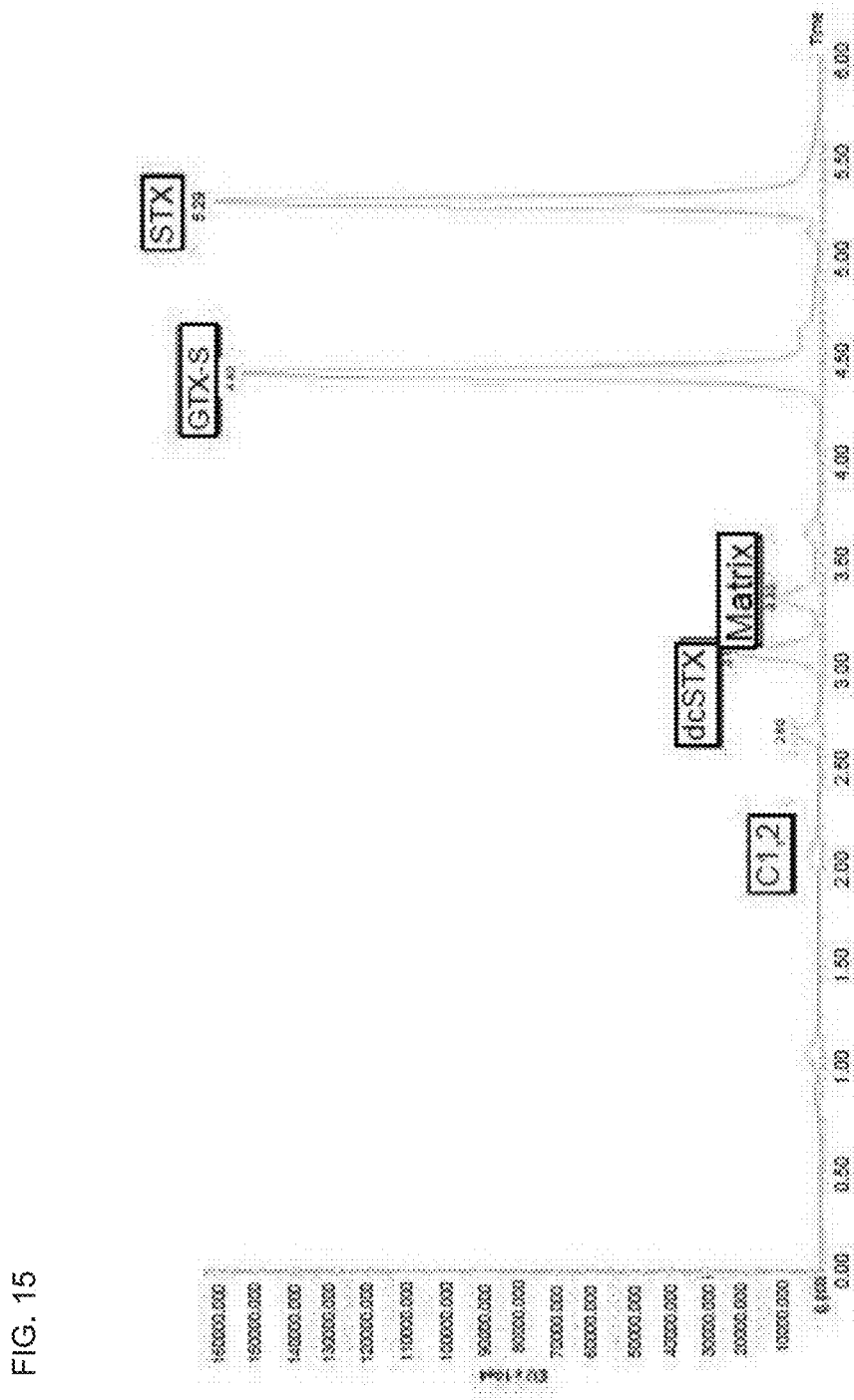
FIG. 15 is a toxin profile of ATNWB01 using HPLC, peaks as indicated were determined against PSP toxin standards.

Of the three strains of *A. tamarense*, Group V, approximately $1.5\text{-}2.2\times10^6$ cells were tested for toxicity using HPLC. Two strains, ATCJ33 and ATEB01, had negative profiles, with no detectable toxins. One strain, ATNWB01, showed positive results with a profile consisting of mostly GTX5, with some STX, C1,2 and deSTX (FIG. 15, Table 7), and a cell quota of 15.3 fmol cell$^{-1}$.

Environmental Samples

*Alexandrium* cells were detected at levels of 350 cells L-1 in routine monitoring samples collected from the Hastings River on 25 Oct. 2010 (Table 6). Subsequent Jellet tests on oyster samples from the same site collected on 9 Nov. 2010 were positive for PSP toxins. *Alexandrium* cells in the samples were single cells and had a generally rounded shape. Cells were 35 μm in length, and 32-35 μm in width. Examination of *Alexandrium* theca revealed a ventral pore in the 1' plate, a 1' plate of the size and shape of *A. tamarense*, and the absence of a connecting pore in the APC.

Of the species of *Alexandrium* observed in Australian waters, the size and shape of cells, the shape of the 1' plate, the presence of the ventral pore on the 1' plate, and the shape of the APC, appear most consistent with *Alexandrium tamarense*. No cultures were established from this bloom event, however, and molecular sequences nor toxin profiles could be confirmed.

TABLE 6

Results from phytoplankton and oyster toxicity monitoring, Hastings River.

| Site | Species | Cells L$^{-1}$ | Date | Jellet test result on oyster samples |
|---|---|---|---|---|
| Hastings River | Alexandrium tamarense | 350 | 25 Oct. 2010 | Negative |
| | Alexandrium tamarenze | 350 | 9 Nov. 2010 | Positive (PSP) |

TABLE 7

Toxin profiles of strains of *Alexandrium catenella/fundyense/tamarense* species complex, showing molar % and total toxin content.

| Species | Strain | Clade | Profile C1,2 | C3,4 | GTX 1,4 | GTX 2,3 | GTX5 (B1) | GTX6 (B2) | neoSTX | STX | dcSTX | Toxin content fmol/cell | Reference |
|---|---|---|---|---|---|---|---|---|---|---|---|---|---|
| *Alexandrium tamarense* | ATBR2c | I | 70 | — | 10 | 3 | — | — | 16 | 1 | — | 42-199* | Persich et al 2006 |
| *Alexandrium tamarense* | ATBR2d | I | 80 | — | 10 | 2 | — | — | 8 | — | — | 42-199 | Persich et al 2006 |
| *Alexandrium tamarense* | ATBR2e | I | 60 | — | 19 | 2 | — | — | 19 | — | — | 42-199 | Persich et al 2006 |
| *Alexandrium tamarense* | ATBR2g | I | 63 | — | 33 | 2 | — | — | 2 | — | — | 42-199 | Persich et al 2006 |
| *Alexandrium catenella* | PFB38 | I | — | — | 23.0 | 77.1 | — | — | — | — | — | 18.5 | Aguilera-Belmonte et al 2011 |
| *Alexandrium catenella* | PFB39 | I | 44.4 | — | 9.2 | 4.2 | 14.2 | 26.4 | — | 1.6 | — | 24.7 | Aguilera-Belmonte et al 2011 |
| *Alexandrium catenella* | PFB36 | I | 26.2 | — | 13.7 | 13.7 | 33.7 | 0.1 | 12.5 | — | — | 92.0 | Aguilera-Belmonte et al 2011 |
| *Alexandrium catenella* | PFB42 | I | — | — | 25.9 | 74.0 | — | — | — | — | — | 18.3 | Aguilera-Belmonte et al 2011 |
| *Alexandrium catenella* | PFB45 | I | 1.1 | — | 13.3 | 27.6 | 15.9 | 15.5 | 20.1 | 2.5 | — | 96.9 | Aguilera-Belmonte et al 2011 |
| *Alexandrium catenella* | PFB37 | I | — | — | 59.6 | 40.3 | — | — | — | — | — | 11.7 | Aguilera-Belmonte et al 2011 |
| *Alexandrium catenella* | PFB41 | I | — | — | 38.1 | 60.2 | — | — | — | — | — | 8.5 | Aguilera-Belmonte et al 2011 |
| *Alexandrium tamarense* | SZN01 | II | | | | | | | | — | | ND | John et al 2003 |
| *Alexandrium tamarense* | SZN08 | II | | | | | | | | | | ND | John et al 2003 |
| *Alexandrium tamarense* | SZN19 | II | | | | | | | | | | ND | John et al 2003 |
| *Alexandrium tamarense* | SZN21 | II | | | | | | | | | | ND | John et al 2003 |
| *Alexandrium tamarense* | Various strains | III | | | | | | | | | | ND | Higman et al 2001 |
| *Alexandrium catenella* | ATTL01 | IV | 54 | 2 | — | — | 44 | — | — | — | — | 44.3 | Lilly et al 2002 |
| *Alexandrium catenella* | ATTL02 | IV | 33 | 20 | 1 | — | 46 | — | — | — | — | 5.3 | Lilly et al 2002 |
| *Alexandrium catenella* | ACPP09 | IV | 22.2 | 13.7 | 30.1 | 0.5 | 1.9 | 30.4 | 1.0 | — | — | | Hallegraeff et al 1991 |
| *Alexandrium catenella* | ACPP02 | IV | 11.9 | 4.6 | 21.3 | 0.2 | 4.0 | 57.3 | 0.4 | — | — | | Hallegraeff et al 1991 |
| *Alexandrium catenella* | CAWD44 | IV | 53 | 35 | 8 | 2 | — | — | 2 | — | — | 150.2 | MacKenzie et al 2004*(mean of 13 isolates) |
| *Alexandrium tamarense* | CAWD121 | IV | 8 | 90 | 2 | — | — | — | — | — | — | 328.5 | MacKenzie et al 2004 |
| *Alexandrium catenella* | ACSH02 | IV | 41 | — | 35 | — | 10 | 13 | — | — | — | 12.1 | Murray et al 2011 |
| *Alexandrium catenella* | ACCC01 | IV | 36 | 14 | 16 | — | — | 34 | — | — | — | 14.7 | Murray et al 2011 |
| *Alexandrium catenella* | ACTRA02 | IV | 59 | — | 40 | — | — | — | — | — | — | 3.5 | Murray et al 2011 |
| *Alexandrium tamarense* | ATBB01 | V | | | | | | | | | | ND | Orr et al 2011 |
| *Alexandrium tamarense* | ATBB01 | V | | | | | | | | | | ND with HPLC, but some response with saxiphilin assay | Negri et al 2003 |
| *Alexandrium tamarense* | ATCJ33 | V | | | | | | | | | | ND | This study |
| *Alexandrium tamarense* | ATEB01 | V | | | | | | | | | | ND | This study |
| *Alexandrium tamarense* | ATNWB01 | V | 0.1 | — | — | — | 86 | — | — | 11 | 2 | 15.3 | This study |

ND = not detected

Discussion

In general among strains of toxic species of the genus *Alexandrium*, the toxin profile appears to remain largely constant over time (Cembella and Destombe, 1996) apart from situations of extreme nutrient depletion (Boczar et al., 1988). In contrast the amount of toxin produced (cell quota) has been found to vary over time. While toxin profiles appear to be stable within a strain, the relationship between a particular toxin profile and the identification of a strain to a particular genetic group (I-V) of this species complex is unclear. Considerable variation in toxin profiles have been found amongst strains of each group examined (Table 7).

This study is the first report of the toxin profile of a strain of *Alexandrium tamarense*, Group V. The study shows that, based on morphological features such as the presence of the ventral pore, and long sequences of rDNA genes, including the variable ITS1/5.8s/ITS2 regions, the strain ATNWB01 was a member of Group V. Previously, strains of this group have been tested for toxicity by means of HPLC and found non-toxic (Hallegraeff et al., 1991; Salas et al., 2001; Bolch and De Salas, 2007). Negri et al (2003) reported that the strain *A. tamarense*, ATBB01 showed STX activity when tested with the saxiphilin assay, but had no detectable toxins when tested with HPLC methods. In the same study, a culture that had been identified as *A. tamarense* from Australian waters (strain ATTRA03) was found to produce STX (Negri et al., 2003). Strain ATTRA03 subsequently died without verification of its identity, and it is therefore unclear which species or group this strain represented. It may have been derived from an introduced cyst, as it was isolated as a cyst from a shipping port used for exports (Bolch and de Salas, 2007).

Figure 14:
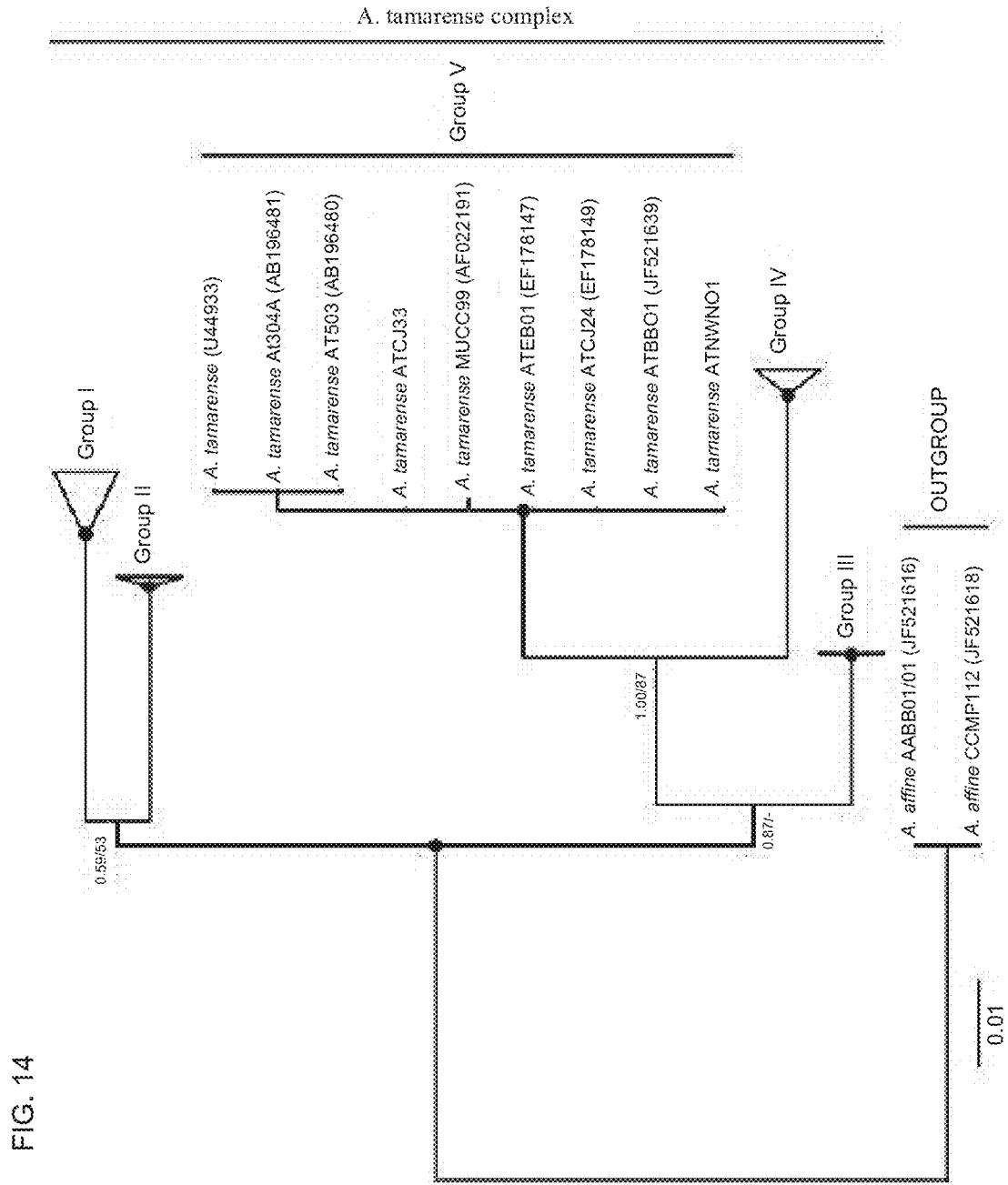
FIG. 14 shows 18S+ITS1-5.8S-ITS2+28S rDNA concatenated phylogeny of the *A. tamarense* complex (2821 characters). The tree is reconstructed with Bayesian inference (Phylobayes). Numbers on the internal nodes represent posterior probability and bootstrap values (>50%) for Phylobayes and RAxML (ordered; Phylobayes/RaxML). Black circles indicate a posterior probability value of 1.00 and bootstrap >90%. Group 1-4 clades have been collapsed, for an expanded version of the phylogeny see

Three strains from Japan, including At304, isolated from Mikawa Bay, Japan, were found to be members of the Group V clade in the phylogenetic analysis (FIG. 14). This is the first report of a Group V strain being present in the north western Pacific region, as it was previously thought to be confined to southern Australia (Bolch and de Salas 2007). The toxicity of strains from Japan was not determined, and needs to be examined.

The strain ATNWB01 had a STX cell quota well within the detectable range using standard HPLC methods (15.3 fmol cell-1 Table 7). This is similar to the toxin quota reported for many common STX-producing strains of this species complex (Table 7, 3.5-328 fmol cell$^{-1}$, 0.66-9.8 pg STX equivalents cell$^{-1}$). The toxin profile of this strain was relatively unusual, as GTX5 has not commonly been reported to be a major part of the toxin profile of strains of *Alexandrium tamarense* species complex (Table 7; Anderson et al., 1994). In general, strains of *Alexandrium catenella* (Group IV), the most common source of PSTs in shellfish in New South Wales, have contained high proportions of C1/2 and GTX1/4 as major components (Murray et al, 2011; Negri et al 2003; Hallegraeff et al., 1991). GTX5 has been found to be a major component of a strain of *Alexandrium tamarense* Group I from Chile, (33.7%, Aguilera-Belmonte et al., 2011), and two strains of *Alexandrium catenella* (Group IV) from France, (44-46%, Lilly et al., 2002).

No cultures were made of the *A. tamarense* strain identified from the Hastings River sample, and no molecular sequences were determined, therefore it is not possible to definitively identify it as *A. tamarense* Group V. Fortnightly phytoplankton monitoring has been undertaken at 69 sites in 32 estuaries in New South Wales for the past 7 years. *Alexandrium catenella* has been identified on 8 sampling occasions in 2010 and 2011. On 7 of these, PSP toxins were subsequently found in sample oysters from neighbouring oyster harvest areas, using Jellet PSP tests (NSW Food Authority, unpublished data). *Alexandrium tamarense* was identified from 4 samples in 2010 and 2011. The sample from the Hastings River is the first report of it being associated with PSP toxicity in Australian oysters. The analogues produced by *Alexandrium tamarense* Group V, in particular, the high proportion of GTX5, has a low equivalent toxicity when compared to the most toxic analogues such as STX, and it is estimated to be about 10% as toxic as STX (Oshima, 1995). This low STX equivalent toxicity may explain why this is the first report of an incident of shellfish toxicity in this region that is putatively linked to a bloom of this species. Further sampling of *Alexandrium tamarense* Group V populations in NSW coastal waters is required in order to verify whether local populations can indeed produce toxins.

The three strains of *A. tamarense* have all been found to possess the gene sxtA (Stüken et al., 2011). It was found that sxtA genes were closely related to each other in all Group V strains (0.5-2.5% differences in aligned sequences for domains sxtA1 and sxtA4). The presence or absence of these genes in these strains therefore appears to be unrelated to toxin production.

Differences in growth and toxin production in the species *Alexandrium* catenella, *Alexandrium tamarense* and *Alexandrium minutum* have been previously reported, related to the environmental conditions of the culture, such as salinity, light and nutrients, and the growth phase of the culture (Hamasaki et al., 2001; Hu et al., 2006; Lippemeier et al., 2003; Anderson et al. 1990; Grzebyk et al., 2003). In the present study, each of the three *A. tamarense* strains were cultured under identical light conditions, in the same media and seawater, and were inoculated and then harvested on the same days. Therefore, it seems unlikely that the lack of toxicity found in the other two *Alexandrium tamarense* Group V strains is a result of differences in environmental conditions promoting the differential expression of STX production.

Some cultured strains of *Alexandrium* may lose toxicity over time in culture, for example, in *Alexandrium minutum* (reported as *A. lusitanicum* in Martins et al., 2004). This was initially thought to be related to antibiotic exposure, as co-cultured and symbiotic bacteria have been shown to play a role in mediating toxin production in *Alexandrium* species (Ho et al., 2006). In the present study, the cultures of Group V examined most likely contain mixed bacterial communities in line with that of the seawater at the site of isolation, and none had been exposed to antibiotics.

Mating experiments have found that subclones of a toxic clonal strain of *Alexandrium tamarense*, (Group IV) can be non-toxic (Cho et al., 2008). The non-toxic characteristics of one strain of *A. tamarense*, an axenic non-toxic subclone of a toxic strain, were confirmed at the attomole per cell level. Three out of nine toxic subclones of this same strain became non-toxic over a relatively short period of time (4-6 years), while the other toxic subclones retained their toxicity and the non-toxic subclones remained non-toxic (Cho et al., 2008).

High levels of population genetic differences have been found within the species *Alexandrium catenella* Group IV (Masseret et al., 2009), *Alexandrium tamarense* Group I (Nagai et al., 2007), (Alpermann et al., 2009), *A. fundyense* Group I (Erdner et al., 2011) and *A. minutum* (McCauley et al., 2009), using microsatellite markers. This, in combination with the results of strains with differing toxin production following intraspecific mating experiments (Cho et al., 2008), suggests that significant population level differences in toxin production may also exist within *A. tamarense* (Group V). Further studies using microsatellite markers on multiple clonal cultures of this strain may help to determine whether toxin production is restricted to one particular population of this species, which may allow for the design of predictive genetic tools for the identification of this population.

REFERENCES

Aguilera-Belmonte, A., Inostroza, I., Franco, J. M., Riobà, P., Gomez, P. I., 2011. The growth, toxicity and genetic characterization of seven strains of *Alexandrium catenella* (Whedon and Kofoid) Balech 1985 (Dinophyceae) isolated during the 2009 summer outbreak in southern Chile. Harmful Algae. In Press.

Alpermann, T. J., Beszteri, B., John, U., Tillmann, U., Cembella, A. D., 2009. Implications of life history transitions on the population genetic structure of the toxigenic marine dinoflagellate *Alexandrium tamarense*. Mol. Ecol. 18(10), 2122-2133.

Anderson, D., Kulis, D., Doucette, G., Gallagher, J., Balech, E., 1994. Biogeography of toxic dinoflagellates in the genus *Alexandrium* from the northeastern United States and Canada. Mar. Biol. 120(3), 467-478.

Anderson, D., Kulis, D., Sullivan, J., Hall, S., 1990. Toxin composition variations in one isolate of the dinoflagellate *Alexandrium fundyense*. Toxicon 28(8), 885-893.

Balech, E. 1995. The genus *Alexandrium* Halim (Dinoflagellata). Shenkin Island Press.

Boczar, B. A., Beitler, M. K., Liston, J., Sullivan, J. J., Cattolico, R. A., 1988. Paralytic shellfish toxins in *Protogonyaulax tamarensis* and *Protogonyaulax catenella* in axenic culture. Plant Physiol. 88(4), 1285.

Bolch, C. J. S., de Salas, M. F., 2007. A review of the molecular evidence for ballast water introduction of the toxic dinoflagellates *Gymnodinium catenatum* and the *Alexandrium*. Harmful Algae 6(4), 465-485.

Castresana, J., 2000. Selection of conserved blocks from multiple alignments for their use in phylogenetic analysis. Mol. Biol. Evol. 17(4), 540-552.

Cembella, A., Destombe, C., 1996. Genetic differentiation among *Alexandrium* populations from eastern Canada. In: Harmful and Toxic Algal Blooms. Intergovernmental Oceanographic Commission, UNESCO, Paris, 447-450.

Cembella, A., Taylor, F., Therriault, J. C., 1988. Cladistic analysis of electrophoretic variants within the toxic dinoflagellate genus *Protogonyaulax*. Bot. Mar. 31(1), 39-52.

Cho, Y., Hiramatsu, K., Ogawa, M., Omura, T., Ishimaru, T., Oshima, Y., 2008. Non-toxic and toxic subclones obtained from a toxic clonal culture of *Alexandrium tamarense* (Dinophyceae): Toxicity and molecular biological feature. Harmful Algae 7(6), 740-751.

de Salas, M. F., Emmerik, M. J., Hallegraeff, G., Negri, A., Vaillancourt, R., Bolch, C., 2001. Toxic Australian *Alexandrium* Dinoflagellates: Introduced or indigenous? In: Hallegraeff, G. M., Blackburn, S. I., Bolch, C. J., Lewis, R. J. (Eds.), Proceedings of the Ninth International Conference on Harmful Algal Blooms. Intergovernmental Oceanographic Commission of UNESCO, Hobart, Tasmania, Harmful Algal Blooms 2000., pp 477-480.

Erdner, D. L., Richlen, M., McCauley, L. A. R., Anderson, D. M., 2011. Diversity and dynamics of a widespread bloom of the toxic dinoflagellate *Alexandrium* fundyense. PloS One 6(7), e22965.

Fukuyo, Y., 1985. Morphology of *Protogonyaulax tamarensis* (Lebour) Taylor and *Protogonyaulax catenella* (Whedon and Kofoid) Taylor from Japanese coastal waters. Bull. Mar. Sci. 37(2), 529-537.

Gayoso, A. M., Fulco, V. K., 2006. Occurrence patterns of *Alexandrium tamarense* (Lebour) Balech populations in the Golfo Nuevo (Patagonia, Argentina), with observations on ventral pore occurrence in natural and cultured cells. Harmful Algae 5(3), 233-241.

Genovesi, B., Shin-Grzebyk, M. S., Grzebyk, D., Laabir, M., Gagnaire, P. A., Vaguer, A., Pastoureaud, A., Lasserre, B., Collos, Y., Berrebi, P., 2011. Assessment of cryptic species diversity within blooms and cyst bank of the *Alexandrium tamarense* complex (Dinophyceae) in a Mediterranean lagoon facilitated by semi-multiplex PCR. J. Plankt. Res. 33(3), 405.

Grzebyk, D., Bechemin, C., Ward, C. J., Verite, C., Codd, G. A., Maestrini, S. Y., 2003. Effects of salinity and two coastal waters on the growth and toxin content of the dinoflagellate *Alexandrium minutum*. J. Plankt. Res. 25(10), 1185.

Hallegraeff, G., Bolch, C., Blackburn, S., Oshima, Y., 1991. Species of the toxigenic dinoflagellate genus *Alexandrium* in southeastern Australian waters. Bot. Mar. 34(6), 575-588.

Hallegraeff, G., Steffensen, D., Wetherbee, R., 1988. Three estuarine Australian dinoflagellates that can produce paralytic shellfish toxins. J. Plankt. Res. 10(3), 533.

Hamasaki, K., Horie, M., Tokimitsu, S., Toda, T., Taguchi, S., 2001. Variability in toxicity of the dinoflagellate *Alexandrium tamarense* isolated from Hiroshima Bay, western Japan, as a reflection of changing environmental conditions. J. Plankt. Res. 23(3), 271.

Higman, W. A., Stone, D. M., Lewis, J. M., 2001. Sequence comparisons of toxic and non-toxic *Alexandrium tamarense* (Dinophyceae) isolates from UK waters. Phycologia 40 (3), 256-262.

Ho, A. Y. T., Hsieh, D. P. H., Qian, P. Y., 2006. Variations in paralytic shellfish toxin and homolog production in two strains of *Alexandrium tamarense* after antibiotic treatments. Aquat. Microb. Ecol. 42(1), 41-53.

Hofacker, I. L., Fekete, M., Stadler, P. F., 2002. Secondary structure prediction for aligned RNA sequences. J. Mol. Biol. 319(5), 1059-1066.

Hu, H., Chen, W., Shi, Y., Cong, W., 2006. Nitrate and phosphate supplementation to increase toxin production by the marine dinoflagellate *Alexandrium tamarense*. Mar. Poll. Bull. 52(7), 756-760.

John, U., Fensome, R. A., Medlin, L. K., 2003. The application of a molecular clock based on molecular sequences and the fossil record to explain biogeographic distributions within the *Alexandrium tamarense* species complex (Dinophyceae). Mol. Biol. Evol. 20(7), 1015-1027.

Katoh, K., Toh, H., 2008. Recent developments in the MAFFT multiple sequence alignment program. Briefings Bioinf. 9(4), 286-298.

Kim, C. J., Sako, Y., 2005. Molecular identification of toxic *Alexandrium tamiyavanichii* (Dinophyceae) using two DNA probes. Harmful Algae 4(6), 984-991.

Kiryu, H., Tabei, Y., Kin, T., Asai, K., 2007. Murlet: a practical multiple alignment tool for structural RNA sequences. Bioinformatics 23(13), 1588-1598.

Kumar, S., SkjÃ¦veland, A., Orr, R., Enger, P., Ruden, T., Mevik, B. H., Burki, F., Botnen, A., Shalchian-Tabrizi, K., 2009. AIR: A batch-oriented web program package for construction of supermatrices ready for phylogenomic analyses. BMC Bioinformatics 10(1), 357.

Lartillot, N., Brinkmann, H., Philippe, H., 2007. Suppression of long-branch attraction artefacts in the animal phylogeny using a site-heterogeneous model. BMC Evol. Biol. 7(Suppl 1), S4.

Lartillot, N., Philippe, H., 2004. A Bayesian mixture model for across-site heterogeneities in the amino-acid replacement process. Mol. Biol. Evol. 21(6), 1095-1109.

Leaw, C. P., Lim, P. T., Ng, B. K., Cheah, M. Y., Ahmad, A., Usup, G., 2005. Phylogenetic analysis of *Alexandrium* species and *Pyrodinium bahamense* (Dinophyceae) based on theca morphology and nuclear ribosomal gene sequence. J. Phycol. 44(5).

Lilly, E., Kulis, D., Gentien, P., Anderson, D., 2002. Paralytic shellfish poisoning toxins in France linked to a human-introduced strain of *Alexandrium catenella* from the western Pacific: evidence from DNA and toxin analysis. J. Plankt. Res. 24(5), 443.

Lilly, E. L., Halanych, K. M., Anderson, D. M., 2007. Species boundaries and global biogeography of the *Alexandrium tamarense* complex (Dinophyceae) 1. J. Phycol. 43(6), 1329-1338.

Lin, S., Zhang, H., Hou, Y., Zhuang, Y., Miranda, L., 2009. High-level diversity of dinoflagellates in the natural environment, revealed by assessment of mitochondrial cox1 and cob genes for dinoflagellate DNA barcoding. Appl. Environ. Microbiol. 75(5), 1279.

Lippemeier, S., Frampton, D. M. F., Blackburn, S. I., Geier, S. C., Negri, A. P., 2003. Influence of phosphorous limitation on toxicity and photosynthesis of *Alexandrium minutum* (Dinophyceae) monitored by online detection of variable chorlophyll fluorescence. J. Phycol. 39(2), 320-331.

Litaker, R. W, Vandersea, M. W., Kibler, S. R., Reece, K. S., Stokes, N. A., Lutzoni, F. M., Yonish, B. A., West, M. A., Black, M. N. D., Tester, P. A., 2007. Recognizing dinoflagellate species using ITS rDNA sequences. J. Phycol. 43(2), 344-355.

Madison, W., Madison, D., 1992. MacClade: interactive analysis of phylogeny and character evolution. Sunderland, Mass.: Sinnauer Associates.

Martins, C. A., Kulis, D., Franca, S., Anderson, D. M., 2004. The loss of PSP toxin production in a formerly toxic *Alexandrium lusitanicum* clone. Toxicon 43(2), 195-205.

Masseret, E., Grzebyk, D., Nagai, S., Genovesi, B., Lasserre, B., Laabir, M., Collos, Y., Vaguer, A., Berrebi, P., 2009. Unexpected genetic diversity among and within populations of the toxic dinoflagellate *Alexandrium catenella* as revealed by nuclear microsatellite markers. Appl. Environ. Microbiol. 75(7), 2037-2045.

McCauley, L. A. R., Erdner, D. L., Nagai, S., Richlen, M. L., Anderson, D. M., 2009. Biogeographic analysis of the globally distributed harmful algal bloom species *Alexandrium minutum* (Dinophyceae) based on rRNA gene sequences and microsatellite markers. J. Phycol. 45(2), 454-463.

Medlin, L., Elwood, H. J., Stickel, S., Sogin, M. L., 1988. The characterization of enzymatically amplified eukaryotic 16S-like rRNA-coding regions. Gene 71(2), 491-499.

Montresor, M., John, U., Beran, A., Medlin, L. K., 2004. *Alexandrium tamatum* sp. nov. (dinophyceae): A new nontoxic species in the genus *Alexandrium*. J. Phycol. 40(2), 398-411.

Murray, S. A., O'Connor, W. A., Alvin, A., Mihali, T. K., Kalaitzis, J., Neilan, B. A., 2009. Differential accumulation of paralytic shellfish toxins from *Alexandrium minutum* in the pearl oyster, *Pinctada imbricata*. Toxicon 54(3), 217-223.

Murray, S. A., Wiese M., Stüken, A., Brett, S. Kellmann, R., Hallegraeff, G. M., Neilan, B. A, 2011. sxtA-based quantitative molecular assay to identify saxitoxin-producing harmful algal blooms in marine waters. Appl. Environ. Microbiol. 77:7050-7057.

Nagai, S., Lian, C., Yamaguchi, S., Hamaguchi, M., Matsuyama, Y., Itakura, S., Shimada, H., Kaga, S., Yamauchi, H., Sonda, Y., 2007. Microsatellite markers reveal population genetic structure of the toxic dinoflagellate *Alexandrium tamarense* (dinophyceae) in Japanese coastal waters. J. Phycol. 43(1), 43-54.

Negri, A., Llewellyn, L., Doyle, J., Webster, N., Frampton, D., Blackburn, S., 2003. Paralytic shellfish toxins are restricted to few species among Australia's taxonomic diversity of cultured microalgae. J. Phycol. 39(4), 663-667.

Orlova, T. Y., Selina, M. S., Lilly, E. L., Kulis, D. M., Anderson, D. M., 2007. Morphogenetic and toxin composition variability of *Alexandrium tamarense* (Dinophyceae) from the east coast of Russia. J. Phycol. 46(5).

Orr, R. J. S., Stüken, A., Rundberget, T., Eikrem, W., Jakobsen, K. S., 2011. Improved phylogenetic resolution of toxic and non-toxic *Alexandrium* strains using a concatenated rDNA approach. Harmful Algae 10(6), 676-688.

Oshima, Y., 1995. Postcolumn derivatization liquid chromatographic method for paralytic shellfish toxins. J. AOAC International 78(2), 528-532.

Parkhill, J. P., Cembella, A. D., 1999. Effects of salinity, light and inorganic nitrogen on growth and toxigenicity of the marine dinoflagellate *Alexandrium tamarense* from northeastern Canada. J Plankt. Res. 21(5), 939-955.

Penna, A., Magnani, M., 1999. Identification of *Alexandrium* (Dinophyceae) species using PCR and rRNA targeted probes. J. Phycol. 35(3), 615-621.

Persich, G., Kulis, D., Lilly, E, Anderson D. M., Garcia V. M. T. 2006. Probable origin and toxin profile of *Alexandrium tamarense* (Lebour) Balech from southern Brazil. Harmful Algae 5, 36-44.

Posada, D., Crandall, K. A., 1998. Modeltest: testing the model of DNA substitution. Bioinformatics 14(9), 817-818.

Rogers, J. E., Leblond, J. D., Moncreiff, C. A., 2006. Phylogenetic relationship of *Alexandrium monilatum* (Dinophyceae) to other *Alexandrium* species based on 18S ribosomal RNA gene sequences. Harmful Algae 5(3), 275-280.

Sako, Y., Kim, C. H., Ninomiya, H., Adachi, M., Ishida, Y., 1990. Isozyme and cross analysis of mating populations in the *Alexandrium catenella/tamarense* species complex. In: Toxic Marine Phytoplankton. Elsevier, New York, 320-323.

Scholin, C. A., Herzog, M., Sogin, M., Anderson, D. M., 1994. Identification of group and strain specific genetic markers for globally distributed *Alexandrium* (dinophyceae). II Sequence analysis of a fragment of the LSU rRNA gene. J. Phycol. 30(6), 999-1011.

Stamatakis, A., 2006. RAxML-VI-HPC: maximum likelihood-based phylogenetic analyses with thousands of taxa and mixed models. Bioinformatics 22(21), 2688.

Steidinger, K. A., 1990. Species of the *tamarensis/catenella* group of *Gonyaulax* and the fucoxanthin derivative-containing gymnodiniods. In: Graneli, E., Sundsstrom, B., Edler, L., Anderson, D. M. (Eds.), Toxic Marine Phytoplankton. Elsevier, New York, pp. 11-16.

Stüken, A., Orr, R. J. S., Kellmann, R., Murray, S. A., Neilan, B. A., Jakobsen, K. S., 2011. Discovery of nuclear-encoded genes for the neurotoxin saxitoxin in dinoflagellates. PloS One 6(5), e20096.

Wohlrab, S., M. H. Iversen, and U. John. 2010. A molecular and co-evolutionary context for grazer induced toxin production in *Alexandrium tamarense*. PloS One 5:e15039.

Yang, I., U. John, S. Beszteri, G. Glockner, B. Krock, A. Goesmann, and A. D. Cembella. 2010. Comparative gene expression in toxic versus non-toxic strains of the marine dinoflagellate *Alexandrium minutum*. BMC Genomics 11:248.

Example 6: qPCR Reactions for the Detection of sxtA4 and Discerning Between Toxic and Non-Toxic Strains of *Alexandrium minutum*

Materials and Methods

10 µl or 20 µl qPCR reactions were run on a Roche LightCycler®480 system in a white 96 well plate. Each reaction contained 5 or 10 µl LightCycler® 480 SYBR Green I Master, 125 nM of each primer (sxt072 and sxt073) and template (*Alexandrium* cDNA or gDNA). Reactions were run in duplicate. Standard curves and non-template controls were included on each plate. Standard curves were generated with 10× serial dilutions of a gel-purified PCR amplicon generated from strain CCMP113 with primers sxt007 & sxt008 (PCR to get amplicon as as described in Stüken et al. 2011, PlosOne). qPCR cycling parameters were: hot-start: 1×(95° C., 10 min); amplification: 45×(94° C., 10s; 64° C., 20s; 72° C., 10s, single acquisition; melting curve: 1×(95° C., 5s; 65° C., 1 min; up to 97° C. continuous measurements); Cooling: 1×(40° C., 10s). Crossing point and meltcurve ananylses were carried out using the software supplied by Roche.

The qPCR primers used for the detection of sxtA in these experiments were:

```
                                        (SEQ ID NO: 228)
sxt072          CTTGCCCGCCATATGTGCTT (SEQ ID NO: 229)
sxt073          GCCCGGCGTAGATGATGTTG
```

Results

The following strains were tested by the qPCR outlined above.

| Species | Strain | SXT-synthesis? | Result |
|---|---|---|---|
| Alexandrium minutum | 1022 Rance | under investigation | double peak |
| Alexandrium minutum | 771 Penzé | under investigation | double peak |
| Alexandrium tamarense | ATNWB01 | yes | single peak |
| Alexandrium tamarense | ATCJ33 | no | single peak |
| Alexandrium tamarense | ATEB01 | no | single peak |
| Alexandrium catenella | ACTRA | yes | single peak |
| Alexandrium catenella | ACCC01 | yes | single peak |
| Alexandrium andersonii | CCMP2222 | no | *unclear |
| Alexandrium insuetum | CCMP2082 | no | *unclear |
| Alexandrium affine | CCMP112 | no | *unclear |
| Alexandrium affine | PA8V | no | no amplification |
| Alexandrium minutum | CCMP113 | yes | single peak |
| Alexandrium minutum | AL24V | yes | single peak |
| Alexandrium minutum | Min3 | yes | single peak |
| Alexandrium minutum | VGO650 | no | double peak |
| Alexandrium minutum | VGO651 | no | double peak |
| Alexandrium minutum | AL10C | yes | single peak |
| Alexandrium catenella | CCMP1493 | yes | single peak |
| Alexandrium fundyense | CCMP1719 | yes | single peak |
| Alexandrium fundyense | MDQ1096 | yes | single peak |

Sequences for saxitoxin-producing strains were generated as follows:

*Alexandrium minutum* CCMP113_sxtA4_gDNA_consensus (SEQ ID NO: 230)
*Alexandrium minutum* CCMP113_sxtA4_cDNA_consensus (SEQ ID NO: 231)
*Alexandrium minutum* AL24V_sxtA4_gDNA_consensus (SEQ ID NO: 232)
*Alexandrium minutum* AL24V_sxtA4_cDNA_consensus (SEQ ID NO: 233)
*Alexandrium minutum* Min3_sxtA4_gDNA_consensus (SEQ ID NO: 234)
*Alexandrium minutum* Min3_sxtA4_cDNA_consensus (SEQ ID NO: 235)
*Alexandrium minutum* VGO650_sxtA4_DNA_consensus (SEQ ID NO: 236)
*Alexandrium minutum* VGO651_sxtA4_DNA_consensus (SEQ ID NO: 237)
*Alexandrium minutum* VGO651_sxtA4_cDNA_consensus (SEQ ID NO: 238)
*Alexandrium minutum* AL10C_sxtA4_cDNA_consensus (SEQ ID NO: 239)
*Alexandrium catenella* CCMP1493_sxtA4_cDNA_consensus (SEQ ID NO: 240)
*Alexandrium fundyense* CCMP1719_sxtA4_cDNA_consensus (SEQ ID NO: 241)
*Alexandrium fundyense* MDQ1096_sxtA4_cDNA_consensus (SEQ ID NO: 242)

Figure 17:
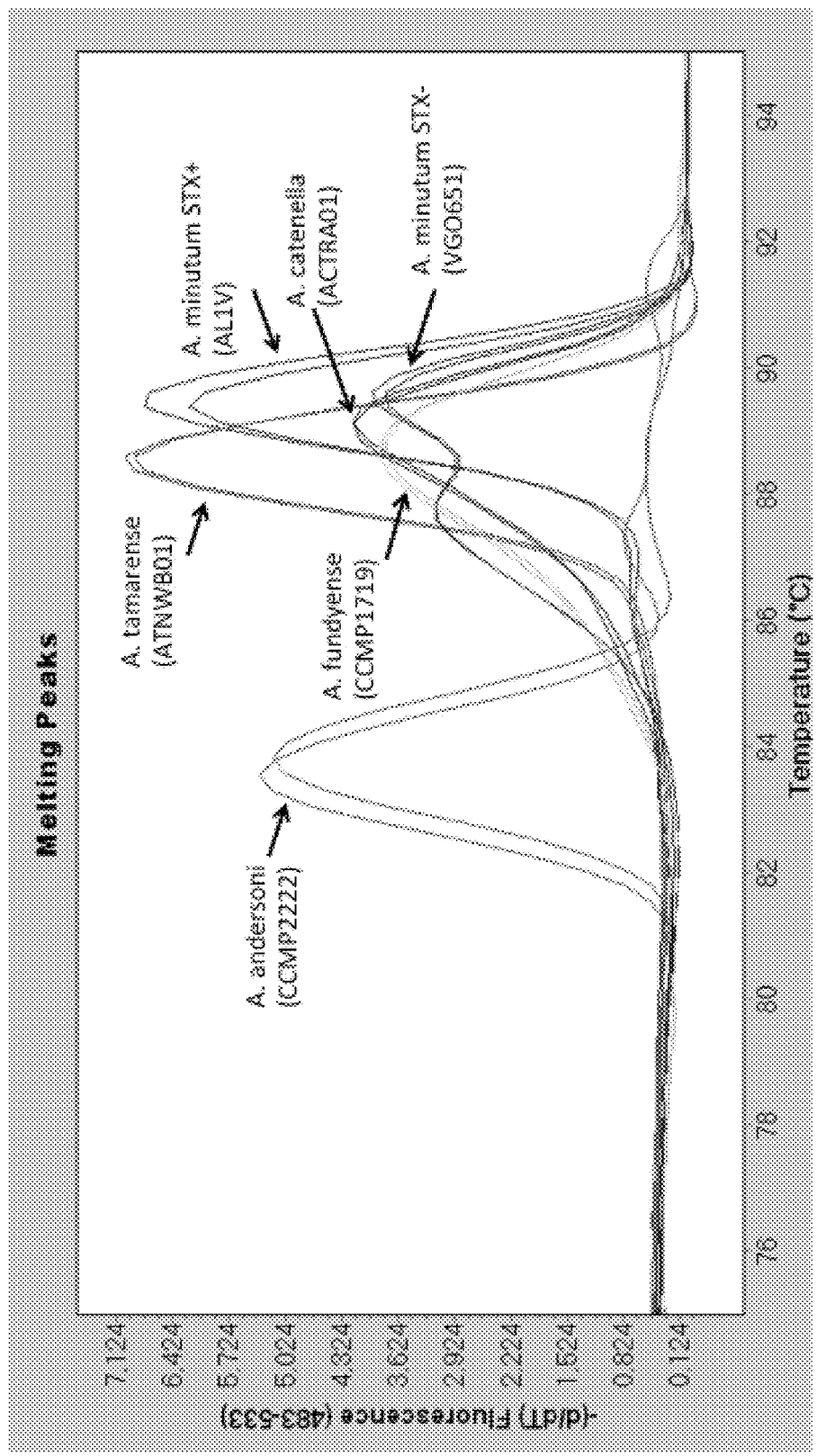
FIG. 17 shows toxic *A. minutum* AL1V, two curves; non-STX *A. minutum* VGO651, one curve.

The primers utilised detected sxtA in STX producing species and can also discriminate between toxic and non-toxic strains of *Alexandrium minutum*. Non-toxic *A. minutum* have two different sxtA copies in their genome, which results in a bimodal melting curve, when a Sybr Green assay is used (see FIG. 17: toxic *A. minutum* AL1V, two curves; non-STX *A. minutum* VGO651, one curve). Other species also have characteristic melt-curves, but discrimination between toxic and non-toxic species based on the meltcurve only works for *A. minutum*.

The primers sxt072 and sxt073 were also demonstrated to work well with the Universal Probe Library probe from Roche, #142 (data not shown). This assay is very specific and useful for detection of sxtA in environmental samples.

Example 7: sxtA1 and sxtA4 are Absent in Dinoflagellate Strains that do not Produce Saxitoxins Materials and Methods sxtA1 and sxtA4 PCRs were performed as described in Example 1 above.

Results sxtA (1/4) was not detected in any of the dinoflagellate strains listed below:

| Species/Taxon | sxtA (1/4) |
|---|---|
| Adenoides eludens CCMP1891 | n.d. |
| Alexandrium insuetum CCMP2082 | n.d. |

-continued

| Species/Taxon | sxtA (1/4) |
|---|---|
| *Amphidinium carteri* UIO081 | n.d. |
| *Amphidinium mootonorum* CAWD161 | n.d. |
| *Azadinium spinosum* RCC2538 | n.d. |
| *Ceratium longipes* CCMP1770 | n.d. |
| *Coolia monotis* | n.d. |
| *Gambierdiscus australes* CAWD148 | n.d. |
| *Gymnodinium aureolum* SCCAP K-1561 | n.d. |
| *Heterocapsa triquetra* RCC2540 | n.d. |
| *Karlodinium veneficum* RCC2539 | n.d. |
| *Lepidodinium chlorphorum* RCC2537 | n.d. |
| *Lingulodinium polyedrum* CCMP1931 | n.d. |

-continued

| Species/Taxon | sxtA (1/4) |
|---|---|
| *Pentapharsodinium dalei* SCCAP K-1100 | n.d. |
| *Polarella glacialis* CCMP2088 | n.d. |
| *Prorocentrum micans* UIO292 | n.d. |
| *Prorocentrum minimum* UIO085 | n.d. |
| *Protoceratium reticulatum* | n.d. |
| *Pyrocystis noctiluca* CCMP732 | n.d. |
| *Scrippsiella trochoideae* BS-46 | n.d. |
| *Thecadinium kofoidii* SCCAP K-1504 | n.d. | n.d. not detected

The invention claimed is:

1. A method comprising:
   obtaining a sample for use in the method; and
   detecting whether a saxitoxin-producing dinoflagellate is present in the sample by contacting the sample with a nucleic acid primer specific for a dinoflagellate saxitoxin A catalytic domain polynucleotide sequence or an antibody specific for a dinoflagellate saxitoxin A catalytic domain polypeptide, wherein the saxitoxin A catalytic domain is selected from: saxitoxin A1 catalytic domain, saxitoxin A4 catalytic domain, or a fragment of a saxitoxin A1 or A4 catalytic domain, and wherein:
   the saxitoxin A4 catalytic domain sequence consists of a nucleotide sequence having 95% or more similarity with nucleotides 3115-4121 of the polynucleotide sequence set forth in SEQ ID NO: 3, or a nucleotide sequence having 95% or more similarity with nucleotides 3597-3721 of the polynucleotide sequence set forth in SEQ ID NO: 3, and
   the saxitoxin A1 catalytic domain sequence consists of a nucleotide sequence having 95% or more similarity with nucleotides 160-1821 of the polynucleotide sequence set forth in SEQ ID NO: 1, or a nucleotide sequence having 95% or more similarity with nucleotides 277-2022 of the polynucleotide sequence set forth in SEQ ID NO: 3.

2. The method according to claim 1, wherein the polynucleotide comprises a saxitoxin A nucleotide sequence selected from a nucleotide sequence having 95% or more similarity with any one of SEQ ID NOS: 224-227, 230-242 and 247.

3. The method according to claim 1, wherein the saxitoxin A catalytic domain is a saxitoxin A4 catalytic domain sequence or fragment thereof consisting of a nucleotide sequence having 95% or more similarity with nucleotides 3115-4121 of the polynucleotide sequence set forth in SEQ ID NO: 3, or a nucleotide sequence having 95% or more similarity with nucleotides 3597-3721 of the polynucleotide sequence set forth in SEQ ID NO: 3.

4. The method according to claim 1, wherein the saxitoxin A catalytic domain is a saxitoxin A1 catalytic domain sequence consisting of a nucleotide sequence having 95% or more similarity with nucleotides 160-1821 of the polynucleotide sequence set forth in SEQ ID NO: 1, or a nucleotide sequence having 95% or more similarity with nucleotides 277-2022 of the polynucleotide sequence set forth in SEQ ID NO: 3.

5. The method according to claim 1, wherein said detecting comprises amplification of polynucleotides from the sample by polymerase chain reaction and said polymerase chain reaction utilises one or more primers comprising a sequence set forth in any one of SEQ ID NOs: 198-199, 200-211, 228-229, and 243-244, or a fragment of any one of those sequences.

6. The method according to claim 1, wherein the polypeptide comprises:
   (i) a saxitoxin A1 catalytic domain amino acid sequence having 95% or more similarity with residues 1-554 of SEQ ID NO: 2 or a saxitoxin A1 catalytic domain amino acid sequence having 95% or more similarity with residues 1-582 of SEQ ID NO: 4; or
   (ii) a saxitoxin A4 catalytic domain amino acid sequence having 95% or more similarity with residues 947-1281 of SEQ ID NO: 4.

7. The method according to claim 1, wherein the saxitoxin-producing dinoflagellate is from the *Alexandrium*, *Pyrodinium* or *Gymnodinium* genus.

8. The method according to claim 7, wherein the saxitoxin-producing dinoflagellate is selected from the group consisting of *A. catenella*, *A. fundyense*, *A lusitanicum*, *A. minutum*, *A. ostenfeldii*, *A. tamarense*, *G. catenatum* and *P. bahamense* var *compressum*.

* * * * *

UNITED STATES PATENT AND TRADEMARK OFFICE
CERTIFICATE OF CORRECTION

| | | |
|---|---|---|
| PATENT NO. | : 10,947,601 B2 | Page 1 of 1 |
| APPLICATION NO. | : 15/370752 | |
| DATED | : March 16, 2021 | |
| INVENTOR(S) | : Brett A. Neilan et al. | |

It is certified that error appears in the above-identified patent and that said Letters Patent is hereby corrected as shown below:

On the Title Page

Item (73), should read:
NewSouth Innovations Pty Limited, New South Wales (AU);
Universitetet i Oslo, Oslo (NO)

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*